US008778964B2

(12) United States Patent
Vakalopoulos et al.

(10) Patent No.: US 8,778,964 B2
(45) Date of Patent: Jul. 15, 2014

(54) HYDROXY-SUBSTITUTED IMIDAZO[1,2-A]-PYRIDINECARBOXAMIDES AND THEIR USE

(71) Applicant: Bayer Pharma Aktiengesellschaft, Berlin (DE)

(72) Inventors: Alexandros Vakalopoulos, Hilden (DE); Ingo Hartung, Berlin (DE); Markus Follmann, Köln (DE); Rolf Jautelat, Haan (DE); Alexander Straub, Wuppertal (DE); Jorma Haβfeld, Düsseldorf (DE); Niels Lindner, Wuppertal (DE); Dirk Schneider, Wuppertal (DE); Frank Wunder, Wuppertal (DE); Johannes-Peter Stasch, Solingen (DE); Gorden Redlich, Bochum (DE); Volkhart Min-Jian Li, Velbert (DE); Eva-Maria Becker, Wuppertal (DE); Andreas Knorr, Erkrath (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 13/789,208

(22) Filed: Mar. 7, 2013

(65) Prior Publication Data
US 2014/0128424 A1 May 8, 2014

(30) Foreign Application Priority Data
Nov. 5, 2012 (EP) ..................... 12191200

(51) Int. Cl.
A61K 31/44 (2006.01)
C07D 491/02 (2006.01)
C07D 498/02 (2006.01)

(52) U.S. Cl.
USPC .......................... 514/300; 546/121

(58) Field of Classification Search
USPC .......................... 546/121; 514/300
See application file for complete search history.

(56) References Cited

U.S. PATENT DOCUMENTS

| | | | |
|---|---|---|---|
| 5,691,336 | A | 11/1997 | Dorn et al. |
| 5,698,704 | A | 12/1997 | Jackson |
| 6,180,656 | B1 | 1/2001 | Fürstner et al. |
| 8,212,041 | B2 | 7/2012 | Albrecht et al. |
| 2008/0051409 | A1 | 2/2008 | Gmeiner et al. |
| 2008/0103183 | A1 | 5/2008 | Ackermann et al. |
| 2009/0124612 | A1 | 5/2009 | Albrecht et al. |
| 2010/0092966 | A1 | 4/2010 | Burkhardt et al. |
| 2013/0203751 | A1 | 8/2013 | Hübsch et al. |

FOREIGN PATENT DOCUMENTS

| | | |
|---|---|---|
| EP | 0266890 A1 | 5/1988 |
| EP | 1277754 A1 | 2/2003 |
| JP | H01258674 | 10/1989 |
| WO | 8903833 | 5/1989 |
| WO | 9634866 A1 | 11/1996 |
| WO | 2008082490 A2 | 7/2008 |
| WO | 2008134553 A1 | 11/2008 |
| WO | 2010030538 A2 | 3/2010 |
| WO | 2011113606 A1 | 9/2011 |
| WO | 2011141409 | 11/2011 |
| WO | 2012143796 A2 | 10/2012 |
| WO | 2012165399 | * 12/2012 |

OTHER PUBLICATIONS

Lasker et al., Expert Rev Respir Med. Apr. 2001; 5(2): 153-161.*
Witte et al., "Experimental heart failure in rats: effects on cardiovascular circadian rhythms and on myocardial β-adrenergic signaling," Cardiovascular Research, 2000, 47:350-358.
Chien-nien et al., "Cyclic Guanosine Monophasphate Signalling Pathway in Pulmonary Arterial Hypertension," 2013, vol. 58, 211-218.
Dembinski et al.,"Recent Advances in the Mitsunobu Reaction: Modified Reagents and the Quest for Chromatography-Free Separation," Eur. J. Org. Chem. 2004, vol. 13, 2763-2772.
Deng et al., "Studies on Phosphoroheterocycle Chemistry II: A Simple and New Route to 1,3,2-Diazaphospholidine-4-thione 2-sulfide Derivatives," Synthesis 2001, 16:2445-2449.
Gensini et al., "3-Azabicyclo[3.1.0]hex-1-ylamines by Ti-Mediated Intramolecular Reductive Cyclopropanation of α-(N-Allylamino)-Substituted N,N-Dialkylcarboxamides and Carbonitriles," Eur. J. Org. Chem., 2002, 15:2499-2507.
Glass et al., "Stimulation of Human Platelet Guanylate Cyclase by Fatty Acids," J. Biol. Chem., Feb. 1977, 252:1279-1285.
Greene et al., Greene's Protective Groups in Organic Synthesis, 4th ed, chapter 1, "The Role of Protective Groups in Organic Synthesis," 2007, Published by John Wiley & Sons, New York.
Hjorringgaard et al., "An Automatic Solid-Phase Synthesis of Peptaibols," J. Org. Chem., 2009, 74:1329-1332.
Hoenicka et al., "Purified Soluble Guanylyl Cyclase Expressed in a Baculovirus/Sf9 System: Stimulation by YC-1, Nitric Oxide, and Carbon Monoxide," J. Mol. Med., 1999, 77:14-23.
Hughes et al., Organic Reactions, vol. 42, 1992, Chapter 2, "The Mitsunobu Reaction," Published by John Wiley & Sons, Inc, pp. 335-395 and 636-656.
Kozo et al., International Review of Experimental Pathololgy, vol. 7, 1969, chapter 2, "Spontaneous Hypertension in Rats," Published by Academic Press, Inc., New York, pp. 227-270.
Maarten van den Buuse, "Circadian Rhythms of Blood Pressure, Heart Rate,and Locomotor Activity in Spontaneously Hypertensive Rats as Measured With Radio-Telemetry," Physiology & Behavior, 1994, 55:(4) 783-787.

(Continued)

Primary Examiner — Niloofar Rahmani
(74) Attorney, Agent, or Firm — Karen B. King

(57) ABSTRACT

The present application relates to novel substituted imidazo [1,2-a]pyridine-3-carboxamides, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

6 Claims, No Drawings

(56) References Cited

OTHER PUBLICATIONS

McElroy et al., "The Preparation and Properties of Crystalline Firefly Luciferin," Archives of Biochemistry and Biophysics 1957, 72:358-368.

Mülsch et al., "Effect of YC-1, an NO-independent, Superoxide-senstive Stimulator of Soluble Guanylyl Cyclase, on Smooth Muscle Responsiveness to Nitrovasodilators," British Journal Pharmacology 1997, 120:681-689.

Ogrel et al., "Synthesis of 15N-Labelled D-Isovaline and á-Aminoisobutyric Acid," Eur. J. Org. Chem., 2000, 5:857-859.

Pettibone et al., "A Structurally Novel Stimulator of Guanylate Cyclase With Long-Lasting Hypotensive Activity in the Dog," European Journal of Pharmacology, 1985, 116:307-312.

Soler et al., "Betulinic Acid Derivatives: A New Class of Specific Inhibitors of Human Immunodeficiency Virus Type 1 Entry," Journal Med. Chem., 1996, 39:1069-1083.

Stasch et al., "Cardiovascular actions of a novel NO-independent guanylyl cyclase stimulator, BAY 41-8543: in vivo studies," British Journal of Pharmacology, 2002, 135(2):344-355.

Ko et al., "YC-1, a novel activator of platelet guanylate cyclase," Blood, 1994, 84(12): 4226-4233.

Wunder et al., "A cell-based cGMP assay useful for ultra-high-throughput screening and identification of modulators of the nitric oxide/cGMP pathway," Analytical Biochemistry, 2005, 339:104-112.

Yu et al., "Vasorelaxant Effect of Isoliquiritigenin, a Novel Soluble Guanylate Cyclase Activator, in Rat Aorta," British Journal of Pharmacology, 1995, 114:1587-1594.

Lasker et al., "Targeting soluble guanylate cyclase for the treatment of pulmonary hypertension," Expert Rev Respir Med., Apr. 2011, 5:(2)153-161.

U.S. Appl. No. 13/789,655, filed Mar. 7, 2013.
U.S. Appl. No. 14/071,274, filed Nov. 1, 2013.
U.S. Appl. No. 14/071,274, filed Nov. 4, 2013.
U.S. Appl. No. 13/789,414, filed Mar. 7, 2013.

* cited by examiner

HYDROXY-SUBSTITUTED IMIDAZO[1,2-A]-PYRIDINECARBOXAMIDES AND THEIR USE

The present application relates to novel substituted imidazo[1,2-a]pyridine-3-carboxamides, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Over the last years, a number of substances which stimulate soluble guanylate cyclase directly. i.e. without prior release of NO, have been described, for example 3-(5'-hydroxymethyl-2'-furyl)-1-benzylindazole [YC-1; Wu et al., Blood 84 (1994), 4226; Mulsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587], and also various substituted pyrazole derivatives (WO 98/16223). EP 0 266 890-A1, WO 89/03833-A1, JP 01258674-A [cf. Chem. Abstr. 112:178986], WO 96/34866-A1, EP 1 277 754-A1, WO 2006/015737-A1, WO 2008/008539-A2, WO 2008/082490-A2, WO 2008/134553-A1, WO 2010/030538-A2 and WO 2011/113606-A1, inter alia, describe various imidazo[1,2-a]pyridine derivatives which can be used for treating disorders.

It was an object of the present invention to provide novel substances which act as stimulators of soluble guanylate cyclase and, as such, are suitable for the treatment and/or prophylaxis of diseases.

The present invention provides compounds of the general formula (I)

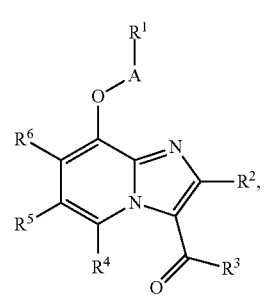

in which
A represents $CH_2$, $CD_2$ or $CH(CH_3)$,
$R^1$ represents $(C_4-C_6)$-alkyl, $(C_3-C_7)$-cycloalkyl or phenyl,
where $(C_4-C_6)$-alkyl may be substituted up to six times by fluorine,
where $(C_3-C_7)$-cycloalkyl may be substituted by 1 to 4 substituents independently of one another selected from the group consisting of fluorine, trifluoromethyl and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy, difluoromethoxy and trifluoromethoxy or at two adjacent carbon atoms of the phenyl group by a difluoromethylenedioxy bridge,
$R^2$ represents hydrogen, $(C_1-C_4)$-alkyl, cyclopropyl, monofluoromethyl, difluoromethyl or trifluoromethyl,
$R^3$ represents a group of the formula

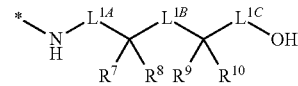

or

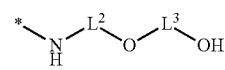

where
* represents the point of attachment to the carbonyl group,
$L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy, $L^{1B}$ represents a bond or $(C_1-C_4)$-alkanediyl,
$L^{1C}$ represents a bond or $(C_1-C_4)$-alkanediyl,
  where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
    where phenyl, phenoxy and benzyloxy for their part may be substituted by 1 to 3 halogen substituents,
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^8$ represents hydrogen or $(C_1-C_4)$-alkyl,
  where $(C_1-C_4)$-alkyl may be substituted by hydroxy,
or
$R^7$ and $R^8$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine and $(C_1-C_4)$-alkyl,
$R^9$ represents hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
  where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
    where phenyl, phenoxy and benzyloxy for their part may be substituted by
  where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
  and
  where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^{10}$ represents hydrogen or $(C_1-C_4)$-alkyl,
  where $(C_1-C_4)$-alkyl may be substituted by hydroxy,
or
$R^9$ and $R^{10}$ together with the carbon atom to which they are attached form a 3- to 7-membered carbocycle or a 4- to 7-membered heterocycle,
  where the 3- to 7-membered carbocycle and the 4- to 7-membered heterocycle for their part may be substituted by 1 or 2 substituents independently of one another selected from the group consisting of fluorine and $(C_1-C_4)$-alkyl,
  with the proviso that the radicals $R^7$ and $R^9$ do not both represent phenyl,
or
$R^7$ and $R^9$ together with the carbon atoms to which they are attached and with the group $L^{1B}$ form a 5- to 10-membered carbocycle,
with the proviso that not more than one of the radical pairs $R^7$ and $R^8$, $R^9$ and $R^{10}$ and $R^7$ and $R^9$, respectively, forms a carbo- or heterocycle,
$L^2$ represents straight-chain $(C_2-C_4)$-alkanediyl,
$L^3$ represents straight-chain $(C_2-C_4)$-alkanediyl,
$R^4$ represents hydrogen,
$R^5$ represents hydrogen, halogen, cyano, difluoromethyl, trifluoromethyl, $(C_1-C_4)$-alkyl, $(C_3-C_7)$-cycloalkyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and their N-oxides, salts, solvates, salts of the N-oxides and solvates of the N-oxides and salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of conventional mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanol-amine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl in the context of the invention represents a straight-chain or branched alkyl radical having the number or carbon atoms stated in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Carbocycle or cycloalkyl in the context of the invention represents a mono- or bicyclic saturated or partially unsaturated carbocycle having the number of ring carbon atoms stated in each case and up to 3 double bonds. The following may be mentioned by way of example and by way of preference: cyclopropyl, cyclobutyl, cyclopentyl, cyclohexyl, cycloheptyl, cyclopentenyl, cyclohexenyl, cyclohexadienyl, cycloheptenyl, cycloheptadienyl, indanyl, tetralinyl.

Alkenyl in the context of the invention represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkynyl in the context of the invention represents a straight-chain or branched alkynyl radical having 2 to 6 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkanediyl in the context of the invention represents a straight-chain or branched divalent alkyl radical having 1 to 4 carbon atoms. The following may be mentioned by way of example and by way of preference: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkoxycarbonyl in the context of the invention represents a straight-chain or branched alkoxy radical having 1 to 4 carbon atoms and a carbonyl group attached at the oxygen atom. The following may be mentioned by way of example and by way of preference: methoxycarbonyl, ethoxycarbonyl, n-propoxycarbonyl, isopropoxycarbonyl and tert-butoxycarbonyl.

Alkylthio in the context of the invention represents a thio group having a straight-chain or branched alkyl substituent having 1 to 4 carbon atoms. The following may be mentioned by way of example and by way of preference: methylthio, ethylthio, n-propylthio, isopropylthio, n-butylthio and tert-butylthio.

Alkylsulphonyl in the context of the invention represents a straight-chain or branched alkyl radical which has 1 to 4 carbon atoms and is attached via a sulphonyl group. The following may be mentioned by way of example and by way of preference: methylsulphonyl, ethylsulphonyl, n-propylsulphonyl, isopropylsulphonyl, n-butylsulphonyl and tert-butylsulphonyl.

A 4- to 7-membered heterocycle in the context of the invention represents a monocyclic saturated heterocycle which has a total of 4 to 7 ring atoms, which contains one or two ring heteroatoms from the group consisting of N, O, S, SO and $SO_2$ and which is attached via a ring carbon atom or, if appropriate, a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention represents a monocyclic aromatic heterocycle (heteroaromatic) which has a total of 5 or 6 ring atoms, which contains up to three identical or different ring heteroatoms from the group consisting of N, O and S and is attached via a ring carbon atom or, if appropriate, a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group which may represent $R^3$ or $R^1$, the end point of the line marked by a * or # label does not represent a carbon atom or a $CH_2$ group but forms part of the bond to the atom which is designated in each case and to which $R^3$ and $R^1$, respectively, are attached.

If radicals in the compounds according to the invention are substituted, the radicals may, unless specified otherwise, be mono- or polysubstituted. In the context of the present invention, all radicals which occur more than once are defined independently of one another. Substitution by one, two or three identical or different substituents is preferred.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

In the context of the present invention, preference is given to compounds of the formula (I) in which
A represents $CH_2$, $CD_2$ or $CH(CH_3)$,
$R^1$ represents $(C_4-C_6)$-alkyl, $(C_4-C_6)$-cycloalkyl or phenyl,
  where $(C_4-C_6)$-alkyl may be substituted up to six times by fluorine,
  where $(C_4-C_6)$-cycloalkyl may be substituted by 1 or 2 substituents independently of one another selected from the group consisting of fluorine, trifluoromethyl and methyl,
  and
  where phenyl may be substituted by 1 to 4 substituents independently of one another selected from the group consisting of fluorine, chlorine, bromine, difluoromethyl, trifluoromethyl and methyl or at 2 adjacent carbon atoms of the phenyl group by a difluoromethylenedioxy bridge,
$R^2$ represents hydrogen, $(C_1-C_4)$-alkyl, trifluoromethyl or cyclopropyl,
$R^3$ represents a group of the formula

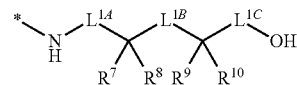

or

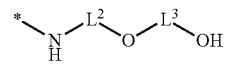

where
* represents the point of attachment to the carbonyl group,
$L^{1A}$ represents a bond or methylene,
$L^{1B}$ represents a bond, methylene or 1,2-ethanediyl,
$L^{1C}$ represents a bond or methylene,
  where methylene may be substituted by 1 or 2 substituents independently of one another selected from the group consisting of trifluoromethyl and $(C_1-C_4)$-alkyl,
$R^7$ represents hydrogen, trifluoromethyl, $(C_1-C_6)$-alkyl, $(C_2-C_4)$-alkenyl, $(C_3-C_6)$-cycloalkyl, $(C_1-C_4)$-alkoxycarbonyl, 5- or 6-membered heteroaryl or phenyl,
  where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, $(C_1-C_4)$-alkylthio, $(C_1-C_4)$-alkylsulphonyl, phenyl, phenoxy and benzyloxy,
    where phenyl, phenoxy and benzyloxy for their part may be substituted by 1 or 2 substituents selected from the group consisting of fluorine and chlorine,
  where $(C_3-C_6)$-cycloalkyl may be substituted by 1 or 2 substituents independently of one another selected from the group consisting of fluorine, trifluoromethyl, methyl and ethyl,
  and
  where phenyl and 5- or 6-membered heteroaryl may be substituted by 1 or 2 substituents independently of one another selected from the group consisting of fluorine, chlorine, cyano, trifluoromethyl, $(C_1-C_4)$-alkyl, methoxy and ethoxy,
$R^8$ represents hydrogen, methyl or ethyl,
  where methyl and ethyl may be substituted by hydroxy,
or
$R^7$ and $R^8$ together with the carbon atom to which they are attached form a 3- to 6-membered carbocycle,
  where the 3- to 6-membered carbocycle may be substituted by 1 or 2 substituents independently of one another selected from the group consisting of fluorine and methyl,
$R^9$ represents hydrogen, trifluoromethyl, $(C_1-C_6)$-alkyl, $(C_2-C_4)$-alkenyl, $(C_3-C_6)$-cycloalkyl, $(C_1-C_4)$-alkoxycarbonyl, 5- or 6-membered heteroaryl or phenyl,
  where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, $(C_1-C_4)$-alkylthio, $(C_1-C_4)$-alkylsulphonyl, phenyl, phenoxy and benzyloxy,
    where phenyl, phenoxy and benzyloxy for their part may be substituted by 1 or 2 substituents selected from the group consisting of fluorine and chlorine,
  where $(C_3-C_6)$-cycloalkyl may be substituted by 1 or 2 substituents independently of one another selected from the group consisting of fluorine, trifluoromethyl, methyl and ethyl, and
where phenyl and 5- or 6-membered heteroaryl may be substituted by 1 or 3 substituents independently of one another selected from the group consisting of fluorine, chlorine, cyano, trifluoromethyl, $(C_1-C_4)$-alkyl, methoxy and ethoxy, $R^{10}$ represents hydrogen, methyl or ethyl,
where methyl and ethyl may be substituted by hydroxy,
or
$R^9$ and $R^{10}$ together with the carbon atom to which they are attached form a 3- to 6-membered carbocycle,
where the 3- to 6-membered carbocycle may be substituted by 1 or 2 substituents independently of one another selected from the group consisting of fluorine and methyl, with the proviso that the radicals $R^7$ and $R^9$ do not both represent phenyl,
or
$R^7$ and $R^9$ together with the carbon atoms to which they are attached and with the group $L^{1B}$ form a 5- to 10-membered carbocycle,
with the proviso that not more than one of the radical pairs $R^7$ and $R^8$, $R^9$ and $R^{10}$ and $R^7$ and $R^9$, respectively, forms one of the carbo- or heterocycles mentioned above, $L^2$ represents 1,2-ethanediyl,
$L^3$ represents 1,2-ethanediyl,
$R^4$ represents hydrogen,
$R^5$ represents hydrogen, fluorine, chlorine, bromine, cyano, difluoromethyl, trifluoromethyl, methyl, ethyl, cyclopropyl, ethynyl, morpholinyl or pyrrolidinyl,
$R^6$ represents hydrogen or fluorine,
and to N-oxides, salts, solvates, salts of the N-oxides and solvates of the N-oxides and salts thereof.

In the context of the present invention, particular preference is given to compounds of the formula (I) in which
A represents $CH_2$,
$R^1$ represents a phenyl group of the formula

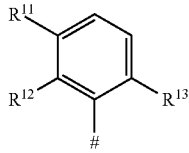

where
# represents the point of attachment to A,
and
$R^{11}$, $R^{12}$ and $R^{13}$ independently of one another represent hydrogen, fluorine or chlorine,
with the proviso that at least two of the radicals $R^{11}$, $R^{12}$, $R^{13}$ are different from hydrogen,
$R^2$ represents methyl,
$R^3$ represents a group of the formula

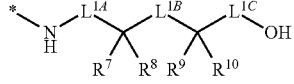

where
* represents the point of attachment to the carbonyl group,
$L^{1A}$ represents a bond,
$L^{1B}$ represents a bond, methylene or 1,2-ethanediyl,
$L^{1C}$ represents a bond,
$R^7$ represents hydrogen, trifluoromethyl, $(C_1-C_6)$-alkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl, and
where phenyl may be substituted by 1 or 2 substituents independently of one another selected from the group consisting of fluorine and chlorine,
$R^8$ represents hydrogen, methyl or ethyl,
$R^9$ represents hydrogen, trifluoromethyl, $(C_1-C_6)$-alkyl or phenyl,
where $(C_1-C_6)$-alkyl may be substituted by 1 or 2 substituents independently of one another selected from the group consisting of fluorine, trifluoromethyl, hydroxy, $(C_1-C_4)$-alkoxy and phenyl,
and
where the phenyl groups mentioned above may be substituted by 1 or 2 substituents independently of one another selected from the group consisting of fluorine and chlorine,
$R^{10}$ represents hydrogen, methyl or ethyl,
or
$R^9$ and $R^{10}$ together with the carbon atom to which they are attached form a 3- to 6-membered carbocycle,
with the proviso that the radicals $R^7$ and $R^9$ do not both represents phenyl,
or
$R^7$ and $R^9$ together with the carbon atoms to which they are attached and the group $L^{1B}$ form a 5- to 9-membered carbocycle,
with the proviso that not more than one of the radical pairs $R^9$ and $R^{10}$ and $R^7$ and $R^9$, respectively, forms a carbocycle,
$R^4$ represents hydrogen,
$R^5$ represents hydrogen, fluorine, chlorine, cyano, methyl or ethyl,
$R^6$ represents hydrogen,
and to N-oxides, salts, solvates, salts of the N-oxides and solvates of the N-oxides and salts thereof.

In the context of the present invention, preference is also given to compounds of the formula (I) in which
$R^1$ represents a group of the formula

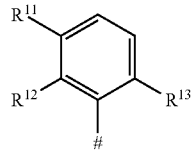

where
# represents the point of attachment to A,
and
$R^{11}$, $R^{12}$ and $R^{13}$ independently of one another represent hydrogen, fluorine or chlorine,
with the proviso that at least two of the radicals $R^{11}$, $R^{12}$, $R^{13}$ are different from hydrogen, and to N-oxides, salts, solvates, salts of the N-oxides and solvates of the N-oxides and salts thereof.

In the context of the present invention, preference is also given to compounds of the formula (I) in which
$R^2$ represents methyl,
and to N-oxides, salts, solvates, salts of the N-oxides and solvates of the N-oxides and salts thereof.

In the context of the present invention, preference is also given to compounds of the formula (I) in which
$R^3$ represents a group of the formula

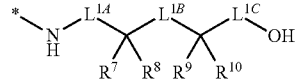

where
* represents the point of attachment to the carbonyl group,
$L^{1A}$ represents a bond,
$L^{1B}$ represents a bond, methylene or 1,2-ethanediyl,
$L^{1C}$ represents a bond or methylene,
where methylene may be substituted by 1 or 2 substituents independently of one another selected from the group consisting of trifluoromethyl, $(C_1-C_4)$-alkyl cyclopropyl and cyclobutyl,
and to N-oxides, salts, solvates, salts of the N-oxides and solvates of the N-oxides and salts thereof.

In the context of the present invention, preference is also given to compounds of the formula (I) in which
$R^3$ represents a group of the formula

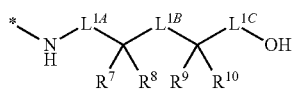

where
* represents the point of attachment to the carbonyl group,
$R^8$ represents hydrogen,
and
$R^{10}$ represents hydrogen, methyl or ethyl,
and to N-oxides, salts, solvates, salts of the N-oxides and solvates of the N-oxides and salts thereof.

In the context of the present invention, preference is also given to compounds of the formula (I) in which
$R^6$ represents hydrogen,
and to N-oxides, salts, solvates, salts of the N-oxides and solvates of the N-oxides and salts thereof.

In the context of the present invention, preference is also given to compounds of the formula (I) in which
$R^5$ represents hydrogen, fluorine, chlorine or methyl,
and to N-oxides, salts, solvates, salts of the N-oxides and solvates of the N-oxides and salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the preferred ranges mentioned above are particularly preferred.

The invention furthermore provides a process for preparing the compounds of the formula (I) according to the invention, characterized in that
[A] a compound of the formula (II)

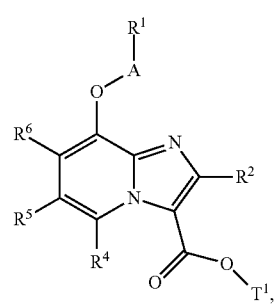

in which A, $R^1$, $R^2$, $R^4$, $R^5$ and $R^6$ each have the meanings given above and
$T^1$ represents $(C_1-C_4)$-alkyl or benzyl, is reacted in an inert solvent in the presence of a suitable base or acid to give a carboxylic acid of the formula (III)

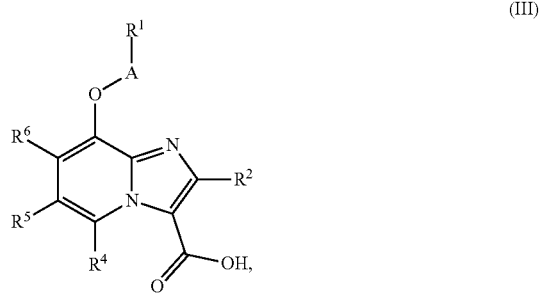

in which A, $R^1$, $R^2$, $R^4$, $R^5$ and $R^6$ each have the meanings given above,
and this is subsequently reacted in an inert solvent under amide coupling conditions with an amine of the formula (IV-A) or (IV-B)

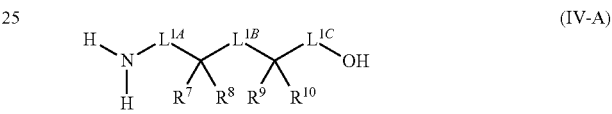

or

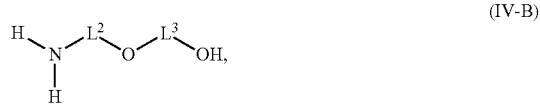

in which $L^{1A}$, $L^{1B}$, $L^{1C}$, $L^2$, $L^3$, $R^7$, $R^8$, $R^9$ and $R^{10}$ each have the meanings given above
or
[B] a compound of the formula (III-B)

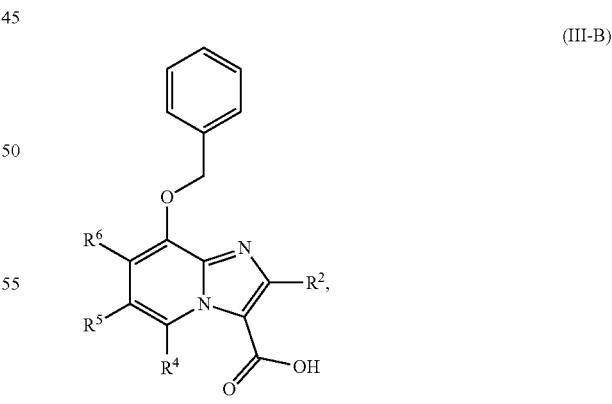

in which $R^2$, $R^4$, $R^5$ and $R^6$ each have the meanings given above,
is reacted in an inert solvent under amide coupling conditions with an amine of the formula (IV-A) or (IV-B) to give a compound of the formula (I-A) and (I-B)

13

(I-A)

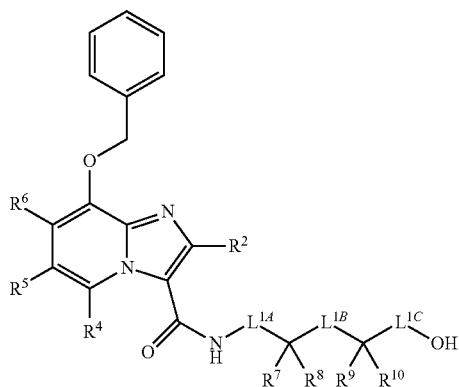

or (I-B)

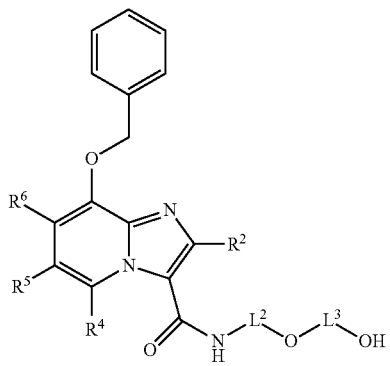

in which $R^2$, $R^4$, $R^5$, $R^6$, $L^{1A}$, $L^{1B}$, $L^{1C}$, $L^2$, $L^3$, $R^7$, $R^8$, $R^9$ and $R^{10}$ each have the meanings given above, from this compound, the benzyl group is subsequently removed using methods known to the person skilled in the art and the resulting compound of the formula (V-A) or (V-B)

(V-A)

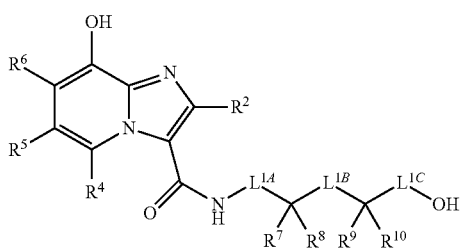

(V-B)

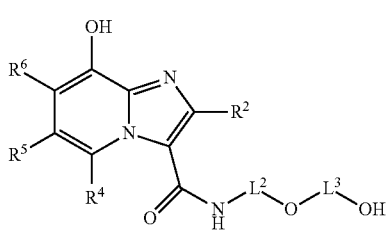

in which $R^2$, $R^4$, $R^5$, $R^6$, $L^{1A}$, $L^{1B}$, $L^{1C}$, $L^2$, $L^3$, $R^7$, $R^8$, $R^9$ and $R^{10}$ each have the meanings given above, is reacted in an inert solvent in the presence of a suitable base with a compound of the formula (VI)

(VI)

in which A and $R^1$ have the meanings given above and $X^1$ represents a suitable leaving group, in particular chlorine, bromine, iodine, mesylate, triflate or tosylate, and the resulting compounds of the formula (I) are optionally converted with the appropriate (i) solvents and/or (ii) acids or bases into their solvates, salts and/or solvates of the salts.

The compounds of the formulae (I-A) and (I-B) form a subset of the compounds of the formula (I) according to the invention.

The preparation processes described can be illustrated in an exemplary manner by the synthesis schemes below (Schemes 1 and 2):

Scheme 1:

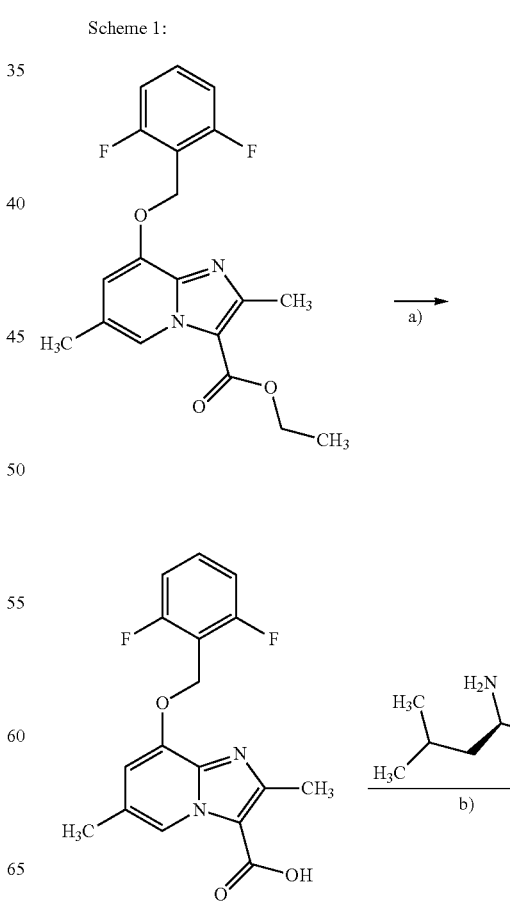

15

-continued

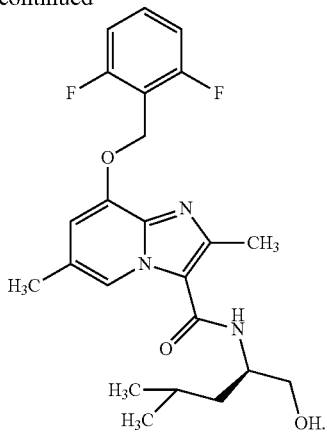

[a]: lithium hydroxide, THF/methanol/H$_2$O, RT;
b): TBTU, 4-methylmorpholine, DMF, RT]

Scheme 2:

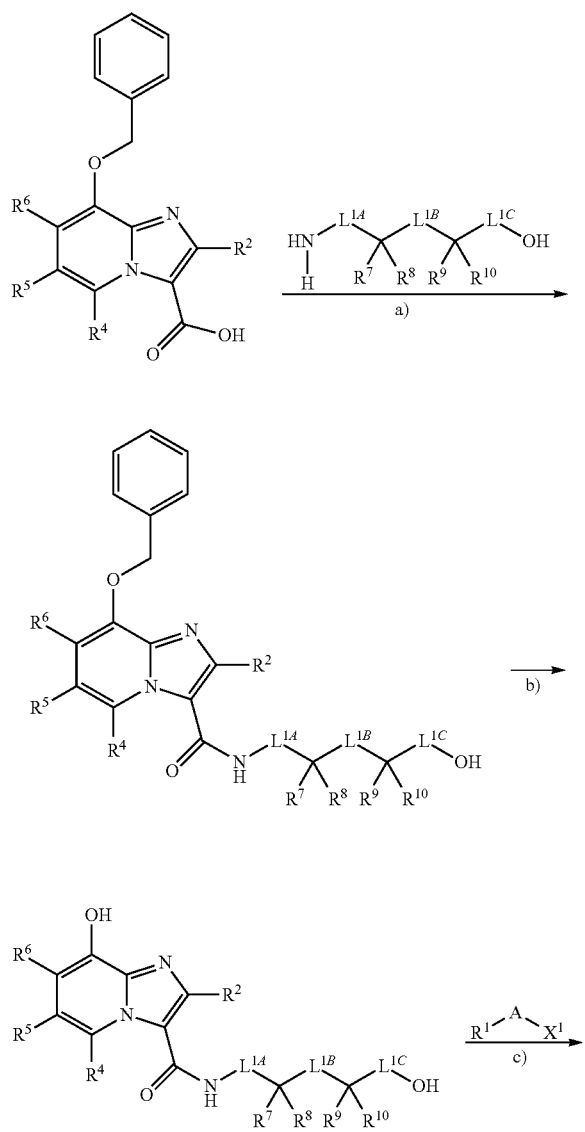

16

-continued

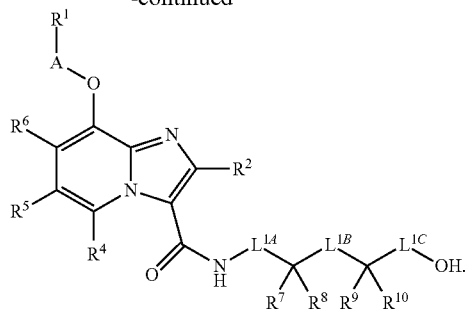

[a]: TBTU, N-methylmorpholine, DMF;
b): H$_2$, Pd/C, ethyl acetate;
c): Cs$_2$CO$_3$, DMF]

The compounds of the formulae (IV) and (VI) are commercially available, known from the literature or can be prepared analogously to processes known from the literature.

Inert solvents for the process steps (III)+(IV)→(I), (III-A)+(IV-A)→(I-A) and (III-B)+(IV)→(I-B) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to dichloromethane, tetrahydrofuran, dimethylformamide or mixtures of these solvents.

Suitable condensing agents for the amide formation in process steps (III)+(IV)→(I), (III-A)+(IV-A)→(I-A) and (III-B)+(IV)→(I-B) are, for example, carbodiimides such as N,N'-diethyl-, N,N'-dipropyl-, N,N'-diisopropyl-, N,N'-dicyclohexylcarbodiimide (DCC) or N-(3-dimethylamino-propyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethyl-prop1-ene-1-amine, diethyl cyanophosphonate, bis-(2-oxo-3-oxazolidinyl)phosphoryl chloride, benzotriazol-1-yloxytris(dimethylamino)phosphonium hexafluorophosphate, benzotriazol-1-yloxytris(pyrrolidino) phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxybenzotriazole (HOBt) or N-hydroxysuccinimide (HOSu), and also as bases alkali metal carbonates, for example sodium carbonate or potassium carbonate or sodium bicarbonate or potassium bicarbonate, or organic bases such as trialkylamines, for example triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-ene-1 amine.

The condensations (III)+(IV)→(I), (III-A)+(IV-A)→(I-A) and (III-B)+(IV)→(I-B) are generally carried out in a temperature range of from −20° C. to +100° C., preferably at from 0° C. to +60° C. The reaction can be performed at atmospheric, elevated or at reduced pressure (for example from 0.5 to 5 bar). In general, the reaction is carried out at atmospheric pressure.

Alternatively, the carboxylic acids of the formula (III) can also initially be converted into the corresponding carbonyl chloride and this can then be reacted directly or in a separate reaction with an amine of the formula (IV) to give the compounds according to the invention. The formation of carbonyl chlorides from carboxylic acids is carried out by methods known to the person skilled in the art, for example by treatment with thionyl chloride, sulphuryl chloride or oxalyl chloride in the presence of a suitable base, for example in the presence of pyridine, and also optionally with addition of dimethylformamide, optionally in a suitable inert solvent.

The hydrolysis of the ester group $T^1$ of the compounds of the formula (II) is carried out by customary methods by treating the esters in inert solvents with acids or bases, where in the latter case the salts initially formed are converted into the free carboxylic acids by treatment with acid. In the case of the tert-butyl esters the ester cleavage is preferably carried out with acids. In the case of benzyl esters, the ester cleavage is preferably carried out hydrogenolytically using palladium on activated carbon or Raney nickel.

Suitable inert solvents for this reaction are water or the organic solvents customary for an ester cleavage. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates such as sodium carbonate, potassium carbonate or calcium carbonate. Particular preference is given to sodium hydroxide or lithium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, if appropriate with addition of water. Preference is given to hydrogen chloride or trifluoroacetic acid in the case of the tert-butyl esters and hydrochloric acid in the case of the methyl esters.

The ester cleavage is generally carried out in a temperature range of from 0° C. to +100° C., preferably at from +0° C. to +50° C.

The reactions mentioned can be carried out at atmospheric, elevated or reduced pressure (for example from 0.5 to 5 bar). In general, the reactions are in each case carried out at atmospheric pressure.

Suitable inert solvents for the process step (V)+(VI)→(I) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (V)+(VI)→(I) are the customary inorganic or organic bases. These preferably include alkali metal hydroxides, for example lithium hydroxide, sodium hydroxide or potassium hydroxide, alkali metal or alkaline metal carbonates such as lithium carbonate, sodium carbonate, potassium carbonate, calcium carbonate or caesium carbonate, if appropriate with addition of an alkali metal iodide, for example sodium iodide or potassium iodide, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)-amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 4-(N,N-dimethylamino)pyridine (DMAP), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally carried out in a temperature range of from 0° C. to +120° C., preferably at from +20° C. to +80° C., if appropriate in a microwave. The reaction can be carried out at atmospheric, elevated or reduced pressure (for example from 0.5 to 5 bar).

In the process steps described above, any functional groups present—such as, in particular amino, hydroxyl and carboxyl groups—may, if expedient or required, also be present in protected form. Here, the introduction and removal of such protective groups is carried out by customary methods [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protected groups is present, their release may, if appropriate, take place simultaneously in a one-pot reaction or else in separate reaction steps.

Preferred for use as amino protective group is tert-butoxycarbonyl (Boc) or benzyloxycarbonyl (Z). As protective group for a hydroxyl or carboxyl function, preference is given to using tert-butyl or benzyl. The removal of these protective groups is carried out by customary methods, preferably by reaction with a strong acid such as hydrogen chloride, hydrogen bromide or trifluoroacetic acid in an inert solvent such as dioxane, diethyl ether, dichloromethane or acetic acid; if appropriate, the removal can also be carried out without any additional inert solvent. In the case of benzyl and benzyloxycarbonyl as protective group, these can also be removed by hydrogenolysis in the presence of a palladium catalyst. If appropriate, the removal of the protective groups mentioned can be performed simultaneously in a one-pot reaction or in separate reaction steps.

Here, the removal of the benzyl group in reaction steps (I-A)→(V-A) and (I-B)→(V-B) is carried out by customary methods known from protective group chemistry, preferably by hydrogenolysis in the presence of a palladium catalyst such as palladium on activated carbon in an inert solvent, for example ethanol or ethyl acetate [see also, for example, T. W. Greene and P. G. M. Wuts, *Protective Groups in Organic Synthesis*, Wiley, New York, 1999].

The compounds of the formula (II) are known from the literature or can be prepared by reacting a compound of the formula (VII)

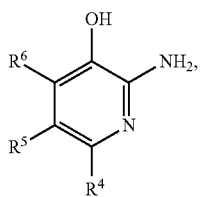

(VII)

in which $R^4$, $R^5$ and $R^6$ have the meanings given above, in an inert solvent in the presence of a suitable base with a compound of the formula (VI) to give a compound of the formula (VIII)

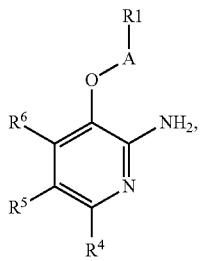

(VIII)

in which $R^1$, $R^4$, $R^5$ and $R^6$ each have the meanings given above, and this is then reacted in an inert solvent with a compound of the formula (IX)

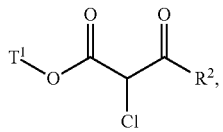

(IX)

in which $R^2$ and $T^1$ each have the meanings given above.

The process described is illustrated in an exemplary manner by the scheme below (Scheme 3):

Scheme 3:

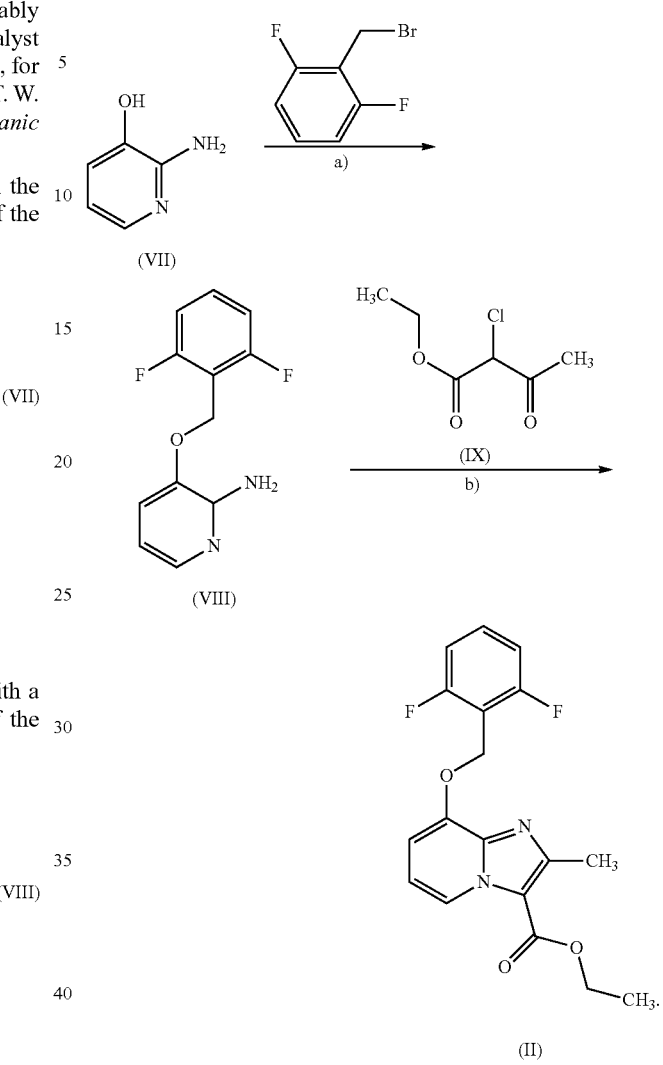

[a): i) NaOMe, MeOH, RT; ii) DMSO, RT;
b): EtOH, molecular sieve, reflux]

The synthesis sequence shown can be modified such that the respective reaction steps are carried out in a different order. An example of such a modified synthesis sequence is shown in Scheme 4.

Scheme 4:

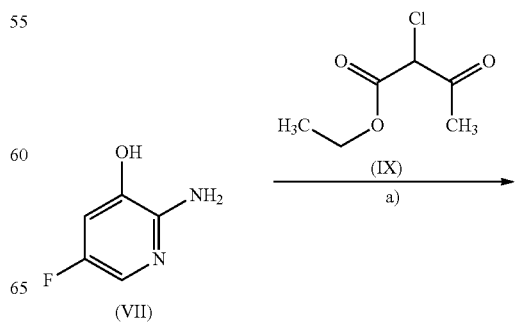

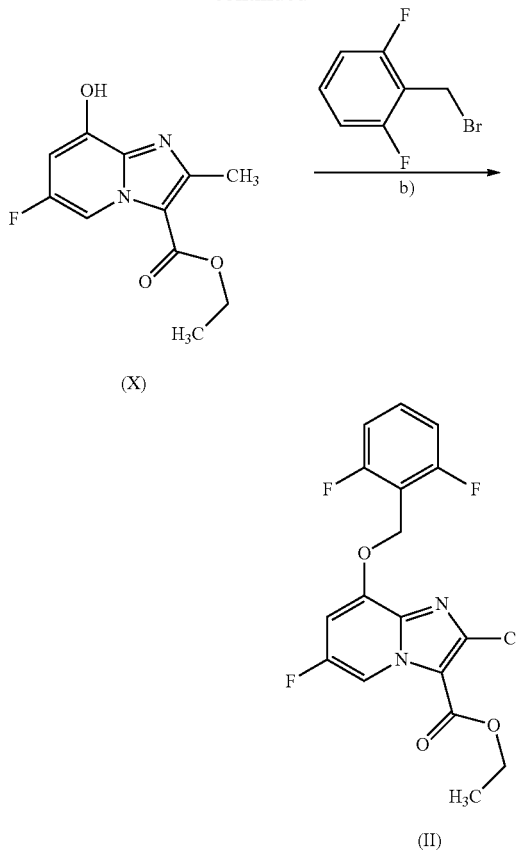

[a]: EtOH, molecular sieve, 80° C.;
b): b) Cs₂CO₃, DMF, 50° C.]

Inert solvents for the ring closure affording the imidazo[1,2-a]pyridine skeleton (VIII)+(IX)→(II) or (VII)+(IX)→(X) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol.

The ring closure is usually carried out in a temperature range from +50° C. to +150° C., preferably at from +50° C. to +100° C., if appropriate in a microwave oven.

The ring closure (VIII)+(IX)→(II) or (VII)+(IX)→(X) is optionally carried out in the presence of dehydrating agwents, for example in the presence of molecular sieve (pore size 4 Å) or using a water separator. The reaction (VIII)+(IX)→(II) or (VII)+(IX)→(X) is carried out using an excess of the reagent of the formula (IX), for example using 1 to 20 equivalents of reagent (IX), if appropriate with addition of bases (such as sodium bicarbonate), where the addition of this reagent can be carried out once or in several portions.

Alternatively to the introductions of R¹ shown in Schemes 1 to 4 by reaction of the compounds (V), (VII) or (X) with compounds of the formula (VI), it is also possible—as shown in Scheme 5—to react these intermediates with alcohols of the formula (XI) under the conditions of the Mitsunobu reaction.

Scheme 5:

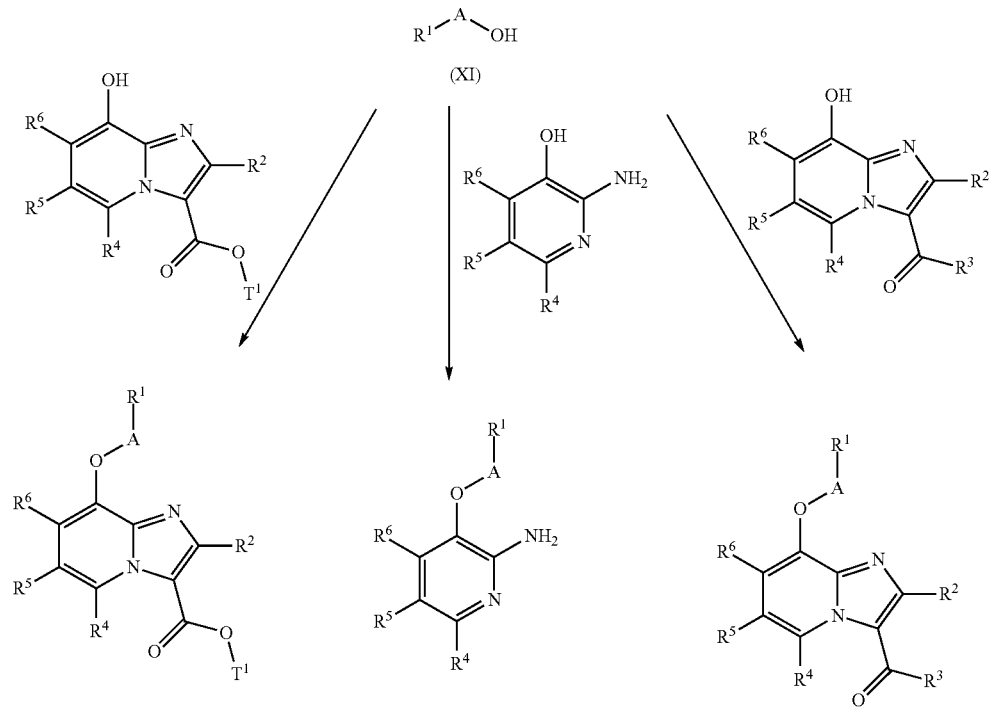

Typical reaction conditions for such Mitsunobu condensations of phenols with alcohols can be found in the relevant literature, for example Hughes, D. L. *Org. React.* 1992, 42, 335; Dembinski, R. *Eur. J. Org. Chem.* 2004, 2763. Typically, the compound is reacted with an activating agent, for example diethyl azodicarboxylate (DEAD) or diisopropyl azodicarboxylate (DIAD), and a phosphine reagent, for example triphenylphosphine or tributylphosphine, in an inert solvent, for example THF, dichloromethane, toluene or DMF, at a temperature between 0° C. and the boiling point of the solvent employed.

Further compounds according to the invention can optionally also be prepared by converting functional groups of individual substituents, in particular those listed under $R^3$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylations, aminations, esterifications, ester cleavages, etherifications, ether cleavages, formation of carboxamides, and also the introduction and removal of temporary protective groups.

The compounds according to the invention have useful pharmacological properties and can be employed for the prevention and treatment of disorders in humans and animals. The compounds according to the invention open up a further treatment alternative and are therefore an enrichment of pharmacy.

The compounds according to the invention bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention intensify the action of substances that raise the cGMP level, for example EDRF (endothelium-derived relaxing factor), NO donors, protoporphyrin IX, arachidonic acid or phenylhydrazine derivatives.

The compounds according to the invention are suitable for the treatment and prophylaxis of cardiovascular, pulmonary, thromboembolic and fibrotic diseases.

The compounds according to the invention can therefore be used in medicinal products for the treatment and prophylaxis of cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for the treatment and/or prophylaxis of thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for the treatment and/or prophylaxis of erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (myocarditis), chronic myocarditis, acute myocarditis, viral myocarditis, diabetic heart failure, alcoholic cardiomyopathy, storage cardiomyopathies, diastolic heart failure and also systolic heart failure and acute phases of an existing chronic heart failure (worsening heart failure).

In addition, the compounds according to the invention can also be used for the treatment and/or prophylaxis of arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention can be used for the treatment and/or prophylaxis of primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention are suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention are suitable for the treatment and/or prophylaxis of kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention are also suitable for the treatment and/or prophylaxis of asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention are also active substances for controlling diseases in the central nervous system that are characterized by disturbances of the NO/cGMP system. In particular, they are suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, post-traumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They are also suitable for the treatment and/or prophylaxis of diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention are also suitable for controlling cerebral perfusion and are effective agents for combating migraines. They are also suitable for the prophylaxis and control of consequences of cerebral infarctions (apoplexia cerebri) such as stroke, cerebral ischaemias and head injury. The compounds according to the invention can also be used for controlling pain states and tinnitus.

In addition, the compounds according to the invention possess anti-inflammatory action and can therefore be used as anti-inflammatory agents for the treatment and/or prophylaxis of sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention can also be used for the treatment and prophylaxis of autoimmune diseases.

Furthermore, the compounds according to the invention are suitable for the treatment and/or prophylaxis of fibrotic diseases of the internal organs, for example of the lung, heart, kidney, bone marrow and in particular of the liver, and dermatological fibroses and fibrotic diseases of the eye. In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention are suitable for controlling postoperative scarring, e.g. as a result of glaucoma operations.

The compounds according to the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further relates to the use of the compounds according to the invention for the treatment and/or prophylaxis of diseases, in particular the aforementioned diseases.

The present invention further relates to the use of the compounds according to the invention for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the compounds according to the invention for use in a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the use of the compounds according to the invention for producing a medicinal product for the treatment and/or prophylaxis of diseases, in particular the aforementioned diseases.

The present invention further relates to the use of the compounds according to the invention for producing a medicinal product for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to a method for the treatment and/or prophylaxis of diseases, in particular the aforementioned diseases, using an effective amount of at least one of the compounds according to the invention.

The present invention further relates to a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for the treatment and/or prophylaxis of the aforementioned diseases. As suitable combination active substances, we may mention for example and preferably:

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;

antithrombotic agents, for example and preferably from the group of platelet aggregation inhibitors, anticoagulants or profibrinolytic substances;

active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with a HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicinal products that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application.

Inhaled pharmaceutical forms (including powder inhalers, nebulizers), nasal drops, solutions or sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

Oral or parenteral administration is preferred, especially oral administration.

The compounds according to the invention can be transformed to the aforementioned dosage forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

In general, it has proved advantageous, in the case of parenteral administration, to administer amounts of about 0.001 to 1 mg/kg, preferably about 0.01 to 0.5 mg/kg body weight to achieve effective results. For oral application, the dosage is about 0.001 to 2 mg/kg, preferably about 0.001 to 1 mg/kg body weight.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

| Abbreviations and acronyms: | |
|---|---|
| aq. | aqueous solution |
| calc. | calculated |
| br. | broad signal (NMR coupling pattern) |
| δ | shift in the NMR spectrum (stated in ppm) |
| d | doublet (NMR coupling pattern) |
| DCI | direct chemical ionization (in MS) |
| DMAP | 4-N,N-dimethylaminopyridine |
| DMF | dimethylformamide |
| DMSO | dimethyl sulphoxide |
| ent | enantiomerically pure |
| eq. | equivalent(s) |
| ESI | electrospray ionization (in MS) |
| Et | ethyl |
| h | hour(s) |
| HATU | O-(7-azabenzotriazol-1-yl)-N,N,N'N'-tetramethyluronium hexafluorophosphate |
| HPLC | high pressure, high performance liquid chromatography |
| HRMS | high resolution mass spectrometry |
| konz. | concentrated |
| l | litre |
| LC/MS | liquid chromatography-coupled mass spectrometry |
| LiHMDS | lithium hexamethyldisilazide |
| m | multiplet |
| Me | methyl |
| min | minute(s) |
| MS | mass spectrometry |
| NMR | nuclear magnetic resonance spectrometry |
| Pd$_2$dba$_3$ | tris(dibenzylideneacetone)dipalladium |
| Ph | phenyl |
| q | quartet (NMR coupling pattern) |
| quint. | quintet (NMR coupling pattern) |
| rac | racemic |
| RT | room temperature |
| R$_t$ | retention time (in HPLC) |
| s | singlet (NMR coupling pattern) |
| t | triplet (NMR coupling pattern) |
| THF | tetrahydrofuran |
| TFA | trifluoroacetic acid |
| TBTU | (benzotriazol-1-yloxy)bisdimethylaminomethylium fluoroborate |
| UV | ultraviolet spectrometry |
| v/v | ratio by volume (of a solution) |
| Xantphos | 4,5-bis(diphenylphosphino)-9,9-dimethylxanthene |
| XPHOS | dicyclohexyl-(2',4',6'-triisopropylbiphenyl-2-yl)phosphine |

The percentages in the tests and examples below are, unless indicated otherwise, percentages by weight; parts are parts by weight. Solvent ratios, dilution ratios and concentrations of liquid/liquid solutions are in each case based on volume. Statements about coupling patterns in NMR spectra are descriptive, coupling patterns of a higher order are not described as such.

LC/MS and HPLC Methods:

Method 1 (LC-MS):
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
Instrument: Micromass Quattro Premier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):
MS instrument type: Waters Micromass Quattro Micro; HPLC instrument type: Agilent 1100 Series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):
MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 5 (LC-MS):
MS instrument: Waters ZQ 2000; HPLC instrument: Agilent 1100, 2-column system, autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A—0.2 min 95% A—1.8 min 25% A—1.9 min 10% A—2.0 min 5% A—3.2 min 5% A—3.21 min 100% A—3.35 min 100% A; oven: 40° C.; flow rate: 3.0 ml/min; UV detection: 210 nm.

Method 6 (Preparative HPLC):
Column: Macherey-Nagel VP 50/21 Nucleosil 100-5 C18 Nautilus. Flow rate: 25 ml/min. Gradient: A=acetonitrile, B=water+0.1% formic acid, 0 min 10% A; 2.00 min 10% A; 6.00 min 90% A; 7.00 min 90% A; 7.10 min 10% A; 8 min 10% A; UV detection: 220 nm Method 7 (Preparative HPLC):
Column: Phenomenex Gemini C18; 110A, AXIA, 5 μm, 21.2×50 mm 5 micron; gradient: A=water+0.1% conc ammonia, B=acetonitrile, 0 min=10% B, 2 min=10% B, 6 min=90% B, 7 min=90% B, 7.1 min=10% B, 8 min=10% B, flow rate 25 ml/min, UV detection 220 nm.

Method 8 (Preparative HPLC):
Column: Axia Gemini 5μ C18 110 A, 50×21.5 mm, P/NO: 00B-4435-PO-AX, S/NO: 35997-2, gradient: A=water+0.1% conc. aqueous ammonia, B=acetonitrile, 0 min=30% B, 2 min=30% B, 6 min=100% B, 7 min=100% B, 7.1 Min=30% B, 8 Min=30% B, flow rate 25 ml/min, UV detection 220 nm.

Method 9 (Preparative HPLC):
Column: Macherey-Nagel VP 50/21 Nucleosil 100-5 C18 Nautilus. Flow rate: 25 ml/min. gradient: A=water+0.1% formic acid, B=methanol, 0 min=30% B, 2 min=30% B, 6 min=100% B, 7 min=100% B, 7.1 min=30% B, 8 min=30% B, flow rate 25 ml/min, UV detection 220 nm.

Method 10 (Preparative HPLC):
Column: Macherey-Nagel VP 50/21 Nucleosil 100-5 C18 Nautilus. Flow rate: 25 ml/min. gradient: A=water+0.1% conc. aq ammonia, B=methanol, 0 min=30% B, 2 min=30% B, 6 min=100% B, 7 min=100% B, 7.1 min=30% B, 8 min=30% B, flow rate 25 ml/min, UV detection 220 nm.

Method 11 (Preparative HPLC):
MS instrument: Waters, HPLC instrument: Waters (column Waters X-Bridge C18, 18 mm×50 mm, 5 μm, mobile phase A: water+0.05% triethylamine, mobile phase B: acetonitrile (ULC)+0.05% triethylamine, gradient: 0.0 min 95% A—0.15 min 95% A—8.0 min 5% A—9.0 min 5% A; flow rate: 40 ml/min; UV detection: DAD; 210-400 nm).

or:

MS instrument: Waters, HPLC instrument: Waters (column Phenomenex Luna 5μ C18(2) 100A, AXIA Tech. 50×21.2 mm, mobile phase A: water+0.05% formic acid, mobile phase B: acetonitrile (ULC)+0.05% formic acid, gradient: 0.0 min 95% A—0.15 min 95% A—8.0 min 5% A—9.0 min 5% A; flow rate: 40 ml/min; UV detection: DAD; 210-400 nm).

Method 12 (LC-MS):

MS instrument: Waters SQD; HPLC instrument: Waters UPLC; Saeule: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 13 (DCI-MS):

Instrument: DSQ II; Thermo Fisher-Scientific; DCI with $NH_3$, flow rate: 1.1 ml/min; source temperature: 200° C.; ionization energy 70 eV; DCI heating coil heated to 800° C.; mass range 80-900.

Method 14 (GC-MS):

Instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min).

Method 15 (MS):

Instrument: Waters ZQ; ionization type: ESI (+); mobile phase; acetonitrile/water.

Method 16 (GC-MS):

Instrument: Thermo DFS, Trace GC Ultra; column: Restek RTX-35, 15 m×200 μm×0.33 μm; constant helium flow: 1.20 ml/min; oven: 60° C.; inlet: 220° C.; gradient: 60° C., 30° C./min→300° C. (maintained for 3.33 min)

Method 17 (LC-MS):

Instrument: Waters ACQUITY SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.

Method 18 (LC-MS):

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.

If compounds according to the invention are purified by preparative HPLC according to the methods described above where the mobile phases contain additives such as trifluoroacetic acid, formic acid or ammonia, the compounds according to the invention may be obtained in salt form, for example as trifluoroacetate, formate or ammonium salt, if the compounds according to the invention contain a functionality which is sufficiently basic or acidic. Such a salt may be converted by various methods known to the person skilled in the art into the corresponding base or acid, respectively.

Salts may be present in substoichiometric or superstoichiometric amounts, in particular if an amine or a carboxylic acid is present. In addition, in the case of the present imidazopyridines, under acidic conditions there may always be salts present, even in substoichiometric amounts, without this being obvious from the $^1$H NMR, and without particular specification and indication of these in the respective IUPAC named and structural formulae.

The multiplicities of proton signals in the $^1$H NMR spectra given in the paragraphs below indicate the signal form observed in each case and do not take into account any higher order signal phenomena.

Starting Materials and Intermediates

Example 1A

Ethyl 8-(benzyloxy)-2-methylimidazo[1,2-a]pyridine-3-carboxylate

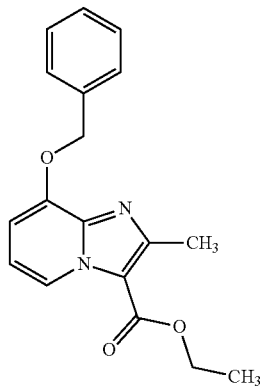 [SMILES: CCOC(=O)c1c(C)nc2c(OCc3ccccc3)cccn12]

25 g (124.8 mmol) of 2-amino-3-benzyloxypyridine were dissolved in 781 ml of ethanol, 102.7 g (624.2 mmol) of ethyl 2-chloroacetoacetate and two tablespoons of 4 A molecular sieve were added, and the reaction mixture was then heated at reflux (bath temperature 100° C.) for 2 days. The mixture was concentrated, and excess ethyl 2-chloroacetoacetate was removed on a rotary evaporator with dry ice cooling. The residue was purified by silica gel chromatography (mobile phase cyclohexane:ethyl acetate gradient 9:1, 4:1). This gave 20.81 g of the target compound (54% of theory, purity 99%).

LC-MS (Method 2): $R_t$=1.12 min

MS (ESpos): m/z=311 (M+H)$^+$ $^1$H NMR (400 MHz, DMSO-$d_6$): δ=1.35 (t, 3H), 2.59 (s, 3H), 4.34 (q, 2H), 5.32 (s, 2H), 7.01-7.09 (m, 2H), 7.33-7.48 (m, 3H), 7.52 (d, 2H), 8.81-8.86 (m, 1H).

Example 2A 8-(Benzyloxy)-2-methylimidazo[1,2-a]pyridine-3-carboxylic acid

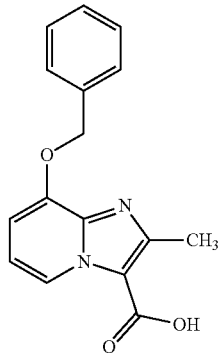 [SMILES: Cc1nc2c(OCc3ccccc3)cccn2c1C(=O)O]

253 ml of 2N aqueous sodium hydroxide solution were added to a solution of 15.7 g (50.59 mmol) of ethyl 8-(benzyloxy)-2-methylimidazo[1,2-a]pyridine-3-carboxylate in 253 ml of dioxane, and the mixture was stirred at room temperature for 14 hours. 101 ml of 6N hydrochloric acid were then added to the mixture. The solid formed was filtered off, washed with water and with methyl tert-butyl ether and then dried in a vacuum drying cabinet at 40° C. overnight. This gave 15.49 g (108% of theory) of 8-(benzyloxy)-2-methylimidazo[1,2-a]pyridine-3-carboxylic acid as a colourless solid. The yield was more than 100% owing to water of crystallization ($^1$H NMR).

LC-MS (Method 1): $R_t$=0.66 min
MS (ESpos): m/z=283.0 (M+H)$^+$
1H NMR (400 MHz, DMSO-$d_6$): δ=2.67 (s, 3H), 3.2-3.8 (very broad water peak), 5.41 (s, 2H), 7.30 (m, 1H), 7.35-7.48 (m, 4H), 7.57 (d, 2H), 9.02 (d, 1H).

Example 3A

Ethyl 8-hydroxy-2-methylimidazo[1,2-a]pyridine-3-carboxylate

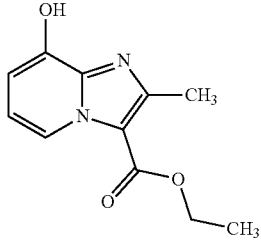 [SMILES: CCOC(=O)c1c(C)nc2c(O)cccn12]

31.45 g (101.3 mmol) of ethyl 8-(benzyloxy)-2-methylimidazo[1,2-a]pyridine-3-carboxylate were dissolved in 2 l of ethyl acetate, 3.15 g of 10% Pd/carbon were added and the mixture was stirred at RT and atmospheric pressure with hydrogen for 5 h. The mixture was filtered through kieselguhr, the filter cake was washed thoroughly with ethyl acetate/methanol and the filtrate was evaporated to dryness. This gave 21.94 g of the target compound (98% of theory, purity 99%).

LC-MS (Method 1): $R_t$=0.61 min
MS (ESpos): m/z=221 (M+H)$^+$
$^1$H NMR (400 MHz, DMSO-$d_6$): δ=1.36 (t, 3H), 2.60 (s, 3H), 4.36 (q, 2H), 6.78 (d, 1H), 6.98 (t, 1H), 8.73 (d, 1H), 10.60 (br s, 1H).

Example 4A

3-[(2,6-Difluorobenzyl)oxy]pyridine-2-amine

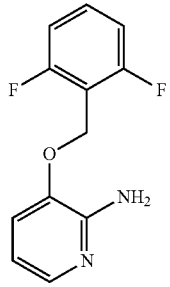

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was poured into 20 l of water and stirred for 15 min, and the solid was filtered off. The solid was washed with 1 l of water, 100 ml of isopropanol and 500 ml of petroleum ether and dried under high vacuum. This gave 171 g of the title compound (78% of theory).

$^1$H NMR (400 MHz, DMSO-$d_6$): δ=5.10 (s, 2H); 5.52 (br. s, 2H), 6.52 (dd, 1H); 7.16-7.21 (m, 3H); 7.49-7.56 (m, 2H).

Example 5A

Ethyl 8-[(2,6-difluorobenzyl)oxy]-2-methylimidazo[1,2-a]pyridine-3-carboxylate

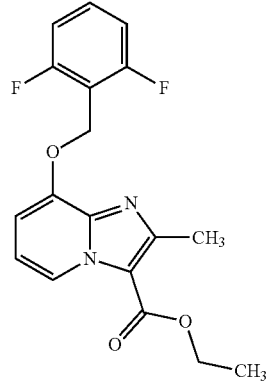 [SMILES: CCOC(=O)c1c(C)nc2c(OCc3c(F)cccc3F)cccn12]

170 g of 3-[(2,6-difluorobenzyl)oxy]pyridine-2-amine (Example 4A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The resulting reaction mixture was heated under reflux for 24 h and then filtered off through kieselguhr and concentrated under reduced pressure. After relatively long standing (48 h) at RT, a solid precipitated out. This solid was filtered off, three times suspended in a little isopropanol and in each case filtered off again and finally washed with diethyl ether. This gave 60.8 g (23.4% of theory) of the title compound. The combined mother liquor of the filtration steps was chromatographed on silica gel using cyclohexane/diethyl ether as mobile phase. This gave a further 46.5 g (18.2% of theory; total yield: 41.6% of theory) of the title compound.

LC-MS (Method 1): $R_t$=1.01 min
MS (ESpos): m/z=347 (M+H)$^+$
$^1$H NMR (400 MHz, DMSO-$d_6$): δ=1.36 (t, 3H); 2.54 (s, 3H; obscured by DMSO signal); 4.36 (q, 2H); 5.33 (s, 2H); 7.11 (t, 1H); 7.18-7.27 (m, 3H); 7.59 (quint, 1H); 8.88 (d, 1H).

Example 6A

8-[(2,6-Difluorobenzyl)oxy]-2-methylimidazo[1,2-a]pyridine-3-carboxylic acid

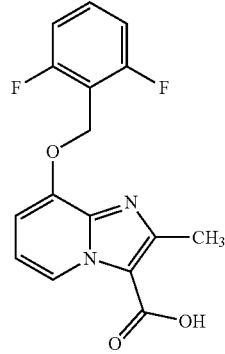 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 5A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was adjusted in an ice bath to pH 3-4 using 1 N aqueous hydrochloric acid. The resulting solid was filtered off, washed with water and isopropanol and dried under reduced pressure. This gave 92 g (95% of theory) of the title compound.

LC-MS (Method 1): $R_t$=0.62 min

MS (ESpos): m/z=319.1 (M+H)$^+$ $^1$H NMR (400 MHz, DMSO-d$_6$): δ=2.55 (s, 3H; superimposed by DMSO signal); 5.32 (s, 2H); 7.01 (t, 1H); 7.09 (d, 1H); 7.23 (t, 2H); 7.59 (quint, 1H); 9.01 (d, 1H).

Example 7A 3-(Cyclohexylmethoxy)pyridine-2-amine

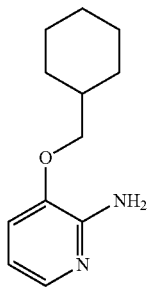 [SMILES: Nc1ncccc1OCC1CCCCC1]

At RT, 96 g of sodium hydroxide (45%; 1081 mmol, 1 equivalents) were initially charged in 1170 ml of methanol, 119 g of 2-amino-3-hydroxypyridine (1080 mmol, 1 equivalent) were added and the mixture was stirred at RT for 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was stirred into 6 l of water, and the aqueous solution was extracted twice, in each case with 2 l of ethyl acetate. The combined organic phases were washed with in each case 1 l of saturated aqueous sodium bicarbonate solution and water, dried, filtered and concentrated. The residue was stirred with 500 ml of pentane, filtered off and dried under reduced pressure. This gave 130 g (58.3% of theory) of the title compound.

LC-MS (Method 3): $R_t$=1.41 min

MS (ESpos): m/z=207.1 (M+H)$^+$

Example 8A

Ethyl 8-(cyclohexylmethoxy)-2-methylimidazo[1,2-a]pyridine-3-carboxylate

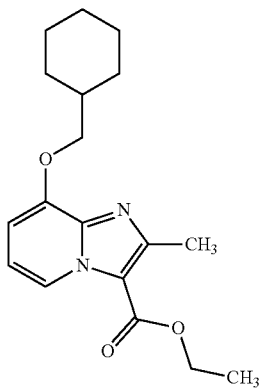 [SMILES: CCOC(=O)c1c(C)nc2c(OCC3CCCCC3)cccn12]

130 g of 3-(cyclohexylmethoxy)pyridine-2-amine (Example 7A; 630 mmol, 1 equivalent) were initially charged in 3950 ml of ethanol, and 436 ml of ethyl 2-chloroacetoacetate (3.2 mol, 5 equivalents) were added. The resulting reaction mixture was heated under reflux for 24 h and then concentrated under reduced pressure. The crude product obtained in this manner was chromatographed on silica gel using cyclohexane/diethyl ether as mobile phase, giving 66.2 g (33.2% of theory) of the title compound.

LC-MS (Method 1): $R_t$=1.17 min

MS (ESpos): m/z=317.1 (M+H)$^+$ $^1$H NMR (400 MHz, DMSO-d$_6$): δ=1.02-1.31 (m, 5H); 1.36 (t, 3H); 1.64-1.77 (m, 3H); 1.79-1.90 (m, 3H); 2.60 (s, 3H); 3.97 (d, 2H); 4.35 (q, 2H); 6.95 (d, 1H); 7.03 (t, 1H); 8.81 (d, 1H).

Example 9A 8-(Cyclohexylmethoxy)-2-methylimidazo[1,2-a]pyridine-3-carboxylic acid

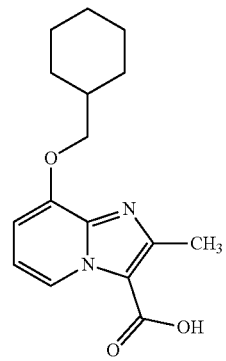 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 8A; 158 mmol, 1 equivalent) were dissolved in 600 ml of dioxane, 790 ml of 2 N aqueous sodium hydroxide solution (1.58 mol, 10 equivalents) were added and the mixture was stirred at RT for 16 h. 316 ml of 6 N hydrochloric acid were added, and the mixture was concentrated to about ⅕ of the total volume. The resulting solid was filtered off, washed with water and tert-butyl methyl ether and dried under reduced pressure. This gave 35 g (74% of theory) of the title compound.

LC-MS (Method 1): $R_t$=0.81 min

MS (ESpos): m/z=289.0 (M+H)$^+$ $^1$H NMR (400 MHz, DMSO-d$_6$): δ=1.03-1.44 (m, 5H); 1.64-1.78 (m, 3H); 1.81-1.92 (m, 3H); 2.69 (s, 3H); 4.07 (d, 2H); 7.30-7.36 (m, 2H); 9.01 (d, 1H).

Example 10A

5-Fluoro-2-nitropyridin-3-ol

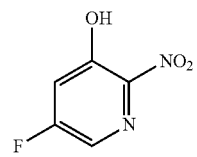 [SMILES: O=[N+]([O-])c1ncc(F)cc1O]

With ice cooling, 5 g of 5-fluoropyridin-3-ol (44 mmol, 1 equivalent) were dissolved in 43 ml of concentrated sulphuric acid, and 2.8 ml of concentrated nitric acid were added at 0° C. over a period of 5 min. The reaction was warmed to RT and stirred overnight. The mixture was added to 100 g of ice and stirred for 30 min. The solid formed was filtered off and dried under reduced pressure. This gave 5.6 g (81% of theory) of the title compound which was used without further purification for the next reaction.

LC-MS (Method 1): $R_t$=0.45 min
MS (ESneg): m/z=156.9 (M−H)⁻
¹H NMR (400 MHz, DMSO-$d_6$): δ=7.5 (dd, 1H); 8.08 (d, 1H); 12.2 (br. s, 1H).

Example 11A

2-Amino-5-fluoropyridin-3-ol

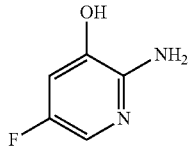

5.6 g of 5-fluoro-2-nitropyridin-3-ol (Example 10A; 36 mmol) were dissolved in 2 l of ethanol, a catalytic amount of palladium on activated carbon (10%) was added and the mixture was hydrogenated under hydrogen standard pressure for 16 h. The mixture was filtered off through kieselguhr and the filtrate was concentrated (product batch 1). The residue was rinsed with methanol until the colour of the filtrate was no longer yellowish. The filtrate was concentrated, giving a second product batch. This gave a total of 4.26 g (85% of theory) of the title compound.

LC-MS (Method 1): $R_t$=0.17 min
MS (ESpos): m/z=128.9 (M+H)⁺
¹H NMR (400 MHz, DMSO-$d_6$): δ=5.4 (br. s, 2H); 6.8 (dd, 1H); 7.4 (d, 1H).

Example 12A

Ethyl 6-fluoro-8-hydroxy-2-methylimidazo[1,2-a]pyridine-3-carboxylate

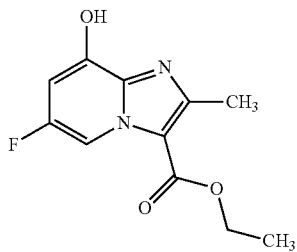 [SMILES: CCOC(=O)c1c(C)nc2c(O)cc(F)cn12]

3.2 g of 2-amino-5-fluoropyridin-3-ol (Example 11A; 25 mmol, 1 equivalent) were initially charged in 155 ml of ethanol, 1.5 g of powdered molecular sieve 3 Å and 20.6 g of ethyl 2-chloroacetoacetate (125 mmol, 5 equivalents) were added and the mixture was heated at reflux overnight. The reaction solution was concentrated and chromatographed (Biotage Isolera Four; SNAP Cartridge KP-Sil 50 g; cyclohexane/ethyl acetate gradient; then dichloromethane/methanol gradient). The crude product was partly dissolved in a little methanol, and tert-butyl methyl ether was added. The solid obtained was filtered off and rinsed with tert-butyl methyl ether. This gave 570 mg (10% of theory) of the title compound.

LC-MS (Method 1): $R_t$=0.77 min
MS (ESpos): m/z=239.2 (M+H)⁺
¹H NMR (400 MHz, DMSO-$d_6$): δ=1.39 (t, 3H); 2.64 (s, 3H); 4.40 (q, 2H); 7.20 (br. d, 1H); 8.9 (dd, 1H); 12.5 (br., 1H).

Example 13A

Ethyl 8-[(2,6-difluorobenzyl)oxy]-6-fluoro-2-methylimidazo[1,2-a]pyridine-3-carboxylate

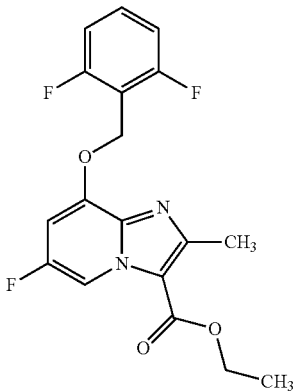 [SMILES: CCOC(=O)c1c(C)nc2c(OCc3c(F)cccc3F)cc(F)cn12]

560 mg of ethyl 6-fluoro-8-hydroxy-2-methylimidazo[1,2-a]pyridine-3-carboxylate (Example 12A; 2.4 mmol, 1.0 equivalent), 1.7 g of caesium carbonate (5.17 mmol, 2.2 equivalents) and 535 mg of 2,6-difluorobenzyl bromide (2.6 mmol, 1.1 equivalents) were initially charged in 34 ml of dry DMF, and the mixture was heated at 50° C. for 15 min. Water was added and the mixture was stirred for 30 min. The solid was filtered off and washed with water. This gave 560 mg of the title compound (65% of theory).

LC-MS (Method 1): $R_t$=1.18 min
MS (ESpos): m/z=365.1 (M+H)⁺
¹H NMR (400 MHz, DMSO-$d_6$): δ=1.37 (t, 3H); 2.55 (s, 3H; superimposed by DMSO signal); 4.38 (q, 2H); 5.89 (s, 2H); 7.23 (t, 2H); 7.44 (dd, 1H); 7.60 (quint., 1H); 8.90 (dd, 1H).

Example 14A

8-[(2,6-Difluorobenzyl)oxy]-6-fluoro-2-methylimidazo[1,2-a]pyridine-3-carboxylic acid

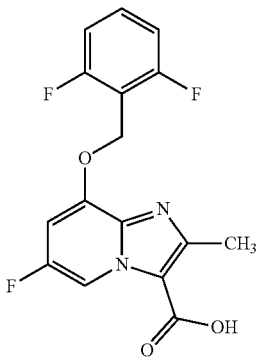 [SMILES: Cc1nc2c(OCc3c(F)cccc3F)cc(F)cn2c1C(=O)O]

550 mg of ethyl 8-[(2,6-difluorobenzyl)oxy]-6-fluoro-2-methylimidazo[1,2-a]pyridine-3-carboxylate (Example 13A; 1.5 mmol, 1 equivalent) were dissolved in 64 ml of THF and 12 ml of methanol, 7.5 ml of 1 N aqueous lithium hydroxide solution were added and the mixture was stirred at RT overnight. 8 ml of 1 N aqueous hydrochloric acid were then added, and the mixture was concentrated under reduced pressure. The solid formed was filtered off and washed with water. This gave 429 mg of the title compound (80% of theory).

LC-MS (Method 2): $R_t$=0.90 min

MS (ESpos): m/z=337.1 (M+H)$^+$ $^1$H NMR (400 MHz, DMSO-d$_6$): δ=2.54 (s, 3H; superimposed by DMSO signal); 5.84 (s, 2H); 7.23 (t, 2H); 7.40 (dd, 1H); 7.51 (quint., 1H); 8.92 (dd, 1H); 13.28 (br. s, 1H).

Example 15A

5-Chloro-2-nitropyridin-3-ol

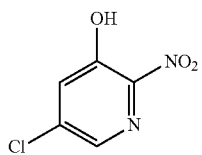 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulphuric acid, and, at 0° C., 24 ml of concentrated nitric acid were added slowly. The reaction was warmed to RT and stirred overnight. The mixture was stirred into an ice/water mixture and stirred for another 30 min. The solid was filtered off, washed with cold water and air-dried. This gave 33 g (82% of theory) of the title compound, which were used without further purification for the next reaction.

LC-MS (Method 1): $R_t$=0.60 min

MS (ESneg): m/z=172.9/174.9 (M−H)$^−$ $^1$H NMR (400 MHz, DMSO-d$_6$): δ=7.71 (d, 1H); 8.10 (d, 1H); 12.14 (br. 1H).

Example 16A

5-Chloro-3-[(2,6-difluorobenzyl)oxy]-2-nitropyridine

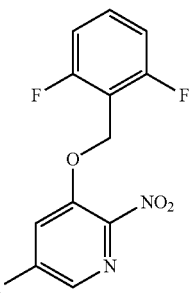

33 g of 5-chloro-2-nitropyridin-3-ol (Example 15A; 189 mmol, 1 equivalent) and 61.6 g of caesium carbonate (189 mmol, 1 equivalent) were initially charged in 528 ml of DMF, 40.4 g of 2,6-difluorobenzyl bromide (189 mmol, 1 equivalent) were added and the mixture was stirred at RT overnight. The reaction mixture was stirred into water/1N aqueous hydrochloric acid and the solid was filtered off, washed with water and air-dried. This gave 54.9 g (97% of theory) of the title compound.

$^1$H NMR (400 MHz, DMSO-d$_6$): δ=5.46 (s, 2H); 7.22 (t, 2H); 7.58 (quint., 1H); 8.28 (d, 1H); 8.47 (d, 1H).

Example 17A

5-Chloro-3-[(2,6-difluorobenzyl)oxy]pyridine-2-amine

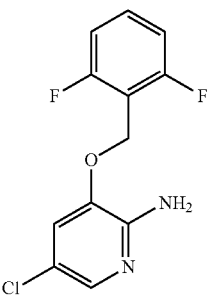 [SMILES: O=[N+]([O-])c1ncc(Cl)cc1OCc1c(F)cccc1F]

59.7 g of 5-chloro-3-[(2,6-difluorobenzyl)oxy]-2-nitropyridine (Example 16A; 199 mmol, 1 equivalent) were initially charged in 600 ml of ethanol, 34.4 g of iron powder (616 mmol, 3.1 equivalents) were added and the mixture was heated to reflux. 152 ml of concentrated hydrochloric acid were slowly added dropwise and the mixture was boiled at reflux for a further 30 min. The reaction mixture was cooled and stirred into an ice/water mixture. The resulting mixture was adjusted to pH 5 using sodium acetate, and the solid was filtered off, washed with water, air-dried and then dried under reduced pressure at 50° C. This gave 52.7 g (98% of theory) of the title compound.

LC-MS (Method 1): $R_t$=0.93 min

MS (ESpos): m/z=271.1/273.1 (M+H)$^+$ $^1$H NMR (400 MHz, DMSO-d$_6$): δ=5.14 (s, 2H); 5.82 (br. s, 2H); 7.20 (t, 2H); 7.35 (d, 1H); 7.55 (quint., 1H); 7.56 (d, 1H).

Example 18A

Ethyl 6-chloro-8-[(2,6-difluorobenzyl)oxy]-2-methylimidazo[1,2-a]pyridine-3-carboxylate

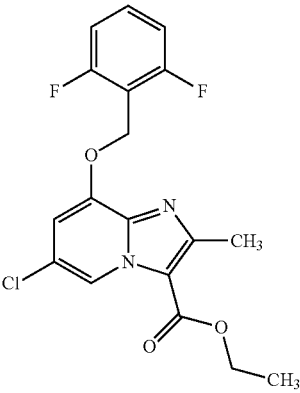

40 g of 5-chloro-3-[(2,6-difluorobenzyl)oxy]pyridine-2-amine (Example 17A; 147.8 mmol; 1 equivalent) were initially charged in 800 ml of ethanol, 30 g of powdered molecular sieve 3 Å and 128 g of ethyl 2-chloroacetoacetate (739 mmol, 5 equivalents) were added and the mixture was heated at reflux overnight. The reaction mixture was concentrated and the residue was taken up in ethyl acetate and filtered. The ethyl acetate phase was washed with water, dried, filtered and concentrated. This gave 44 g (78% of theory) of the title compound.

LC-MS (Method 1): $R_t$=1.27 min
MS (ESpos): m/z=381.2/383.2 (M+H)$^+$
$^1$H NMR (400 MHz, DMSO-d$_6$): δ=1.36 (t, 3H); 2.54 (s, 3H; obscured by DMSO signal); 4.37 (q, 2H); 5.36 (s, 2H); 7.26 (t, 2H); 7.38 (d, 1H); 7.62 (quint., 1H); 8.92 (d, 1H).

Example 19A

6-Chloro-8-[(2,6-difluorobenzyl)oxy]-2-methylimidazo[1,2-a]pyridine-3-carboxylic acid

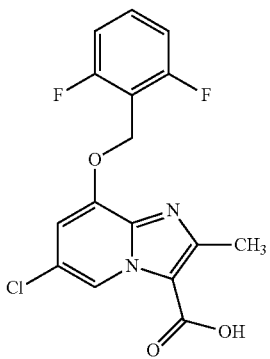

44 g of ethyl 6-chloro-8-[(2,6-difluorobenzyl)oxy]-2-methylimidazo[1,2-a]pyridine-3-carboxylate (Example 18A; 115 mmol, 1 equivalent) were dissolved in 550 ml of THF and 700 ml of methanol, 13.8 g of lithium hydroxide (dissolved in 150 ml of water; 577 mmol, 5 equivalents) were added and the mixture was stirred at RT overnight. 1 N aqueous hydrochloric acid was added and the mixture was concentrated under reduced pressure. The solid obtained was filtered off and washed with water. This gave 34 g of the title compound (84% of theory).

LC-MS (Method 2): $R_t$=1.03 min
MS (ESpos): m/z=353.0/355.0 (M+H)$^+$
$^1$H NMR (400 MHz, DMSO-d$_6$): δ=2.54 (s, 3H; superimposed by DMSO signal); 5.36 (s, 2H); 7.26 (t, 2H); 7.34 (d, 1H); 7.61 (quint., 1H); 8.99 (d, 1H); 13.36 (br. s, 1H).

Example 20A

5-Bromo-3-[(2,6-difluorobenzyl)oxy]pyridine-2-amine

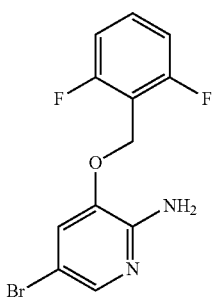 [SMILES: Nc1ncc(Cl)cc1OCc1c(F)cccc1F]

32.6 g of 3-[(2,6-difluorobenzyl)oxy]pyridine-2-amine (Example 4A; 138 mmol, 1 equivalent) were suspended in 552 ml of 10% strength sulphuric acid, and the mixture was cooled to 0° C. 8.5 ml of bromine (165 mmol, 1.2 equivalents) were dissolved in 85 ml of acetic acid and then, over a period of 90 min, added dropwise to the ice-cooled reaction solution. After the dropwise addition had ended, the mixture was stirred at 0° C. for 90 min and then diluted with 600 ml of ethyl acetate, and the aqueous phase was separated off. The aqueous phase was re-extracted with ethyl acetate and the organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound. LC-MS (Method 1): $R_t$=0.96 min MS (ESpos): m/z=315.1/317.1 (M+H)$^+$
$^1$H NMR (400 MHz, DMSO-d$_6$): δ=5.14 (s, 2H); 5.83 (br. s, 2H); 7.20 (t, 2H); 7.42 (d, 1H); 7.54 (quint., 1H); 7.62 (d, 1H).

Example 21A

Ethyl 6-bromo-8-[(2,6-difluorobenzyl)oxy]-2-methylimidazo[1,2-a]pyridine-3-carboxylate

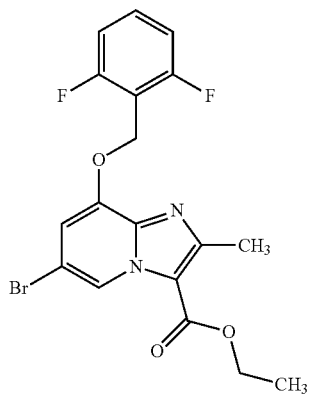 [SMILES: CCOC(=O)c1c(C)nc2c(OCc3c(F)cccc3F)cc(Cl)cn12]

24 g of 5-bromo-3-[(2,6-difluorobenzyl)oxy]pyridine-2-amine (Example 20A; 76.2 mmol; 1 equivalent) were initially charged in 400 ml of ethanol, 16 g of powdered molecular sieve 3 Å and 52.7 ml of ethyl 2-chloroacetoacetate (380.8 mmol; 5 equivalents) were added and the mixture was heated at reflux overnight. A further 8 g of molecular sieve were added, and the mixture was heated at reflux for a further 24 h. The reaction mixture was concentrated under reduced pressure and the residue was taken up in dichloromethane and chromatographed on silica gel (dichloromethane/methanol 20:1 as mobile phase). The product-containing fractions were concentrated and the residue was stirred with 100 ml of diethyl ether for 30 min, filtered off, washed with a little diethyl ether and dried. This gave 15 g (45% of theory) of the title compound.

LC-MS (Method 2): $R_t$=1.43 min
MS (ESpos): m/z=414.9/416.8 (M+H)$^+$

¹H NMR (400 MHz, DMSO-d₆): δ=1.36 (t, 3H); 2.54 (s, 3H; obscured by DMSO signal); 4.37 (q, 2H); 5.36 (s, 2H); 7.25 (t, 2H); 7.42 (d, 1H); 7.61 (quint., 1H); 9.00 (d, 1H).

Example 22A

6-Bromo-8-[(2,6-difluorobenzyl)oxy]-2-methylimidazo[1,2-a]pyridine-3-carboxylic acid

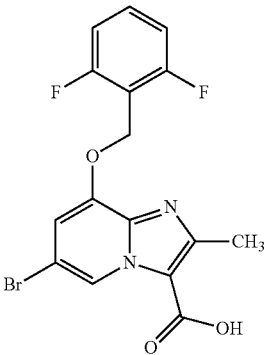 [SMILES: Cc1nc2c(OCc3c(F)cccc3F)cc(Cl)cn2c1C(=O)O]

1.5 g of ethyl 6-bromo-8-[(2,6-difluorobenzyl)oxy]-2-methylimidazo[1,2-a]pyridine-3-carboxylate (Example 21A; 3.5 mmol, 1 equivalent) were dissolved in 72 ml of THF/methanol 5:1, 17.6 ml of 1N aqueous lithium hydroxide solution (17.6 mmol, 5 equivalents) were added and the mixture was warmed to 40° C. and stirred at this temperature for 6 h. Using 6 N aqueous hydrochloric acid, the mixture was then adjusted to pH 4 and concentrated. Water was added to the solid formed and the solid was triturated, filtered off, washed with water and dried under reduced pressure. This gave 1.24 g of the title compound (88% of theory).

LC-MS (Method 1): R_f=0.93 min
MS (ESpos): m/z=397.0/399.1 (M+H)⁺
¹H NMR (400 MHz, DMSO-d₆): δ=2.54 (s, 3H; superimposed by DMSO signal); 5.36 (s, 2H); 7.25 (t, 2H); 7.40 (d, 1H); 7.61 (quint., 1H); 9.06 (d, 1H); 13.35 (br. s, 1H).

Example 23A

Ethyl 8-[(2,6-difluorobenzyl)oxy]-2,6-dimethylimidazo[1,2-a]pyridine-3-carboxylate

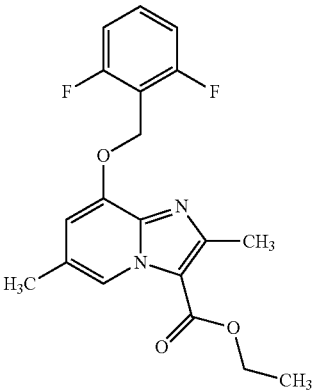 [SMILES: CCOC(=O)c1c(C)nc2c(OCc3c(F)cccc3F)cc(C)cn12]

20.00 g (85.38 mmol) of ethyl 8-hydroxy-2,6-dimethylimidazo[1,2-a]pyridine-3-carboxylate from Example 239A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then poured into 6.4 l of 10% strength aqueous sodium chloride solution and then extracted twice with ethyl acetate. The combined organic phases were washed with 854 ml of 10% strength aqueous sodium chloride solution, dried, concentrated and dried under high vacuum at RT overnight. This gave 28.2 g (92% of theory; purity about 90%) of the title compound.

LC-MS (Method 1): R_f=1.05 min
MS (ESpos): m/z=361.1 (M+H)⁺
¹H NMR (400 MHz, DMSO-d₆): δ=1.38 (t, 3H); 2.36 (s, 3H); 4.35 (q, 2H); 5.30 (s, 2H); 7.10 (s, 1H); 7.23 (t, 2H); 7.59 (quint., 1H); 8.70 (s, 1H).

Example 24A

8-[(2,6-Difluorobenzyl)oxy]-2,6-dimethylimidazo[1,2-a]pyridine-3-carboxylic acid

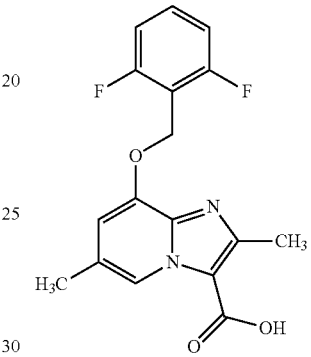

220 mg of ethyl 8-[(2,6-difluorobenzyl)oxy]-2,6-dimethylimidazo[1,2-a]pyridine-3-carboxylate (Example 23A; 0.524 mmol, 1 equivalent) were dissolved in 7 ml of THF/methanol 1:1, 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N hydrochloric acid. The solid was triturated, filtered off, washed with water and dried under reduced pressure. This gave 120 mg of the title compound (60% of theory).

LC-MS (Method 1): R_f=0.68 min
MS (ESpos): m/z=333.1 (M+H)⁺
¹H NMR (400 MHz, DMSO-d₆): δ=2.34 (s, 3H); 5.28 (s, 2H); 7.09 (s, 1H); 7.23 (t, 2H); 7.58 (quint., 1H); 8.76 (s, 1H); 13.1 (br. s, 1H).

Example 25A

8-[(2,6-Difluorobenzyl)oxy]-2-methylimidazo[1,2-a]pyridine-3-carbonyl chloride hydrochloride

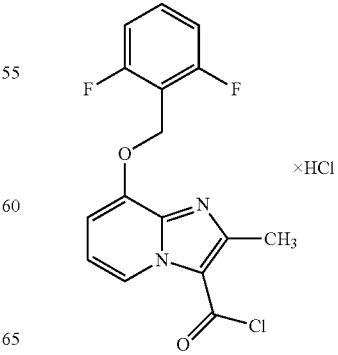

2.0 g of 8-[(2,6-difluorobenzyl)oxy]-2-methylimidazo[1,2-a]pyridine-3-carboxylic acid (6.28 mmol) were initially charged in abs. THF, 4 drops of DMF were added and 3.19 g of oxalyl chloride (25.14 mmol) were then added dropwise. The reaction mixture was stirred at RT for 3 h. Another 0.80 g of oxalyl chloride (6.29 mmol) were added, and the reaction was stirred at RT for a further 4 h. The reaction mixture was concentrated and co-evaporated with toluene three times, and the residue was dried under high vacuum. This gave 2.43 g of the title compound (103% of theory).

DCI-MS (Method 13): MS (ESpos): m/z=437 (M−HCl+H)$^+$

Example 26A

Ethyl 2-chloro-3-cyclopropyl-3-oxopropanoate

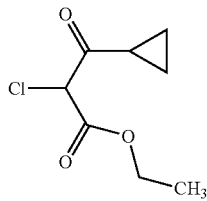

3.1 ml of sulphuryl chloride (38.2 mmol, 1.05 equivalents) were initially charged in 21 ml of dichloromethane, and 5.68 g of ethyl 3-cyclopropyl-3-oxopropanoate (36.4 mmol) were added dropwise on a water bath. The reaction mixture was stirred at RT for 2 h and then washed with water, 5% strength aqueous sodium bicarbonate solution and saturated aqueous sodium chloride solution, dried over magnesium sulphate and concentrated. The crude product (6.8 g) was used without further purification for the next reaction.

Example 27A

Ethyl 2-cyclopropyl-8-[(2,6-difluorobenzyl)oxy]imidazo[1,2-a]pyridine-3-carboxylate

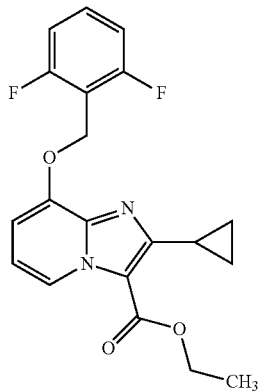 [SMILES: CCOC(=O)c1c(C2CC2)nc2c(OCc3c(F)cccc3F)cccn12]

1.69 g of 3-[(2,6-difluorobenzyl)oxy]pyridine-2-amine (Example 4A; 7.13 mmol, 1 equivalent) were initially charged in 44.4 ml of ethanol, and 425 mg of powdered molecular sieve 3 Å and 6.8 g of ethyl 2-chloro-3-cyclopropyl-3-oxopropanoate (crude product from Example 26A) were added. The resulting reaction mixture was heated at reflux for 48 h and then concentrated, and the residue was chromatographed (cyclohexane/ethyl acetate as mobile phase). The product-containing fractions were combined and concentrated under reduced pressure. The residue obtained in this manner was taken up in methanol, dimethyl sulphoxide and water and the solid formed was filtered off and dried under high vacuum. This gave 410 mg (15.4% of theory) of the title compound.

LC-MS (Method 1): R$_t$=1.22 min
MS (ESpos): m/z=373.2 (M+H)$^+$
$^1$H NMR (400 MHz, DMSO-d$_6$): δ=0.95-1.05 (m, 4H); 1.39 (t, 3H); 2.36 (s, 3H); 2.70-2.80 (m, 1H); 4.39 (q, 2H); 5.30 (s, 2H); 7.08 (t, 1H); 7.15 (d, 1H); 7.20 (t, 2H); 7.59 (quint., 1H); 8.88 (d, 1H).

Example 28A

2-Cyclopropyl-8-[(2,6-difluorobenzyl)oxy]imidazo[1,2-a]pyridine-3-carboxylic acid

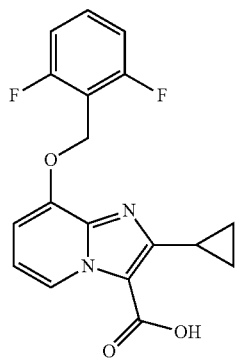 [SMILES: O=C(O)c1c(C2CC2)nc2c(OCc3c(F)cccc3F)cccn12]

410 mg of ethyl 2-cyclopropyl-8-[(2,6-difluorobenzyl)oxy]imidazo[1,2-a]pyridine-3-carboxylate (Example 27A, 1.1 mmol, 1 equivalent) were initially charged in 15 ml of methanol/tetrahydrofuran (1:1), and 5.5 ml of a 1 N aqueous lithium hydroxide solution (5.5 mmol, 5 equivalents) were added. The reaction mixture was stirred at RT overnight, another 5.5 ml of 1 N aqueous lithium hydroxide solution were added, and the mixture was stirred at RT for another night. The mixture was concentrated and the residue was taken up in water and acidified with 1 N aqueous hydrochloric acid. The precipitated product was filtered off and dried under high vacuum. This gave 293 mg (77% of theory) of the title compound.

LC-MS (Method 1): R$_t$=0.83 min
MS (ESpos): m/z=345.2 (M+H)$^+$
$^1$H NMR (400 MHz, DMSO-d$_6$): δ=0.95-1.02 (m, 4H); 2.80 (quint., 1H); 5.30 (s, 2H); 7.02 (t, 1H); 7.15 (d, 1H); 7.22 (t, 2H); 7.59 (quint., 1H); 8.92 (s, 1H); 13.3 (br. s, 1H).

Example 29A

Ethyl 2-chloro-3-oxopropanoate

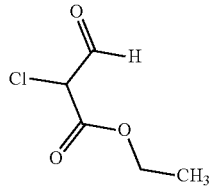

139 ml of a 21% strength solution of sodium ethoxide in ethanol (371 mmol, 0.91 equivalents) were initially charged in 200 ml of diethyl ether, and a solution consisting of 43.7 ml of ethyl chloroacetate (408 mmol, 1 equivalent) and 32.9 ml of ethyl formate (408 mmol, 1 equivalent) in 150 ml of diethyl ether was added dropwise at RT. The reaction mixture was stirred overnight and the solid was filtered off and washed with diethyl ether. The solid was dissolved in water and the aqueous phase was, with ice bath cooling, adjusted to pH4 using concentrated hydrochloric acid. The mixture was extracted repeatedly with diethyl ether and the combined organic phases were washed with saturated aqueous sodium chloride solution, dried with magnesium sulphate, filtered and concentrated. The crude product obtained (8.2 g) was freed from residual solvent under high vacuum and used without further purification for the next reaction.

Example 30A

Ethyl 8-[(2,6-difluorobenzyl)oxy]imidazo[1,2-a]pyridine-3-carboxylate

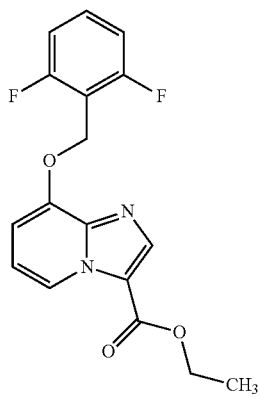 [SMILES: CCOC(=O)c1cnc2c(OCc3c(F)cccc3F)cccn12]

1.93 g of 3-[(2,6-difluorobenzyl)oxy]pyridine-2-amine (Example 4A; 8.2 mmol, 1 equivalent) were initially charged in 50 ml of ethanol, and 8.2 g of ethyl 2-chloro-3-oxopropanoate (75% pure, crude product from Example 29A, 40.8 mmol, 5 equivalents) were added. The resulting reaction mixture was heated at reflux overnight. The reaction solution was concentrated and the crude product obtained was chromatographed on 340 g of silica gel (Biotage Isolera) (mobile phase: cyclohexane:ethyl acetate gradient; $R_f$ value of the product in cyclohexane:ethyl acetate 2:1=0.36). The product fractions were combined and concentrated and the residue obtained was triturated with diisopropyl ether. The solid was filtered off and dried under high vacuum. This gave 2.02 g of the title compound (71% of theory).

LC-MS (Method 1): $R_t$=1.08 min

MS (ESpos): m/z=333.1 (M+H)$^+$ $^1$H NMR (400 MHz, DMSO-d$_6$): δ=1.35 (t, 3H); 4.39 (q, 2H); 5.35 (s, 2H); 7.15-7.28 (m, 4H); 7.58 (quint., 1H); 8.18 (s, 1H); 8.90 (d, 1H).

Example 31A

8-[(2,6-Difluorobenzyl)oxy]imidazo[1,2-a]pyridine-3-carboxylic acid

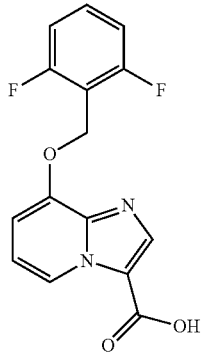 [SMILES: O=C(O)c1cnc2c(OCc3c(F)cccc3F)cccn12]

1 g of ethyl 8-[(2,6-difluorobenzyl)oxy]imidazo[1,2-a]pyridine-3-carboxylate (Example 30A, 3 mmol, 1 equivalent) was initially charged in 60 ml of methanol/tetrahydrofuran (5:1), 15 ml of a 1 N aqueous lithium hydroxide solution (15 mmol, 5 equivalents) were added and the mixture was warmed to 40° C. and stirred at this temperature for 4 h. The mixture was then cooled and, with ice cooling, adjusted to pH=4 using 6 N hydrochloric acid. The organic solvents were removed on a rotary evaporator, water was added to the precipitated product and the product was filtered off. The filter cake was washed with water and dried under high vacuum. This gave 797 mg (87% of theory) of the title compound.

LC-MS (Method 1): $R_t$=0.66 min

MS (ESpos): m/z=305.1 (M+H)$^+$ $^1$H NMR (400 MHz, DMSO-d$_6$): δ=5.38 (s, 2H); 7.10-7.28 (m, 4H); 7.59 (quint., 1H); 8.12 (s, 1H); 8.92 (s, 1H); 13.1 (br. s, 1H).

Example 32A

Ethyl 8-[(2,6-difluorobenzyl)oxy]-2-methyl-6-(pyrrolidin-1-yl)imidazo[1,2-a]pyridine-3-carboxylate

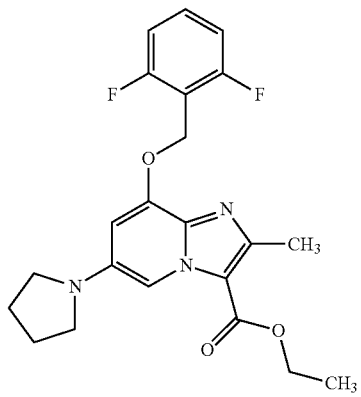 [SMILES: CCOC(=O)c1c(C)nc2c(OCc3c(F)cccc3F)cc(N3CCCC3)cn12]

500 mg of ethyl 6-bromo-8-[(2,6-difluorobenzyl)oxy]-2-methylimidazo[1,2-a]pyridine-3-carboxylate (1.18 mmol, 1 equivalent), 43 mg of tris(dibenzylideneacetone)dipalladium (0.047 mmol, 4 mol%), 158 mg of sodium tert-butoxide (1.65 mmol, 1.4 equivalents), 67 mg of XPHOS (0.141 mmol, 12 mol %) and 294 µl of pyrrolidine (3.5 mmol, 3 equivalents) were dissolved in 30 ml of dry toluene and reacted in an oil bath preheated to 100° C. After 16 h at this temperature, the reaction mixture was cooled, filtered through kieselguhr, concentrated and chromatographed (Biotage Isolera Four; cyclohexane/ethyl acetate gradient as mobile phase). This gave 100 mg (19% of theory) of the title compound.

LC-MS (Method 1): R$_t$=1.08 min

MS (ESpos): m/z=416.2 (M+H)$^+$ $^1$H NMR (400 MHz, DMSO-d$_6$): δ=1.34 (t, 3H); 1.95-2.04 (m, 4H); 2.55 (s, 3H; obscured by DMSO signal); 3.21-3.29 (m, 4H); 4.31 (q, 2H); 5.38 (s, 2H); 6.80 (s, 1H); 7.22 (t, 2H); 7.58 (quint., 1H); 8.13 (s, 1H).

Example 33A

8-[(2,6-Difluorobenzyl)oxy]-2-methyl-6-(pyrrolidin-1-yl)imidazo[1,2-a]pyridine-3-carboxylic acid

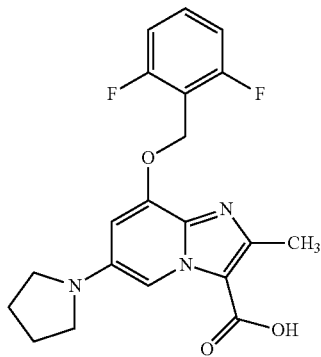 [SMILES: Cc1nc2c(OCc3c(F)cccc3F)cc(N3CCCC3)cn2c1C(=O)O]

90 mg of ethyl 8-[(2,6-difluorobenzyl)oxy]-2-methyl-6-(pyrrolidin-1-yl)imidazo[1,2-a]pyridine-3-carboxylate (Example 32A; 0.217 mmol, 1 equivalent) were dissolved in 6 ml of THF/methanol 5:1, 1.1 ml of 1N aqueous lithium hydroxide solution (1.1 mmol, 5 equivalents) were added and the mixture was warmed to 40° C. and stirred at this temperature for 20 h. The mixture was cooled, acidified to pH 4 with 6 N hydrochloric acid and concentrated. Water was added to the solid formed and the product was triturated, filtered off with suction, washed with water and dried under reduced pressure. This gave 87 mg of the title compound (93% of theory).

LC-MS (Method 1): R$_t$=0.83 min

MS (ESpos): m/z=388.2 (M+H)$^+$ $^1$H NMR (400 MHz, DMSO-d$_6$): δ=2.00-2.08 (m, 4H); 2.60 (s, 3H); 3.30-3.38 (m, 4H); 5.52 (s, 2H); 7.24 (s, 1H); 7.25 (t, 2H); 7.60 (quint., 1H); 8.30 (s, 1H).

Example 34A

Ethyl 8-[(2,6-difluorobenzyl)oxy]-2-methyl-6-(morpholin-4-yl)imidazo[1,2-a]pyridine-3-carboxylate

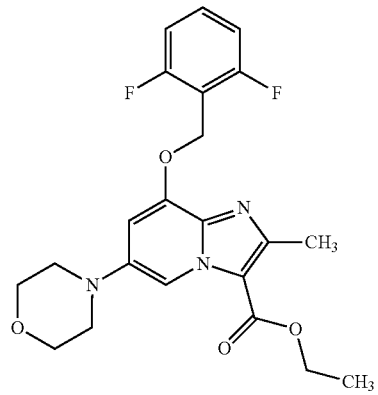 [SMILES: CCOC(=O)c1c(C)nc2c(OCc3c(F)cccc3F)cc(N3CCOCC3)cn12]

500 mg of ethyl 6-bromo-8-[(2,6-difluorobenzyl)oxy]-2-methylimidazo[1,2-a]pyridine-3-carboxylate (1.18 mmol, 1 equivalent), 43 mg of tris(dibenzylideneacetone)dipalladium (0.047 mmol, 4 mol %), 158 mg of sodium tert-butoxide (1.65 mmol, 1.4 equivalents), 67 mg of XPHOS (0.141 mmol, 12 mol %) and 307 µl of morpholine (3.5 mmol, 3 equivalents) were dissolved in 30 ml of dry toluene and reacted in an oil bath preheated to 100° C. After 16 h at this temperature, the reaction mixture was cooled, filtered through kieselguhr, concentrated and chromatographed (Biotage Isolera Four; cyclohexane/ethyl acetate gradient as mobile phase). This gave 352 mg (63% of theory) of the title compound.

LC-MS (Method 1): R$_t$=1.05 min

MS (ESpos): m/z=432.2 (M+H)$^+$ $^1$H NMR (400 MHz, DMSO-d$_6$): δ=1.35 (t, 3H); 2.55 (s, 3H; obscured by DMSO signal); 3.08-3.13 (m, 4H); 3.75-3.80 (m, 4H); 4.31 (q, 2H); 5.30 (s, 2H); 7.20 (s, 1H); 7.23 (t, 2H); 7.59 (quint., 1H); 8.40 (s, 1H).

Example 35A

8-[(2,6-Difluorobenzyl)oxy]-2-methyl-6-(morpholin-4-yl)imidazo[1,2-a]pyridine-3-carboxylic acid

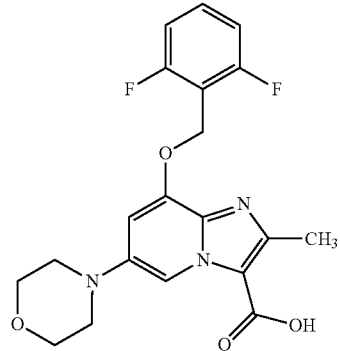 [SMILES: Cc1nc2c(OCc3c(F)cccc3F)cc(N3CCOCC3)cn2c1C(=O)O]

400 mg of ethyl 8-[(2,6-difluorobenzyl)oxy]-2-methyl-6-(pyrrolidin-1-yl)imidazo[1,2-a]pyridine-3-carboxylate (Example 34A; 0.927 mmol, 1 equivalent) were dissolved in 24 ml of THF/methanol 5:1, 4.6 ml of 1N aqueous lithium hydroxide solution (4.6 mmol, 5 equivalents) were added and the mixture was warmed to 40° C. and stirred at this temperature for 4 h. The mixture was cooled, acidified to pH 4 with 6 N hydrochloric acid and concentrated. Water was added to the residue and the mixture was extracted repeatedly with dichloromethane. The combined organic phases were washed with saturated aqueous sodium chloride solution, dried, filtered and concentrated. This gave 145 mg of the title compound (35% of theory) which was reacted further without further work-up.

LC-MS (Method 1): $R_t$=0.72 min
MS (ESpos): m/z=404.2 (M+H)$^+$
$^1$H NMR (400 MHz, DMSO-$d_6$): δ=2.55 (s, 3H; superimposed by DMSO signal); 3.10-3.20 (m, 4H); 3.75-3.82 (m, 4H); 5.38 (s, 2H); 7.23 (t, 2H); 7.25 (s, 1H); 7.58 (quint., 1H); 8.48 (s, 1H).

Example 36A

6-Chloro-8-[(2,3-difluorobenzyl)oxy]-2-methylimidazo[1,2-a]pyridine-3-carboxylic acid

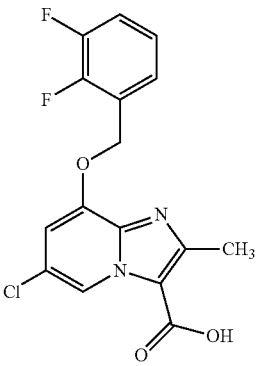 [SMILES: Cc1nc2c(OCc3cccc(F)c3F)cc(Cl)cn2c1C(=O)O]

Step a): 2-Amino-5-chloropyridin-3-ol

Nitro reduction of 5-chloro-2-nitropyridin-3-ol (Example 15A) analogously to the preparation of Example 11A to give 2-amino-5-chloropyridin-3-ol; 84% yield (contained 33% dechlorinated product).

LC-MS (Method 1): $R_t$=0.20 min
MS (ESpos): m/z=144.9/146.9 (M+H)$^+$

Step b): 5-Chloro-3-[(2,6-difluorobenzyl)oxy]pyridine-2-amine

Reaction of 2-amino-5-chloropyridin-3-ol with 1.1 equivalents of 2,3-difluorobenzyl bromide and 2.2 equivalents of caesium carbonate in DMF (15 min at 50° C.), aqueous work-up, extraction with ethyl acetate and subsequent chromatography of the organic residue (gradient: cyclohexane/ethyl acetate 8:1 to pure ethyl acetate) to give 5-chloro-3-[(2,6-difluorobenzyl)oxy]pyridine-2-amine; 10% yield.

LC-MS (Method 1): $R_t$=0.94 min
MS (ESpos): m/z=271.0/273.0 (M+H)$^+$

Step c): Ethyl 6-chloro-8-[(2,3-difluorobenzyl)oxy]-2-methylimidazo[1,2-a]pyridine-3-carboxylate Cyclization (analogously to the preparation of Example 18A) to give ethyl 6-chloro-8-[(2,3-difluorobenzyl)oxy]-2-methylimidazo[1,2-a]pyridine-3-carboxylate; 48% yield.

LC-MS (Method 1): $R_t$=1.25 min
MS (ESpos): m/z=381.1/383.0 (M+H)$^+$

Step d): 6-Chloro-8-[(2,3-difluorobenzyl)oxy]-2-methylimidazo[1,2-a]pyridine-3-carboxylic acid Ester hydrolysis (analogously to the preparation of Example 19A) to give 6-chloro-8-[(2,3-difluorobenzyl)oxy]-2-methylimidazo[1,2-a]pyridine-3-carboxylic acid; 67% yield.

LC-MS (Method 1): $R_t$=0.87 min
MS (ESpos): m/z=353.1/355.1 (M+H)$^+$
$^1$H NMR (400 MHz, DMSO-$d_6$): δ=2.54 (s, 3H; superimposed by DMSO signal); 5.41 (s, 2H); 7.27 (s, 1H); 7.25-7.31 (m, 1H); 7.43-7.55 (m, 2H); 8.99 (s, 1H); 13.39 (br. s, 1H).

Example 37A

Ethyl 8-[(2,6-difluorobenzyl)oxy]-2-methyl-6-[(trimethylsilyl)ethynyl]imidazo[1,2-a]pyridine-3-carboxylate

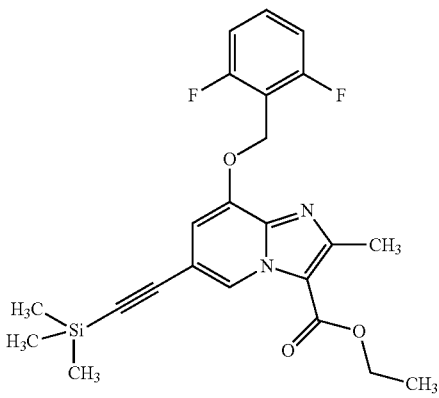 [SMILES: CCOC(=O)c1c(C)nc2c(OCc3c(F)cccc3F)cc(C#C[Si](C)(C)C)cn12]

1 g of ethyl 6-bromo-8-[(2,6-difluorobenzyl)oxy]-2-methylimidazo[1,2-a]pyridine-3-carboxylate (Example 21A; 2.35 mmol; 1 equivalent) was initially charged in 52 ml of dioxane/diisopropylethylamine 1:1, and 165 mg of dichlorobis(triphenylphosphine)palladium(II) (0.24 mmol, 0.1 equivalents) and 45 mg of copper(I) iodide (0.24 mmol, 0.1 equivalents) were added. At RT, 1.3 ml of trimethylsilylacetylene (9.4 mmol, 4 equivalents) were slowly added dropwise. The resulting reaction mixture was stirred at 50° C. for 16 h. The mixture was then concentrated, water was added and the mixture was extracted three times with ethyl acetate. The combined organic phases were washed twice with 10% strength aqueous sodium thiosulphate solution and then with saturated sodium chloride solution and dried over magnesium sulphate, and the filtrate was concentrated. The residue was dissolved in methanol and purified by preparative HPLC (column: Nucleodur C18 Gravity 50×200 mm, 10 μm, gradient: A=water+0.1% concentrated aqueous ammonia solution, B=acetonitrile, 0 min=30% B, 5 min=30% B, 23 min=100% B, 28 min=100% B, 28.2 min=30% B, 34 min=30% B, flow rate 110 ml/min, wavelength 220 nm). This gave 726 mg of a solid (89% pure, 62% of theory).

LC-MS (Method 1): $R_t$=1.48 min
MS (ESpos): m/z=443.3 (M+H)$^+$ $^1$H NMR (400 MHz, DMSO-d$_6$): δ=0.3 (s, 9H), 1.36 (t, 3H), 2.54 (s, 3H; obscured by DMSO signal), 4.37 (q, 2H), 5.33 (s, 2H), 7.20-7.28 (m, 3H), 7.61 (quint., 1H), 8.93 (s, 1H).

Example 38A

Ethyl 8-[(2,6-difluorobenzyl)oxy]-6-ethynyl-2-methylimidazo[1,2-a]pyridine-3-carboxylate

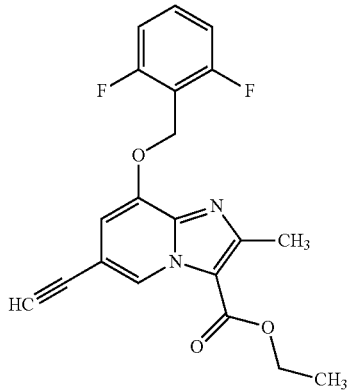 [SMILES: C#Cc1cc(OCc2c(F)cccc2F)c2nc(C)c(C(=O)OCC)n2c1]

720 mg ethyl 8-[(2,6-difluorobenzyl)oxy]-2-methyl-6-[(trimethylsilyl)ethynyl]imidazo[1,2-a]-pyridine-3-carboxylate (Example 37A; 1.63 mmol; 1 equivalent) were initially charged in 16 ml of methanol, and 674 mg of potassium carbonate (4.81 mmol, 3 equivalents) were added. The resulting reaction mixture was stirred at room temperature for 2 h. The reaction mixture was then concentrated, water was added and the mixture was extracted three times with ethyl acetate. The combined organic phases were washed with saturated sodium chloride solution and dried over magnesium sulphate, and the filtrate was concentrated. This gave 587.7 mg of crude product (which contained 35% of the methyl ester of the target compound; quantitative yield) which was used without further purification for the next reaction.

LC-MS (Method 1): R$_t$=1.22 min (methyl ester: 1.14 min)
MS (ESpos): m/z=371.2 (M+H)$^+$ (ethyl ester: 357.1)
$^1$H NMR (400 MHz, DMSO-d$_6$): δ=1.36 (t, 3H), 2.54 (s, 3H; obscured by DMSO signal), 4.38 (q, 2H), 4.40 (s, 1H), 5.33 (s, 2H), 7.20-7.28 (m, 3H), 7.61 (quint., 1H), 8.93 (s, 1H).

Example 39A

8-[(2,6-Difluorobenzyl)oxy]-6-ethynyl-2-methylimidazo[1,2-a]pyridine-3-carboxylic acid

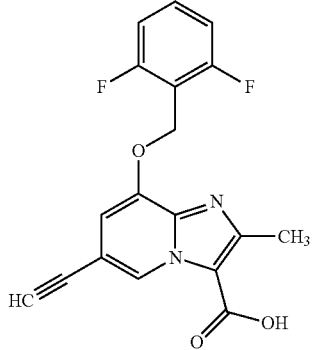 [SMILES: C#Cc1cc(OCc2c(F)cccc2F)c2nc(C)c(C(=O)O)n2c1]

580 mg of ethyl 8-[(2,6-difluorobenzyl)oxy]-6-ethynyl-2-methylimidazo[1,2-a]pyridine-3-carboxylate (Example 38A; contained 35% of the methyl ester) were initially charged in 30 ml of tetrahydrofuran and 5 ml of methanol, and 7.8 ml of 1N aqueous lithium hydroxide solution were added. The resulting reaction mixture was stirred at room temperature for 6 h and then kept at 0° C. for 16 h. The mixture was then acidified with 6 N hydrochloric acid and concentrated. The solid which formed was filtered off, triturated with a little water and filtered off again. Drying under reduced pressure gave 521 mg of the desired product (quantitative yield).

LC-MS (Method 1): R$_t$=0.87 min
MS (ESpos): m/z=343.1 (M+H)$^+$
$^1$H NMR (400 MHz, DMSO-d$_6$): δ=2.54 (s, 3H; obscured by DMSO signal), 4.40 (s, 1H), 5.33 (s, 2H), 7.20-7.28 (m, 3H), 7.61 (quint., 1H), 9.06 (s, 1H).

Example 40A

Ethyl 6-cyclopropyl-8-[(2,6-difluorobenzyl)oxy]-2-methylimidazo[1,2-a]pyridine-3-carboxylate

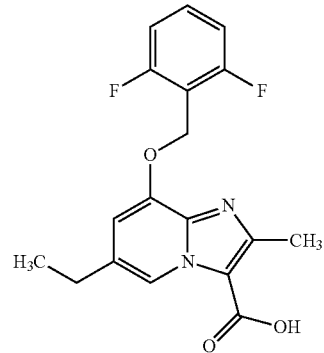 [SMILES: CCc1cc(OCc2c(F)cccc2F)c2nc(C)c(C(=O)O)n2c1]

150 mg of 8-[(2,6-difluorobenzyl)oxy]-6-ethynyl-2-methylimidazo[1,2-a]pyridine-3-carboxylic acid (Example 39A) were initially charged in 50 ml of ethanol and 20 ml of ethyl acetate, a spatula tip of Pd/C (10%) was added and the mixture was hydrogenated at atmospheric pressure for 4 h. The reaction mixture was filtered and the residue obtained (137 mg of a solid; 95% pure, 86% of theory) was reacted further without purification.

LC-MS (Method 1): R$_t$=0.80 min
MS (ESpos): m/z=347.1 (M+H)$^+$
$^1$H NMR (400 MHz, DMSO-d$_6$): δ=1.22 (t, 3H), 2.54 (s, 3H; obscured by DMSO signal), 2.69 (q, 2H), 5.31 (s, 2H), 7.09 (s, 1H), 7.23 (t, 2H), 7.61 (quint., 1H), 8.80 (s, 1H).

Example 41A

Ethyl 6-cyclopropyl-8-[(2,6-difluorobenzyl)oxy]-2-methylimidazo[1,2-a]pyridine-3-carboxylate

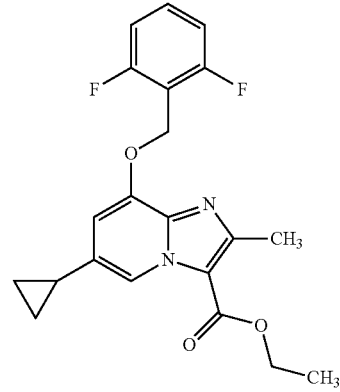 [SMILES: CCOC(=O)c1c(C)nc2c(OCc3c(F)cccc3F)cc(C3CC3)cn12]

500 mg of ethyl 6-bromo-8-[(2,6-difluorobenzyl)oxy]-2-methylimidazo[1,2-a]pyridine-3-carboxylate (Example 21A; 1.18 mmol; 1 equivalent), 131 mg of cyclopropaneboronic acid (1.53 mmol, 1.3 equivalents), 873 mg of potassium phosphate (4.12 mmol, 3.5 equivalents), 33 mg of tricyclohexylphosphine (0.12 mmol, 0.1 equivalents) and 13 mg of palladium(II) acetate (0.059 mmol, 5 mol %) were initially charged in 10.5 ml of toluene/water 20:1 and stirred at 80° C. for 16 h.

The mixture was then filtered through silica gel and concentrated. The residue was chromatographed on a 50 g silica gel cartridge (Biotage Isolera, cyclohexane/ethyl acetate gradient as mobile phase). This gave 473 mg of a yellowish solid (98% pure, quantitative yield).

LC-MS (Method 1): $R_t$=1.17 min

MS (ESpos): m/z=387.3 $(M+H)^+$ $^1$H NMR (500 MHz, DMSO-$d_6$): δ=0.78-0.82 (m, 2H), 0.95-1.05 (m, 2H), 1.36 (t, 3H), 2.05-2.10 (m, 1H), 2.54 (s, 3H; obscured by DMSO signal), 4.37 (q, 2H), 5.33 (s, 2H), 6.80 (s, 1H), 7.23 (t, 2H), 7.59 (quint., 1H), 8.70 (s, 1H).

Example 42A

6-Cyclopropyl-8-[(2,6-difluorobenzyl)oxy]-2-methylimidazo[1,2-a]pyridine-3-carboxylic acid

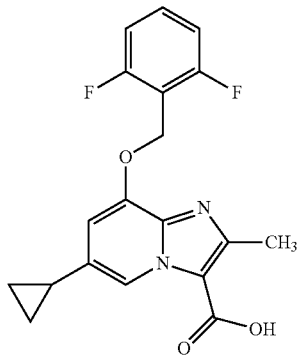 [SMILES: Cc1nc2c(OCc3c(F)cccc3F)cc(C3CC3)cn2c1C(=O)O]

470 mg of ethyl 6-cyclopropyl-8-[(2,6-difluorobenzyl)oxy]-2-methylimidazo[1,2-a]pyridine-3-carboxylate (Example 41A) were initially charged in 36 ml of tetrahydrofuran/methanol 5:1, and 6.1 ml of 1N aqueous lithium hydroxide solution were added. The mixture was stirred at 40° C. for 4 h and then acidified with 6 N hydrochloric acid and concentrated. The residue was taken up in water and repeatedly extracted with dichloromethane. The combined organic phases were washed with saturated aqueous sodium chloride solution, dried with magnesium sulphate and filtered, and the filtrate was concentrated. This gave 470 mg of the desired product (90% pure; 97% of theory) which was reacted without further purification.

LC-MS (Method 2): $R_t$=0.92 min

MS (ESpos): m/z=359.1 $(M+H)^+$ $^1$H NMR (400 MHz, DMSO-$d_6$): δ=0.88-0.92 (m, 2H), 1.05-1.10 (m, 2H), 2.12-2.20 (m, 1H), 2.60 (s, 3H), 4.40 (s, 1H), 5.40 (s, 2H), 7.14 (s, 1H), 7.22 (t, 2H), 7.61 (quint., 1H), 8.90 (s, 1H).

Example 43A 2,6-Difluorophenyl)($^2$H$_2$)methanol

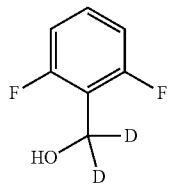 [SMILES: [2H]C([2H])(O)c1c(F)cccc1F]

At 0° C., 1.00 g (5.81 mmol) of methyl 2,6-difluorobenzoate were initially charged in 20 ml of THF, and 11.62 ml of (11.62 mmol) of lithium aluminium deuteride [=LiAlD$_4$=lithium tetrahydrido($^2$H$_4$)aluminate] (1 M solution in THF) were added dropwise. The mixture was stirred for 1 h in an ice bath that slowly thawed. 0.58 ml of water, 0.58 ml of 2 N aqueous sodium hydroxid solution and 1.16 ml of water were then added in succession to the reaction solution. The precipitate formed was filtered off and washed thoroughly with THF. The filtrate was concentrated and the residue was dried under high vacuum. This gave 0.743 g of the product (88% of theory, purity about 90%), which was reacted further without purification.

LC-MS (Method 14): $R_t$=2.38 min

MS (EIpos): m/z=146 $(M)^+$ $^1$H NMR (400 MHz, DMSO-$d_6$): δ=5.20 (s, 1H), 7.08 (t, 2H), 7.39 (quint, 1H).

Example 44A

Ethyl 8-{[(2,6-difluorophenyl)($^2$H$_2$)methyl]oxy}-2-methylimidazo[1,2-a]pyridine-3-carboxylate

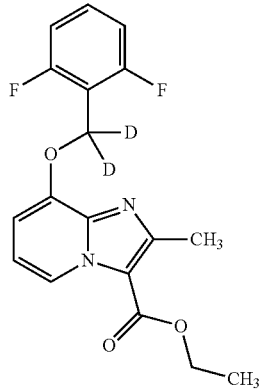 [SMILES: [2H]C([2H])(Oc1cccn2c(C(=O)OCC)c(C)nc12)c1c(F)cccc1F]

493 mg (2.24 mmol) of ethyl 8-hydroxy-2-methylimidazo[1,2-a]pyridine-3-carboxylate (Example 3 A) were initially charged in 13.5 ml of dry toluene, and then first 490 mg (3.35 mmol) of 2,6-difluorophenyl)($^2$H$_2$)methanol (Example Compound 43A) and 938 mg (3.58 mmol) of triphenylphosphine and then 769 mg (3.58 mmol) of diisopropyl azodicarboxylate were added, and the mixture was stirred at RT overnight. The reaction solution was concentrated and the residue was applied to silica gel and purified chromatographically (mobile phase: cyclohexane/ethyl acetate=8:1). This gave 467 mg of the target compound (60% of theory, purity 100%).

LC-MS (Method 2): $R_t$=1.16 min
MS (ESpos): m/z=349 (M+H)$^+$
$^1$H NMR (400 MHz, DMSO-d$_6$): δ=1.36 (t, 3H), 2.54 (s, 3H), 4.36 (q, 2H), 7.11 (t, 1H); 7.18-7.27 (m, 3H); 7.59 (quint, 1H); 8.88 (d, 1H).

Example 45A

8-{[(2,6-Difluorophenyl)($^2$H$_2$)methyl]oxy}-2-methylimidazo[1,2-a]pyridine-3-carboxylic acid

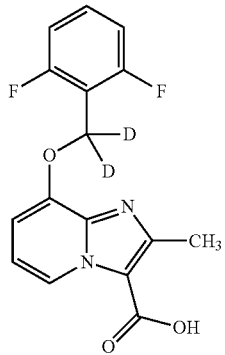 [SMILES: [2H]C([2H])(Oc1cccn2c(C(=O)O)c(C)nc12)c1c(F)cccc1F]

1.57 g (4.52 mmol) of ethyl 8-{[(2,6-difluorophenyl)($^2$H$_2$)methyl]oxy}-2-methylimidazo[1,2-a]-pyridine-3-carboxylate (Example Compound 44A) were dissolved in 96 ml of THF:methanol (5:1), 22.6 ml (22.6 mmol) of 1 N aqueous lithium hydroxide solution were added and the mixture was stirred at RT overnight. With cooling, the mixture was adjusted to pH 4 using 2 N aqueous hydrochloric acid solution, and the organic solvents were removed under reduced pressure. The resulting solid was filtered off, washed with water and dried under reduced pressure. This gave 1.29 g (89% of theory, purity 99%) of the product.

LC-MS (Method 2): $R_t$=0.76 min
MS (ESpos): m/z=321 (M+H)$^+$
$^1$H NMR (400 MHz, DMSO-d$_6$): δ=2.55 (s, 3H), 7.01 (t, 1H), 7.09 (d, 1H), 7.23 (t, 2H), 7.59 (quint, 1H), 8.92 (d, 1H), 13.08 (br s, 1H).

Example 46A

8-Hydroxy-N-[(2R)-1-hydroxyhexan-2-yl]-2-methylimidazo[1,2-a]pyridine-3-carboxamide

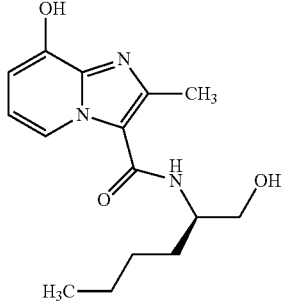

350 mg of 10% palladium/carbon were added to a solution of 3.5 g (9.18 mmol) of 8-(benzyloxy)-N-[(2R)-1-hydroxyhexan-2-yl]-2-methylimidazo[1,2-a]pyridine-3-carboxamide in 250 ml of ethyl acetate, and hydrogen was applied at room temperature and atmospheric pressure. After 3 h, the mixture was filtered off through kieselguhr, the filter cake was washed intensively with ethyl acetate/methanol and the filtrate was evaporated to dryness. Methyl tert-butyl ether was added to the crude product obtained, the product was triturated and the solid was then filtered off and dried at 40° C. under high vacuum. This gave 2.1 g (79% of theory) of 8-hydroxy-N-[(2R)-1-hydroxyhexan-2-yl]-2-methylimidazo[1,2-a]pyridine-3-carboxamide LC-MS (Method 1): $R_t$=0.61 min
MS (ESpos): m/z=292.1 (M+H)$^+$
$^1$H NMR (400 MHz, DMSO-d$_6$): δ=0.88 (t, 3H), 1.25-1.70 (m, 6H), 2.55 (s, 3H), 3.45 (m, 2H), 3.98 (m, 1H), 4.72 (s br, 1H), 6.59 (d, 1H), 6.79 (t, 1H). 7.45 (d, 1H), 8.40 (d, 1H).
Specific rotation (589 nm, 20.1° C., c=0.315 g/100 ml) in methanol: +16.9°

Example 47A

8-Hydroxy-N-[(2R)-1-hydroxybutan-2-yl]-2-methylimidazo[1,2-a]pyridine-3-carboxamide

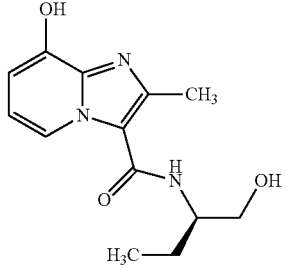

The preparation was carried out analogously to Example 46A by Pd/C-mediated hydrogenation starting with 3.5 g (about 9.72 mmol) of 8-(benzyloxy)-N-[(2R)-1-hydroxybutan-2-yl]-2-methylimidazo[1,2-a]pyridine-3-carboxamide. This gave 1.2 g (58% of theory) of the title compound.

LC-MS (Method 1): $R_t$=0.30 min
MS (ESpos): m/z=264.1 (M+H)$^+$
$^1$H NMR (400 MHz, DMSO-d$_6$): δ=0.93 (t, 3H), 1.48 (m, 1H), 1.70 (m, 1H), 2.53 (s, 3H), 3.48 (m, 2H), 3.92 (m, 1H), 4.72 (br, 1H), 6.59 (d, 1H), 6.79 (t, 1H), 7.45 (d, 1H), 8.40 (d, 1H).
Specific rotation (589 nm, 20.1° C., c=0.285 g/100 ml) in methanol: +23.0°

The following synthesis intermediates were prepared analogously to Example 46A:

TABLE 1A

| Example | IUPAC name/structure (yield) | Analytical data |
|---|---|---|
| 48A | 8-hydroxy-N-[2-(1-hydroxycyclopentyl)ethyl]-2-methylimidazo-[1,2-a]pyridine-3-carboxamide<br><br>(82% of theory) | LC-MS (Method 2): $R_t$ = 0.62 min<br>MS (ESpos): m/z = 304.2 (M + H)$^+$ |
| 49A | N-(1,3-dihydroxypropan-2-yl)-8-hydroxy-2-methylimidazo-[1,2-a]pyridine-3-carboxamide | LC-MS (Method 3): $R_t$ = 0.70 min |

TABLE 1A-continued

| Example | IUPAC name/structure (yield) | Analytical data |
|---|---|---|
| | 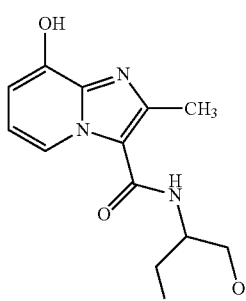<br>(46% of theory) | MS (ESpos):<br>m/z = 266.1<br>(M + H)⁺ |

Example 50A

Methyl 8-(cyclohexylmethoxy)-2-ethylimidazo[1,2-a]pyridine-3-carboxylate

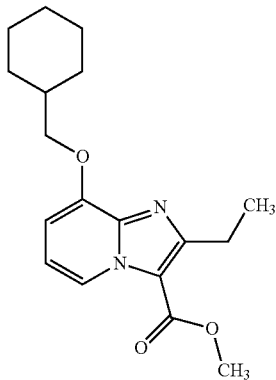 [SMILES: CCc1nc2c(OCC3CCCCC3)cccn2c1C(=O)OC]

A solution of 100 mg (0.485 mmol) of 3-(cyclohexylmethoxy)pyridine-2-amine and 399 mg (2.42 mmol) of methyl 2-chloro-3-oxopentanoate in 4 ml of ethanol was heated at reflux overnight. The mixture was then cooled and concentrated and the residue obtained was purified by preparative HPLC (Method 6). This gave 26 mg (17% of theory) of methyl 8-(cyclohexylmethoxy)-2-ethylimidazo[1,2-a]pyridine-3-carboxylate.

LC-MS (Method 2): $R_t$=1.31 min

MS (ESpos): m/z=317.3 (M+H)⁺

$^1$H NMR (400 MHz, DMSO-d$_6$): δ=1.07-1.17 (m, 2H), 1.16-1.34 (m, 3H), 1.24 (t, 3H), 1.65-1.76 (m, 3H), 1.84-1.90 (m, 3H), 2.50 (obscured by DMSO signal, s, 3H), 3.00 (q, 2H), 3.89 (s, 3H), 3.98 (d, 2H), 6.96 (d, 1H), 7.04 (t, 1H), 8.82 (d, 1H).

The following synthesis intermediates in Table 2A were obtained analogously to Example 50A by reacting the appropriate alkoxylated aminopyridines with the following condensation partners:

Example 51A condensation with ethyl 2-chloro-3-keto-4,4,4-trifluorobutyrate in ethanol;

Example 52A condensation with ethyl 2-chloro-3-oxohexanoate in ethanol;

Example 53A and Example 54A condensation with ethyl 2-chloro-3-oxobutanoate in ethanol;

Example 55A condensation with methyl 2-chloro-3-oxopentanoate in ethanol;

Example 56A condensation with ethyl 2-chloro-3-oxopropanoate in ethanol.

TABLE 2A

| Example | IUPAC name/structure (yield) | Analytical data |
|---|---|---|
| 51A | ethyl 8-(cyclohexylmethoxy)-2-trifluoromethylimidazo[1,2-a]pyridine-3-carboxylate<br>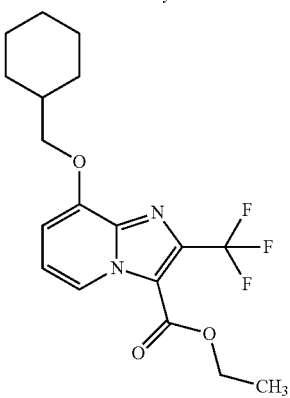<br>(31% of theory) | LC-MS (Method 2):<br>$R_t$ = 1.62 min<br>MS (ESpos):<br>m/z = 371.2<br>(M + H)⁺ |
| 52A | ethyl 8-(cyclohexylmethoxy)-2-propylimidazo[1,2-a]pyridine-3-carboxylate<br>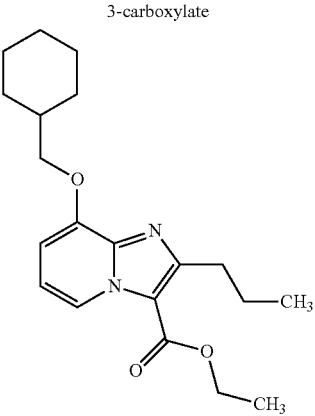<br>(15% of theory) | LC-MS (Method 2):<br>Rt = 1.46 min<br>MS (ESpos):<br>m/z = 345.4<br>(M + H)+ |

TABLE 2A-continued

| Example | IUPAC name/structure (yield) | Analytical data |
|---|---|---|
| 53A | ethyl 8-(cyclohexylmethoxy)-2-methylimidazo[1,2-a]pyridine-3-carboxylate 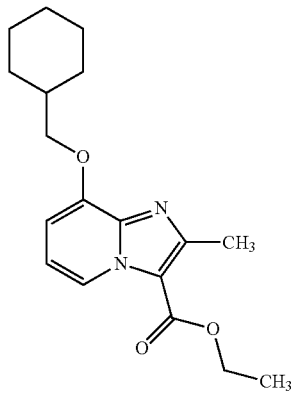 [SMILES: CCOC(=O)c1c(C)nc2c(OCC3CCCCC3)cccn12] (56% of theory) | LC-MS (Method 1): Rt = 1.18 min MS (ESpos): m/z = 317.1 (M + H)+ |
| 54A | ethyl 8-(cyclobutylmethoxy)-2-methylimidazo[1,2-a]pyridine-3-carboxylate 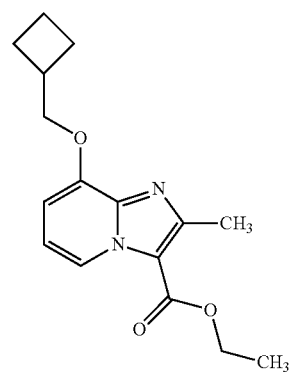 [SMILES: CCOC(=O)c1c(C)nc2c(OCC3CCC3)cccn12] (57% of theory) | LC-MS (Method 1): Rt = 1.01 min MS (ESpos): m/z = 289 (M + H)+ |
| 55A | methyl 8-(cyclobutylmethoxy)-2-ethylimidazo[1,2-a]pyridine-3-carboxylate 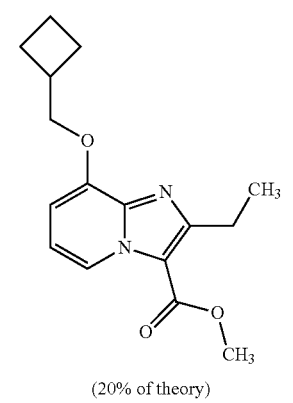 (20% of theory) | LC-MS (Method 2): Rt = 1.12 min MS (ESpos): m/z = 289.2 (M + H)+ |
| 56A | ethyl 8-(cyclohexylmethoxy)imidazo-[1,2-a]-pyridine-3-carboxylate 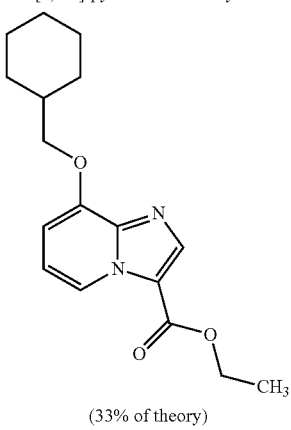 (33% of theory) | LC-MS (Method 2): Rt = 1.36 min MS (ESpos): m/z = 303.0 (M + H)+ |

Example 57A 8-(Cyclohexylmethoxy)-2-ethylimidazo[1,2-a]pyridine-3-carboxylic acid

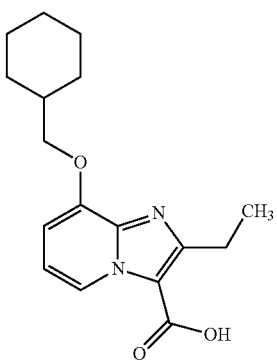 [SMILES: CCc1nc2c(OCC3CCCCC3)cccn2c1C(=O)O]

0.8 ml of 2N aqueous sodium hydroxide solution was added to a solution of 26 mg (0.082 mmol) of ethyl 8-(cyclohexylmethoxy)-2-ethylimidazo[1,2-a]pyridine-3-carboxylate in 1.15 ml of dioxane, and the mixture was stirred at room temperature overnight. The mixture was then acidified with 1.5 ml of 6N aqueous hydrochloric acid, diluted with 5 ml of dichloromethane and filtered over an Extrelut® cartridge. The cartridge was washed with 30 ml of dichloromethane, the filtrate was concentrated and the residue formed was dried under high vacuum. This gave 24 mg (97% of theory) of 8-(cyclohexylmethoxy)-2-ethylimidazo[1,2-a]pyridine-3-carboxylic acid as a crude product which was used as such for the next reaction.

LC-MS (Method 1): $R_t$=0.87 min

MS (ESpos): m/z=303.2 (M+H)+

The following synthesis intermediates in Table 3A were prepared analogously to Example Compound 57A by basic hydrolysis of the corresponding esters:

TABLE 3A

| Example | IUPAC name/structure (yield) | Analytical data |
|---|---|---|
| 58A | 8-(cyclohexylmethoxy)-2-trifluoromethyl-imidazo[1,2-a]pyridine-3-carboxylic acid 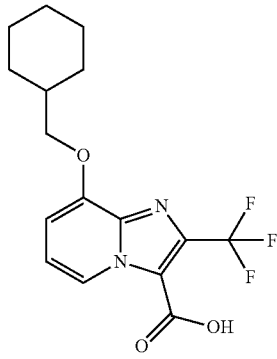 [SMILES: O=C(O)c1c(C(F)(F)F)nc2c(OCC3CCCCC3)cccn12] (99% of theory) | LC-MS (Method 1): $R_t$ = 1.15 min MS (ESpos): m/z = 343.1 $(M + H)^+$ |
| 59A | 8-(cyclohexylmethoxy)-2-propylimidazo-[1,2-a]-pyridine-3-carboxylic acid 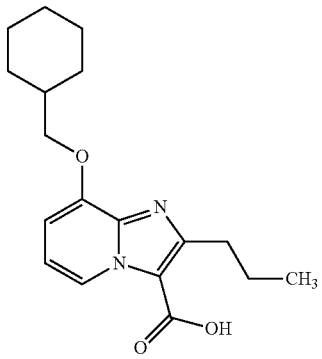 [SMILES: CCCc1nc2c(OCC3CCCCC3)cccn2c1C(=O)O] (73% of theory) | LC-MS (Method 1): $R_t$ = 0.94 min MS (ESpos): m/z = 317.3 $(M + H)^+$ |
| 60A | 8-(cyclohexylmethoxy)-2-methylimidazo-[1,2-a]-pyridine-3-carboxylic acid 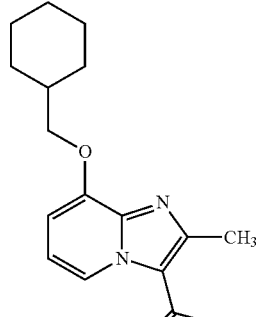 (about 100% of theory) | LC-MS (Method 1): $R_t$ = 0.82 min MS (ESpos): m/z = 289.1 $(M + H)^+$ |
| 61A | 8-(cyclobutylmethoxy)-2-methylimidazo-[1,2-a]-pyridine-3-carboxylic acid 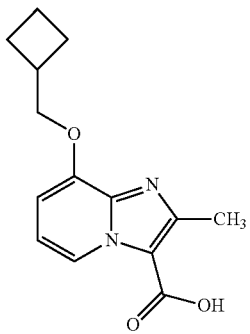 (about 62% of theory) | LC-MS (Method 3): $R_t$ = 1.67 min MS (ESpos): m/z = 289.2 $(M + H)^+$ |
| 62A | 8-(cyclobutylmethoxy)-2-ethylimidazo-[1,2-a]-pyridine-3-carboxylic acid 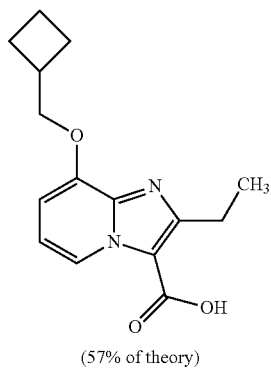 (57% of theory) | LC-MS (Method 1): $R_t$ = 0.73 min MS (ESpos): m/z = 275.1 $(M + H)^+$ |
| 63A | 8-(cyclohexylmethoxy)imidazo-[1,2-a]pyridine-3-carboxylic acid 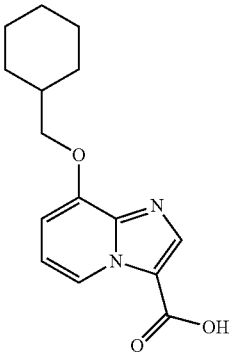 [SMILES: O=C(O)c1cnc2c(OCC3CCCCC3)cccn12] (77% of theory) | LC-MS (Method 2): $R_t$ = 0.90 min MS (ESpos): m/z = 275.2 $(M + H)^+$ |

Example 64A

8-[(2,6-Difluorobenzyl)oxy]-2-methyl-N-[(2R)-1-oxohexan-2-yl]imidazo[1,2-a]pyridine-3-carboxamide

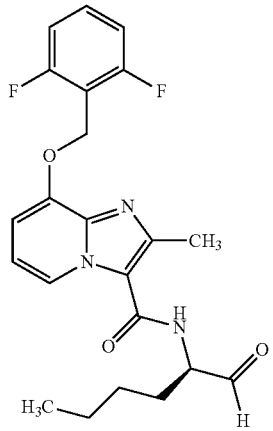 [SMILES: CCCC[C@H](C=O)NC(=O)c1c(C)nc2c(OCc3c(F)cccc3F)cccn12]

655 mg of 1,1,1-triacetoxy-1,1-dihydro-1,2-benziodoxol-3(1H)-one (Dess-Martin periodinane; 97%, Aldrich; 1.5 mmol) were initially charged in 10 ml of anhydrous dichloromethane and cooled to about −30° C. 83 μl (1.03 mmol) of pyridine and 430 mg 8-[(2,6-difluorobenzyl)oxy]-N-[(2R)-1-hydroxyhexan-2-yl]-2-methylimidazo[1,2-a]pyridine-3-carboxamide (1.03 mmol) in 20 ml of dichloromethane were added successively to this suspension. The reaction solution was warmed to room temperature and stirred for a further 4 h. With ice cooling, 1N aqueous aqueous sodium hydroxide solution was then added, and the mixture was extracted three times with ethyl acetate. The combined organic phases were washed with saturated aqueous sodium chloride solution, dried over magnesium sulphate, filtered off and concentrated. The residue obtained was used without further purification for subsequent reactions.

LC-MS (Method 1): $R_t$=1.0 min
MS (ESpos): m/z=416 (M+H)$^+$
$^1$H NMR (400 MHz, DMSO-$d_6$): δ=0.88 (t, 3H), 1.25-1.50 (m, 4H), 1.61-1.71 (m, 1H); 1.85-1.91 (m, 1H); 2.57 (s, 3H); 4.31-4.36 (m, 1H); 5.32 (s, 2H); 6.95 (t, 1H); 7.03 (d, 1H); 7.23 (t, 2H); 7.59 (quint., 1H); 8.21 (d, 1H); 8.57 (d, 1H); 9.56 (s, 1H).

Example 65A

Methyl N-({8-[(2,6-difluorobenzyl)oxy]-2-methylimidazo[1,2-a]pyridin-3-yl}carbonyl)-L-norleucinate

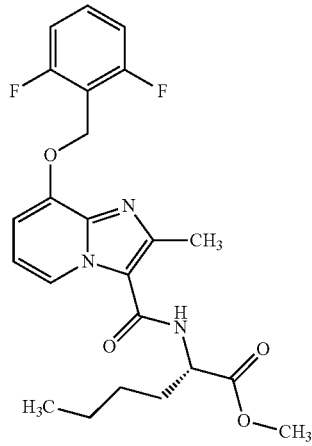 [SMILES: CCCC[C@H](NC(=O)c1c(C)nc2c(OCc3c(F)cccc3F)cccn12)C(=O)OC]

500 mg of 8-[(2,6-difluorobenzyl)oxy]-2-methylimidazo[1,2-a]pyridine-3-carboxylic acid (Example 6A; 1.57 mmol, 1 equivalent) were initially charged in 10 ml of anhydrous dichloromethane, and 313 mg of methyl L-norleucinate hydrochloride (1.73 mmol, 1.1 equivalents), 554 mg of benzotriazol-1-yloxy)bisdimethylaminomethylium fluoroborate (TBTU; 1.73 mmol, 1.1 equivalents) and 0.864 ml of 4-methylmorpholine (7.85 mmol, 5 equivalents) were added in succession. The reaction mixture was stirred at room temperature for 4 h. The mixture was then diluted with dichloromethane, washed with saturated aqueous sodium bicarbonate solution, with water and finally with saturated aqueous sodium chloride solution, dried and concentrated. The residue obtained was chromatographed on a 100 g silica gel cartridge (Biotage Isolera; cyclohexane/ethyl acetate gradient as mobile phase). This gave 644 mg of the target compound (91% of theory).

LC-MS (Method 1): $R_t$=1.05 min
MS (ESpos): m/z=446.2 (M+H)$^+$
$^1$H NMR (400 MHz, DMSO-$d_6$): δ=0.88 (t, 3H), 1.25-1.50 (m, 4H), 1.71-1.91 (m, 2H), 2.57 (s, 3H; obscured by DMSO signal), 3.79 (s, 3H), 4.45 (q, 1H), 5.32 (s, 2H), 6.91 (t, 1H), 7.01 (d, 1H), 7.21 (t, 2H), 7.59 (quint., 1H), 8.21 (d, 1H), 8.51 (d, 1H).

specific rotation: −15.9° (c=0.445 g in 100 ml of methanol, layer thickness 100 mm, 20.2° C., wavelength 589 nm).

Example 66A

Methyl N-({8-[(2,6-difluorobenzyl)oxy]-2-methylimidazo[1,2-a]pyridin-3-yl}carbonyl)-D-norleucinate

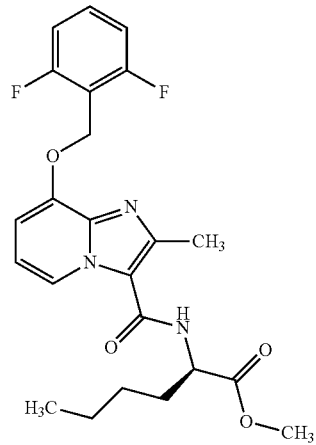 [SMILES: CCCC[C@@H](NC(=O)c1c(C)nc2c(OCc3c(F)cccc3F)cccn12)C(=O)OC]

2 g of 8-[(2,6-difluorobenzyl)oxy]-2-methylimidazo[1,2-a]pyridine-3-carboxylic acid (Example 6A; 6.28 mmol, 1 equivalent) were initially charged in 40 ml of anhydrous dichloromethane, and 1.26 g of methyl DL-norleucinate hydrochloride (6.91 mmol, 1.1 equivalents), 2.2 g of benzotriazol-1-yloxy)bisdimethylaminomethylium fluoroborate (TBTU; 6.91 mmol, 1.1 equivalents) and 3.45 ml of 4-methylmorpholine (31.4 mmol, 5 equivalents) were added in succession. The reaction mixture was stirred at room temperature for 4 h. The mixture was then diluted with dichloromethane, washed with saturated aqueous sodium bicarbonate solution, with water and finally with saturated aqueous sodium chloride solution, dried and concentrated. The residue obtained was chromatographed on a 340 g silica gel cartridge (Biotage Isolera; cyclohexane/ethyl acetate gradient as mobile phase). This gave 2.75 g of the target compound (97% of theory). The racemate was dissolved in 40 ml of ethanol and separated by chiral HPLC into the enantiomers (Daicel Chiralpak AD-H 5

μm 250×20 mm; 15 ml/min flow rate, mobile phase ethanol, detection wavelength 220 nm, injection volume 2.5 ml, temperature 45° C.).

Enantiomer A: corresponds to Example 65A
1.16 g of product (41% of theory)
LC analysis (column 250×4.6 mm filled with Daicel Chiralpak AD-H, 5 μM; flow rate 1.0 ml/min, temperature 40° C., mobile phase: ethanol) $R_t$=19.12 min; 99% ee
specific rotation: −15.3° (c=0.33 g in 100 ml methanol, layer thickness 100 mm, 19.6° C., wavelength 589 nm).

Enantiomer B: corresponds to Examples 65A
1.18 g of product (42% of theory)
LC analysis (column 250×4.6 mm filled with Daicel Chiralpak AD-H, 5 μM; flow rate 1.0 ml/min, temperature 40° C., mobile phase: ethanol) $R_t$=41.01 min; 99% ee
specific rotation: +15.1° (c=0.445 g in 100 ml of methanol, layer thickness 100 mm, 19.9° C., wavelength 589 nm).

$^1$H NMR (400 MHz, DMSO-$d_6$): δ=0.88 (t, 3H), 1.25-1.50 (m, 4H), 1.71-1.91 (m, 2H), 2.57 (s, 3H; obscured by DMSO signal), 3.70 (s, 3H), 4.45 (q, 1H), 5.31 (s, 2H), 6.91 (t, 1H), 7.01 (d, 1H), 7.21 (t, 2H), 7.59 (quint., 1H), 8.25 (d, 1H), 8.51 (d, 1H).

Example 67A (2R)-2-Aminobutan-1,4-diol

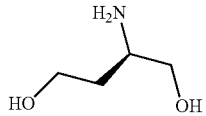

500 mg of (R)-2-Cbz-aminobutan-1,4-diol were dissolved in 250 ml of ethanol, a spatula tip of Pd/C (10%) was added and the mixture was hydrogenated with hydrogen at atmospheric pressure for 90 minutes. The reaction mixture was filtered through kieselguhr, the filter cake was washed with ethanol and the filtrate was concentrated. This gave 199 mg (91% of theory) of the target compound which was reacted further without further purification.

$^1$H NMR (400 MHz, DMSO-$d_6$): δ=1.22-1.32 (m, 1H), 1.46-1.55 (m, 1H), 2.70-2.76 (m, 1H), 3.12 (dd, 1H), 3.30 (dd, 1H), 3.49 (t, 2H).

Example 68A (2R)-2-Aminopentan-1,5-diol

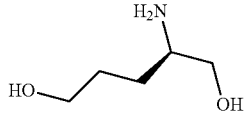

500 mg of (R)-2-Cbz-aminopentan-1,5-diol were dissolved in 250 ml of ethanol, a spatula tip of Pd/C (10%) was added and the mixture was hydrogenated with hydrogen at atmospheric pressure for 90 minutes. The reaction mixture was filtered through kieselguhr, the filter cake was washed with ethanol and the filtrate was concentrated. This gave 183 mg (78% of theory) of the target compound which was reacted further without further purification.

$^1$H NMR (400 MHz, DMSO-$d_6$): δ=1.00-1.15 (m, 1H), 1.30-1.65 (m, 3H), 2.55 (m, 1H; partially obscured by DMSO signal), 3.10 (dd, 1H), 3.28 (dd, 1H), 3.40 (t, 2H; partially obscured by water signal), 4.50 (br.s, 1H).

Representative Working Procedure 1a
Reduction of Amino Acids Using Lithium Borohydride and Chlorotrimethylsilane.

1.7-2.5 equivalents of lithium borohydride were initially charged in THF (about 0.1-0.5 M based on the amino acid), 3.4-5.0 equivalents of chlorotrimethylsilane were added (at 0° C. or RT) and the mixture was stirred at RT for five to 30 min. 1 equivalent of the amino acid was then carefully added a little at a time at 0° C. or RT and the reaction mixture was stirred at RT for 1-2 d. Exemplary work-up of the reaction mixture: Methanol was added and the mixture was concentrated. A 20% potassium hydroxide solution was added to the residue and the mixture was extracted three times with dichloromethane. The combined organic phases were dried over sodium sulphate, filtered and concentrated.

Example 69A

2-Amino-4,4,4-trifluorobutan-1-ol

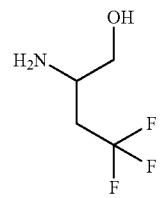

0.32 ml (0.65 mmol) of lithium borohydride (2 M in THF) were initially charged in 0.5 ml of dry THF, 0.16 ml (1.28 mmol) of chlorotrimethylsilane were added at RT and the mixture was stirred at RT for 5 min. 50 mg (0.26 mmol) of 2-amino-4,4,4-trifluorobutanoic acid hydrochloride (1:1) were then added a little at a time, and the reaction mixture was stirred at RT overnight. 0.5 ml of methanol was added, and the mixture was then concentrated. 0.6 ml of a 20% strength solution of potassium hydroxide was then added to the residue, and the mixture was extracted three times with dichloromethane. The combined organic phases were dried over sodium sulphate, filtered and concentrated. This gave 33 mg of the target compound (88% of theory).

DCI-MS (Method 13): MS (ESpos): m/z=144 (M+H)$^+$ $^1$H NMR (400 MHz, DMSO-$d_6$): δ=2.08-2.20 (m, 1H), 2.22-2.38 (m, 1H), 3.25-3.32 (m, 1H), 3.39-3.44 (m, 1H), 3.59-3.65 (m, 1H).

The examples shown in Table 4A were prepared analogously to Example 69A by reacting lithium borohydride (1.7-2.5 equivalents) and chlorotrimethylsilane (3.4-5 equivalents) with the appropriate commercially available amino acids according to the reaction conditions described:

TABLE 4A

| Example | IUPAC name/structure (yield) | Analytical data |
|---|---|---|
| 70A | 2-amino-5,5,5-trifluoropentan-1-ol (65% of theory) | DCI-MS (Method 13): MS (ESpos): m/z = 158 (M + H)$^+$ |
| 71A | 2-Amino-6,6,6-trifluorohexan-1-ol | DCI-MS (Method 13): |

TABLE 4A-continued

| Example | IUPAC name/structure (yield) | Analytical data |
|---|---|---|
| | 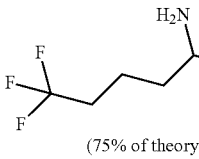 (75% of theory) | MS (ESpos): m/z = 172 (M + H)+ |
| 72A | 2-amino-3,3,3-trifluoropropan-1-ol 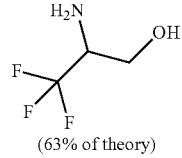 (63% of theory) | LC-MS (Method 13): MS (ESpos): m/z = 130 (M + H)+ |
| 73A | 2-amino-6,6,6-trifluorohexane-1,5-diol hydrochloride (1:1) 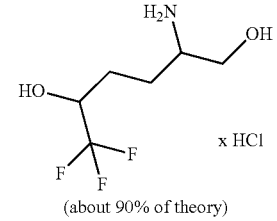 x HCl (about 90% of theory) | LC-MS (Method 13): MS (ESpos): m/z = 188 (M – HCl + H)+ |
| 74A | 2-amino-2-[4-(methylsulphonyl)-phenyl]ethanol 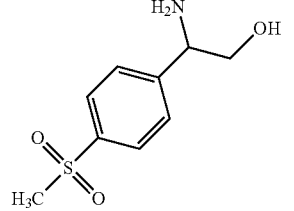 (about 98% of theory, purity about 80%) | LC-MS (Method 2): MS (ESpos): m/z = 216 (M + H)+ |

Example 75A

Methyl 2-amino-4,4,4-trifluorobutanoate hydrochloride (1:1)

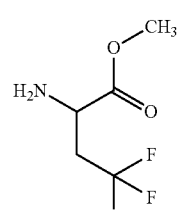

1.186 g (6.127 mmol) of 2-amino-4,4,4-trifluorobutanoic acid hydrochloride (1:1) were initially charged in 11.6 ml of methanol which had been saturated with hydrogen chloride, and the mixture was stirred under reflux for 4 h. The reaction solution was concentrated and dried under high vacuum. This gave 1.275 g of the target compound (100% of theory).

DCI-MS (Method 13): MS (ESpos): m/z=172 (M–HCl+H)+

$^1$H NMR (400 MHz, DMSO-$d_6$): δ=2.90-3.08 (m, 2H), 3.78 (s, 3H), 3.41 (t, 1H), 8.89 (br s, 3H).

The example compounds shown in Table 5A were prepared analogously to Example 75A by reacting hydrogen chloride in methanol with the corresponding commercially available amino acids under the reaction conditions described:

TABLE 5A

| Example | IUPAC name/structure (yield) | Analytical data |
|---|---|---|
| 76A | methyl 5,5,5-trifluoronorvalinate hydrochloride (1:1) 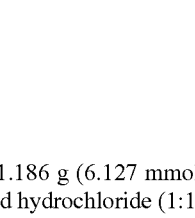 x HCl (94% of theory) | DCI-MS (Method 15): MS (ESpos): m/z = 186 (M + H)+ |
| 77A | methyl 6,6,6-trifluoronorleucinate hydrochloride (1:1) 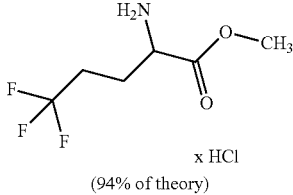 x HCl (100% of theory) | DCI-MS (Method 13): MS (ESpos): m/z = 200 (M – HCl + H)+ $^1$H NMR (400 MHz, DMSO-$d_6$): δ = 1.48-1.73 (m, 2H), 1.82-1.96 (m, 2H), 2.24-2.38 (m, 2H), 3.76 (s, 3H), 4.06-4.12 (m, 1H), 8.54-8.70 (br s, 3H). |

Representative Working Procedure 2a
Amide Formation Using TBTU as Coupling Agent.

1 equivalent of the carboxylic acid to be coupled, 1.1-1.5 equivalents of (benzotriazol-1-yloxy)bisdimethylaminomethylium fluoroborate (TBTU) and 3-6 equivalents of 4-methylmorpholine were initially charged in DMF or dichloromethane (about 0.1-0.2 M based on the carboxylic acid to be coupled). 1.1 to 1.5 equivalents of the amine to be coupled were then added, and the mixture was stirred at RT overnight.

Exemplary work-up of the reaction mixture: Water was added to the reaction solution and the precipitate formed was stirred for 0.5-1.0, filtered off, washed thoroughly with water and dried under high vacuum overnight. Alternatively, the reaction mixture was concentrated directly, purified further by preparative HPLC and dried under high vacuum overnight.

Example 78A

Methyl N-({8-[(2,6-difluorobenzyl)oxy]-2-methylimidazo[1,2-a]pyridin-3-yl}carbonyl)-beta-alaninate

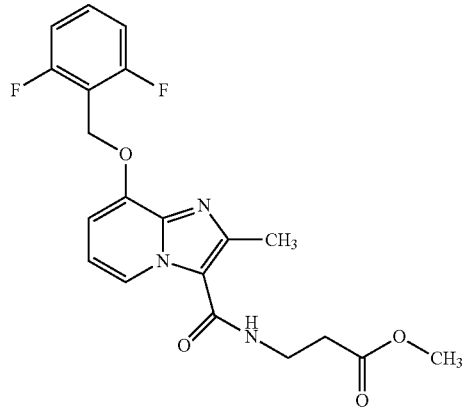 [SMILES: COC(=O)CCNC(=O)c1c(C)nc2c(OCc3c(F)cccc3F)cccn12]

300 mg (0.94 mmol) of 8-[(2,6-difluorobenzyl)oxy]-2-methylimidazo[1,2-a]pyridine-3-carboxylic acid, 454 mg (1.41 mmol) of (benzotriazol-1-yloxy)bisdimethylaminomethylium fluoroborate (TBTU) and 477 mg (4.71 mmol) of 4-methylmorpholine were initially charged in 6.0 ml of DMF. After 10 min at RT, 158 mg (1.13 mmol) of methyl beta-alaninate hydrochloride were added and the mixture was stirred at room temperature overnight. About 48 ml of water were added to the reaction solution, and the precipitate formed was stirred for another 30 min, filtered off, washed with diethyl ether and dried under high vacuum overnight. This gave 334 mg of the target compound (88% of theory).

LC-MS (Method 1): $R_t$=0.78 min

MS (ESpos): m/z=404 (M+H)$^+$ $^1$H NMR (400 MHz, DMSO-d$_6$): δ=2.48 (s, 3H), 2.63 (t, 2H), 3.58 (q, 2H), 3.63 (s, 3H), 5.30 (s, 2H), 6.92 (t, 1H), 7.01 (d, 1H), 7.23 (t, 2H), 7.59 (quint, 1H), 7.94 (t, 1H), 8.62 (d, 1H).

The example compounds shown in Table 6A were prepared analogously to Example Compound 78A by reacting 8-[(2,6-difluorobenzyl)oxy]-2-methylimidazo[1,2-a]pyridine-3-carboxylic acid with the appropriate commercially available amines in DMF or dichloromethane under the reaction conditions described in the Representative Working Procedure 2a:

TABLE 6A

| Example | IUPAC name/structure (yield) | Analytical data |
|---|---|---|
| 79A | rac-methyl 2-[({8-[(2,6-difluorobenzyl)oxy]-2-methylimidazo[1,2-a]pyridin-3-yl}-carbonyl)amino]-4,4,4-trifluorobutanoate<br><br>(80% of theory) | LC-MS (Method 1): $R_t$ = 0.95 min<br>MS (ESpos): m/z = 472 (M + H)$^+$<br>$^1$H NMR (400 MHz, DMSO-d$_6$): δ = 2.50 (s, 3H), 2.88-3.04 (m, 2H), 3.72 (s, 3H), 4.80-4.87 (m, 1H), 5.31 (s, 2H), 6.98 (t, 1H), 7.07 (d, 1H), 7.22 (t, 2H), 7.59 (quint, 1H), 8.49 (d, 1H), 8.58 (d, 1H). |

TABLE 6A-continued

| Example | IUPAC name/structure (yield) | Analytical data |
|---|---|---|
| 80A | rac-methyl N-({8-[(2,6-difluorobenzyl)oxy]-2-methylimidazo[1,2-a]pyridin-3-yl}carbonyl)-5,5,5-trifluoronorvalinate<br>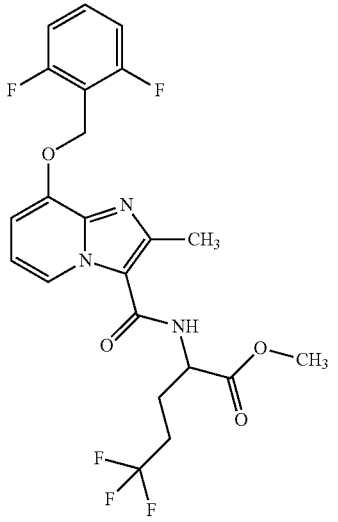 [SMILES: COC(=O)C(CCC(F)(F)F)NC(=O)c1c(C)nc2c(OCc3c(F)cccc3F)cccn12]<br>(91% of theory) | LC-MS (Method 3): $R_t$ = 2.05 min<br>MS (ESpos): m/z = 486 (M + H)$^+$<br>$^1$H NMR (400 MHz, DMSO-d$_6$): δ = 1.97-2.18 (m, 2H), 2.30-2.54 (m, 2H), underneath at 2.50 (s, 3H), 3.71 (s, 3H), 4.59-4.67 (m, 1H), 5.32 (s, 2H), 6.96 (t, 1H), 7.04 (d, 1H), 7.22 (t, 2H), 7.60 (quint, 1H), 8.34 (d, 1H), 8.55 (d, 1H). |
| 81A | rac-methyl N-({8-[(2,6-difluorobenzyl)oxy]-2-methylimidazo[1,2-a]pyridin-3-yl}carbonyl)-6,6,6-trifluoronorleucinate<br>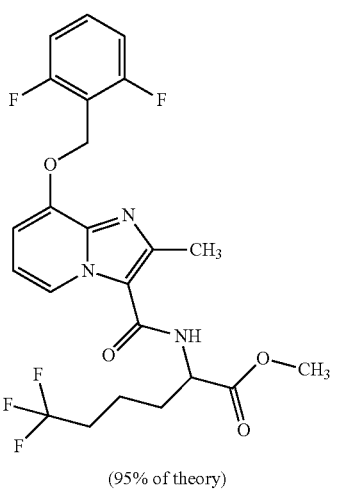<br>(95% of theory) | LC-MS (Method 1): $R_t$ = 1.04 min<br>MS (ESpos): m/z = 500 (M + H)$^+$<br>$^1$H NMR (400 MHz, DMSO-d$_6$): δ = 1.59-1.69 (m, 2H), 1.80-2.01 (m, 2H), 2.20-2.43 (m, 2H), 2.50 (s, 3H), 3.70 (s, 3H), 4.49-4.57 (m, 1H), 5.31 (s, 2H), 6.94 (t, 1H), 7.03 (d, 1H), 7.22 (t, 2H), 7.60 (quint, 1H), 8.33 (d, 1H), 8.49 (d, 1H). |

TABLE 6A-continued

| Example | IUPAC name/structure (yield) | Analytical data |
|---|---|---|
| 82A | rac-methyl (4-chlorophenyl)[({8-[(2,6-difluorobenzyl)oxy]-2-methylimidazo[1,2-a]pyridin-3-yl}carbonyl)amino]acetate<br>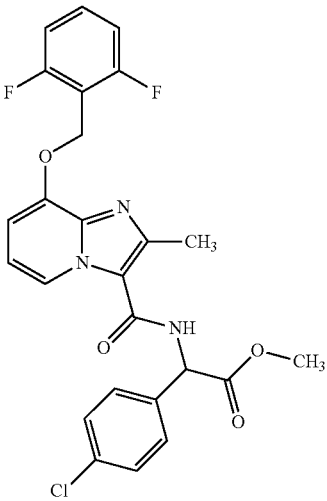 [SMILES: COC(=O)C(NC(=O)c1c(C)nc2c(OCc3c(F)cccc3F)cccn12)c1ccc(Cl)cc1]<br>(72% of theory) | LC-MS (Method 1): $R_t$ = 1.10 min<br>MS (ESpos): m/z = 500 (M + H)$^+$<br>$^1$H NMR (400 MHz, DMSO-d$_6$): δ = 2.50 (s, 3H), 3.70 (s, 3H), 5.31 (s, 2H), 5.71 (d, 1H), 6.98 (t, 1H), 7.03 (d, 1H), 7.22 (t, 2H), 7.49 (d, 2H), 7.53-7.63 (m, 3H), 8.53 (d, 1H), 8.73 (d, 1H). |
| 83A | rac-methyl [({8-[(2,6-difluorobenzyl)oxy]-2-methylimidazo[1,2-a]pyridin-3-yl}carbonyl)amino](4-fluorophenyl)acetate<br>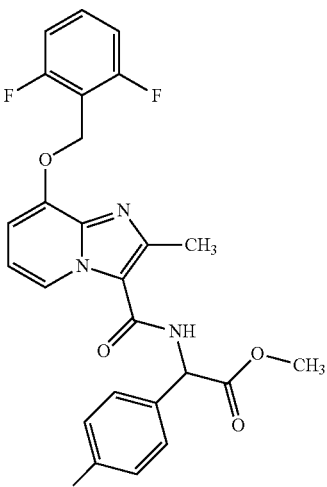<br>(84% of theory) | LC-MS (Method 1): $R_t$ = 1.04 min<br>MS (ESpos): m/z = 484 (M + H)$^+$<br>$^1$H NMR (400 MHz, DMSO-d$_6$): δ = 2.50 (s, 3H), 3.69 (s, 3H), 5.31 (s, 2H), 5.70 (d, 1H), 6.96 (t, 1H), 7.03 (d, 1H), 7.19-7.28 (m, 4H), 7.53-7.63 (m, 3H), 8.53 (d, 1H), 8.72 (d, 1H). |

Example 84A 3-(Benzyloxy)-5-bromopyridine-2-amine

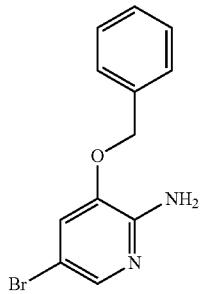 [SMILES: Nc1ncc(Br)cc1OCc1ccccc1]

200 g (1 mol) of 2-amino-3-benzyloxypyridine were initially charged in 4 l of dichloromethane, and a solution of 62 ml (1.2 mol) of bromine in 620 ml of dichloromethane was added at 0° C. over a period of 30 min. After the addition had ended, the reaction solution was stirred at 0° C. for 60 min. About 4 l of saturated aqueous sodium bicarbonate solution were then added to the mixture. The organic phase was separated off and concentrated. The residue was purified by silica gel column chromatography (petroleum ether:ethyl acetate 6:4), and the product fractions were concentrated. This gave 214 g (77% of theory) of the title compound.

LC-MS (Method 1): $R_t$=0.92 min
MS (ESpos): m/z=279 (M+H)$^+$
$^1$H NMR (400 MHz, DMSO-$d_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 85A

Ethyl 8-(benzyloxy)-6-bromo-2-methylimidazo[1,2-a]pyridine-3-carboxylate

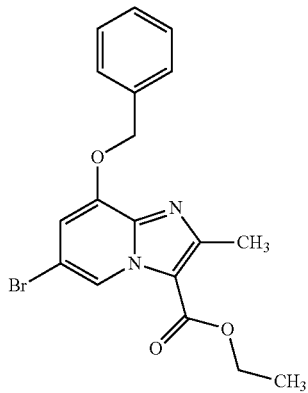

Under argon, 200 g (0.72 mol) of 3-(benzyloxy)-5-bromopyridine-2-amine Example 84A, 590 g (3.58 mol) of ethyl 2-chloroacetoacetate and 436 g 3 A molecular sieve were suspended in 6 l of ethanol and boiled at reflux for 72 h. The reaction mixture was filtered off through kieselguhr and concentrated. The residue was purified by silica gel chromatography (petroleum ether:ethyl acetate 9:1, then 6:4) and the product fractions were concentrated. This gave 221 g (79% of theory) of the target compound.

LC-MS (Method 17): $R_t$=1.31 min
MS (ESpos): m/z=389 (M+H)$^+$
$^1$H NMR (400 MHz, DMSO-$d_6$): δ=1.36 (t, 3H), 2.58 (s, 3H), 4.32-4.41 (m, 2H), 5.33 (s, 2H), 7.28-7.32 (m, 1H), 7.36-7.47 (m, 3H), 7.49-7.54 (m, 2H), 8.98 (d, 1H).

Example 86A

Ethyl 8-(benzyloxy)-2,6-dimethylimidazo[1,2-a]pyridine-3-carboxylate

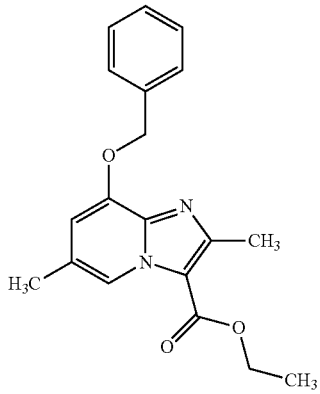 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate Example 85A were suspended in 4.2 l of 1,4-dioxane, 135.4 g (539 mmol, purity 50%) of trimethylboroxine, 31.2 g (27 mmol) of tetrakis(triphenylphosphine)palladium(0) and 78.3 g (566 mmol) of potassium carbonate were added in succession and the mixture was stirred under reflux for 8 h. The reaction mixture was cooled to RT, the precipitate was filtered off over silica gel and the filtrate was concentrated. The residue was dissolved in dichloromethane and purified by silica gel chromatography (dichloromethane:ethyl acetate=9:1). This gave 74 g (84.6% of theory; purity 100%) of the target compound.

LC-MS (Method 17): $R_t$=1.06 min
MS (ESpos): m/z=325 (M+H)$^+$
$^1$H NMR (400 MHz, DMSO-$d_6$): δ=1.35 (t, 3H), 2.34 (br. s, 3H), 2.56 (s, 3H), 4.31-4.38 (m, 2H), 5.28 (br. s, 2H), 6.99-7.01 (m, 1H), 7.35-7.47 (m, 3H), 7.49-7.54 (m, 2H), 8.68-8.70 (m, 1H).

Example 87A

Ethyl 8-hydroxy-2,6-dimethylimidazo[1,2-a]pyridine-3-carboxylate

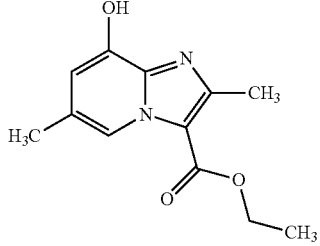 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate Example 86A were initially charged in 1254 ml of dichloromethane and 251 ml of ethanol, and 20.1 g of 10% palladium on activated carbon (moistened with water 50%) were added under argon. The reaction mixture was hydrogenated overnight at RT and atmospheric pressure. The reaction mixture was filtered off through kieselguhr and concentrated. The crude product was purified by silica gel chromatography (dichloromethane:methanol=95:5). This gave 50.4 g (94% of theory) of the target compound.

DCI-MS: (Method 13) (ESpos): m/z=235.2 (M+H)$^+$ $^1$H NMR (400 MHz, DMSO-d$_6$): δ=1.35 (t, 3H), 2.27 (s, 3H), 2.58 (s, 3H), 4.30-4.38 (m, 2H), 6.65 (d, 1H), 8.59 (s, 1H), 10.57 (br. s, 1H).

Example 88A

Ethyl 2,6-dimethyl-8-(3-methylbutoxy)imidazo[1,2-a]pyridine-3-carboxylate

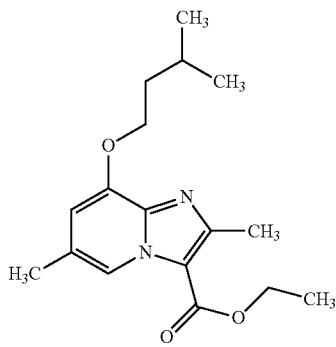 [SMILES: CCOC(=O)c1c(C)nc2c(OCCC(C)C)cc(C)cn12]

2.0 g (8.5 mmol) of ethyl 8-hydroxy-2,6-dimethylimidazo[1,2-a]pyridine-3-carboxylate Example 87A were initially charged in 122.3 ml of DMF, and 1.23 ml (9.4 mmol) of 1-iodo-3-methylbutane and 6.12 g (18.8 mmol) of caesium carbonate were added. The mixture was stirred at 60° C. for 40 min. The reaction mixture was cooled to RT, 900 ml of water were added and the mixture was stirred at RT for 1 h. The precipitated solid was filtered off, washed with water and dried under high vacuum. This gave 2.25 g (84% of theory; purity 97%) of the title compound.

LC-MS (Method 17): R$_t$=1.12 min

MS (ESpos): m/z=305 (M+H)$^+$ $^1$H NMR (400 MHz, DMSO-d$_6$): δ=0.96 (d, 6H), 1.35 (t, 3H), 1.70 (q, 2H), 1.77-1.89 (m, 1H), 2.33 (s, 3H), 2.56 (s, 3H), 4.17 (t, 2H), 4.34 (q, 2H), 6.88 (s, 1H), 8.64 (s, 1H).

Example 89A 2,6-Dimethyl-8-(3-methylbutoxy)imidazo[1,2-a]pyridine-3-carboxylic acid

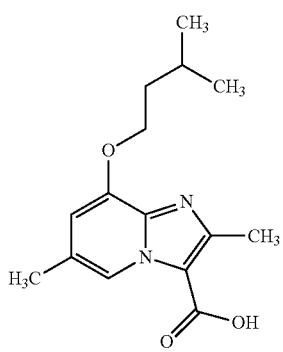

2.25 g (7.4 mmol) of ethyl 2,6-dimethyl-8-(3-methylbutoxy)imidazo[1,2-a]pyridine-3-carboxylate Example 88A were initially charged in 157 ml of THF/methanol (5:1), 37 ml (37 mmol) of 1N aqueous lithium hydroxide solution were added and the reaction mixture was stirred at RT over the weekend. The mixture was then cooled to 0° C., acidified to pH 4 with 6 N aqueous hydrochloric acid and freed from organic solvent on a rotary evaporator. The precipitated solid was filtered off, washed with water and dried under high vacuum. This gave 1.64 g (80% of theory; purity 100%) of the title compound.

LC-MS (Method 1): R$_t$=0.71 min

MS (ESpos): m/z=277 (M+H)$^+$ $^1$H NMR (400 MHz, DMSO-d$_6$): δ=0.96 (d, 6H), 1.70 (q, 2H), 1.78-1.89 (m, 1H), 2.32 (s, 3H), 2.56 (s, 3H), 4.17 (t, 2H), 6.85 (s, 1H), 8.69 (s, 1H), 12.86-13.08 (m, 1H).

Example 90A

Ethyl 2,6-dimethyl-8-[4,4,4-trifluoro-3-(trifluoromethyl)butoxy]imidazo[1,2-a]pyridine-3-carboxylate

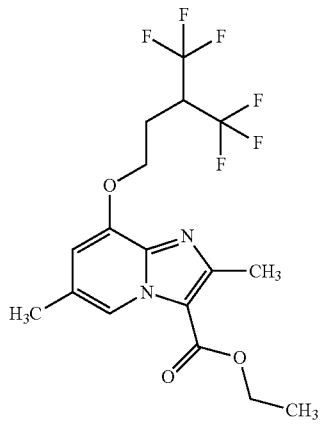 [SMILES: CCOC(=O)c1c(C)nc2c(OCCC(C(F)(F)F)C(F)(F)F)cc(C)cn12]

1.89 g (8.07 mmol) of ethyl 8-hydroxy-2,6-dimethylimidazo[1,2-a]pyridine-3-carboxylate Example 87A were initially charged in 60 ml of DMF, 7.89 g (24.2 mmol) of caesium carbonate and 2.30 g (8.88 mmol) of 4,4,4-trifluoro-3-(trifluoromethyl)butyl bromide were added and the reaction mixture was stirred at RT for 90 min. 60 ml of water were then added, the precipitated solid was filtered off and the filter residue was washed with 100 ml of water and twice with 20 ml of tert-butyl methyl ether. The precipitate obtained from the filtrate was filtered off and washed with mother liquor. Both filter residues were taken up in 50 ml of ethyl acetate. The solution was concentrated on a rotary evaporator and the residue was dried under reduced pressure overnight. This gave 2.25 g of the target compound (95% pure, 64% of theory).

LC-MS (Method 1): R$_t$=1.16 min

MS (ESpos): m/z=413 (M+H)$^+$

¹H NMR (400 MHz, DMSO-d₆): δ=1.36 (t, 3H), 2.34 (s, 3H), 2.32-2.38 (m, 2H), 2.58 (s, 3H), 4.18-4.30 (m, 1H), 4.31-4.38 (m, 4H), 6.93 (s, 1H), 8.71 (s, 1H).

Example 91A 2,6-Dimethyl-8-[4,4,4-trifluoro-3-(trifluoromethyl)butoxy]imidazo[1,2-a]pyridine-3-carboxylic acid

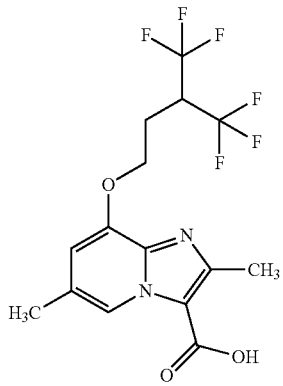 [SMILES: Cc1cc(OCCC(C(F)(F)F)C(F)(F)F)c2nc(C)c(C(=O)O)n2c1]

1.95 g (4.73 mmol) of ethyl 2,6-dimethyl-8-[4,4,4-trifluoro-3-(trifluoromethyl)butoxy]imidazo[1,2-a]pyridine-3-carboxylate Example 90A were initially charged in 30 ml of methanol, 3.28 g (10.4 mmol) of barium hydroxide octahydrate were added and the mixture was stirred at RT for 3 days. The suspension was diluted with 30 ml of water and adjusted to pH 6 using 1 M aqueous hydrochloric acid. The solid was filtered off, washed with 50 ml of water and dried under reduced pressure at 70° C. for 2 h. This gave 1.64 g of the target compound (90% pure, 81% of theory).

LC-MS (Method 1): R$_t$=0.78 min
MS (ESpos): m/z=385 (M+H)⁺
¹H NMR (400 MHz, DMSO-d₆): δ=2.29 (s, 3H), 2.28-2.37 (m, 2H), 2.56 (s, 3H), 4.22-4.35 (m, 3H), 6.74 (s, 1H), 8.99 (s, 1H), acid OH not visible.

Example 92A rac-Ethyl 8-[1-(2,6-difluorophenyl)ethoxy]-2,6-dimethylimidazo[1,2-a]pyridine-3-carboxylate

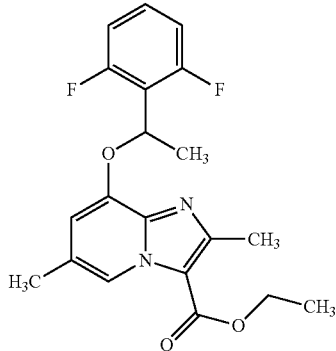 [SMILES: CCOC(=O)c1c(C)nc2c(OC(C)c3c(F)cccc3F)cc(C)cn12]

5.50 g (23.5 mmol) of ethyl 8-hydroxy-2,6-dimethylimidazo[1,2-a]pyridine-3-carboxylate Example 87A, 4.46 g (28.2 mmol) of 1-(2,6-difluorophenyl)ethanol, 5.35 ml (27.0 mmol) of diisopropyl azodicarboxylate and 7.08 g (27.0 mmol) of triphenylphosphine were dissolved in 141 ml of THF, and the mixture was stirred at RT for 2 h. 0.70 ml (3.5 mmol) of diisopropyl azodicarboxylate and 0.62 g (2.3 mmol) of triphenylphosphine were added to the reaction mixture, and the reaction solution was stirred at RT for 1 h. The precipitated solid was filtered off and dried under high vacuum. This gave 4.6 g (52.8% of theory; purity 100%) of the title compound. The filtrate was concentrated and purified twice by silica gel chromatography (cyclohexane:ethyl acetate gradient=from 8:1 to 4:1). All product-containing fractions were re-purified by preparative HPLC (RP18 column, mobile phase: acetonitrile/water gradient with addition of 0.1% TFA). This gave another 2.16 g (25% of theory) of the target compound.

LC-MS (Method 1): R$_t$=1.08 min
MS (ESpos): m/z=375 (M+H)⁺
¹H NMR (400 MHz, DMSO-d₆): δ=1.34 (t, 3H), 1.79 (d, 3H), 2.25 (s, 3H), 2.58 (s, 3H), 4.33 (q, 2H), 6.17 (q, 1H), 6.73 (s, 1H), 7.06-7.16 (m, 2H), 7.37-7.48 (m, 1H), 8.67 (s, 1H).

Example 93A ent-Ethyl 8-[1-(2,6-difluorophenyl)ethoxy]-2,6-dimethylimidazo[1,2-a]pyridine-3-carboxylate (enantiomer B)

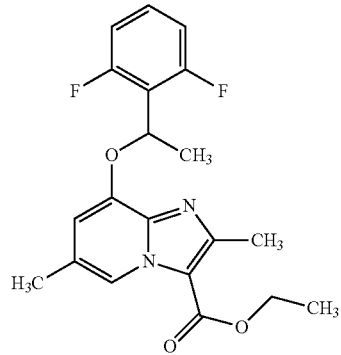 [SMILES: CCOC(=O)c1c(C)nc2c(OC(C)c3c(F)cccc3F)cc(C)cn12]

6.8 g of Example 92A were separated into the enantiomers by preparative separation on a chiral phase [column: Daicel Chiralpak AD-H, 5 μm, 250×30 mm, mobile phase: 70% isohexane, 30% ethanol, flow rate: 50 ml/min; 40° C., detection: 210 nm].
Enantiomer B:
Yield: 2.7 g (98.4% ee)
R$_t$=5.18 min [Daicel Chiralpak AD-H, 5 μm, 250×4.6 mm; mobile phase: 70% isohexane, 30% ethanol; flow rate 1.0 ml/min; 30° C.; detection: 220 nm].

Example 94A ent-8-[1-(2,6-Difluorophenyl)ethoxy]-2,6-dimethylimidazo[1,2-a]pyridine-3-carboxylic acid (enantiomer B)

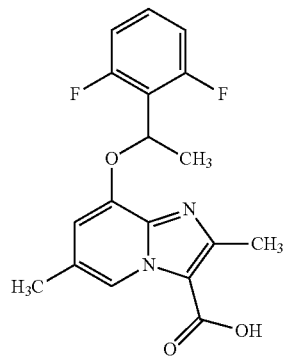

2.58 g (6.9 mmol) of ent-ethyl 8-[1-(2,6-difluorophenyl)ethoxy]-2,6-dimethylimidazo[1,2-a]-pyridine-3-carboxylate Example 93A (enantiomer B) were dissolved in 154 ml of THF/methanol (5:1), 34.5 ml (34.5 mmol) of 1 N aqueous lithium hydroxide solution were added and the mixture was stirred at 40° C. for 5 h. The reaction mixture was cooled to RT and acidified with 6 N aqueous hydrochloric acid solution and then concentrated. The solid was filtered off, washed with water and dried under high vacuum. This gave 2.26 g (95% of theory; purity 100%) of the title compound.

LC-MS (Method 1): $R_t$=0.74 min

MS (ESpos): m/z=347 (M+H)$^+$ $^1$H NMR (400 MHz, DMSO-$d_6$): δ=1.79 (d, 3H), 2.24 (s, 3H), 2.57 (s, 3H), 6.16 (q, 1H), 6.67 (s, 1H), 7.06-7.16 (m, 2H), 7.38-7.48 (m, 1H), 8.74 (s, 1H), 12.24-13.90 (br. s, 1H).

Example 95A rac-Methyl N-[(benzyloxy)carbonyl]norleucinate

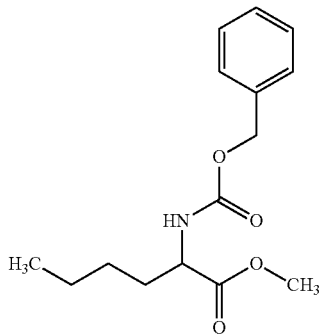 [SMILES: CCCCC(NC(=O)OCc1ccccc1)C(=O)OC]

12 g (66.1 mmol) of rac-methyl norleucinate hydrochloride were initially charged in 974 ml of water/THF (8:1), and 28.3 g (204.8 mmol) of potassium carbonate were added. The reaction mixture was cooled to 0° C. 12.3 ml (72.7 mmol) of benzyl chloroformate were slowly added dropwise and the reaction mixture was stirred at RT overnight. The mixture was diluted with 480 ml of water and extracted three times with dichloromethane. The combined organic phases were dried over sodium sulphate, filtered off and concentrated. The residue was purified by silica gel chromatography (cyclohexane/ethyl acetate=4:1). This gave 18.0 g (97.6% of theory, purity 100%) of the target compound.

LC-MS (Method 1): $R_t$=1.10 min.

MS (ESIpos): m/z=280 (M+H)$^+$.

$^1$H NMR (400 MHz, DMSO-$d_6$): δ=0.79-0.90 (m, 3H), 1.21-1.35 (m, 4H), 1.52-1.73 (m, 2H), 3.63 (s, 3H), 3.95-4.05 (m, 1H), 4.97-5.11 (m, 2H), 7.24-7.42 (m, 5H), 7.74 (d, 1H).

Example 96A rac-Benzyl (2-hydroxy-2-methylheptan-3-yl)carbamate

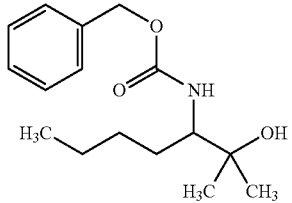 [SMILES: CCCCC(NC(=O)OCc1ccccc1)C(C)(C)O]

Under argon, 16.87 g (60.4 mmol) of rac-methyl N-[(benzyloxy)carbonyl]norleucinate Example 95A were initially charged in 584 ml of THF. The reaction mixture was cooled to 0° C., 70.5 ml (211.4 mmol) of 3 M methylmagnesium bromide in diethyl ether were added dropwise and the mixture was stirred at 0° C. for 15 min. The mixture was then allowed to warm slowly to RT and stirred at room temperature overnight. The reaction mixture was acidified carefully with 1 N aqueous hydrochloric acid, Celite was added to the reaction solution and the solid was filtered off. The solid was washed thoroughly with THF and the filtrate was concentrated. The residue was partitioned between dichloromethane and water, and the organic phase was washed twice with water, dried over sodium sulphate, filtered and concentrated. The residue was purified by silica gel chromatography (cyclohexane/ethyl acetate=from 9:1 to 7:3) and the product fractions were concentrated. This gave 13.46 g (80% of theory) of the target compound.

LC-MS (Method 1): $R_t$=0.98 min.

MS (ESIpos): m/z=280 (M+H)$^+$.

$^1$H NMR (400 MHz, DMSO-$d_6$): δ=0.80-0.89 (m, 3H), 0.98 (s, 3H), 1.05 (s, 3H), 1.09-1.37 (m, 5H), 1.58-1.74 (m, 1H), 3.25-3.32 (m, 1H), 4.24 (s, 1H), 4.99-5.08 (m, 2H), 6.85 (d, 1H), 7.26-7.40 (m, 5H).

Example 97A ent-Benzyl (2-hydroxy-2-methylheptan-3-yl)carbamate (enantiomer A)

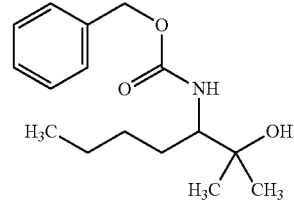 [SMILES: CCCCC(NC(=O)OCc1ccccc1)C(C)(C)O]

15.85 g of Example 96A were separated into the enantiomers by preparative separation on a chiral phase [column: Daicel Chiralpak AD-H, 5 μm, 250×20 mm, mobile phase: 80% isohexane, 20% ethanol, flow rate: 20 ml/min; 35° C., detection: 210 nm].

Enantiomer A:

Yield: 5.43 g (97% ee)

$R_t$=5.93 min [Daicel Chiralpak AD-H, 5 μm, 250×4.6 mm; mobile phase: 80% isohexane, 20% ethanol; flow rate 1.0 ml/min; 40° C.; detection: 220 nm].

Example 98A ent-3-Amino-2-methylheptan-2-ol hydrochloride (enantiomer A)

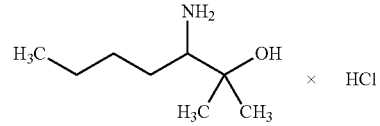

Under argon, 381 mg (0.36 mmol, 10% pure) of palladium on activated carbon and 10.9 ml (107.38 mmol) of cyclohexene were added to 1.0 g (3.58 mmol) of ent-benzyl (2-hydroxy-2-methylheptan-3-yl)carbamate (enantiomer A) Example 97A in ethanol (25 ml), and the reaction mixture was stirred at reflux for 3 h. The mixture was filtered through a Millipore® filter and the filter cake was washed with ethanol. 3.6 ml (7.16 mmol) of 2 N aqueous hydrochloric acid in diethyl ether were added to the filtrate, and the mixture was then concentrated and dried under high vacuum. This gave 801 mg (123% of theory) of the target compound. The product was used without further purification for the next reaction.

DCI-MS (Method 13): m/z=146 (M−HCl+H)+

$^1$H NMR (400 MHz, DMSO-d$_6$): δ=0.88 (t, 3H), 1.07 (s, 3H), 1.18 (s, 3H), 1.21-1.58 (m, 6H), 2.73-2.83 (m, 1H), 7.69-7.84 (m, 2H).

Example 99A rac-Methyl 6,6,6-trifluoronorleucinate hydrochloride

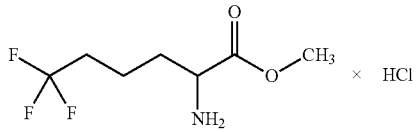

2.70 g (14.58 mmol) of rac-6,6,6-trifluoronorleucine were initially charged in 27.6 ml of saturated hydrochloric acid in methanol, and the mixture was stirred under reflux for 4 h. Another 10 ml of saturated hydrochloric acid in methanol were then added to the reaction solution, and the mixture was stirred at reflux for a further 4 h. The reaction solution was concentrated and the residue was dried under high vacuum. This gave 3.77 g of the target compound (99% of theory; purity 90%).

DCI-MS (Method 13): (ESpos): m/z=200 (M−HCl+H)+

$^1$H NMR (400 MHz, DMSO-d$_6$): δ=1.48-1.73 (m, 2H), 1.80-1.96 (m, 2H), 2.24-2.38 (m, 2H), 3.76 (s, 3H), 4.06-4.14 (m, 1H), 8.49-8.68 (br. s, 3H).

Example 100A rac-Methyl N-[(benzyloxy)carbonyl]-6,6,6-trifluoronorleucinate

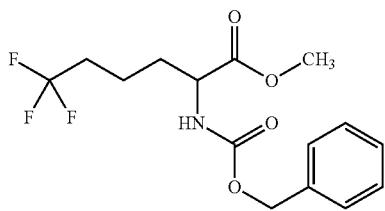 [SMILES: COC(=O)C(CCCC(F)(F)F)NC(=O)OCc1ccccc1]

3.77 g (14.4 mmol, purity about 90%) of rac-methyl 6,6,6-trifluoronorleucinate hydrochloride Example 99A were initially charged in 212 ml of water/THF (8:1), and 6.17 g (44.6 mmol) of potassium carbonate were added. The reaction mixture was cooled to 0° C., 2.68 ml (15.8 mmol) of benzyl chloroformate were slowly added dropwise and the mixture was then stirred at RT overnight. The mixture was diluted with 100 ml of water and extracted three times with dichloromethane. The combined organic phases were dried over sodium sulphate, filtered off and concentrated. The residue was purified by silica gel chromatography (cyclohexane/ethyl acetate 4:1). This gave 3.64 g (76% of theory, purity 100%) of the target compound.

LC-MS (Method 18): R$_t$=2.32 min.

MS (ESIpos): m/z=334 (M+H)+.

$^1$H NMR (400 MHz, DMSO-d$_6$): δ=1.47-1.59 (m, 2H), 1.61-1.72 (m, 1H), 1.73-1.85 (m, 1H), 2.14-2.34 (m, 2H), 3.64 (s, 3H), 4.04-4.12 (m, 1H), 5.04 (s, 2H), 7.25-7.40 (m, 5H), 7.81 (d, 1H).

Example 101A rac-Benzyl (7,7,7-trifluoro-2-hydroxy-2-methylheptan-3-yl)carbamate

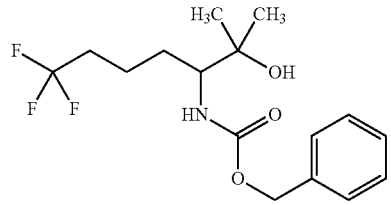 [SMILES: CC(C)(O)C(CCCC(F)(F)F)NC(=O)OCc1ccccc1]

Under argon, 3.23 g (9.70 mmol) of rac-methyl N-[(benzyloxy)carbonyl]-6,6,6-trifluoronorleucinate Example 100A were initially charged in 94 ml of THF. The reaction mixture was cooled to 0° C., 11.32 ml (33.96 mmol) of 3M methylmagnesium bromide in diethyl ether were added dropwise and the mixture was stirred at 0° C. for 15 min. The mixture was allowed to warm to RT slowly and stirred at room temperature overnight. Carefully, saturated aqueous ammonium chloride solution and then Celite were added to the reaction mixture. The solid was filtered off and washed thoroughly with THF, and the filtrate was concentrated. The aqueous residue was partitioned between dichloromethane and water. The organic phase was washed two more times with water, dried over sodium sulphate and filtered, and the filtrate was concentrated. The residue was purified by silica gel chromatography (cyclohexane/ethyl acetate 7:3) and the product fractions were concentrated. This gave 2.83 g (87% of theory, purity 97%) of the target compound.

LC-MS (Method 17): R$_t$=1.02 min.

MS (ESIpos): m/z=334 (M+H)+.

$^1$H NMR (400 MHz, DMSO-d$_6$): δ=0.99 (s, 3H), 1.06 (s, 3H), 1.25-1.45 (m, 2H), 1.47-1.60 (m, 1H), 1.67-1.80 (m, 1H), 2.06-2.35 (m, 2H), 3.29-3.32 (m, 1H, partially obscured by the water peak), 4.32 (s, 1H), 5.05 (q, 2H), 6.95 (d, 1H), 7.26-7.38 (m, 5H).

Example 102A ent-Benzyl (7,7,7-trifluoro-2-hydroxy-2-methylheptan-3-yl)carbamate (enantiomer A)

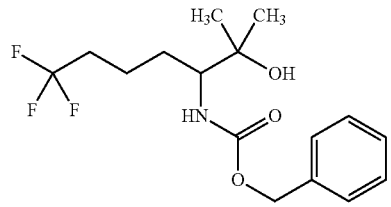

1.91 g of Example 101A were separated into the enantiomers by preparative separation on a chiral phase [column: Daicel Chiralpak AY-H, 5 μm, 250×20 mm, mobile phase: 90% isohexane, 10% ethanol, flow rate: 15 ml/min; 35° C., detection: 220 nm].

Enantiomer A:

Yield: 766 mg (99% ee)

$R_t$=5.12 min [Daicel Chiralpak AY-H, 5 μm, 250×4.6 mm; mobile phase: 90% isohexane, 10% ethanol; flow rate 1.0 ml/min; 30° C.; detection: 220 nm].

Example 103A rac-3-Amino-7,7,7-trifluoro-2-methylheptan-2-ol hydrochloride

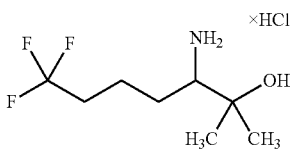

Under argon, 319 mg (0.30 mmol, 10% pure) of palladium on activated carbon and 9.1 ml (90.0 mmol) of cyclohexene were added to 1.0 g (3.0 mmol) of rac-benzyl (7,7,7-trifluoro-2-hydroxy-2-methylheptan-3-yl)carbamate Example 101A in ethanol (21 ml), and the reaction mixture was stirred at reflux overnight. The mixture was filtered through a Millipore® filter and the filter cake was washed with ethanol. 3 ml (6.0 mmol) of 2 N hydrochloric acid in diethyl ether were added to the filtrate and the mixture was concentrated and dried under high vacuum. This gave 785 mg (111% of theory) of the target compound. The product was used without further purification for the next reaction.

MS (Method 13): m/z=200 (M−HCl+H)$^+$.

$^1$H NMR (400 MHz, DMSO-d$_6$): δ=1.08 (s, 3H), 1.19 (s, 3H), 1.40-1.59 (m, 2H), 1.60-1.82 (m, 2H), 2.15-2.41 (m, 2H), 2.80-2.91 (m, 1H), 5.17-5.35 (br. s, 1H), 7.65-7.93 (br. s, 2H).

Example 104A ent-3-Amino-7,7,7-trifluoro-2-methylheptan-2-ol hydrochloride (enantiomer A)

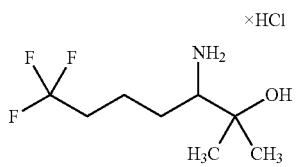

Under argon, 765 mg (2.30 mmol) of ent-benzyl (7,7,7-trifluoro-2-hydroxy-2-methylheptan-3-yl)carbamate (enantiomer A) Example 102A were initially charged in ethanol (16.1 ml), 244 mg (0.23 mmol, 10% pure) of palladium on activated carbon and 7.0 ml (68.85 mmol) of cyclohexene were added and the reaction mixture was stirred at reflux for 3 h. The mixture was filtered through a Millipore® filter and washed with ethanol. 2.3 ml (4.59 mmol) of 2 N hydrochloric acid in diethyl ether were added to the filtrate, and the mixture was concentrated and dried under high vacuum. This gave 559 mg (99% of theory) of the target compound.

DCI-MS (Method 13): m/z=200 (M−HCl+H)$^+$.

$^1$H NMR (400 MHz, DMSO-d$_6$): δ=1.08 (s, 3H), 1.19 (s, 3H), 1.40-1.59 (m, 2H), 1.60-1.69 (m, 1H), 1.70-1.82 (m, 1H), 2.15-2.27 (m, 1H), 2.28-2.42 (m, 1H), 2.80-2.91 (m, 1H), 5.17-5.35 (br. s, 1H), 7.73-7.97 (br. s, 2H).

Example 105A (3,3-Difluorocyclobutyl)methyl methanesulphonate

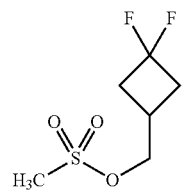

1.35 g (11.06 mmol) of (3,3-difluorocyclobutyl)methanol were initially charged in 41.8 ml of abs. dichloromethane, 3.08 ml (22.11 mmol) of triethylamine and 1.03 ml (13.27 mmol) of methanesulphonyl chloride were added and the mixture was stirred at room temperature overnight. Water was added to the reaction mixture and the aqueous phase was extracted twice with dichloromethane. The combined organic phases were washed with saturated aqueous sodium chloride solution, dried over sodium sulphate and filtered, and the filtrate was concentrated. This gave 2.37 g (quantitative yield) of the target compound.

DCI-MS (Method 16): $R_t$=4.18 min. m/z=218 (M+NH$_4$)$^+$.

$^1$H NMR (400 MHz, DMSO-d$_6$): δ=2.34-2.59 (m, 3H), 2.62-2.74 (m, 2H), 3.21 (s, 3H), 4.26 (d, 2H).

Example 106A

Ethyl 8-[(3,3-difluorocyclobutyl)methoxy]-2,6-dimethylimidazo[1,2-a]pyridine-3-carboxylate

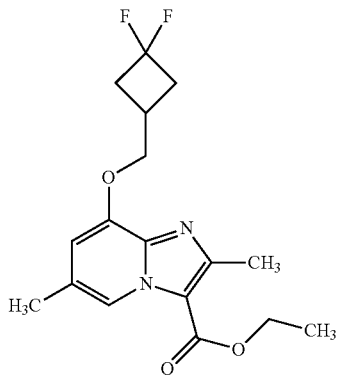 [SMILES: CCOC(=O)c1c(C)nc2c(OCC3CC(F)(F)C3)cc(C)cn12]

1.85 g (7.89 mmol) of ethyl 8-hydroxy-2,6-dimethylimidazo[1,2-a]pyridine-3-carboxylate Example 87A and 2.37 g (9.47 mmol) of (3,3-difluorocyclobutyl)methyl methanesulphonate Example 105A were initially charged in 104 ml of DMF, and 10.28 g (31.56 mmol) of caesium carbonate were added. The reaction mixture was stirred at 60° C. overnight. After cooling, the reaction mixture was filtered, the solid was washed thoroughly with ethyl acetate, the filtrate was concentrated and about 150 ml of water were added to the residue. The solid formed was filtered off and dried under high vacuum. This gave 2.51 g (89% of theory; purity 95%) of the title compound.

LC-MS (Method 1): $R_t$=1.00 min

MS (ESpos): m/z=339 (M+H)$^+$

¹H NMR (400 MHz, DMSO-d₆): δ=1.35 (t, 3H), 2.32 (s, 3H), 2.42-2.60 (m, 5H), 2.62-2.84 (m, 3H), 4.22 (d, 2H), 4.33 (q, 2H), 6.90 (s, 1H), 8.68 (s, 1H).

Example 107A

8-[(3,3-Difluorocyclobutyl)methoxy]-2,6-dimethylimidazo[1,2-a]pyridine-3-carboxylic acid

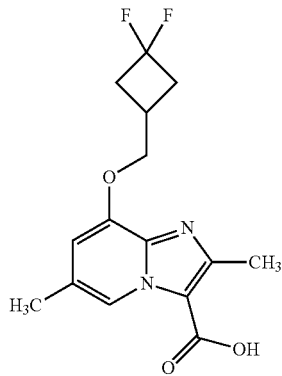

2.39 g (7.06 mmol) of ethyl 8-[(3,3-difluorocyclobutyl)methoxy]-2,6-dimethylimidazo[1,2-a]-pyridine-3-carboxylate Example 106A were dissolved in 151 ml of THF/methanol (5:1), 35.3 ml (35.3 mmol) of 1 N aqueous lithium hydroxide solution were added and the mixture was stirred at RT for 2 d. The reaction mixture was acidified with 1 N aqueous hydrochloric acid solution to pH 4 and concentrated. The solid was filtered off, washed with water and dried under high vacuum. This gave 1.63 g (71% of theory; purity 95%) of the title compound.

LC-MS (Method 1): $R_t$=0.63 min

MS (ESpos): m/z=311 (M+H)⁺

¹H NMR (500 MHz, DMSO-d₆): δ=2.32 (s, 3H), 2.42-2.60 (m, 5H), 2.62-2.82 (m, 3H), 4.22 (d, 2H), 6.87 (s, 1H), 8.71 (s, 1H), 12.93 (br. s, 1H).

Example 108A

4-Fluoro-2-nitropyridin-3-ol

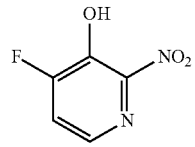 [SMILES: O=[N+]([O-])c1nccc(F)c1O]

With ice cooling, 500 mg (3.43 mmol) of 4-fluoropyridin-3-ol hydrochloride were dissolved carefully in 3.2 ml of concentrated sulphuric acid, and 0.21 ml of concentrated nitric acid was added carefully at 0° C. The reaction was warmed to RT and stirred overnight. The mixture was added to 10 g of ice, and 6 ml of 45% strength aqueous sodium hydroxide solution were added dropwise with ice cooling. The solid formed was filtered off and then dried under reduced pressure overnight. This gave 191 mg (36% of theory) of the title compound.

LC-MS (Method 1): $R_t$=0.36 min

MS (ESneg): m/z=157 (M−H)⁻

¹H NMR (400 MHz, DMSO-d₆): δ=7.69 (dd, 1H); 7.95-8.01 (m, 1H); 11.97 (br. s, 1H).

Example 109A

2-Amino-4-fluoropyridin-3-ol

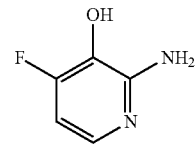

Under argon, 90 mg (0.57 mmol) of 4-fluoro-2-nitropyridin-3-ol Example 108A were dissolved in 30 ml of ethanol, and a spatula tip of palladium on activated carbon (10%) was added. The mixture was hydrogenated at RT under reduced pressure for 1.5 h. The reaction mixture was filtered off through silica gel and the filter cake was washed with plenty of ethanol. The solution was concentrated and dried. This gave 56 mg (77% of theory) of the title compound.

LC-MS (Method 1): $R_t$=0.16 min

MS (ESpos): m/z=129 (M+H)⁺

¹H NMR (400 MHz, DMSO-d₆): δ=5.78 (br. s, 2H); 6.42 (dd, 1H); 7.37-7.43 (m, 1H); 9.47 (br. s, 1H).

Example 110A

3-[(2,6-Difluorobenzyl)oxy]-4-fluoropyridine-2-amine

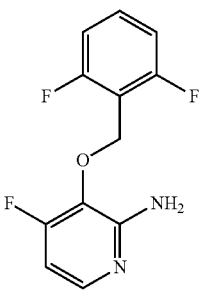 [SMILES: Nc1nccc(F)c1OCc1c(F)cccc1F]

55 mg (0.43 mmol) of 2-amino-4-fluoropyridin-3-ol Example 109A, 98 mg (0.47 mmol) of 2-(bromomethyl)-1,3-difluorobenzene and 308 mg (0.95 mmol) of caesium carbonate were initially charged in 1 ml of dry DMF and heated in an oil bath warmed to 50° C. for 15 min. The mixture was then filtered off and purified by preparative HPLC (Method 9). This gave 70 mg of the title compound (64% of theory).

LC-MS (Method 1): $R_t$=0.70 min

MS (ESpos): m/z=255 (M+H)⁺

¹H NMR (400 MHz, DMSO-d₆): δ=5.06 (s, 2H); 6.04 (br. s, 2H); 6.42 (dd, 1H); 7.08-7.16 (m, 2H); 7.45-7.54 (m, 1H); 7.62-7.69 (m, 1H).

Example 111A

Ethyl 8-[(2,6-difluorobenzyl)oxy]-7-fluoro-2-methylimidazo[1,2-a]pyridine-3-carboxylate

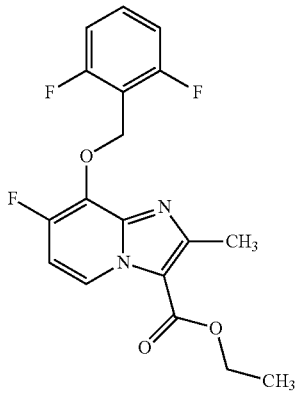 [SMILES: CCOC(=O)c1c(C)nc2c(OCc3c(F)cccc3F)c(F)ccn12]

Under argon, 500 mg (1.97 mmol) of 3-[(2,6-difluorobenzyl)oxy]-4-fluoropyridine-2-amine Example 110A were initially charged in 10 ml of ethanol, and 500 mg of powdered molecular sieve 4 Å and 3.24 g (19.67 mmol) of ethyl 2-chloroacetoacetate were added. The resulting reaction mixture was heated at reflux for 48 h. All volatile components were substantially evaporated on a dry ice rotary evaporator at a water bath temperature of 85° C. The crude product was purified by silica gel chromatography (mobile phase: cyclohexane/ethyl acetate=9/1 isocratic). This gave 368 mg (39% of theory; purity about 76%) of the title compound.

LC-MS (Method 1): $R_f$=1.19 min

MS (ESpos): m/z=365 (M+H)$^+$ $^1$H NMR (400 MHz, DMSO-d$_6$): δ=1.37 (t, 3H); 2.62 (s, 3H); 4.38 (q, 2H); 5.60 (s, 2H); 7.09-7.22 (m, 3H); 7.47-7.56 (m, 1H); 8.98 (dd, 1H).

Example 112A

8-[(2,6-Difluorobenzyl)oxy]-7-fluoro-2-methylimidazo[1,2-a]pyridine-3-carboxylic acid

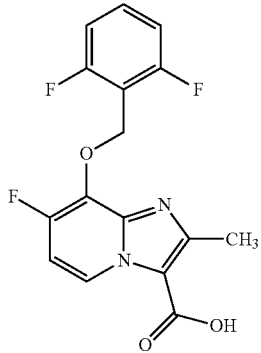 [SMILES: Cc1nc2c(OCc3c(F)cccc3F)c(F)ccn2c1C(=O)O]

365 mg (0.76 mmol; purity about 76%) of ethyl 8-[(2,6-difluorobenzyl)oxy]-7-fluoro-2-methylimidazo[1,2-a]pyridine-3-carboxylate Example 111A were dissolved in 16.6 ml of THF/ethanol (5:1), 1.14 ml (1.14 mmol) of 1 N aqueous lithium hydroxide solution were added and the mixture was stirred at RT overnight. Another 2.67 ml (2.67 mmol) of 1 N aqueous lithium hydroxide solution were added, and the mixture was stirred at RT overnight. The mixture was concentrated and the aqueous phase was acidified to pH 4 using 6 N hydrochloric acid. A precipitate formed, and the suspension was cooled with ice water. The solid was filtered off and dried under high vacuum. This gave 236 mg of the target compound (87% of theory, purity 94%).

LC-MS (Method 1): $R_f$=0.83 min

MS (ESpos): m/z=337 (M+H)$^+$ $^1$H NMR (400 MHz, DMSO-d$_6$): δ=2.62 (s, 3H); 5.60 (s, 2H); 7.09-7.18 (m, 3H); 7.47-7.55 (m, 1H); 9.04 (dd, 1H); 13.22 (br. s, 1H).

WORKING EXAMPLES

Example 1

8-[(2,6-Difluorobenzyl)oxy]-N-[(2R)-1-hydroxyhexan-2-yl]-2-methylimidazo[1,2-a]pyridine-3-carboxamide

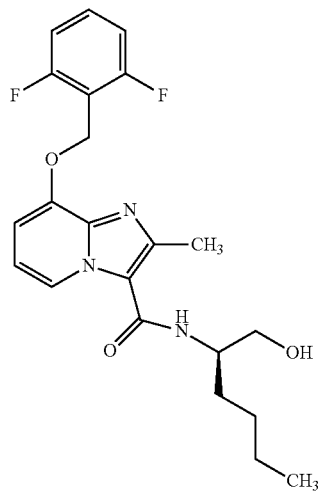 [SMILES: CCCC[C@H](CO)NC(=O)c1c(C)nc2c(OCc3c(F)cccc3F)cccn12]

1.2 ml of 1-methyl-2-pyrrolidone were added to 50 mg (0.172 mmol) of 8-hydroxy-N-[(2R)-1-hydroxyhexan-2-yl]-2-methylimidazo[1,2-a]pyridine-3-carboxamide, 39 mg (0.189 mmol) of 2,6-difluorobenzyl bromide, 52 mg (0.378 mmol) of potassium carbonate and 14 mg (0.086 mmol) of potassium iodide, and the reaction mixture was heated in a microwave at 120° C. for 40 min. The supernatant was decanted off from the solid, and the latter was washed twice with methanol. The combined solutions were concentrated and the residue was purified by preparative HPLC (Method 7). This gave 43.5 mg (60% of theory) of 8-[(2,6-difluorobenzyl)oxy]-N-[(2R)-1-hydroxyhexan-2-yl]-2-methylimidazo[1,2-a]pyridine-3-carboxamide.

LC-MS (Method 2): $R_f$=0.96 min

MS (ESpos): m/z=418.2 (M+H)$^+$ $^1$H NMR (400 MHz, DMSO-d$_6$): δ=0.88 (t, 3H), 1.25-1.70 (m, 6H), 2.58 (s, 3H), 3.48 (m, 2H), 3.95 (m, 1H), 4.71 (t, 1H), 5.29 (s, 2H), 6.90 (t, 1H), 6.98 (d, 1H), 7.22 (t, 2H), 7.48 (d, 1H), 7.57 (m, 1H), 8.52 (d, 1H).

Specific rotation (589 nm, 20.1° C., c=0.365 g/ml) in methanol: +15.7°

The example compounds shown in Table 1 were prepared analogously to Example 1 by reacting 8-hydroxy-N-[(2R)-1-hydroxyhexan-2-yl]-2-methylimidazo[1,2-a]pyridine-3-carboxamide with the appropriate commercially available benzyl halides:

TABLE 1

| Example | IUPAC name/structure (yield) | Analytical data |
|---|---|---|
| 2 | N-[(2R)-1-hydroxyhexan-2-yl]-2-methyl-8-[(2,3,6-trifluorobenzyl)oxy]imidazo[1,2-a]pyridine-3-carboxamide 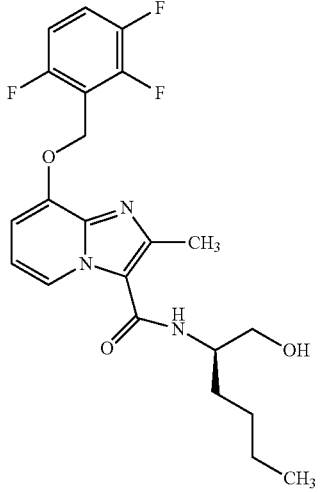 [SMILES: CCCC[C@H](CO)NC(=O)c1c(C)nc2c(OCc3c(F)ccc(F)c3F)cccn12] (61% of theory) | LC-MS (Method 1): $R_t$ = 0.89 min MS (ESpos): m/z = 436.1 (M + H)$^+$ $^1$H NMR (400 MHz, DMSO-d$_6$): δ = 0.88 (t, 3H), 1.25-1.70 (m, 6H), 2.58 (s, 3H), 3.48 (m, 2H), 3.95 (m, 1H), 4.71 (t, 1H), 5.35 (s, 2H), 6.92 (t, 1H), 6.98 (d, 1H), 7.29 (m, 2H), 7.50 (d, 1H), 7.65 (m, 1H), 8.54 (d, 1H). |
| 3 | 8-[(2-chloro-6-fluorobenzyl)oxy]-N-[(2R)-1-hydroxyhexan-2-yl]-2-methylimidazo[1,2-a]pyridine-3-carboxamide 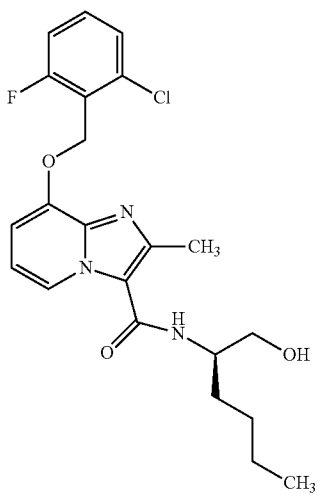 (56% of theory) | LC-MS (Method 1): $R_t$ = 0.91 min MS (ESpos): m/z = 434.1 (M + H)$^+$ $^1$H NMR (400 MHz, DMSO-d$_6$): δ = 0.88 (t, 3H), 1.25-1.70 (m, 6H), 2.58 (s, 3H), 3.48 (m, 2H), 3.95 (m, 1H), 4.71 (t, 1H), 5.35 (s, 2H), 6.93 (t, 1H), 7.01 (d, 1H), 7.34-7.40 (m, 1H), 7.45-7.60 (m, 3H), 8.55 (d, 1H). |

TABLE 1-continued

| Example | IUPAC name/structure (yield) | Analytical data |
|---|---|---|
| 4 | 8-[(2-chlorobenzyl)oxy]-N-[(2R)-1-hydroxyhexan-2-yl]-2-methylimidazo[1,2-a]pyridine-3-carboxamide<br>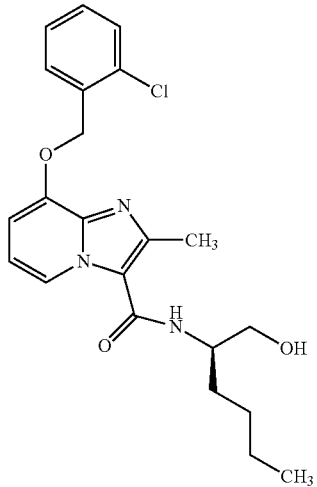 [SMILES: CCCC[C@H](CO)NC(=O)c1c(C)nc2c(OCc3ccccc3Cl)cccn12]<br>(68% of theory) | LC-MS (Method 1):<br>$R_t$ = 0.93 min<br>MS (ESpos): m/z = 416.2<br>(M + H)$^+$ |
| 5 | 8-[(2-fluorobenzyl)-oxy]-N-[(2R)-1-hydroxyhexan-2-yl]-2-methylimidazo[1,2-a]pyridine-3-carboxamide<br>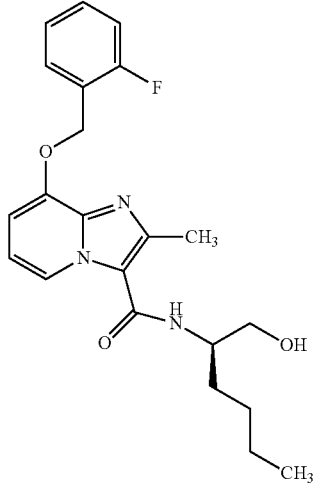 [SMILES: CCCC[C@H](CO)NC(=O)c1c(C)nc2c(OCc3ccccc3F)cccn12]<br>(58% of theory) | LC-MS (Method 1):<br>$R_t$ = 0.86 min<br>MS (ESpos): m/z = 400.2<br>(M + H)$^+$ |

TABLE 1-continued

| Example | IUPAC name/structure (yield) | Analytical data |
|---|---|---|
| 6 | 8-[(3-fluorobenzyl)-oxy]-N-[(2R)-1-hydroxyhexan-2-yl]-2-methylimidazo[1,2-a]pyridine-3-carboxamide<br>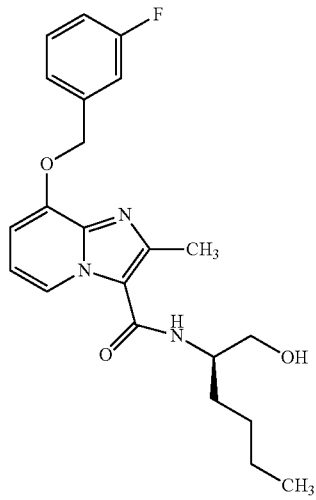 [SMILES: CCCC[C@H](CO)NC(=O)c1c(C)nc2c(OCc3cccc(F)c3)cccn12]<br>(58% of theory) | LC-MS (Method 1):<br>$R_t$ = 0.86 min<br>MS (ESpos): m/z = 400.2<br>$(M + H)^+$ |
| 7 | N-[(2R)-1-hydroxyhexan-2-yl]-2-methyl-8-[(2,3,5,6-tetrafluorobenzyl)oxy]imidazo[1,2-a]pyridine-3-carboxamide<br>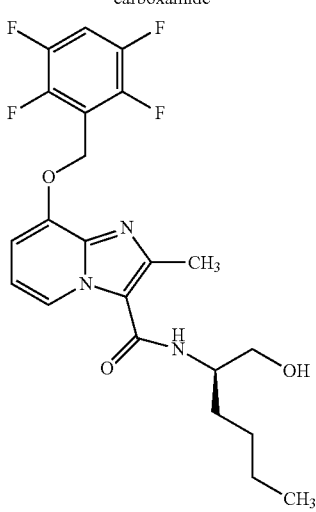<br>(60% of theory) | LC-MS (Method 3):<br>$R_t$ = 1.80 min<br>MS (ESpos): m/z = 454.2<br>$(M + H)^+$ |

TABLE 1-continued

| Example | IUPAC name/structure (yield) | Analytical data |
|---|---|---|
| 8 | 8-[(2,6-dichlorobenzyl)oxy]-N-[(2R)-1-hydroxyhexan-2-yl]-2-methylimidazo[1,2-a]pyridine-3-carboxamide<br>(64% of theory) | LC-MS (Method 1):<br>$R_t$ = 0.96 min<br>MS (ESpos): m/z = 450.0<br>$(M + H)^+$ |
| 9 | 8-[(2,3-dichlorobenzyl)oxy]-N-[(2R)-1-hydroxyhexan-2-yl]-2-methylimidazo[1,2-a]pyridine-3-carboxamide<br>(52% of theory) | LC-MS (Method 1):<br>$R_t$ = 1.00 min<br>MS (ESpos): m/z = 450.1<br>$(M + H)^+$<br>specific rotation (589 nm, 19.8° C., c = 0.445 g/100 ml) in methanol: +14.0° |

TABLE 1-continued

| Example | IUPAC name/structure (yield) | Analytical data |
|---|---|---|
| 10 | 8-[(2,3-difluorobenzyl)oxy]-N-[(2R)-1-hydroxyhexan-2-yl]-2-methylimidazo[1,2-a]pyridine-3-carboxamide<br>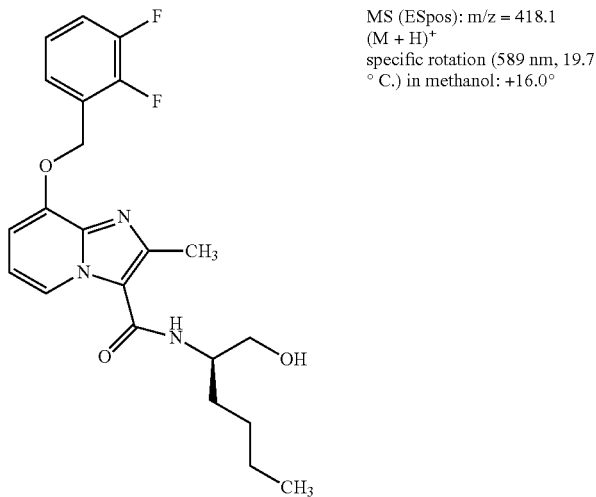<br>(63% of theory) | LC-MS (Method 1): $R_t$ = 0.89 min<br>MS (ESpos): m/z = 418.1 (M + H)$^+$<br>specific rotation (589 nm, 19.7 ° C.) in methanol: +16.0° |
| 11 | 8-[(2-fluoro-3-methylbenzyl)oxy]-N-[(2R)-1-hydroxyhexan-2-yl]-2-methylimidazo[1,2-a]pyridine-3-carboxamide<br>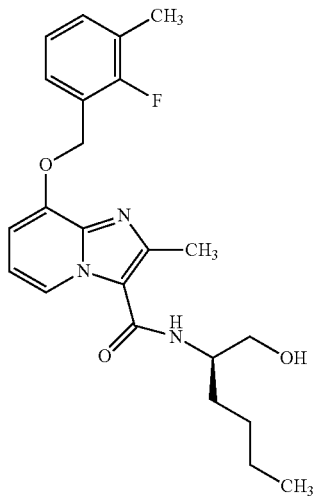 [SMILES: CCCC[C@H](CO)NC(=O)c1c(C)nc2c(OCc3cccc(C)c3F)cccn12]<br>(56% of theory) | LC-MS (Method 2): $R_t$ = 1.02 min<br>MS (ESpos): m/z = 414.3 (M + H)$^+$ |

TABLE 1-continued
| Example | IUPAC name/structure (yield) | Analytical data |
|---|---|---|
| 12 | 8-[(2,2-difluoro-1,3-benzodioxol-4-yl)methoxy]-N-[(2R)-1-hydroxyhexan-2-yl]-2-methylimidazo[1,2-a]pyridine-3-carboxamide 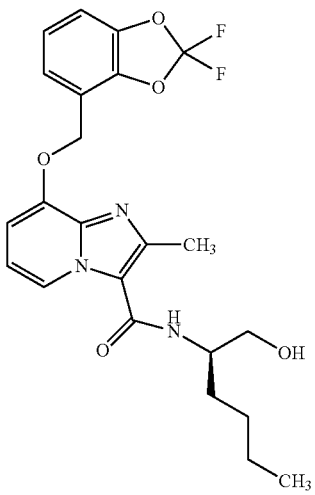 [SMILES: CCCC[C@H](CO)NC(=O)c1c(C)nc2c(OCc3cccc4c3OC(F)(F)O4)cccn12] (57% of theory) | LC-MS (Method 1): $R_t$ = 0.97 min MS (ESpos): m/z = 462.1 $(M + H)^+$ |
| 13 | 8-[(2,6-dimethylbenzyl)oxy]-N-[(2R)-1-hydroxyhexan-2-yl]-2-methylimidazo[1,2-a]pyridine-3-carboxamide 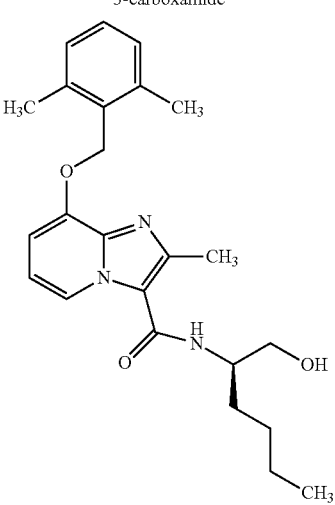 (63% of theory) | LC-MS (Method 1): $R_t$ = 0.95 min MS (ESpos): m/z = 410.2 $(M + H)^+$ |

TABLE 1-continued

| Example | IUPAC name/structure (yield) | Analytical data |
|---|---|---|
| 14 | 8-{[2-fluoro-3-(trifluoromethyl)benzyl]oxy}-N-[(2R)-1-hydroxyhexan-2-yl]-2-methylimidazo[1,2-a]pyridine-3-carboxamide<br><br>(65% of theory) | LC-MS (Method 1):<br>$R_t$ = 0.98 min<br>MS (ESpos): m/z = 468.1 $(M + H)^+$ |

Example 15

N-[(2R)-1-Hydroxyhexan-2-yl]-2-methyl-8-[(2,4,6-trifluorobenzyl)oxy]imidazo[1,2-a]pyridine-3-carboxamide

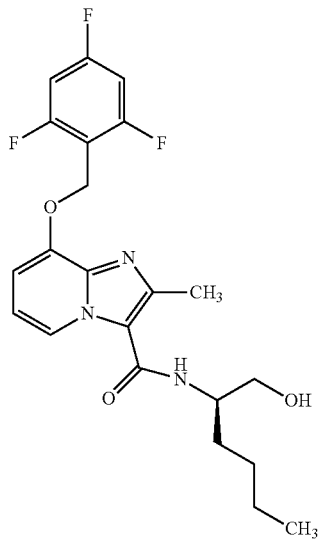 [SMILES: CCCC[C@H](CO)NC(=O)c1c(C)nc2c(OCc3c(F)cc(F)cc3F)cccn12]

50 mg (0.172 mmol) of 8-hydroxy-N-[(2R)-1-hydroxyhexan-2-yl]-2-methylimidazo[1,2-a]-pyridine-3-carboxamide, 42 mg (0.189 mmol) of 2,4,6-trifluorobenzyl bromide and 123 mg (0.378 mmol) of caesium carbonate were initially charged in 2.5 ml of dimethylformamide, and the mixture was heated at 50° C. for 15 min. After cooling to room temperature, water was added. Ethyl acetate was then added, the phases were separated and the aqueous phase was extracted twice with ethyl acetate. The combined organic phases were concentrated and the residue was purified by preparative HPLC (Method 8). This gave 54.5 mg (72% of theory) of the target compound.

LC-MS (Method 1): $R_t$=0.88 min

MS (ESpos): m/z=436.3 $(M+H)^+$ $^1$H NMR (400 MHz, DMSO-$d_6$): δ=0.88 (t, 3H), 1.25-1.40 (m, 4H), 1.40-1.51 (m, 1H), 1.60-1.68 (m, 1H), 2.55 (s, 3H; obscured by DMSO signal), 3.40-3.51 (m, 2H), 3.90-4.02 (m, 1H), 4.71 (t, 1H), 5.29 (s, 2H), 6.90 (t, 1H), 6.98 (d, 1H), 7.31 (t, 2H), 7.52 (d, 1H), 8.52 (d, 1H).

General Working Procedure 1: Amide Formation Using TBTU as Coupling Agent

Under argon, 1 equivalent of the carboxylic acid to be coupled was initially charged with 1.0 to 1.2 equivalents of the amine to be coupled and 5 equivalents of 4-methylmorpholine in dry dichloromethane (for example 0.1 to 0.5 M based on the acid to be coupled). 1.1 equivalents of TBTU were then added, and the mixture was stirred at room temperature overnight. After complete conversion of the carboxylic acid to be coupled had been achieved (usually after 16 h at room temperature; analysis by LC-MS), the mixture was diluted with additional dichloromethane and worked up extractively. An exemplary work-up consisted of washing with 10% strength aqueous citric acid solution (or alternatively saturated aqueous sodium bicarbonate solution), with water, finally with saturated aqueous sodium chloride solution, subsequent drying of the organic phase, for example with magnesium sulphate, filtration and concentration of the filtrate. The residue obtained in this manner was purified for example by column chromatography (e.g. Biotage Isolera using dichloromethane/methanol or cyclohexane/ethyl acetate mixture as mobile phase) or by preparative HPLC. Example 16 described a representative embodiment of this General Working Procedure.

Example 16

8-(Benzyloxy)-N-[(2R)-1-hydroxyhexan-2-yl]-2-methylimidazo[1,2-a]pyridine-3-carboxamide

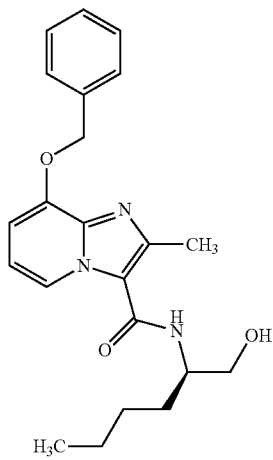 [SMILES: CCCC[C@H](CO)NC(=O)c1c(C)nc2c(OCc3ccccc3)cccn12]

Under argon, 4 g (14.17 mmol) of 8-(benzyloxy)-2-methylimidazo[1,2-a]pyridine-3-carboxylic acid, 1.83 g (15.59 mmol) of (R)-(−)-2-aminohexanol and 7.166 g (70.85 mmol) of 4-methylmorpholine were suspended in 28 ml of dichloromethane. 5 g (15.59 mmol) of TBTU were then added, and the mixture was stirred at room temperature overnight. After 16 h, the mixture was diluted with 200 ml of dichloromethane and washed with 10% strength aqueous citric acid solution, with water and with saturated aqueous sodium chloride solution. The organic phase was concentrated and the residue obtained was purified on a silica gel cartridge (mobile phase dichloromethane:methanol=100:3). Concentration of the product fractions thus gave 3.83 g (71% of theory) of 8-(benzyloxy)-N-[(2R)-1-hydroxyhexan-2-yl]-2-methylimidazo[1,2-a]pyridine-3-carboxamide.

LC-MS (Method 1): $R_t$=0.84 min
MS (ESpos): m/z=381.2 (M+H)$^+$
$^1$H NMR (400 MHz, DMSO-d$_6$): δ=0.88 (t, 3H), 1.29-1.69 (m, 6H), 2.59 (s, 3H), 3.45 (m, 2H), 3.98 (m, 1H), 4.73 (t, 1H), 5.29 (s, 2H), 6.88 (m, 2H), 7.34-7.52 (m, 6H). 8.49 (d, 1H).

Specific rotation (589 nm, 20.1° C., c=0.55 g/100 ml) in methanol: +15.5°

Example 17

8-(Benzyloxy)-N-[(2R)-1-hydroxybutan-2-yl]-2-methylimidazo[1,2-a]pyridine-3-carboxamide The preparation was carried out analogously to the General Working Procedure 1 and Example 16 starting with 4.00 g (14.17 mmol) of 8-(benzyloxy)-2-methylimidazo[1,2-a]pyridine-3-carboxylic acid. This gave 3.52 g (56% of theory) of the target product in a purity of 80%.

LC-MS (Method 1): $R_t$=0.71 min
MS (ESpos): m/z=354.1 (M+H)$^+$
$^1$H NMR (400 MHz, DMSO-d$_6$): δ=0.93 (t, 3H), 1.48 (m, 1H), 1.68 (m, 1H), 2.53 (s, 3H), 3.49 (m, 2H), 3.92 (m, 1H), 4.73 (tr br, 1H), 5.29 (s, 2H), 6.88 (m, 2H), 7.34-7.52 (m, 6H), 8.50 (dd, 1H).

The example compounds shown in Table 2 were prepared analogously to Example 17 by reacting 8-[(2,6-difluorobenzyl)oxy]-2-methylimidazo[1,2-a]pyridine-3-carboxylic acid with the appropriate commercially available amines under the TBTU conditions described (General Working Procedure 1):

TABLE 2

| Example | IUPAC name/structure (yield) | Analytical data |
|---|---|---|
| 18 | 8-[(2,6-difluorobenzyl)oxy]-N-[(2R)-1-hydroxypentan-2-yl]-2-methylimidazo[1,2-a]pyridine-3-carboxamide<br><br>(59% of theory) | LC-MS (Method 1): $R_t$ = 0.80 min<br>MS (ESpos): m/z = 404.1 (M + H)$^+$ |

TABLE 2-continued

| Example | IUPAC name/structure (yield) | Analytical data |
|---|---|---|
| 19 | 8-[(2,6-difluorobenzyl)oxy]-N-[(1S,2S)-2-hydroxycyclopentyl]-2-methylimidazo[1,2-a]-pyridine-3-carboxamide<br>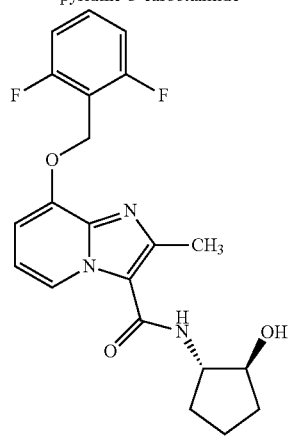<br>(67% of theory) | LC-MS (Method 1): $R_t$ = 0.74 min<br>MS (ESpos): m/z = 402.1 (M + H)$^+$ |
| 20 | 8-[(2,6-difluorobenzyl)oxy]-N-[(3S)-3-hydroxy-2-methylbutan-2-yl]-2-methylimidazo[1,2-a]-pyridine-3-carboxamide<br>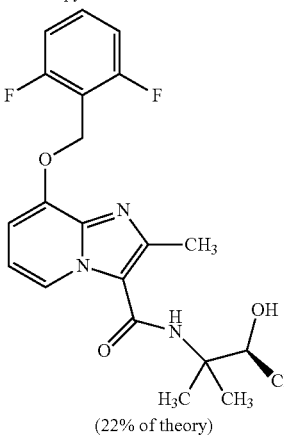<br>(22% of theory) | LC-MS (Method 1): $R_t$ = 0.82 min<br>MS (ESpos): m/z = 404.1 (M + H)$^+$ |
| 21 | 8-[(2,6-difluorobenzyl)oxy]-N-(2-hydroxyethyl)-2-methylimidazo[1,2-a]pyridine-3-carboxamide<br>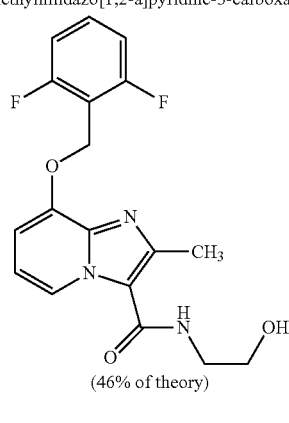<br>(46% of theory) | LC-MS (Method 3): $R_t$ = 1.29 min<br>MS (ESpos): m/z = 362.1 (M + H)$^+$ |

TABLE 2-continued

| Example | IUPAC name/structure (yield) | Analytical data |
|---|---|---|
| 22 | 8-[(2,6-difluorobenzyl)oxy]-N-(3-hydroxy-propyl)-2-methylimidazo[1,2-a]pyridine-3-carboxamide 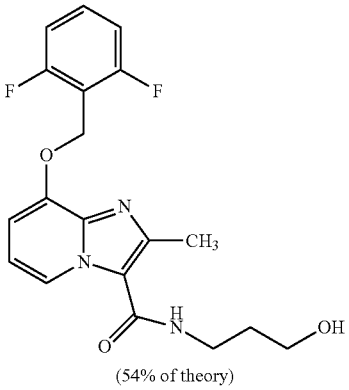 (54% of theory) | LC-MS (Method 1): $R_t$ = 0.67 min<br>MS (ESpos): m/z = 376.2 (M + H)$^+$ |
| 23 | 8-[(2,6-difluorobenzyl)oxy]-N-(4-hydroxybutyl)-2-methylimidazo[1,2-a]pyridine-3-carboxamide 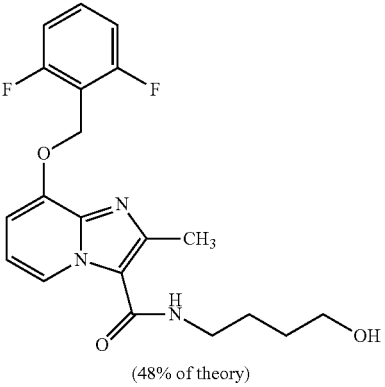 (48% of theory) | LC-MS (Method 3): $R_t$ = 1.37 min<br>MS (ESpos): m/z = 390.2 (M + H)$^+$ |
| 24 | 8-[(2,6-difluorobenzyl)oxy]-N-[2-(2-hydroxy-ethoxy)ethyl]-2-methylimidazo[1,2-a]pyridine-3-carboxamide 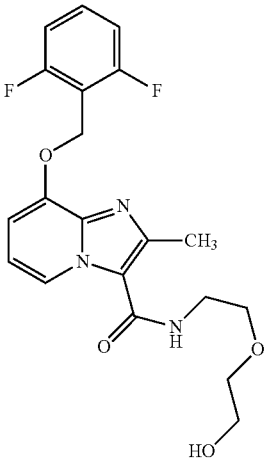 (67% of theory) | LC-MS (Method 3): $R_t$ = 1.33 min<br>MS (ESpos): m/z = 406.2 (M + H)$^+$ |

TABLE 2-continued

| Example | IUPAC name/structure (yield) | Analytical data |
|---|---|---|
| 25 | 8-[(2,6-difluorobenzyl)oxy]-N-[(2R)-1-hydroxy-4-(methylsulphanyl)butan-2-yl]-2-methyl-imidazo[1,2-a]pyridine-3-carboxamide 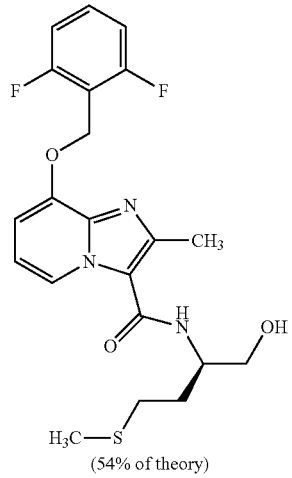 (54% of theory) | LC-MS (Method 3): R$_t$ = 1.55 min<br>MS (ESpos): m/z = 436.2 (M + H)$^+$ |
| 26 | 8-[(2,6-difluorobenzyl)oxy]-N-(1,3-dihydroxypropan-2-yl)-2-methylimidazo[1,2-a]pyridine-3-carboxamide 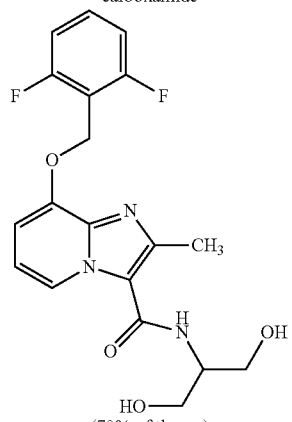 (70% of theory) | LC-MS (Method 1): Rt = 0.61 min<br>MS (ESpos): m/z = 392.0 (M + H)$^+$ |
| 27 | (rac)-trans-8-[(2,6-difluorobenzyl)oxy]-N-[(2-hydroxycyclohexyl)methyl]-2-methylimidazo[1,2-a]pyridine-3-carboxamide 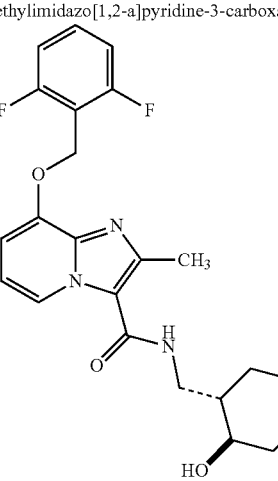 (79% of theory) | LC-MS (Method 3):<br>Rt = 1.66 min<br>MS (ESpos): |

TABLE 2-continued

| Example | IUPAC name/structure (yield) | Analytical data |
|---|---|---|
| 28 | (rac)-8-[(2,6-difluorobenzyl)oxy]-N-(3-hydroxybutyl)-2-methylimidazo[1,2-a]pyridine-3-carboxamide<br />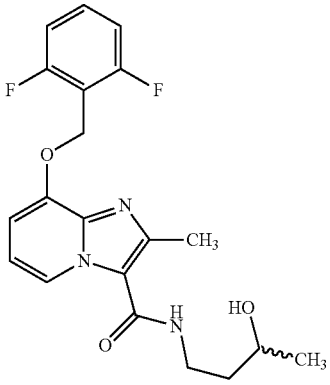<br />(78% of theory) | LC-MS (Method 2):<br />$R_t$ = 0.78 min<br />MS (ESpos):<br />m/z = 390.1 (M + H)$^+$<br />$^1$H NMR (400 MHz, DMSO-d$_6$):<br />δ = 1.11 (d, 3H); 1.53-1.70 (m, 2H); 2.55 (s, 3H, superimposed by DMSO signal); 3.38 (q, 2H); 3.68-3.78 (m, 1H); 4.59 (d, 1H); 5.30 (s, 2H); 6.92 (t, 1H); 7.00 (d, 1H); 7.23 (t, 2H); 7.58 (quint, 1H); 7.83 (t, 1H); 8.65 (d, 1H). |
| 29 | 8-[(2,6-difluorobenzyl)oxy]-N-[(2R)-1-hydroxy-3-methylbutan-2-yl]-2-methylimidazo[1,2-a]pyridine-3-carboxamide<br />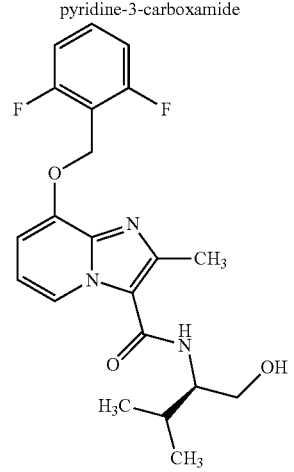<br />(81% of theory) | LC-MS (Method 1):<br />$R_t$ = 0.79 min<br />MS (ESpos):<br />m/z = 404.2 (M + H)$^+$<br />$^1$H NMR (400 MHz, DMSO-d$_6$):<br />δ = 0.92 (d, 3H), 0.96 (d, 3H), 1.92 (dq, 1H); 2.55 (s, 3H, superimposed by DMSO signal); 3.48-3.58 (m, 2H); 3.85-3.95 (m, 1H); 4.63 (t, 1H); 5.30 (s, 2H); 6.92 (t, 1H); 6.99 (d, 1H); 7.21 (t, 2H); 7.47 (d, 1H), 7.58 (quint, 1H); 8.54 (d, 1H). |
| 30 | (rac)-8-[(2,6-difluorobenzyl)oxy]-N-(2-hydroxybutyl)-2-methylimidazo[1,2-a]pyridine-3-carboxamide<br />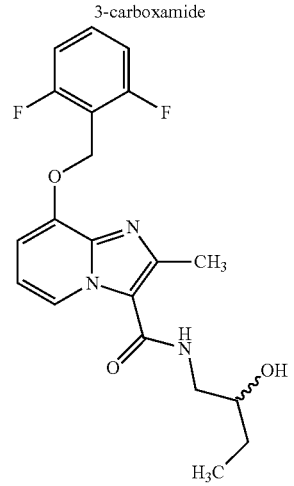<br />(45% of theory) | LC-MS (Method 1):<br />$R_t$ = 0.75 min<br />MS (ESpos):<br />m/z = 390.2 (M + H)$^+$<br />$^1$H NMR (400 MHz, DMSO-d$_6$):<br />δ = 0.90 (d, 3H), 1.32 (sept., 1H), 1.40-1.55 (m, 1H), 2.55 (s, 3H, superimposed by DMSO signal), 3.18-3.28 (m, 1H), 3.33-3.40 (m, 1H), 3.50-3.60 (m, 1H), 4.78 (d, 1H), 5.30 (s, 2H), 6.91 (t, 1H), 6.99 (d, 1H), 7.21 (t, 2H), 7.58 (quint, 1H), 7.70 (t, 1H), 8.61 (d, 1H). |

TABLE 2-continued

| Example | IUPAC name/structure (yield) | Analytical data |
|---|---|---|
| 31 | 8-[(2,6-difluorobenzyl)oxy]-N-[1-(hydroxymethyl)cyclopentyl]-2-methylimidazo[1,2-a]pyridine-3-carboxamide 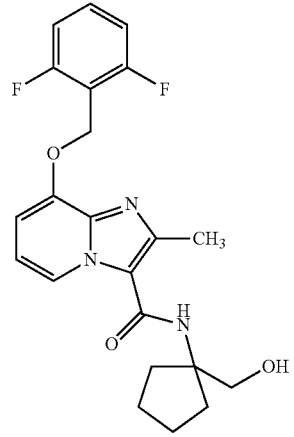 (67% of theory) | LC-MS (Method 1):<br>$R_t$ = 0.82 min<br>MS (ESpos):<br>m/z = 416.2 (M + H)$^+$<br>$^1$H NMR (400 MHz, DMSO-d$_6$):<br>δ = 1.52-1.68 (m, 2H) 1.69-1.78 (m, 4 H), 1.98-2.08 (m, 2H), 2.55 (s, 3H, superimposed by DMSO signal), 3.61 (d, 2H), 4.90 (t, 1H), 5.30 (s, 2H), 6.89 (t, 1H), 6.95 (d, 1H), 7.21 (t, 2H), 7.35 (s, 1H), 7.58 (quint, 1H), 8.51 (d, 1H). |
| 32 | 8-[(2,6-difluorobenzyl)oxy]-N-[(2S)-2-hydroxy-2-phenylethyl]-2-methylimidazo[1,2-a]pyridine-3-carboxamide 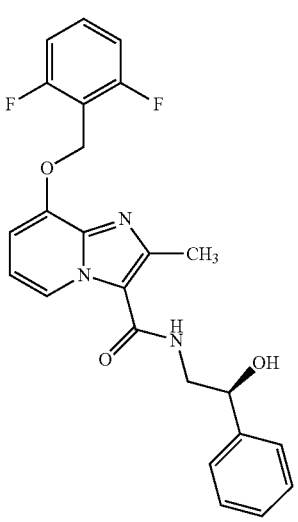 (61% of theory) | LC-MS (Method 3):<br>$R_t$ = 1.67 min<br>MS (ESpos):<br>m/z = 438.2 (M + H)$^+$<br>$^1$H NMR (400 MHz, DMSO-d$_6$):<br>δ = 2.40 (s, 3H, superimposed by DMSO signal), 3.40-3.48 (m, 1H), 3.50-3.60 (m, 1H), 4.80 (dt, 1H), 5.30 (s, 2H), 5.59 (d, 1H), 6.90 (t, 1H), 7.00 (d, 1H), 7.20-7.28 (m, 3H), 7.31 (t, 2H), 7.39 (d, 2H), 7.58 (quint, 1H), 7.79 (t, 1H), 8.61 (d, 1H). |

TABLE 2-continued

| Example | IUPAC name/structure (yield) | Analytical data |
|---|---|---|
| 33 | 8-[(2,6-difluorobenzyl)oxy]-N-[(2R)-2-hydroxy-2-phenylethyl]-2-methylimidazo[1,2-a]pyridine-3-carboxamide<br><br>(43% of theory) | LC-MS (Method 1):<br>$R_t$ = 0.85 min<br>MS (ESpos):<br>m/z = 438.2 (M + H)$^+$<br>$^1$H NMR (400 MHz, DMSO-d$_6$):<br>δ = 2.40 (s, 3H, superimposed by DMSO signal), 3.40-3.48 (m, 1H), 3.50-3.60 (m, 1H), 4.80 (dt, 1H), 5.30 (s, 2H), 5.59 (d, 1H), 6.90 (t, 1H), 7.00 (d, 1H), 7.20-7.28 (m, 3H), 7.31 (t, 2H), 7.39 (d, 2H), 7.58 (quint, 1H), 7.79 (t, 1H), 8.61 (d, 1H). |
| 34 | 8-[(2,6-difluorobenzyl)oxy]-N-(1-hydroxy-2-methylpropan-2-yl)-2-methylimidazo[1,2-a]-pyridine-3-carboxamide<br><br>(30% of theory) | LC-MS (Method 3):<br>$R_t$ = 1.49 min<br>MS (ESpos):<br>m/z = 390.1 (M + H)$^+$<br>$^1$H NMR (400 MHz, DMSO-d$_6$):<br>δ = 1.38 (s, 6H), 2.56 (s, 3H), 3.51 (d, 2H), 5.00 (t, 1H), 5.30 (s, 2H), 6.90 (t, 1H), 6.99 (d, 1H), 7.15 (s, 1H), 7.23 (t, 2H), 7.59 (quint, 1H), 8.60 (d, 1H). |

TABLE 2-continued

| Example | IUPAC name/structure (yield) | Analytical data |
|---|---|---|
| 35 | 8-[(2,6-difluorobenzyl)oxy]-N-[(2R)-1-hydroxy-3,3-dimethylbutan-2-yl]-2-methylimidazo[1,2-a]-pyridine-3-carboxamide<br><br>(51% of theory) | LC-MS (Method 1):<br>$R_t$ = 0.84 min<br>MS (ESpos):<br>m/z = 418.3 (M + H)$^+$<br>$^1$H NMR (400 MHz, DMSO-d$_6$):<br>δ = 0.99 (s, 9H), 2.56 (s, 3H), 3.45-3.53 (m, 1H), 3.68-3.73 (m, 1H), 3.95 (dt, 1H), 4.55 (t, 1H), 5.30 (s, 2H), 6.90 (t, 1H), 6.99 (d, 1H), 7.21 (t, 2H), 7.44 (d, 1H), 7.59 (quint, 1H), 8.50 (d, 1H). |
| 36 | 8-[(2,6-difluorobenzyl)oxy]-N-[(1R,2R)-2-hydroxycyclopentyl]-2-methylimidazo[1,2-a]-pyridine-3-carboxamide<br><br>(33% of theory) | LC-MS (Method 1):<br>$R_t$ = 0.72 min<br>MS (ESpos):<br>m/z = 402.3 (M + H)$^+$<br>$^1$H NMR (400 MHz, DMSO-d$_6$):<br>δ = 1.43-1.57 (m, 2H), 1.60-1.76 (m, 2H), 1.81-1.95 (m, 1H), 2.01-2.12 (m, 1H), 2.53 (s, 3H; superimposed by DMSO signal), 3.95-4.10 (m, 2H), 4.80 (d, 1H), 5.30 (s, 2H), 6.90 (t, 1H), 6.99 (d, 1H), 7.21 (t, 2H), 7.59 (quint, 1H), 7.72 (d, 1H), 8.50 (d, 1H). |

TABLE 2-continued

| Example | IUPAC name/structure (yield) | Analytical data |
|---|---|---|
| 37 | 8-[(2,6-difluorobenzyl)oxy]-N-[(1R,2S)-2-hydroxycyclopentyl]-2-methylimidazo[1,2-a]pyridine-3-carboxamide<br><br>(49% of theory) | LC-MS (Method 3):<br>$R_t$ = 1.47 min<br>MS (ESpos):<br>m/z = 402.2 (M + H)$^+$<br>1H NMR (400 MHz, DMSO-d$_6$):<br>δ = 1.43-1.57 (m, 1H), 1.60-1.70 (m, 2H), 1.70-1.90 (m, 2H), 1.91-2.00 (m, 1H), 2.53 (s, 3H; superimposed by DMSO signal), 4.08-4.18 (m, 2H), 4.96 (d, 1H), 5.30 (s, 2H), 6.91 (t, 1H), 7.00 (d, 1H), 7.20-7.25 (m, 3H), 7.59 (quint, 1H), 8.72 (d, 1H). |
| 38 | 8-[(2,6-difluorobenzyl)oxy]-N-[(2R)-1-hydroxy-3-phenylpropan-2-yl]-2-methylimidazo[1,2-a]pyridine-3-carboxamide<br><br>(67 % of theory) | LC-MS (Method 3):<br>$R_t$ = 1.67 min<br>MS (ESpos):<br>m/z = 452.2 (M + H)$^+$<br>1H NMR (400 MHz, DMSO-d$_6$):<br>δ = 2.34 (s, 3H), 2.79 (dd, 1H), 3.00 (dd, 1H), 3.45-3.60 (m, 2H), 4.20-4.30 (m, 1H), 4.89 (t, 1H), 5.29 (s, 2H), 6.87 (t, 1H), 6.97 (d, 1H), 7.15-7.30 (m, 7 H), 7.53-7.64 (m, 2H), 8.39 (d, 1H). |

Example 39

8-[(2,6-Difluorobenzyl)oxy]-N-[(2R)-1-hydroxy-4-methylpentan-2-yl]-2-methylimidazo[1,2-a]-pyridine-3-carboxamide

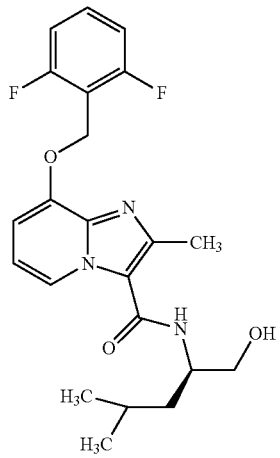 [SMILES: Cc1nc2c(OCc3c(F)cccc3F)cccn2c1C(=O)N[C@@H](CO)CC(C)C]

31 mg (0.1 mmol) of 8-(benzyloxy)-2-methylimidazo[1,2-a]pyridine-3-carboxylic acid, 14 mg (0.12 mmol, 1.2 equivalents) of (2R)-2-amino-4-methylpentan-1-ol, 41 mg of TBTU (0.13 mmol, 1.3 equivalents) and 20.2 mg (0.2 mmol, 2 equivalents) of 4-methylmorpholine were initially charged in 400 μl of DMF and stirred at RT overnight. The target compound was isolated by preparative HPLC (Method 11). This gave 26 mg (55% of theory).

LC-MS (Method 12): $R_t$=0.89 min
MS (ESpos): m/z=418.12 (M+H)$^+$

The example compounds shown in Table 3 were prepared analogously to Example 39 by reacting 8-[(2,6-difluorobenzyl)oxy]-2-methylimidazo[1,2-a]pyridine-3-carboxylic acid with the appropriate commercially available amines under the conditions described:

TABLE 3

| Example | IUPAC name/structure (yield) | Analytical data |
|---|---|---|
| 40 | 8-[(2,6-difluorobenzyl)oxy]-N-[(1S,2R)-2-hydroxy-2,3-dihydro-1H-inden-1-yl]-2-methylimidazo[1,2-a]pyridine-3-carboxamide (82% of theory) | LC-MS (Method 12): $R_t$ = 0.95 min MS (ESpos): m/z = 450.20 (M + H)$^+$ |
| 41 | 8-[(2,6-difluorobenzyl)oxy]-N-(3-hydroxy-2,2-dimethylpropyl)-2-methylimidazo[1,2-a]pyridine-3-carboxamide (30% of theory) | LC-MS (Method 12): $R_t$ = 0.86 min MS (ESpos): m/z = 404.14 (M + H)$^+$ |
| 42 | (rac)-8-[(2,6-difluorobenzyl)oxy]-N-(trans-4-hydroxycyclohexyl)-2-methylimidazo[1,2-a]pyridine-3-carboxamide (56% of theory) | LC-MS (Method 12): $R_t$ = 0.78 min MS (ESpos): m/z = 416.20 (M + H)$^+$ |

Example 43

8-[(2,6-Difluorobenzyl)oxy]-N-[(2R)-1-hydroxybutan-2-yl]-2-methylimidazo[1,2-a]pyridine-3-carboxamide

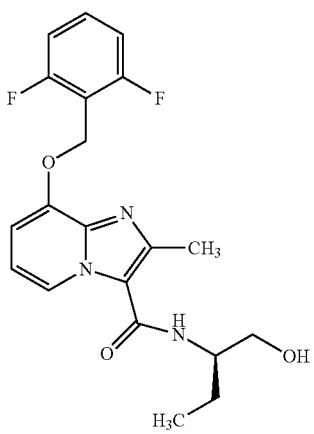 [SMILES: CC[C@H](CO)NC(=O)c1c(C)nc2c(OCc3c(F)cccc3F)cccn12]

1.3 ml of 1-methyl-2-pyrrolidone were added to 50 mg (0.190 mmol) of 8-hydroxy-N-[(2R)-1-hydroxybutan-2-yl]-2-methylimidazo[1,2-a]pyridine-3-carboxamide, 43 mg (0.209 mmol) of 2,6-difluorobenzyl bromide, 58 mg (0.418 mmol) of potassium carbonate and 16 mg (0.095 mmol) of potassium iodide, and the mixture was heated in a microwave at 120° C. for 40 min. The supernatant was then decanted off from the solid, and the latter was washed twice with methanol. The combined solutions were concentrated to dryness under high vacuum and at 60° C., and the residue formed was purified by preparative HPLC (Method 7). This gave 52 mg (69% of theory) of 8-[(2,6-difluorobenzyl)oxy]-N-[(2R)-1-hydroxybutan-2-yl]-2-methylimidazo[1,2-a]pyridine-3-carboxamide.

LC-MS (Method 1): $R_t$=0.73 min
MS (ESpos): m/z=390.1 (M+H)$^+$
$^1$H NMR (400 MHz, DMSO-$d_6$): δ=0.94 (t, 3H), 1.46-1.50 (m, 1H), 1.66-1.70 (m, 1H), 2.53 (s, 3H), 3.47 (m, 2H), 3.87-3.90 (m, 1H), 4.72 (t, 1H), 5.30 (s, 2H), 6.90 (t, 1H). 6.97 (d, 1H). 7.22 (t, 2H). 7.48 (d, 1H). 7.53-7.58 (m, 1H). 8.53 (d, 1H).

The working examples shown in Table 4 were prepared starting with 8-hydroxy-N-[(2R)-1-hydroxybutan-2-yl]-2-methylimidazo[1,2-a]pyridine-3-carboxamide by reaction with the appropriate commercially available benzyl bromides analogously to Example Compound 43.

TABLE 4

| Example | IUPAC name/structure (yield) | Analytical data |
|---|---|---|
| 44 | 8-[(2,3-difluorobenzyl)oxy]-N-[(2R)-1-hydroxybutan-2-yl]-2-methylimidazo[1,2-a]pyridine-3-carboxamide<br><br>(64% of theory) | LC-MS (Method 1): $R_t$ = 0.76 min<br>MS (ESpos): m/z = 390.1 (M + H)$^+$<br>$^1$H NMR (400 MHz, DMSO-$d_6$):<br>δ = 0.94 (t, 3H), 1.40-1.54 (m, 1H), 1.61-1.75 (m, 1H), 2.53 (s, 3H), 3.39-3.55 (m, 2H), 3.85-3.96 (m, 1H), 4.72 (t, 1H), 5.39 (s, 2H), 6.90 (t, 1H). 6.96 (d, 1H). 7.24-7.33 (m, 1H). 7.41-7.54 (m, 3H), 8.53 (d, 1H). |

TABLE 4-continued

| Example | IUPAC name/structure (yield) | Analytical data |
|---|---|---|
| 45 | 8-[(2,3-dichlorobenzyl)oxy]-N-[(2R)-1-hydroxybutan-2-yl]-2-methylimidazo[1,2-a]pyridine-3-carboxamide 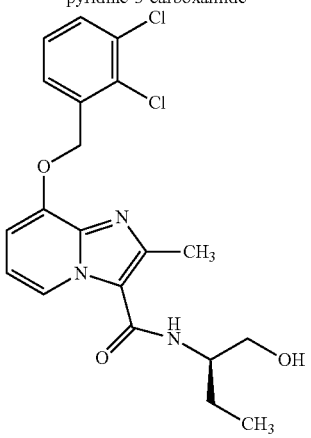 (61% of theory) | LC-MS (Method 1): $R_t$ = 0.88 min MS (ESpos): m/z = 422.0 (M + H)$^+$ $^1$H NMR (400 MHz, DMSO-$d_6$): δ = 0.94 (t, 3H), 1.40-7.54 (m, 1H), 1.62-1.75 (m, 1H), 2.53 (s, 3H), 3.40-3.55 (m, 2H), 3.85-3.96 (m, 1H), 4.75 (t, 1H), 5.40 (s, 2H), 6.87-6.96 (m, 2H). 7.46 (t, 1H). 7.53 (d, 1H). 7.65 (d, 1H), 7.70 (d, 1H), 8.53 (d, 1H). |

Example 46

8-(Benzyloxy)-N-[(2S)-1-hydroxypropan-2-yl]-2-methylimidazo[1,2-a]pyridine-3-carboxamide

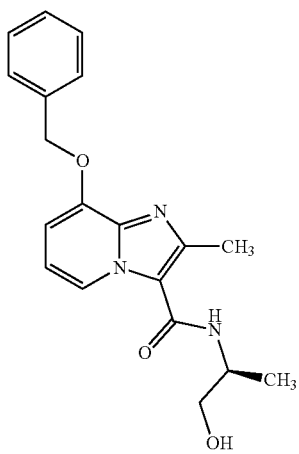 [SMILES: Cc1nc2c(OCc3ccccc3)cccn2c1C(=O)N[C@@H](C)CO]

The preparation was carried out analogously to Example 16 starting with 2.00 g (7.09 mmol) of 8-(benzyloxy)-2-methylimidazo[1,2-a]pyridine-3-carboxylic acid and 0.53 g (7.09 mmol) of L-alaninol. This gave 1.65 g (69% of theory) of the title compound.

LC-MS (Method 1): $R_t$=0.66 min

MS (ESpos): m/z=340.1 (M+H)$^+$

The working examples shown in Table 5 were prepared starting with 8-hydroxy-N-[2-(1-hydroxycyclopentyl)ethyl]-2-methylimidazo[1,2-a]pyridine-3-carboxamide by reaction with the appropriate commercially available benzyl bromides.

TABLE 5

| Example | IUPAC name/structure (yield) | Analytical data |
|---|---|---|
| 47 | 8-[(2,3-dichlorobenzyl)oxy]-N-[2-(1-hydroxycyclopentyl)ethyl]-2-methylimidazo[1,2-a]pyridine-3-carboxamide 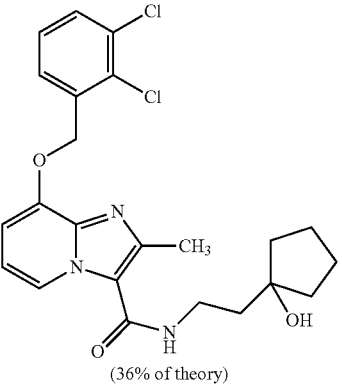 (36% of theory) | LC-MS (Method 1): $R_t$ = 0.98 min MS (ESpos): m/z = 462.1 (M + H)$^+$ |
| 48 | 8-(benzyloxy)-N-[2-(1-hydroxycyclopentyl)ethyl]-2-methylimidazo[1,2-a]pyridine-3-carboxamide 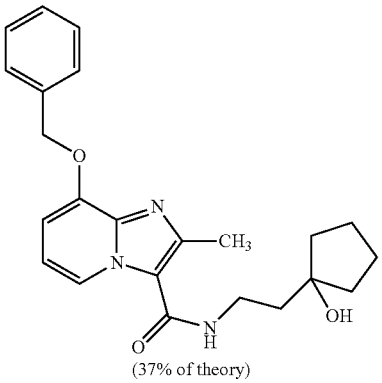 (37% of theory) | LC-MS (Method 1): $R_t$ = 0.82 min MS (ESpos): m/z = 394.2 (M + H)$^+$ |

The example compounds shown in Table 6 were prepared starting with N-(1,3-dihydroxypropan-2-yl)-8-hydroxy-2-methylimidazo[1,2-a]pyridine-3-carboxamide by reaction with the appropriate commercially available benzyl bromides.

TABLE 8

| Example | IUPAC name/structure (yield) | Analytical data |
|---|---|---|
| 49 | 8-[(2,3-dichlorobenzyl)oxy]-N-(1,3-dihydroxypropan-2-yl)-2-methylimidazo[1,2-a]pyridine-3-carboxamide (49% of theory) | LC-MS (Method 1): $R_t$ = 0.77 min MS (ESpos): m/z = 424.0 (M + H)$^+$ |
| 50 | 8-[(2-chlorobenzyl)oxy]-N-(1,3-dihydroxypropan-2-yl)-2-methylimidazo[1,2-a]pyridine-3-carboxamide (9% of theory) or (36% of theory) | LC-MS (Method 4): $R_t$ = 0.74 min MS (ESneg): m/z = 388.0 (M + H)$^+$ |
| 51 | N-(1,3-dihydroxypropan-2-yl)-8-[(2-fluorobenzyl)oxy]-2-methylimidazo[1,2-a]pyridine-3-carboxamide (11% of theory) or (47% of theory) | LC-MS (Method 1): $R_t$ = 0.61 min MS (ESpos): m/z = 374.0 (M + H)$^+$ |
| 52 | 8-[(2-chloro-3-methylbenzyl)oxy]-N-(1,3-dihydroxypropan-2-yl)-2-methylimidazo[1,2-a]pyridine-3-carboxamide (12% of theory) | LC-MS (Method 4): $R_t$ = 0.80 min MS (ESpos): m/z = 404.0 (M + H)$^+$ |
| 53 | 8-[(2,6-dichlorobenzyl)oxy]-N-(1,3-dihydroxypropan-2-yl)-2-methylimidazo[1,2-a]pyridine-3-carboxamide (31% of theory) | LC-MS (Method 4): $R_t$ = 0.79 min MS (ESpos): m/z = 424.0 (M + H)$^+$ |
| 54 | 8-[(2-bromobenzyl)oxy]-N-(1,3-dihydroxypropan-2-yl)-2-methylimidazo[1,2-a]pyridine-3-carboxamide (23% of theory) | LC-MS (Method 4): $R_t$ = 0.76 min MS (ESpos): m/z = 435.1 (M + H)$^+$ |

Example 55

8-(Cyclohexylmethoxy)-2-ethyl-N-[(2R)-1-hydroxypropan-2-yl]imidazo[1,2-a]pyridine-3-carboxamide formic acid salt

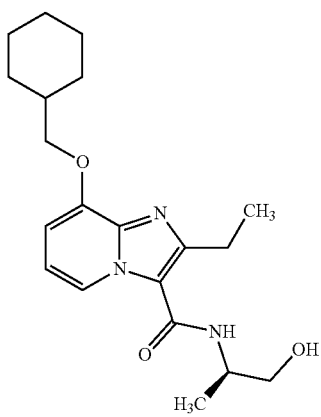 [SMILES: CCc1nc2c(OCC3CCCCC3)cccn2c1C(=O)N[C@H](C)CO]

3.3 mg (0.044 mmol) of L-alaminol, 14 mg (0.044 mmol) of TBTU and 20 mg (0.198 mmol) of N-methylmorpholine were added to a solution of 12 mg (0.040 mmol) of 8-(cyclohexylmethoxy)-2-ethylimidazo[1,2-a]pyridine-3-carboxylic acid in 750 μl of DMSO, and the mixture was then shaken at room temperature overnight. The mixture was then purified by preparative HPLC (Method 6), giving 12 mg (84% of theory) of 8-(cyclohexylmethoxy)-2-ethyl-N-[(2R)-1-hydroxypropan-2-yl]imidazo[1,2-a]pyridine-3-carboxamide as formic acid salt.

LC-MS (Method 1): $R_t$=0.82 min

MS (ESpos): m/z=360.2 (M+H)$^+$ $^1$H NMR (400 MHz, DMSO-d$_6$): δ=1.02-1.16 (m, 2H), 1.19 (d, 3H), 1.22-1.34 (m, 3H), 1.24 (t, 3H), 1.65-1.75 (m, 3H), 1.85-1.89 (m, 3H), 2.50 (partially obscured by DMSO signal, s, 3H), 2.91 (q, 2H), 3.40 (dd, 1H), 3.49 (dd, 1H), 3.95 (d, 2H), 4.05 (quint, 1H), 6.76 (d, 1H), 6.85 (t, 1H), 7.60 (d, 1H), 8.15 (br. s, 1H, formic acid); 8.44 (d, 1H).

The synthesis examples summarized in Table 7 below were prepared analogously to Example 55 and the General Working Procedure 1 by reacting the appropriate carboxylic acid (see synthesis intermediates above) with the appropriate commercially available amines under TBTU conditions.

TABLE 7

| Example | IUPAC name/structure (yield) | Analytical data |
|---|---|---|
| 56 | 8-(cyclohexylmethoxy)-N-[(2S)-1-hydroxypropan-2-yl]-2-(trifluoromethyl)imidazo[1,2-a]pyridine-3-carboxamide<br><br>(45% of theory) | LC-MS (Method 1): $R_t$ = 1.09 min<br>MS (ESpos): m/z = 400.2 (M + H)$^+$<br>$^1$H NMR (400 MHz, DMSO-d$_6$):<br>δ = 1.02-1.33 (m, 6H), 1.14 (d, 3H), 1.65-1.71 (m, 3H), 1.85-1.88 (m, 3H), 3.33-3.41 (m 1H), 3.43-3.49 (m, 1H), 4.00 (d, 2H), 4.04 (quint, 1H), 4.85 (t, 1H), 6.91 (d, 1H), 7.04 (t, 1H), 8.09 (d, 1H), 8.60 (d, 1H). |

TABLE 7-continued

| Example | IUPAC name/structure (yield) | Analytical data |
|---|---|---|
| 57 | 8-(cyclohexylmethoxy)-N-[(2S)-1-hydroxypropan-2-yl]-2-propylimidazo[1,2-a]pyridine-3-carboxamide<br>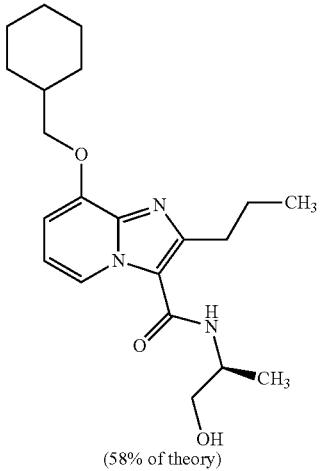<br>(58% of theory) | LC-MS (Method 1): $R_t$ = 0.85 min<br>MS (ESpos): m/z = 374.2 (M + H)$^+$<br>$^1$H NMR (400 MHz, DMSO-d$_6$):<br>δ = 0.90 (t, 3H), 1.04-1.10 (m, 2H), 1.16 (d, 3H), 1.20-1.30 (m, 3H), 1.65-1.75 (m, 5 H), 1.84-1.88 (m, 3H), 2.87 (t, 2H), 3.35-3.42 (m 1H), 3.45-3.53 (m, 1H), 3.95 (d, 2H), 4.05 (quint, 1H), 4.80 (br. s, 1H), 6.75 (d, 1H), 6.85 (t, 1H), 7.63 (d, 1H), 8.42 (d, 1H). |
| 58 | 8-(cyclobutylmethoxy)-2-ethyl-N-[(2S)-1-hydroxypropan-2-yl]imidazo[1,2-a]pyridine-3-carboxamide formic acid salt<br>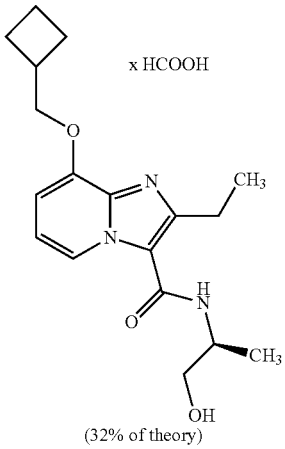<br>(32% of theory) | LC-MS (Method 1): $R_t$ = 0.68 min<br>MS (ESpos): m/z = 332.1 (M + H)$^+$<br>$^1$H NMR (400 MHz, DMSO-d$_6$):<br>δ = 1.16 (d, 3H), 1.24 (t, 3H), 1.83-1.96 (m, 4H), 2.08-2.16 (m, 2H), 2.81 (quint, 1H), 2.91 (q, 2H), 3.40 (dd, 1H), 3.49 (dd, 1H), 4.05 (quint, 1H), 4.14 (d, 2H), 4.80 (br, 1H), 6.78 (d, 1H), 6.85 (t, 1H), 7.60 (d, 1H), 8.18 (br. s, formic acid), 8.45 (d, 1H). |
| 59 | 8-(cyclohexylmethoxy)-N-[(2S)-1-hydroxypropan-2-yl]imidazo[1,2-a]pyridine-3-carboxamide<br>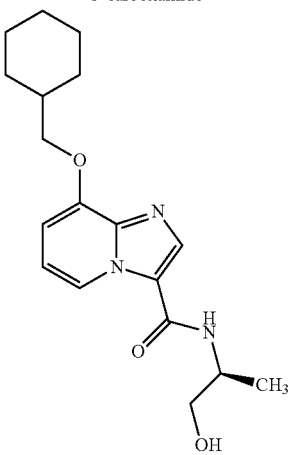<br>(67% of theory) | LC-MS (Method 3): $R_t$ = 1.69 min<br>MS (ESpos): m/z = 332.3 (M + H)$^+$ |

TABLE 7-continued

| Example | IUPAC name/structure (yield) | Analytical data |
|---|---|---|
| 60 | 8-[(2,6-difluorobenzyl)oxy]-6-ethyl-N-[(2R)-1-hydroxyhexan-2-yl]-2-methylimidazo[1,2-a]pyridine-3-carboxamide<br><br>(55% of theory) | LC-MS (Method 1):<br>$R_t$ = 0.94 min<br>MS (ESpos):<br>m/z = 446.3 (M + H)+<br>$^1$H NMR (400 MHz, DMSO-$d_6$):<br>δ = 0.89 (t, 3H), 1.20 (t, 3H), 1.25-1.40 (m, 4 H), 1.40-1.52 (m, 1H), 1.60-1.70 (m, 1H), 2.55 (s, 3H), 2.65 (q, 2H), 3.45-3.53 (m, 2H), 3.94-4.05 (m, 1H), 4.71 (t, 1H), 5.30 (s, 2H), 6.90 (s, 1H), 7.21 (t, 2H), 7.48 (d, 1H), 7.59 (quint, 1H), 8.40 (s, 1H). |
| 61 | 6-cyclopropyl-8-[(2,6-difluorobenzyl)oxy]-N-[(2R)-1-hydroxyhexan-2-yl]-2-methylimidazo[1,2-a]pyridine-3-carboxamide<br><br>(70% of theory) | LC-MS (Method 2):<br>$R_t$ = 1.08 min<br>MS (ESpos):<br>m/z = 458.1 (M + H)+<br>$^1$H NMR (400 MHz, DMSO-$d_6$):<br>δ = 0.72 (q, 2H), 0.89 (t, 3H), 0.95 (q, 2H), 1.22-1.40 (m, 4H), 1.40-1.52 (m, 1H), 1.58-1.70 (m, 1H), 1.98 (quint., 1H), 2.47 (s, 3H), 3.40-3.51 (m, 2H), 3.94-4.02 (m, 1H), 4.71 (t, 1H), 5.30 (s, 2H), 6.65 (s, 1H), 7.21 (t, 2H), 7.48 (d, 1H), 7.59 (quint, 1H), 8.40 (s, 1H). |
| 62 | 8-[(2,6-difluorobenzyl)oxy]-N-[(2R)-1-hydroxyhexan-2-yl]imidazo[1,2-a]pyridine-3-carboxamide<br><br>(59% of theory) | LC-MS (Method 3):<br>$R_t$ = 1.92 min<br>MS (ESpos):<br>m/z = 404.2 (M + H)+<br>$^1$H NMR (400 MHz, DMSO-$d_6$):<br>δ = 0.84 (t, 3H), 1.22-1.40 (m, 4H), 1.40-1.52 (m, 1H), 1.58-1.70 (m, 1H), 3.38-3.51 (m, 2H), 3.91-4.02 (m, 1H), 4.71 (t, 1H ),5.30 (s, 2H), 7.00 (t, 1H), 7.08 (d, 1H), 7.21 (t, 2H), 7.59 (quint, 1H), 8.02 (d, 1H), 8.25 (s, 1H), 9.12 (d, 1H). |

TABLE 7-continued

| Example | IUPAC name/structure (yield) | Analytical data |
|---|---|---|
| 63 | 8-[(2,6-difluorobenzyl)oxy]-N-[(2R)-1-hydroxyhexan-2-yl]-2-methyl-6-(morpholin-4-yl)imidazo[1,2-a]pyridine-3-carboxamide 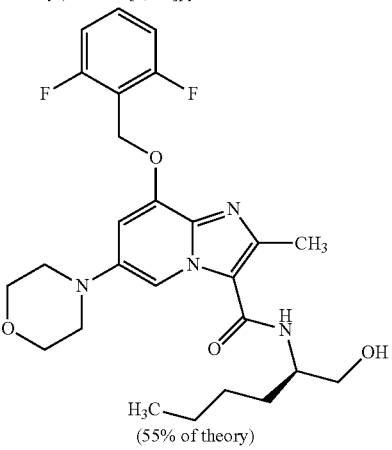 (55% of theory) | LC-MS (Method 1): $R_t$ = 0.88 min MS (ESpos): m/z = 503.3 (M + H)+ $^1$H NMR (400 MHz, DMSO-$d_6$): δ = 0.89 (t, 3H), 1.22-1.35 (m, 4H), 1.40-1.52 (m, 1H), 1.60-1.70 (m, 1H), 2.48 (s, 3H), 3.03-3.07 (m, 4H), 3.38-3.52 (m, 2H), 3.72-3.80 (m, 4H), 3.94-4.01 (m, 1H), 4.71 (t, 1H), 5.30 (s, 2H), 7.00 (s, 1H), 7.21 (t, 2H), 7.38 (d, 1H), 7.59 (quint, 1H), 8.09 (s, 1H). |
| 64 | 8-[(2,6-difluorobenzyl)oxy]-N-[(2R)-1-hydroxyhexan-2-yl]-2-methyl-6-(pyrrolidin-1-yl)imidazo[1,2-a]pyridine-3-carboxamide 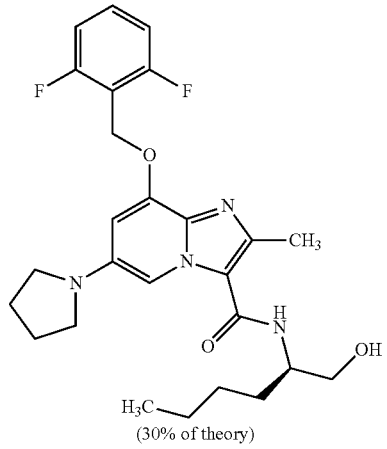 (30% of theory) | LC-MS (Method 1): $R_t$ = 0.97 min MS (ESpos): m/z = 487.3 (M + H)+ 1H NMR (400 MHz, DMSO-$d_6$): δ = 0.87 (t, 3H), 1.22-1.35 (m, 4H), 1.40-1.52 (m, 1H), 1.60-1.70 (m, 1H), 1.96-2.03 (m, 4 H), 2.42 (s, 3H), 3.20-3.28 (m, 4 H), 3.38-3.52 (m, 2H), 3.91-4.01 (m, 1H), 4.71 (t, 1H), 5.32 (s, 2H), 6.70 (s, 1H), 7.21 (t, 2H), 7.23 (d, 1H), 7.59 (quint, 1H), 7.81 (s, 1H). |
| 65 | 6-bromo-8-[(2,6-difluorobenzyl)oxy]-N-[(2R)-1-hydroxyhexan-2-yl]-2-methylimidazo[1,2-a]pyridine-3-carboxamide 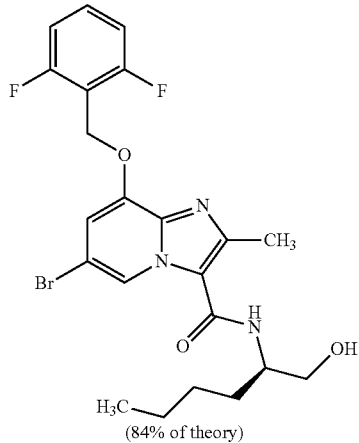 (84% of theory) | LC-MS (Method 1): $R_t$ = 1.13 min MS (ESpos): m/z = 496.2/498.2 (M + H)+ 1H NMR (400 MHz, DMSO-$d_6$): δ = 0.87 (t, 3H), 1.22-1.35 (m, 4H), 1.40-1.52 (m, 1H), 1.60-1.70 (m, 1H), 2.52 (s, 3H; obscured by DMSO signal), 3.38-3.52 (m, 2H), 3.91-4.01 (m, 1H), 4.75 (t, 1H), 5.32 (s, 2H), 7.19-7.25 (m, 3H), 7.55-7.65 (m, 2H), 8.71 (s, 1H). |

The working examples summarized in Table 8 below were prepared by reacting 8-(cyclohexylmethoxy)-2-methylimidazo[1,2-a]pyridine-3-carboxylic acid with the appropriate commercially available amines under TBTU conditions (see also General Working Procedure 1).

TABLE 8

| Example | IUPAC name/structure (yield) | Analytical data |
|---|---|---|
| 66 | 8-(cyclohexylmethoxy)-N-[(2R)-1-hydroxyhexan-2-yl]-2-methylimidazo[1,2-a]pyridine-3-carboxamide 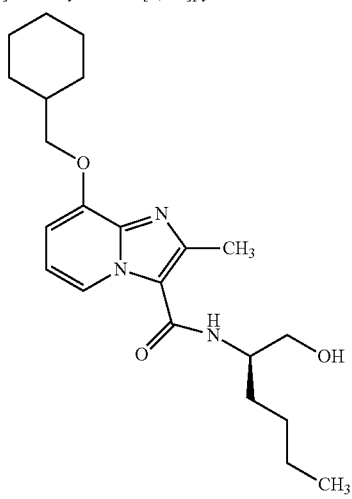 (72% of theory) | LC-MS (Method 1): $R_t$ = 0.94 min MS (ESpos): m/z = 388.2 (M + H)$^+$ |
| 67 | 8-(cyclohexylmethoxy)-N-[(2R)-1-hydroxypentan-2-yl]-2-methylimidazo[1,2-a]pyridine-3-carboxamide 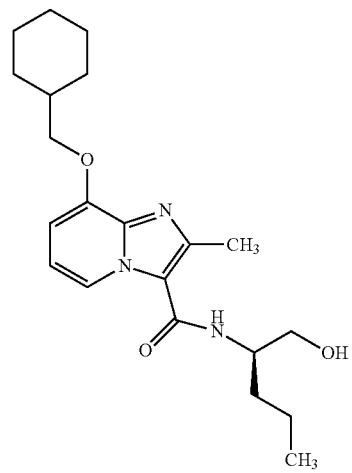 [SMILES: CCC[C@H](CO)NC(=O)c1c(C)nc2c(OCC3CCCCC3)cccn12] (72% of theory) | LC-MS (Method 3): $R_t$ = 1.69 min MS (ESpos): m/z = 374.2 (M + H)$^+$ |

TABLE 8-continued

| Example | IUPAC name/structure (yield) | Analytical data |
|---|---|---|
| 68 | 8-(cyclohexylmethoxy)-N-[(2S)-2,3-dihydroxypropyl]-2-methylimidazo[1,2-a]pyridine-3-carboxamide<br>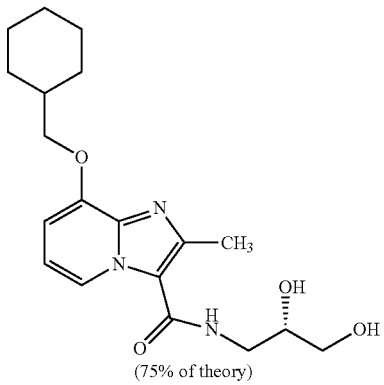<br>(75% of theory) | LC-MS (Method 3): $R_t$ = 1.43 min<br>MS (ESpos): m/z = 362.1 (M + H)⁺ |
| 69 | (rac)-8-(cyclohexylmethoxy)-N-(1-hydroxybutan-2-yl)-2-methylimidazo[1,2-a]pyridine-3-carboxamide formate<br>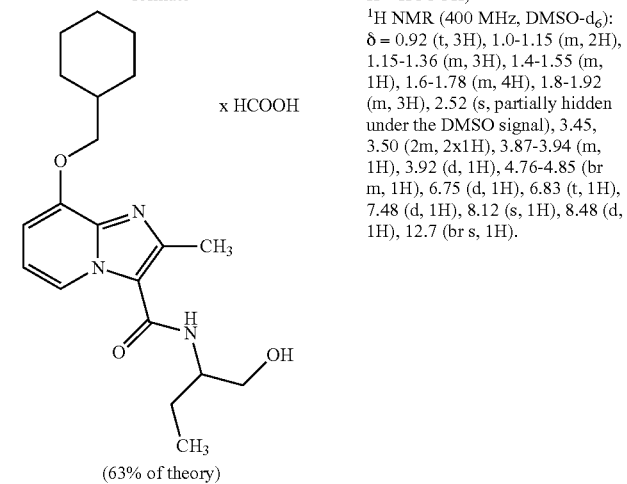<br>(63% of theory) | LC-MS (Method 3): $R_t$ = 1.62 min<br>MS (ESpos): m/z = 360.2 (M + H—HCOOH)⁺<br>¹H NMR (400 MHz, DMSO-d₆):<br>δ = 0.92 (t, 3H), 1.0-1.15 (m, 2H), 1.15-1.36 (m, 3H), 1.4-1.55 (m, 1H), 1.6-1.78 (m, 4H), 1.8-1.92 (m, 3H), 2.52 (s, partially hidden under the DMSO signal), 3.45, 3.50 (2m, 2x1H), 3.87-3.94 (m, 1H), 3.92 (d, 1H), 4.76-4.85 (br m, 1H), 6.75 (d, 1H), 6.83 (t, 1H), 7.48 (d, 1H), 8.12 (s, 1H), 8.48 (d, 1H), 12.7 (br s, 1H). |
| 70 | (rac)-8-(cyclohexylmethoxy)-N-(1-hydroxypent-4-en-2-yl)-2-methylimidazo[1,2-a]pyridine-3-carboxamide<br>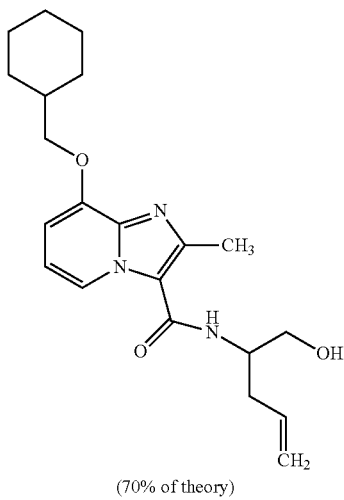<br>(70% of theory) | LC-MS (Method 3): $R_t$ = 1.65 min<br>MS (ESpos): m/z = 372.2 (M + H)⁺ |

TABLE 8-continued

| Example | IUPAC name/structure (yield) | Analytical data |
|---|---|---|
| 71 | (rac)-8-(cyclohexylmethoxy)-N-[trans-2-hydroxycyclopentyl]-2-methylimidazo[1,2-a]pyridine-3-carboxamide (69% of theory) | LC-MS (Method 1): $R_t$ = 0.82 min<br>MS (ESpos): m/z = 372.1<br>$(M + H)^+$ |
| 72 | 8-(cyclohexylmethoxy)-N-[(2R)-1-hydroxybutan-2-yl]-2-methylimidazo[1,2-a]pyridine-3-carboxamide (74% of theory) | LC-MS (Method 3): $R_t$ = 1.57 min<br>MS (ESpos): m/z = 360.2 $(M + H)^+$ |
| 73 | (rac)-8-(cyclohexylmethoxy)-N-(1-hydroxyhexan-2-yl)-2-methylimidazo[1,2-a]pyridine-3-carboxamide (18% of theory)<br>the solvent used was DMSO | LC-MS (Method 5): $R_t$ = 1.63 min<br>MS (ESpos): m/z = 388.3<br>$(M + H)^+$ |

TABLE 8-continued

| Example | IUPAC name/structure (yield) | Analytical data |
|---|---|---|
| 74 | 8-(cyclohexylmethoxy)-N-(4-hydroxybutyl)-2-methylimidazo[1,2-a]pyridine-3-carboxamide<br><br>(9% of theory)<br>the solvent used was DMSO | LC-MS (Method 5): $R_t$ = 1.44 min<br>MS (ESpos): m/z = 360.3<br>$(M + H)^+$ |
| 75 | 8-(cyclohexylmethoxy)-N-[(2S)-1-hydroxypropan-2-yl]-2-methylimidazo[1,2-a]pyridine-3-carboxamide<br><br>(82% of theory) | LC-MS (Method 3): $R_t$ = 1.49 min<br>MS (ESpos): m/z = 346.1<br>$(M + H)^+$ |
| 76 | 8-(cyclohexylmethoxy)-N-(2-hydroxyethyl)-2-methylimidazo[1,2-a]pyridine-3-carboxamide formate<br><br>x HCOOH<br><br>(67% of theory) | LC-MS (Method 1): $R_t$ = 0.76 min<br>MS (ESpos): m/z = 332.1<br>$(M + H)^+$<br>$^1$H NMR (400 MHz, DMSO-d$_6$): δ = 1.0-1.35 (m, 5H), 1.61-1.90 (m, 6H), 2.52 (s, partially hidden under the DMSO signal), 3.36 (q, 2H), 3.52-3.57 (m, 2H), 3.95 (s, 2H), 4.78 (br s, 1H), 6.74 (d, 1H), 6.87 (t, 1H), 7.72 (t, 1H), 8.14 (s, 1H), 8.56 (d, 1H), 12.8 (br s, 1H). |

TABLE 8-continued

| Example | IUPAC name/structure (yield) | Analytical data |
|---|---|---|
| 77 | 8-(cyclohexylmethoxy)-N-[1,3-dihydroxy-2-(hydroxymethyl)propan-2yl]-2-methylimidazo[1,2-a]pyridine-3-carboxamide formate<br>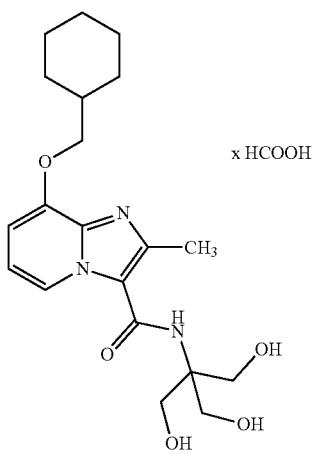 [SMILES: Cc1nc2c(OCC3CCCCC3)cccn2c1C(=O)NC(CO)(CO)CO]<br>(41% of theory) | LC-MS (Method 2): $R_t$ = 0.83 min<br>MS (ESpos): m/z = 392.2<br>$(M + H—HCO_2H)^+$<br><br>$^1$H NMR (400 MHz, DMSO-$d_6$): δ = 1.0-1.15 (m, 2H), 1.15-1.38 (m, 3H), 1.6-1.78 (m, 3H), 1.78-1.90 (m, 3H), 2.53 (s, 3H), 3.7 (s, 6H), 3.95 (d, 2H), 4.85 (br s, 3H), 6.79 (d, 1H), 6.82 (s, 1H), 6.87 (t, 1H), 8.13 (s, 1H), 8.62 (d, 1H), 11.5 (br s, 1H). |
| 78 | (rac)-8-(cyclohexylmethoxy)-N-[(trans)-2-hydroxycyclohexyl]-2-methylimidazo[1,2-a]-pyridine-3-carboxamide<br>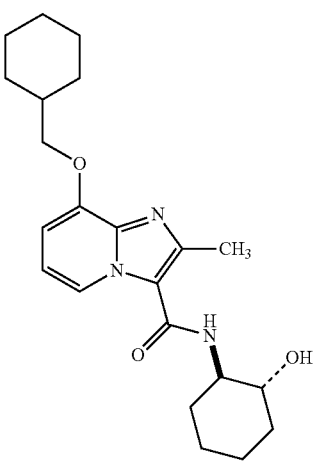<br>(20% of theory) | LC-MS (Method 3): $R_t$ = 1.61 min<br>MS (ESpos): m/z = 386.2 $(M + H)^+$ |

TABLE 8-continued

| Example | IUPAC name/structure (yield) | Analytical data |
|---|---|---|
| 79 | 8-(cyclohexylmethoxy)-N-(2-hydroxy-3-methoxypropyl)-2-methylimidazo[1,2-a]pyridine-3-carboxamide<br>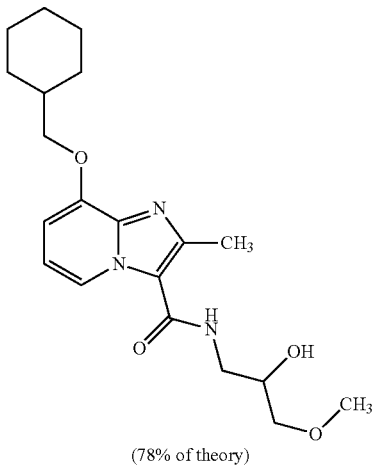<br>(78% of theory) | LC-MS (Method 3): $R_t$ = 1.53 min<br>MS (ESpos): m/z = 376.2 (M + H)$^+$ |
| 80 | 8-(cyclohexylmethoxy)-N-[(2R)-2,3-dihydroxypropyl]-2-methylimidazo[1,2-a]pyridine-3-carboxamide<br>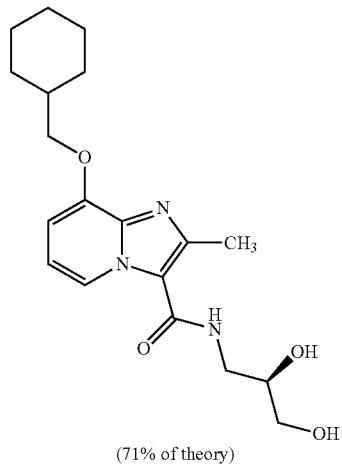<br>(71% of theory) | LC-MS (Method 3): $R_t$ = 1.43 min<br>MS (ESpos): m/z = 362.1 (M + H)$^+$ |
| 81 | 8-(cyclohexylmethoxy)-N-[cis-2-hydroxycyclopentyl]-2-methylimidazo[1,2-a]-pyridine-3-carboxamide<br>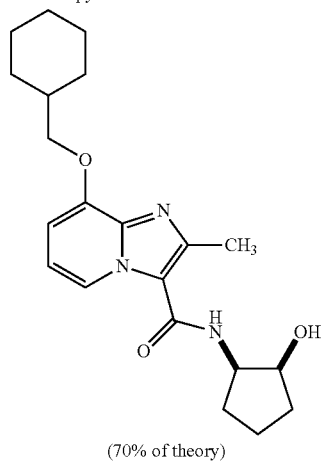<br>(70% of theory) | LC-MS (Method 1): $R_t$ = 0.87 min<br>MS (ESpos): m/z = 372.1<br>(M + H)$^+$ |

TABLE 8-continued

| Example | IUPAC name/structure (yield) | Analytical data |
|---|---|---|
| 82 | 8-(cyclohexylmethoxy)-N-(3-hydroxypropyl)-2-methylimidazo[1,2-a]pyridine-3-carboxamide<br />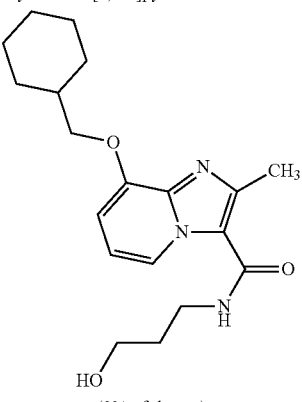<br />(2% of theory)<br />the solvent used was DMSO | LC-MS (Method 5): $R_t$ = 1.42 min<br />MS (ESpos): m/z = 346.3<br />(M + H)$^+$ |
| 83 | 8-(cyclohexylmethoxy)-N-(2-hydroxycyclopentyl)-2-methylimidazo[1,2-a]pyridine-3-carboxamide<br />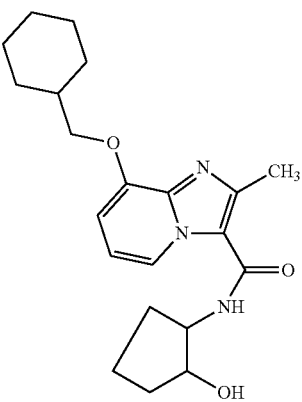 [SMILES: Cc1nc2c(OCC3CCCCC3)cccn2c1C(=O)NC1CCCC1O]<br />(21% of theory)<br />the solvent used was DMSO | LC-MS (Method 5):<br />$R_t$ = 1.47 min<br />MS (ESpos): m/z = 372.3<br />(M + H)$^+$ |
| 84 | 8-(cyclohexylmethoxy)-N-(1-hydroxypropan-2-yl)-2-methylimidazo[1,2-a]pyridine-3-carboxamide<br />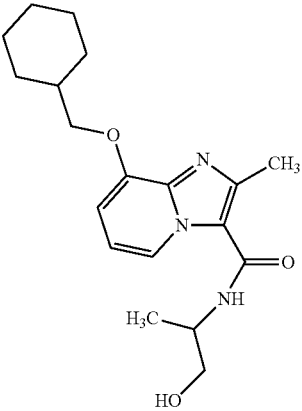 [SMILES: Cc1nc2c(OCC3CCCCC3)cccn2c1C(=O)NC(C)CO]<br />(14% of theory)<br />the solvent used was DMSO | LC-MS (Method 5): $R_t$ = 1.42 min<br />MS (ESpos): m/z = 346.3<br />(M + H)$^+$ |

TABLE 8-continued

| Example | IUPAC name/structure (yield) | Analytical data |
|---|---|---|
| 85 | 8-(cyclohexylmethoxy)-N-(1,3-dihydroxypropan-2-yl)-2-methylimidazo[1,2-a]pyridine-3-carboxamide<br>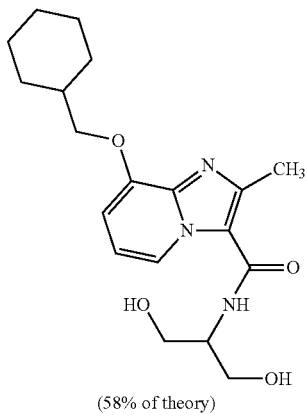<br>(58% of theory) | LC-MS (Method 2): $R_t$ = 0.81 min<br>MS (ESpos): m/z = 362.2<br>$(M + H)^+$ |
| 86 | 8-(cyclohexylmethoxy)-N-[2-(2-hydroxyethoxy)ethyl]-2-methylimidazo[1,2-a]-pyridine-3-carboxamide<br>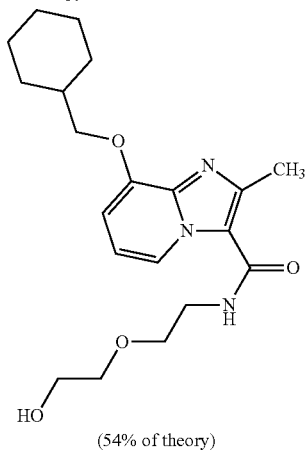<br>(54% of theory)<br>the solvent used was DMSO | LC-MS (Method 2):<br>$R_t$ = 0.87 min<br>MS (ESpos): m/z = 376.2<br>$(M + H)^+$ |
| 87 | 8-(cyclohexylmethoxy)-N-(3-hydroxy-2-methylbutan-2-yl)-2-methylimidazo[1,2-a]pyridine-3-carboxamide<br>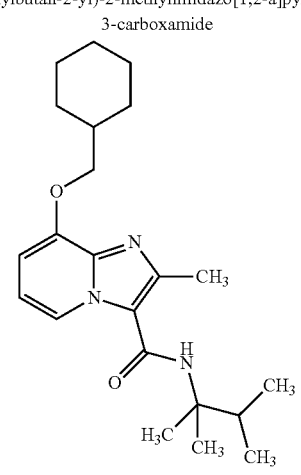<br>(40% of theory, 88% pure) | LC-MS (Method 1):<br>$R_t$ = 0.91 min<br>MS (ESpos): m/z = 374.1<br>$(M + H)^+$<br>$^1$H NMR (400 MHz, DMSO-$d_6$):<br>δ = 1.0-1.09 (m, 1H), 1.1 (d, 1H),<br>1.15-1.35 (m, 3H), 1.35 (d, 6H),<br>1.61-1.09 (m, 6H), 2.51 (s,<br>partially hidden under the DMSO<br>signal), 3.88 (t, 1H), 3.95 (d, 1H),<br>5.05 (d, 1H), 6.78 (d, 1H), 6.88 (t,<br>1H), 7.1 (s, 1H), 8.58 (d, 1H). |

TABLE 8-continued

| Example | IUPAC name/structure (yield) | Analytical data |
|---|---|---|
| 88 | 8-(cyclohexylmethoxy)-N-[(2S)-1-hydroxybutan-2-yl]-2-methylimidazo[1,2-a]pyridine-3-carboxamide<br><br>(74% of theory) | LC-MS (Method 3):<br>$R_t$ = 1.57 min<br>MS (ESpos): m/z = 360.2 (M + H)$^+$ |
| 89 | 8-(cyclohexylmethoxy)-N-[(2S)-1-hydroxypentan-2-yl]-2-methylimidazo[1,2-a]pyridine-3-carboxamide<br><br>(81% of theory) | LC-MS (Method 3):<br>$R_t$ = 1.69 min<br>MS (ESpos): m/z = 374.2 (M + H)$^+$ |
| 90 | 8-(cyclohexylmethoxy)-N-[(2S)-1-hydroxy-4-(methylsulphanyl)butan-2-yl]-2-methylimidazo[1,2-a]pyridine-3-carboxamide<br><br>(27% of theory) | LC-MS (Method 5):<br>$R_t$ = 1.53 min<br>MS (ESpos): m/z = 406.3 (M + H)$^+$ |

TABLE 8-continued

| Example | IUPAC name/structure (yield) | Analytical data |
|---|---|---|
| | the solvent used was DMSO | |
| 91 | 8-(cyclohexylmethoxy)-N-[(2S,3S)-1-hydroxy-3-methylpentan-2-yl]-2-methylimidazo[1,2-a]pyridine-3-carboxamide<br />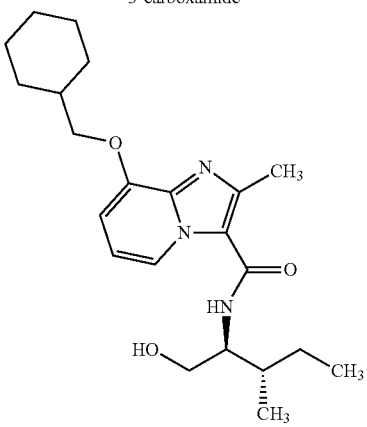<br />(41% of theory)<br />the solvent used was DMSO | LC-MS (Method 5):<br />$R_t$ = 1.58 min<br />MS (ESpos): m/z = 388.3<br />$(M + H)^+$ |
| 92 | 8-(cyclohexylmethoxy)-N-[1-(hydroxymethyl)cyclopentyl]-2-methylimidazo[1,2-a]pyridine-3-carboxamide<br />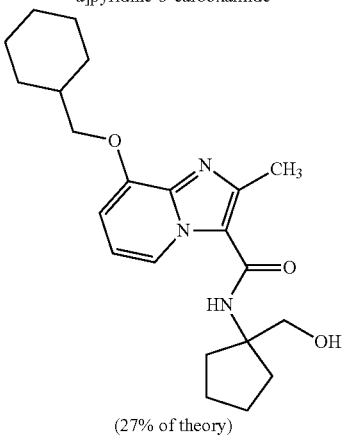<br />(27% of theory)<br />the solvent used was DMSO | LC-MS (Method 5):<br />$R_t$ = 1.56 min<br />MS (ESpos): m/z = 386.3<br />$(M + H)^+$ |
| 93 | 8-(cyclohexylmethoxy)-N-[(2S)-1-hydroxy-3-methylbutan-2-yl]-2-methylimidazo[1,2-a]pyridine-3-carboxamide<br />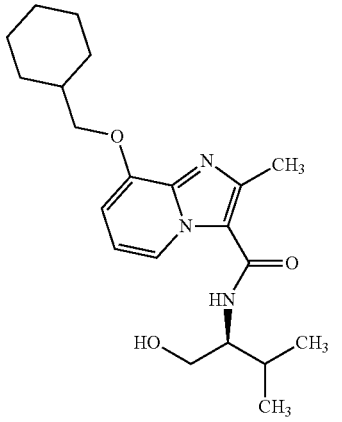 [SMILES: Cc1nc2c(OCC3CCCCC3)cccn2c1C(=O)N[C@H](CO)C(C)C]<br />(23% of theory) | LC-MS (Method 5):<br />$R_t$ = 1.53 min<br />MS (ESpos): m/z = 374.3<br />$(M + H)^+$ |

TABLE 8-continued

| Example | IUPAC name/structure (yield) | Analytical data |
|---|---|---|
| | the solvent used was DMSO | |
| 94 | N-(1-tert-butoxy-3-hydroxypropan-2-yl)-8-(cyclohexylmethoxy)-2-methylimidazo[1,2-a]pyridine-3-carboxamide<br />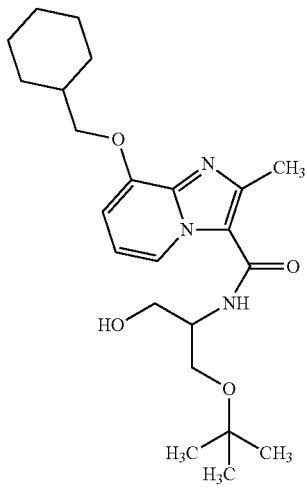 [SMILES: Cc1nc2c(OCC3CCCCC3)cccn2c1C(=O)NC(CO)COC(C)(C)C]<br />(33% of theory)<br />the solvent used was DMSO | LC-MS (Method 5):<br />$R_t$ = 1.62 min<br />MS (ESpos): m/z = 418.3<br />$(M + H)^+$ |
| 95 | 8-(cyclohexylmethoxy)-N-[(2S)-1-hydroxy-4-methylpentan-2-yl]-2-methylimidazo[1,2-a]pyridine-3-carboxamide<br />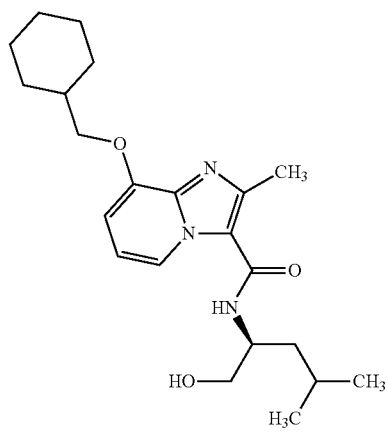 [SMILES: Cc1nc2c(OCC3CCCCC3)cccn2c1C(=O)N[C@H](CO)CC(C)C]<br />(23% of theory)<br />the solvent used was DMSO | LC-MS (Method 5):<br />$R_t$ = 1.60 min<br />MS (ESpos): m/z = 388.3<br />$(M + H)^+$ |

TABLE 8-continued

| Example | IUPAC name/structure (yield) | Analytical data |
|---|---|---|
| 96 | 8-(cyclohexylmethoxy)-N-[(2R)-1-hydroxy-3-methylpentan-2-yl]-2-methylimidazo[1,2-a]pyridine-3-carboxamide<br />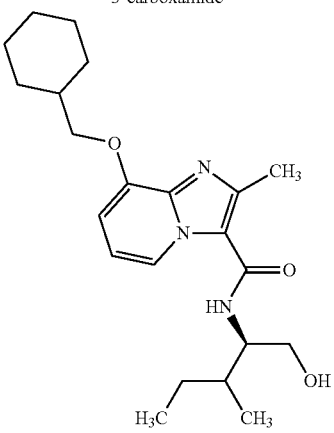<br />(43% of theory)<br />the solvent used was DMSO | LC-MS (Method 5):<br />$R_t$ = 1.60 min<br />MS (ESpos): m/z = 388.3 $(M + H)^+$ |

The further working examples summarized in Table 9 below were prepared by reacting 8-(cyclobutylmethoxy)-2-methylimidazo[1,2-a]pyridine-3-carboxylic acid with the appropriate commercially available amines under TBTU conditions.

TABLE 9

| Example | IUPAC name/structure (yield) | Analytical data |
|---|---|---|
| 97 | 8-(cyclobutylmethoxy)-N-[2-(1-hydroxycyclopentyl)ethyl]-2-methylimidazo[1,2-a]pyridine-3-carboxamide<br />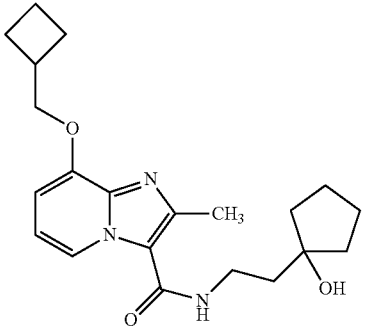 [SMILES: Cc1nc2c(OCC3CCC3)cccn2c1C(=O)NCCC1(O)CCCC1]<br />(48% of theory) | LC-MS (Method 1): $R_t$ = 0.82 min<br />MS (ESpos): m/z = 372.2 $(M + H)^+$ |

TABLE 9-continued

| Example | IUPAC name/structure (yield) | Analytical data |
|---|---|---|
| 98 | 8-(cyclobutylmethoxy)-N-[2-(2-hydroxyethoxy)ethyl]-2-methylimidazo[1,2-a]pyridine-3-carboxamide<br><br>(49% of theory) | LC-MS (Method 1): $R_t$ = 0.65 min<br>MS (ESpos): m/z = 348.1 (M + H)$^+$ |
| 99 | 8-(cyclobutylmethoxy)-N-[2-(1-hydroxycyclohexyl)ethyl]-2-methylimidazo[1,2-a]pyridine-3-carboxamide<br><br>(61% of theory) | LC-MS (Method 2): Rt = 0.98 min<br>MS (ESpos): m/z = 386.2 (M + H)+ |

Representative Working Procedure 2

Amide Formation Using TBTU as Coupling Agent (Variante B)

1 equivalent of the carboxylic acid to be coupled, 1.1-1.5 equivalents of (benzotriazol-1-yloxy)bisdimethylaminomethylium fluoroborate (TBTU) and 3-6 equivalents of 4-methylmorpholine were initially charged in DMF or dichloromethane (about 0.1-0.2 M based on the carboxylic acid to be coupled), 1.1 to 1.5 equivalents of the amine to be coupled were then added and the mixture was stirred at room temperature overnight.

Exemplary work-up of the reaction mixture: Water was added to the reaction solution, and the precipitate formed was stirred for another 0.5-1.0 h, filtered off, washed thoroughly with water and dried under high vacuum overnight. Alternatively, the crude reaction mixture was concentrated directly, purified further by preparative HPLC and dried under high vacuum overnight.

Example 100 rac-8-[(2,6-Difluorobenzyl)oxy]-2-methyl-N-(4,4,4-trifluoro-1-hydroxybutan-2-yl)imidazo[1,2-a]-pyridine-3-carboxamide trifluoroacetate

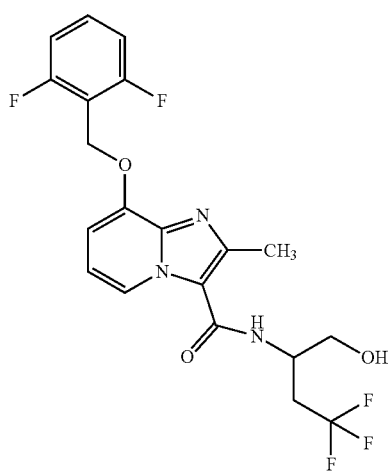 [SMILES: Cc1nc2c(OCc3c(F)cccc3F)cccn2c1C(=O)NC(CO)CC(F)(F)F]

54 mg (0.17 mmol) of 8-[(2,6-difluorobenzyl)oxy]-2-methylimidazo[1,2-a]pyridine-3-carboxylic acid, 59 mg (0.19 mmol) of (benzotriazol-1-yloxy)bisdimethylaminomethylium fluoroborate (TBTU) and 85 mg (0.84 mmol) of 4-methylmorpholine were initially charged in 1.0 ml of dichloromethane. After 10 min at RT, 27 mg (0.19 mmol) of 2-amino-4,4,4-trifluorobutan-1-ol were added and the mixture was stirred at room temperature overnight. The reaction solution was concentrated and purified by preparative HPLC (RP18 column, mobile phase: acetonitrile/water gradient with addition of 0.1% TFA). This gave 48 mg of the target compound (49% of theory, purity 96%).

LC-MS (Method 1): $R_t$=0.82 min
MS (ESpos): m/z=444 (M−TFA+H)$^+$
$^1$H NMR (400 MHz, DMSO-d$_6$): δ=2.50 (s, 3H), 2.55-2.72 (m, 2H), 3.38-3.62 (m, 2H), 4.29-4.40 (m, 1H), 5.39 (s, 2H), 7.10-7.38 (m, 4H), 7.60 (quint, 1H), 8.13 (br s, 1H), 8.60 (d, 1H).

The example compounds shown in Table 10 were prepared analogously to Example Compound 100 by reacting 8-[(2,6-difluorobenzyl)oxy]-2-methylimidazo[1,2-a]pyridine-3-carboxylic acid with the appropriate commercially available amines in DMF or dichloromethane under the reaction conditions described in the Representative Working Procedure 2:

TABLE 10

| Example | IUPAC name/structure (yield) | Analytical data |
|---|---|---|
| 101 | rac-8-[(2,6-difluorobenzyl)oxy]-2-methyl-N-(5,5,5-trifluoro-1-hydroxypentan-2-yl)-imidazo[1,2-a]pyridine-3-carboxamide trifluoroacetate 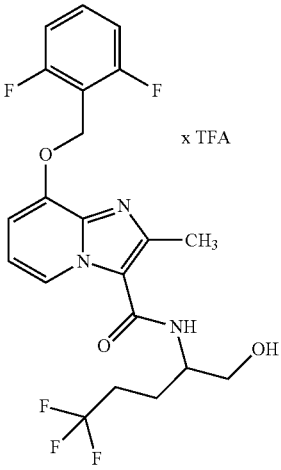 [SMILES: Cc1nc2c(OCc3c(F)cccc3F)cccn2c1C(=O)NC(CO)CCC(F)(F)F ; "x TFA"] (71% of theory) | LC-MS (Method 1): $R_t$ = 0.85 min<br>MS (ESpos): m/z = 458 (M−TFA + H)$^+$<br>$^1$H NMR (400 MHz, DMSO-d$_6$):<br>δ = 1.69-1.79 (m, 1H), 1.83-1.98 (m, 1H), 2.29-2.45 (m, 2H), 2.50 (s, 3H), 3.46-3.60 (m, 2H), 4.00-4.12 (m, 1H), 5.40 (s, 2H), 7.18-7.28 (m, 3H), 7.38 (br s, 1H), 7.60 (quint, 1H), 8.00 (br s, 1H), 8.62 (d, 1H). |
| 102 | rac-8-[(2,6-difluorobenzyl)oxy]-2-methyl-N-(6,6,6-trifluoro-1-hydroxyhexan-2-yl)-imidazo[1,2-a]pyridine-3-carboxamide trifluoroacetate 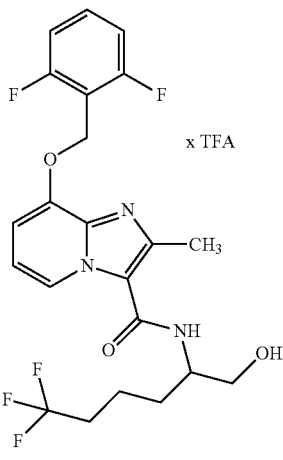 [SMILES: Cc1nc2c(OCc3c(F)cccc3F)cccn2c1C(=O)NC(CO)CCCC(F)(F)F ; "x TFA"] (36% of theory) | LC-MS (Method 1): $R_t$ = 0.88 min<br>MS (ESpos): m/z = 472 (M−TFA + H)$^+$<br>$^1$H NMR (400 MHz, DMSO-d$_6$):<br>δ = 1.51-1.79 (m, 4H), 2.19-2.40 (m, 2H), 2.50 (s, 3H), 3.44-3.59 (m, 2H), 3.98-4.09 (m, 1H), 5.40 (s, 2H), 7.18-7.28 (m, 3H), 7.35 (br s, 1H), 7.60 (quint, 1H), 7.98 (br s, 1H), 8.59 (d, 1H). |

TABLE 10-continued

| Example | IUPAC name/structure (yield) | Analytical data |
|---|---|---|
| 103 | rac-8-[(2,6-difluorobenzyl)oxy]-N-[1-(4-fluorophenyl)-2-hydroxyethyl]-2-methylimidazo-[1,2-a]pyridine-3-carboxamide trifluoroacetate<br>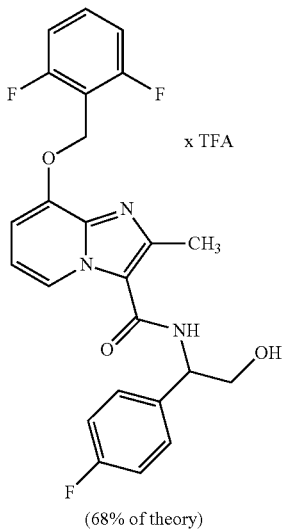<br>(68% of theory) | LC-MS (Method 1): $R_t$ = 0.86 min<br>MS (ESpos): m/z = 456 (M-TFA + H)$^+$<br>$^1$H NMR (400 MHz, DMSO-d$_6$):<br>δ = 2.61 (s, 3H), 3.70 (d, 2H), 5.10 (q, 1H), 5.38 (s, 2H), 7.00-7.32 (m, 6H), 7.48 (dd, 2H), 7.59 (quint, 1H), 8.41 (br s, 1H), 8.58 (d, 1H). |
| 104 | rac-8-[(2,6-difluorobenzyl)oxy]-N-[(1R)-2-hydroxy-1-phenylethyl]-2-methylimidazo[1,2-a]pyridine-3-carboxamide trifluoroacetate<br>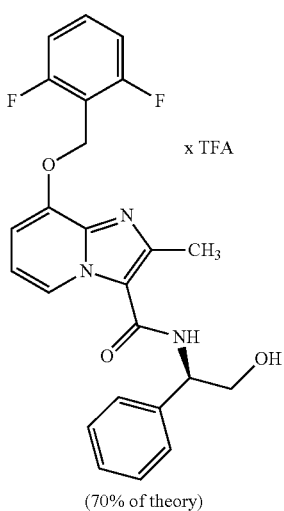<br>(70% of theory) | LC-MS (Method 2): $R_t$ = 0.94 min<br>MS (ESpos): m/z = 456 (M-TFA + H)$^+$<br>$^1$H NMR (400 MHz, DMSO-d$_6$):<br>δ = 2.61 (s, 3H), 3.70 (d, 2H), 5.11 (q, 1H), 5.39 (s, 2H), 7.12-7.30 (m, 4H), 7.33 (t, 2H), 7.40 (d, 2H), 7.60 (quint, 1H), 8.48-8.61 (m, 2H). |

TABLE 10-continued

| Example | IUPAC name/structure (yield) | Analytical data |
|---|---|---|
| 105 | rac-N-[1-(4-chlorophenyl)-2-hydroxyethyl]-8-[(2,6-difluorobenzyl)oxy]-2-methylimidazo[1,2-a]pyridine-3-carboxamide trifluoroacetate<br />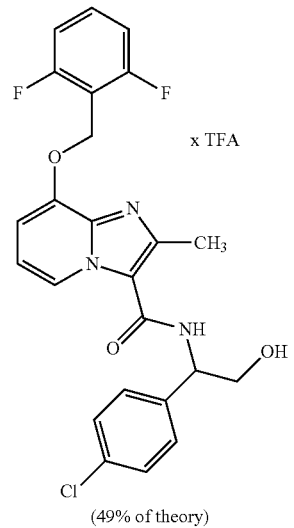<br />(49% of theory) | LC-MS (Method 3): $R_t$ = 1.85 min<br />MS (ESpos): m/z = 472 (M-TFA + H)$^+$<br />$^1$H NMR (400 MHz, DMSO-d$_6$):<br />δ = 2.61 (s, 3H), 3.70 (d, 2H), 5.10 (q, 1H), 5.40 (s, 2H), 7.15-7.28 (m, 3H), 7.31-48 (m, 4H), 7.60 (quint, 1H), 8.52-8.63 (m, 2H). |
| 106 | rac-8-[(2,6-difluorobenzyl)oxy]-2-methyl-N-(3,3,3-trifluoro-2-hydroxypropyl)imidazo[1,2-a]pyridine-3-carboxamide trifluoroacetate<br />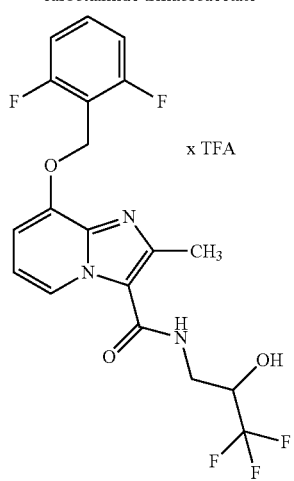<br />(70% of theory) | LC-MS (Method 1): $R_t$ = 0.82 min<br />MS (ESpos): m/z = 430 (M-TFA + H)$^+$<br />$^1$H NMR (400 MHz, DMSO-d$_6$):<br />δ = 2.50 (s, 3H), 3.60-3.70 (m, 2H), 4.20-4.30 (m, 1H), 5.38 (s, 2H), 6.60 (br s, 1H), 7.15-7.28 (m, 3H), 7.33 (br s, 1H), 7.60 (quint, 1H), 8.30 (br s, 1H), 8.59 (d, 1H). |

Example 107 ent-8-[(2,6-Difluorobenzyl)oxy]-N-[1-(4-fluorophenyl)-2-hydroxyethyl]-2-methylimidazo[1,2-a]-pyridine-3-carboxamide (enantiomer B)

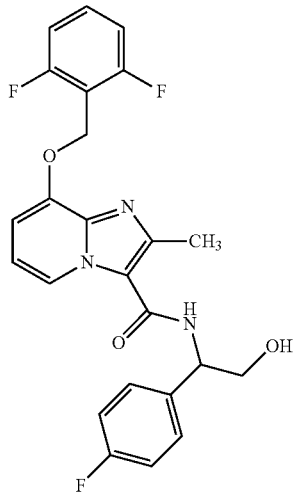 [SMILES: Cc1nc2c(OCc3c(F)cccc3F)cccn2c1C(=O)NC(CO)c1ccc(F)cc1]

112 mg of Example 103 were dissolved in dichloromethane and a few drops of methanol and washed with saturated sodium bicarbonate solution and with water. The organic phase was concentrated (98 mg) and separated into the enantiomers by preparative separation on a chiral phase [column: Daicel Chiralpak AD-H, 5 µm, 250×20 mm, mobile phase: 50% isohexane, 50% ethanol+0.2% diethylamine, flow rate 15 ml/min; 40° C., detection: 220 nm].

Yield: 44 mg (99% pure, >99% ee)

Enantiomer B: $R_f$=22.01 min [Chiralpak AD-H, 5 µm, 250×4.6 mm; mobile phase: 50% isohexane, 50% ethanol+0.2% diethylamine; flow rate 1.0 ml/min; 40° C.; detection: 235 nm].

Example 108 ent-N-[1-(4-Chlorophenyl)-2-hydroxyethyl]-8-[(2,6-difluorobenzyl)oxy]-2-methylimidazo[1,2-a]-pyridine-3-carboxamide (enantiomer A)

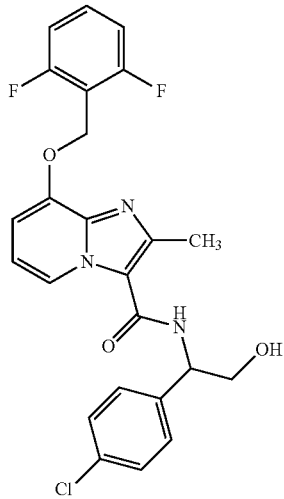 [SMILES: Cc1nc2c(OCc3c(F)cccc3F)cccn2c1C(=O)NC(CO)c1ccc(Cl)cc1]

83 mg of Example 105 were dissolved in ethyl acetate and washed with saturated sodium bicarbonate solution and with saturated sodium chloride solution. The organic phase was dried over sodium sulphate, concentrated (53 mg) and separated into the enantiomers by preparative separation on a chiral phase [column: Daicel Chiralpak AD-H, 5 µm, 250×20 mm, mobile phase: 50% isohexane, 50% ethanol+0.2% diethylamine, flow rate 15 ml/min; 30° C., detection: 220 nm].

Yield: 13 mg (99% pure, >99% ee)

Enantiomer A: $R_f$=6.44 min [Chirakcel OD-H, 5 µm, 250×4.6 mm; mobile phase: 50% isohexane, 50% isopropanol+0.2% diethylamine; flow rate 1.0 ml/min; 40° C.; detection: 235 nm].

Example 109 ent-8-[(2,6-Difluorobenzyl)oxy]-2-methyl-N-(3,3,3-trifluoro-2-hydroxypropyl)imidazo[1,2-a]-pyridine-3-carboxamide (enantiomer B)

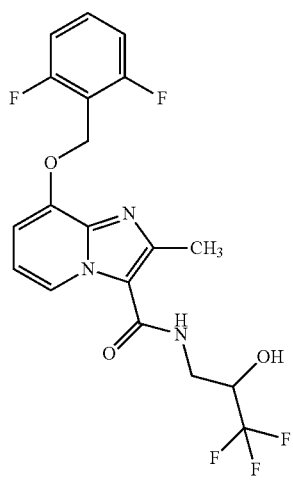 [SMILES: Cc1nc2c(OCc3c(F)cccc3F)cccn2c1C(=O)NCC(O)C(F)(F)F]

108 mg of Example 106 were dissolved in dichloromethane and a few drops of methanol and washed with saturated sodium bicarbonate solution and with water. The organic phase was dried over sodium sulphate, concentrated (73 mg) and separated into the enantiomers by preparative separation on a chiral phase [column: Daicel Chiralpak AD-H, 5 µm, 250×20 mm; mobile phase: 50% isohexane, 50% isopropanol+0.2% diethylamine; flow rate 15 ml/min; temperature: 30° C.; detection: 220 nm].

Yield: 31 mg (99% pure, >98.5% ee)

Enantiomer B: $R_f$=6.50 min [Chiralpak AD-H, 5 µm, 250×4.6 mm; mobile phase: 50% isohexane, 50% isopropanol+0.2% diethylamine; flow rate 1.0 ml/min; 40° C.; detection: 235 nm].

Example 110 rac-8-[(2,6-Difluorobenzyl)oxy]-2-methyl-N-(1,1,1-trifluoro-3-hydroxypropan-2-yl)imidazo[1,2-a]pyridine-3-carboxamide

Example 111 rac-8-[(2,6-Difluorobenzyl)oxy]-N-[1-(3,4-difluorophenyl)-2-hydroxyethyl]-2-methylimidazo[1,2-a]pyridine-3-carboxamide

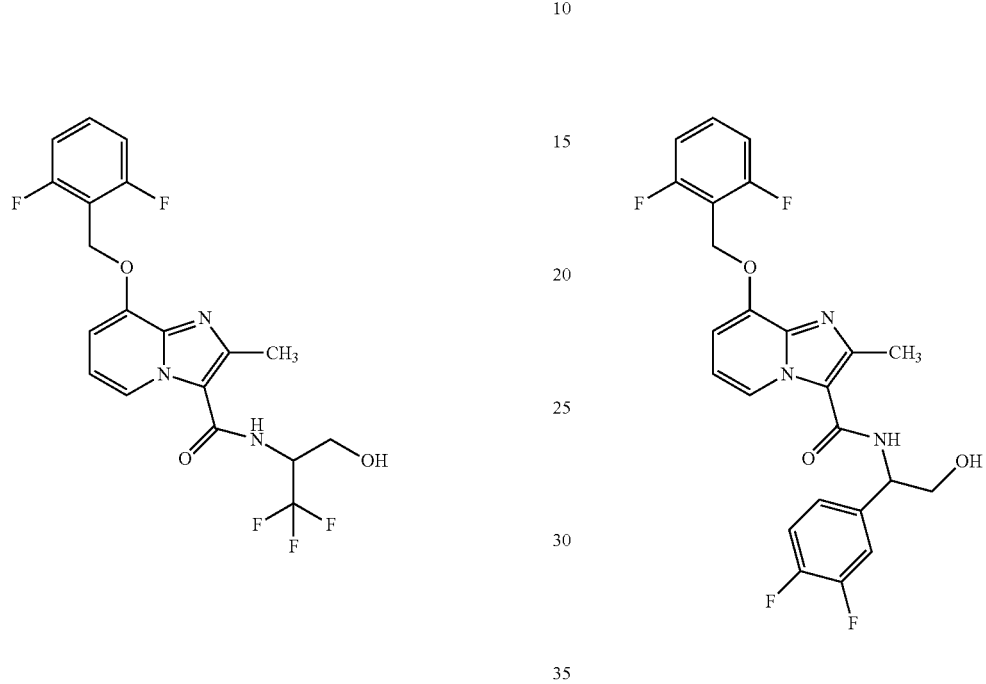

0 mg (0.16 mmol) of 8-[(2,6-difluorobenzyl)oxy]-2-methylimidazo[1,2-a]pyridine-3-carboxylic acid, 55 mg (0.17 mmol) of (benzotriazol-1-yloxy)bisdimethylaminomethylium fluoroborate (TBTU) and 79 mg (0.79 mmol) of 4-methylmorpholine were initially charged in 1.0 ml of dichloromethane. After 10 min at RT, 28 mg (0.17 mmol) of 2-amino-4,4,4-trifluorobutan-1-ol were added and the mixture was stirred at room temperature overnight. 1 ml of DMF and 50 mg (0.39 mmol) of 2-amino-4,4,4-trifluorobutan-1-ol were then added, and the mixture was stirred at 50° C. for 8 h. Another 50 mg (0.39 mmol) of 2-amino-4,4,4-trifluorobutan-1-ol were added, and the mixture was stirred in a microwave at 80° C. for 0.5 h. Another 50 mg (0.39 mmol) of 2-amino-4,4,4-trifluorobutan-1-ol were then added, and the mixture was stirred in a microwave at 80° C. for 1 h. The reaction solution was concentrated and purified by preparative HPLC (RP18 column, mobile phase: acetonitrile/water gradient with addition of 0.1% TFA). All product-containing fractions were combined and concentrated. The residue was dissolved in dichloromethane and washed with saturated aqueous sodium bicarbonate solution. This gave 17 mg of the target compound (25% of theory, purity 100%).

LC-MS (Method 1): $R_t$=0.85 min

MS (ESpos): m/z=430 (M+H)$^+$ $^1$H NMR (400 MHz, DMSO-$d_6$): δ=2.50 (s, 3H), 3.70-3.86 (m, 2H), 4.78-4.88 (m, 1H), 5.28 (t, 1H), 5.32 (s, 2H), 6.98 (t, 1H), 7.06 (d, 1H), 7.23 (t, 2H), 7.60 (quint, 1H), 8.29 (d, 1H), 8.50 (d, 1H).

100 mg (0.31 mmol) of 8-[(2,6-difluorobenzyl)oxy]-2-methylimidazo[1,2-a]pyridine-3-carboxylic acid, 111 mg (0.35 mmol) of (benzotriazol-1-yloxy)bisdimethylaminomethylium fluoroborate (TBTU) and 159 mg (1.57 mmol) of 4-methylmorpholine were initially charged in 2.0 ml of dichloromethane. After 10 min at RT, 142 mg (0.35 mmol) of 2-amino-2-(3,4-difluorophenyl)-ethanol were added and the mixture was stirred at room temperature overnight. The reaction solution was concentrated, and acetonitrile/methanol/water was added. A solid precipitated out, and this solid was filtered off and purified by chromatography on silica gel (mobile phase: dichloromethane:THF=10:1→5:1). The combined product fractions were concentrated and then triturated with acetonitrile, and the solid was filtered off and washed with methanol. This gave 39 mg of the target compound (26% of theory, purity 95%). After some time, the filtrate produced more solid; this gave another 5 mg of the target compound (3.3% of theory, purity 99%).

LC-MS (Method 1): $R_t$=0.91 min

MS (ESpos): m/z=474 (M+H)$^+$ $^1$H NMR (400 MHz, DMSO-$d_6$): δ=2.59 (s, 3H), 3.70 (t, 2H), 5.04-5.13 (m, 2H), 5.30 (s, 2H), 6.90 (t, 1H), 7.00 (d, 1H), 7.18-7.29 (m, 3H), 7.39 (q, 1H), 7.42-7.53 (m, 1H), 7.59 (quint, 1H), 8.12 (d, 1H), 8.52 (d, 1H).

Example 112 ent-8-[(2,6-Difluorobenzyl)oxy]-N-[1-(3,4-difluorophenyl)-2-hydroxyethyl]-2-methylimidazo[1,2-a]pyridine-3-carboxamide (enantiomer B)

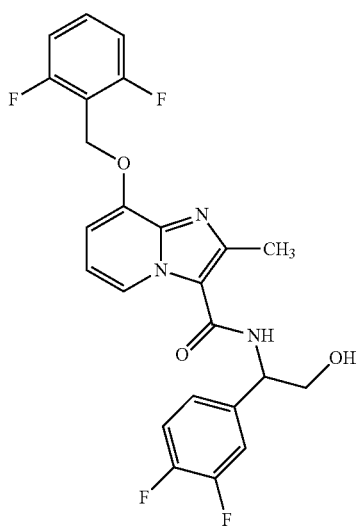 [SMILES: Cc1nc2c(OCc3c(F)cccc3F)cccn2c1C(=O)NC(CO)c1ccc(F)c(F)c1]

Example 111 (130 mg) was separated into the enantiomers by preparative separation on a chiral phase [column: Daicel Chiralpak AD-H, 5 μm, 250×20 mm, mobile phase: 25% isohexane, 75% ethanol+0.2% diethylamine, flow rate 15 ml/min; 45° C., detection: 220 nm]. The product fractions were concentrated, taken up again in water/acetonitrile and freeze-dried.

Yield: 18 mg (99% pure, >99% ee)

Enantiomer B: $R_t$=9.32 min [Chiralpak AD-H, 5 μm, 250× 4.6 mm; mobile phase: 25% isohexane, 75% ethanol+0.2% diethylamine; flow rate 1.0 ml/min; 45° C.; detection: 235 nm].

Example 113 rac-8-[(2,6-Difluorobenzyl)oxy]-2-methyl-N-(4,4,4-trifluoro-1-hydroxybutan-2-yl)imidazo[1,2-a]-pyridine-3-carboxamide

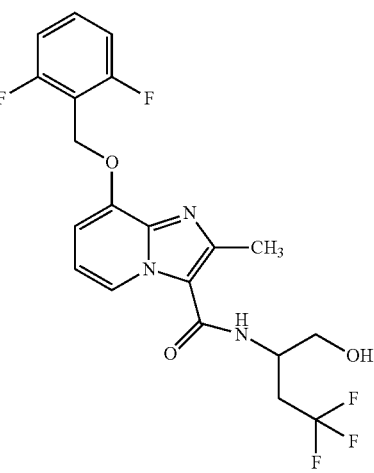

330 mg (1.04 mmol) of 8-[(2,6-difluorobenzyl)oxy]-2-methylimidazo[1,2-a]pyridine-3-carboxylic acid, 399 mg (1.24 mmol) of (benzotriazol-1-yloxy)bisdimethylaminomethylium fluoroborate (TBTU) and 524 mg (5.18 mmol) of 4-methylmorpholine were initially charged in 6.6 ml of DMF. After 10 min at RT, 371 mg (1.56 mmol, purity about 60%) of 2-amino-4,4,4-trifluorobutan-1-ol were added and the mixture was stirred at room temperature overnight. About 200 ml of water were added to the reaction solution, and the precipitate formed was stirred for another 30 min, filtered off, washed thoroughly with water dried under high vacuum overnight. This gave 439 mg of the target compound (96% of theory, purity 100%).

LC-MS (Method 3): $R_t$=1.62 min

MS (ESpos): m/z=444 (M+H)$^+$ $^1$H NMR (400 MHz, DMSO-d$_6$): δ=2.50 (s, 3H), 2.55-2.72 (m, 2H), 3.38-3.47 (m, 1H), 3.51-3.62 (m, 1H), 4.29-4.40 (m, 1H), 5.12 (t, 1H), 5.30 (s, 2H), 6.92 (t, 1H), 7.02 (d, 1H), 7.23 (t, 2H), 7.59 (quint, 1H), 7.80 (d, 1H), 8.56 (d, 1H).

The example compounds shown in Table 11 were prepared analogously to Example 113 by reacting 8-[(2,6-difluorobenzyl)oxy]-2-methylimidazo[1,2-a]pyridine-3-carboxylic acid with the appropriate amines in DMF or dichloromethane under the reaction conditions described in the Representative Working Procedure 2:

TABLE 11

| Example | IUPAC name/structure (yield) | Analytical data |
|---|---|---|
| 114 | rac-8-[(2,6-difluorobenzyl)oxy]-2-methyl-N-(6,6,6-trifluoro-1-hydroxyhexan-2-yl)imidazo[1,2-a]pyridine-3-carboxamide<br>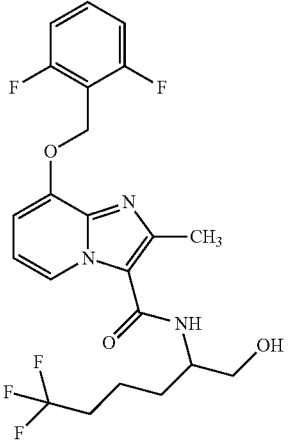 [SMILES: Cc1nc2c(OCc3c(F)cccc3F)cccn2c1C(=O)NC(CO)CCCC(F)(F)F]<br>(76% of theory) | LC-MS (Method 1): $R_t$ = 0.88 min<br>MS (ESpos): m/z = 472 (M + H)$^+$<br>$^1$H NMR (400 MHz, DMSO-d$_6$):<br>δ = 1.51-1.79 (m, 4H), 2.19-2.40 (m, 2H), 2.50 (s, 3H), 3.41-3.57 (m, 2H), 3.96-4.08 (m, 1H), 4.82 (t, 1H), 5.30 (s, 2H), 6.91 (t, 1H), 6.99 (d, 1H), 7.22 (t, 2H), 7.56-7.62 (m, 2H), 8.52 (d, 1H). |
| 115 | 8-{[(2,6-difluorophenyl)($^2$H$_2$)methyl]oxy}-N-[(2R)-1-hydroxyhexan-2-yl]-2-methylimidazo[1,2-a]pyridine-3-carboxamide<br>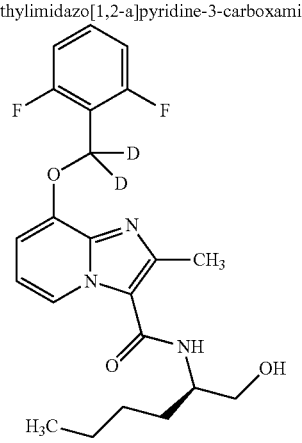<br>(90% of theory) | LC-MS (Method 3): $R_t$ = 1.66 min<br>MS (ESpos): m/z = 420 (M + H)$^+$<br>$^1$H NMR (400 MHz, DMSO-d$_6$):<br>δ = 0.88 (t, 3H), 1.22-1.51 (m, 5H), 1.59-1.70 (m, 1H), 2.50 (s, 3H), 3.39-3.54 (m, 2H), 3.93-4.04 (m, 1H), 4.74 (t, 1H), 6.91 (t, 1H), 6.99 (d, 1H), 7.22 (t, 2H), 7.50-7.63 (m, 2H), 8.52 (d, 1H). |
| 116 | 8-[(2,6-difluorobenzyl)oxy]-N-[2-(1-hydroxycyclohexyl)ethyl]-2-methylimidazo[1,2-a]pyridine-3-carboxamide<br>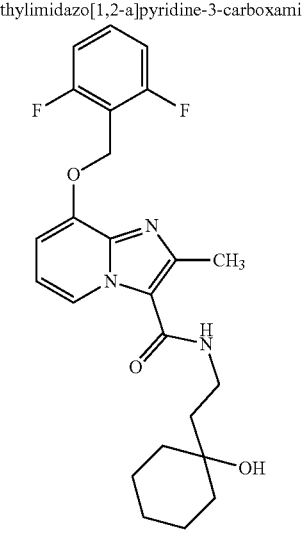<br>(46% of theory) | LC-MS (Method 1): $R_t$ = 0.91 min<br>MS (ESpos): m/z = 444 (M + H)$^+$<br>$^1$H NMR (400 MHz, DMSO-d$_6$):<br>δ = 1.20-1.63 (m, 10H), 1.68 (t, 2H), 2.50 (s, 3H), 3.41 (q, 2H), 4.23 (s, 1H), 5.30 (s, 2H), 6.91 (t, 1H), 7.00 (d, 1H), 7.23 (t, 2H), 7.59 (quintet, 1H), 7.82 (t, 1H), 8.69 (d, 1H). |

TABLE 11-continued

| Example | IUPAC name/structure (yield) | Analytical data |
|---|---|---|
| 117 | 8-[(2,6-difluorobenzyl)oxy]-N-[2-(1-hydroxycyclopentyl)ethyl]-2-methylimidazo[1,2-a]pyridine-3-carboxamide 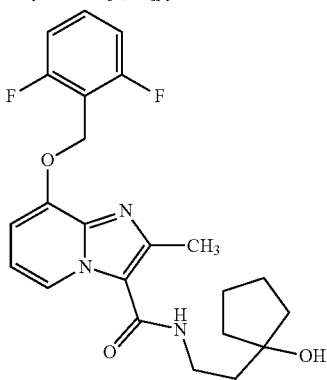 (83% of theory) | LC-MS (Method 1): $R_t$ = 0.84 min<br>MS (ESpos): m/z = 430 (M+H)$^+$<br>$^1$H NMR (400 MHz, DMSO-d$_6$):<br>δ = 1.43-1.76 (m, 8H), 1.78 (t, 2H), 2.50 (s, 3H), 3.44 (q, 2H), 4.31 (s, 1H), 5.30 (s, 2H), 6.92 (t, 1H), 7.00 (d, 1H), 7.23 (t, 2H), 7.59 (quintet, 1H), 7.86 (t, 1H), 8.69 (d, 1H). |
| 118 | 8-[(2,6-difluorobenzyl)oxy]-N-[(2R)-1-hydroxypropan-2-yl]-2-methylimidazo[1,2-a]-pyridine-3-carboxamide 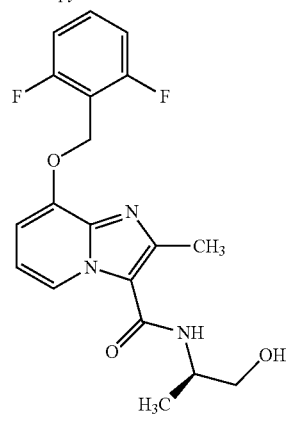 (93% of theory) | LC-MS (Method 1): $R_t$ = 0.68 min<br>MS (ESpos): m/z = 376 (M + H)$^+$<br>$^1$N NMR (400 MHz, DMSO-d$_6$):<br>δ = 1.18 (d, 3H), 2.50 (s, 3H), 3.37-3.54 (m, 2H), 4.00-4.10 (m, 1H), 4.78 (t, 1H), 5.30 (s, 2H), 6.90 (t, 1H), 6.99 (d, 1H), 7.22 (t, 2H), 7.50-7.63 (m, 2H), 8.58 (d, 1H). |
| 119 | rac-8-[(2,6-difluorobenzyl)oxy]-N-[2-hydroxy-1-(pyridin-2-yl)ethyl]-2-methylimidazo[1,2-a]-pyridine-3-carboxamide 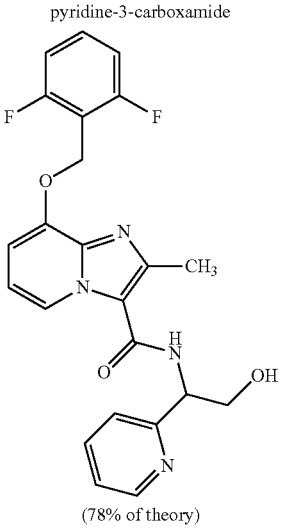 (78% of theory) | LC-MS (Method 1): $R_t$ = 0.72 min<br>MS (ESpos): m/z = 439 (M + H)$^+$<br>$^1$H NMR (400 MHz, DMSO-d$_6$):<br>δ = 2.62 (s, 3H), 3.75-3.88 (m, 2H), 5.01 (t, 1H), 5.19 (q, 1H), 5.32 (s, 2H), 6.92 (t, 1H), 7.03 (d, 1H), 7.19-7.32 (m, 3H), 7.48 (d, 1H), 7.59 (quintet, 1H), 7.79 (t, 1H), 8.09 (d, 1H), 8.58 (d, 1H) 8.68 (d, 1H). |

TABLE 11-continued

| Example | IUPAC name/structure (yield) | Analytical data |
|---|---|---|
| 120 | rac-8-[(2,6-difluorobenzyl)oxy]-N-{2-hydroxy-1-[4-(methylsulphonyl)phenyl]ethyl}-2-methylimidazo[1,2-a]pyridine-3-carboxamide[2]<br><br>(58% of theory) | LC-MS (Method 2): $R_t$ = 0.87 min<br>MS (ESpos): m/z = 516 (M + H)⁺<br>¹H NMR (400 MHz, DMSO-$d_6$):<br>δ = 2.62 (s, 3H), 3.22 (s, 3H), 3.74 (t, 2H), 5.10-5.19 (m, 2H), 5.31 (s, 2H), 6.90 (t, 1H), 7.01 (d, 1H), 7.22 (t, 2H), 7.59 (quintet, 1H), 7.69 (d, 2H), 7.90 (d, 2H), 8.26 (d, 1H), 8.53 (d, 1H). |

[1] Work-up and purification: The mixture was extracted three times with ethyl acetate and the combined organic phases were washed with saturated sodium chloride solution, dried over sodium sulphate, filtered and concentrated. The crude product was purified on a silica gel cartridge (mobile phase: dichloromethane:methanol = 40:1 → 10:1).
[2] The crude product obtained was re-purified by silica gel chromatography (mobile phase: dichloromethane:ethanol = 20:1).

Example 121 ent-8-[(2,6-Difluorobenzyl)oxy]-2-methyl-N-(4,4,4-trifluoro-1-hydroxybutan-2-yl)imidazo[1,2-a]-pyridine-3-carboxamide (enantiomer B)

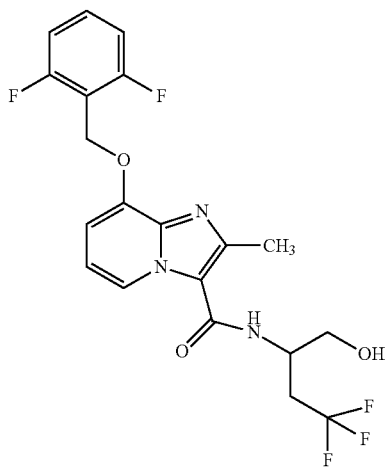 [SMILES: Cc1nc2c(OCc3c(F)cccc3F)cccn2c1C(=O)NC(CO)CC(F)(F)F]

Example 113 (148 mg) was separated into the enantiomers by preparative separation on a chiral phase [column: Daicel Chiralpak AD-H, 5 μm, 250×20 mm; mobile phase: 50% isohexane, 50% ethanol+0.2% diethylamine; flow rate 15 ml/min; 25° C.; detection: 220 nm].

Yield: 64 mg (98% pure, >99% ee)

Enantiomer B: $R_t$=9.71 min [Chiralpak AD-H, 5 μm, 250× 4.6 mm; mobile phase: 50% isohexane, 50% ethanol+0.2% diethylamine; flow rate 1.0 ml/min; 40° C.; detection: 235 nm].

Example 122 ent-8-[(2,6-Difluorobenzyl)oxy]-2-methyl-N-(5,5,5-trifluoro-1-hydroxypentan-2-yl)imidazo[1,2-a]-pyridine-3-carboxamide (enantiomer B)

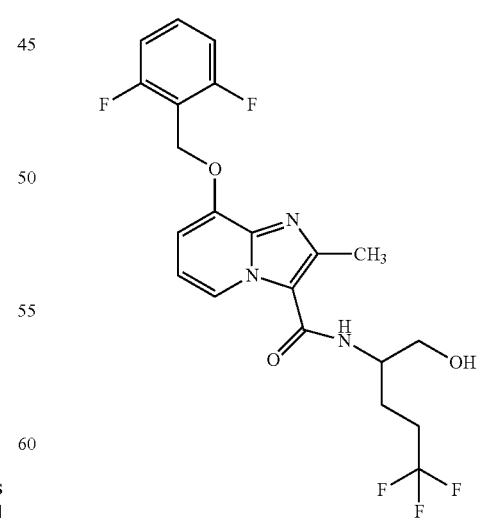

Example 101 (93 mg) was separated into the enantiomers by preparative separation on a chiral phase [column: Daicel Chiralpak AD-H, 5 μm, 250×20 mm, mobile phase: 50% isohexane, 50% ethanol+0.2% diethylamine, flow rate 15 ml/min; 30° C., detection: 220 nm].

Yield: 36 mg (99% pure, >99% ee)

Enantiomer B: $R_t$=8.38 min [Chiralpak AD-H, 5 µm, 250×4.6 mm; mobile phase: 50% isohexane, 50% ethanol+0.2% diethylamine; flow rate 1.0 ml/min; 40° C.; detection: 235 nm].

Example 123 ent-8-[(2,6-Difluorobenzyl)oxy]-2-methyl-N-(6,6,6-trifluoro-1-hydroxyhexan-2-yl)imidazo[1,2-a]-pyridine-3-carboxamide (enantiomer B)

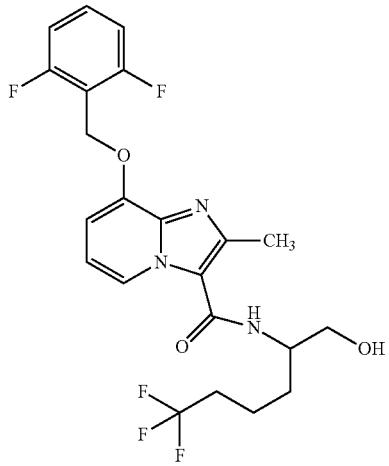 [SMILES: Cc1nc2c(OCc3c(F)cccc3F)cccn2c1C(=O)NC(CO)CCCC(F)(F)F]

Example 114 (157 mg) was separated into the enantiomers by preparative separation on a chiral phase [column: Daicel Chiralpak AD-H, 5 µm, 250×20 mm, mobile phase: 50% isohexane, 50% ethanol+0.2% diethylamine, flow rate 15 ml/min; 25° C., detection: 220 nm].

Yield: 60 mg (99% pure, >99% ee)

Enantiomer B: $R_t$=10.52 min [Chiralpak AD-H, 5 µm, 250×4.6 mm; mobile phase: 50% isohexane, 50% ethanol+0.2% diethylamine; flow rate 1.0 ml/min; 40° C.; detection: 235 nm].

Example 124 rac-8-[(2,6-Difluorobenzyl)oxy]-N-[2-hydroxy-1-(pyridin-3-yl)ethyl]-2-methylimidazo[1,2-a]-pyridine-3-carboxamide

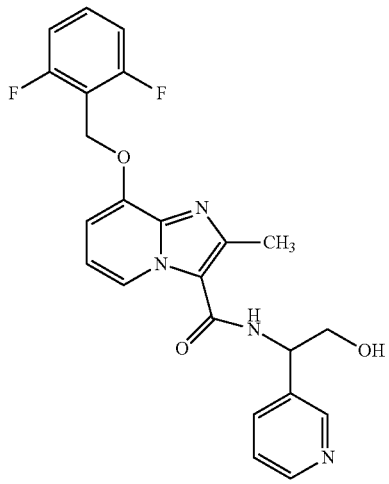 [SMILES: Cc1nc2c(OCc3c(F)cccc3F)cccn2c1C(=O)NC(CO)c1cccnc1]

150 mg (0.47 mmol) of 8-[(2,6-difluorobenzyl)oxy]-2-methylimidazo[1,2-a]pyridine-3-carboxylic acid, 227 mg (0.71 mmol) of (benzotriazol-1-yloxy)bisdimethylaminomethylium fluoroborate (TBTU) and 238 mg (2.36 mmol) of 4-methylmorpholine were initially charged in 3 ml of DMF. After 10 min at RT, 98 mg (0.71 mmol) of 2-amino-2-(pyridin-3-yl)ethanol were added and the mixture was stirred at room temperature overnight. About 25 ml of water were added to the reaction solution and the precipitate formed was stirred for another 30 min, filtered off, washed thoroughly with water and dried under high vacuum overnight. The crude product was purified by silica gel chromatography (mobile phase: dichloromethane:methanol gradient). The product fractions were concentrated and stirred with acetonitrile. The solid obtained was filtered off and dried. This gave 40 mg of the target compound (20% of theory, purity 100%).

LC-MS (Method 1): $R_t$=0.65 min

MS (ESpos): m/z=439 (M+H)$^+$ $^1$H NMR (400 MHz, DMSO-$d_6$): δ=2.58 (s, 3H), 3.70-3.80 (m, 2H), 5.08-5.15 (m, 2H), 5.30 (s, 2H), 6.90 (t, 1H), 7.00 (d, 1H), 7.22 (t, 2H), 7.37 (t, 1H), 7.59 (quint, 1H), 7.82 (d, 1H), 8.23 (d, 1H), 8.47 (d, 1H), 8.53 (d, 1H), 8.64 (s, 1H).

Example 125

8-[(2,6-Difluorobenzyl)oxy]-N-[1-(hydroxymethyl)cyclobutyl]-2-methylimidazo[1,2-a]pyridine-3-carboxamide

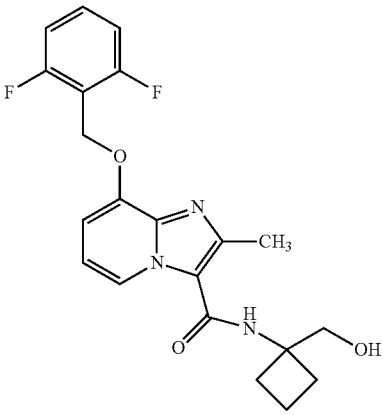 [SMILES: Cc1nc2c(OCc3c(F)cccc3F)cccn2c1C(=O)NC1(CO)CCC1]

75 mg (0.24 mmol) of 8-[(2,6-difluorobenzyl)oxy]-2-methylimidazo[1,2-a]pyridine-3-carboxylic acid, 91 mg (0.28 mmol) of (benzotriazol-1-yloxy)bisdimethylaminomethylium fluoroborate (TBTU) and 143 mg (1.41 mmol) of 4-methylmorpholine were initially charged in 1.6 ml of DMF. After 10 min at RT, 79 mg (0.35 mmol, purity about 45%) of (1-aminocyclobutyl)methanol were added and the mixture was stirred at room temperature overnight. Another 53 mg (0.24 mmol, purity about 45%) of (1-aminocyclobutyl)methanol were then added to the reaction solution. The reaction mixture was stirred at room temperature overnight. Water was then added, and the mixture was extracted three times with dichloromethane. The combined organic phases were washed with water, dried over sodium bisulphate, filtered and concentrated. The crude product was purified by preparative HPLC (RP18 column, mobile phase: acetonitrile/water gradient with addition of 0.1% TFA). The appropriate fractions were substantially freed from acetonitrile, dichloromethane was added to the aqueous phase and the mixture was washed with saturated aqueous sodium bicarbonate solution. The organic phase was dried over sodium sulphate, filtered and concentrated. This gave 42 mg of the target compound (43% of theory, purity 98%).

LC-MS (Method 1): $R_t$=0.75 min

MS (ESpos): m/z=402 (M+H)$^+$ $^1$H NMR (400 MHz, DMSO-d$_6$): δ=1.71-1.93 (m, 2H), 2.09-2.19 (m, 2H), 2.23-2.34 (m, 2H), 2.50 (s, 3H), 3.68 (d, 2H), 4.90 (t, 1H), 5.30 (s, 2H), 6.90 (t, 1H), 6.98 (d, 1H), 7.23 (t, 2H), 7.59 (quint, 1H), 7.71 (s, 1H), 8.56 (d, 1H).

General Working Procedure 3: Amide Formation Using HATU as Coupling Agent.

1 equivalent of the carboxylic acid to be coupled, 1.3 equivalents of O-(7-azabenzotriazol-1-yl)-N,N,N'N'-tetramethyluronium hexafluorophosphate (HATU) and 3 to 4 equivalents of N,N-diisopropylethylamine were initially charged in DMF (about 0.2 M based on the carboxylic acid to be coupled), 1.2 to 1.5 equivalents of the amine to be coupled were added and the mixture was stirred at RT overnight. In individual cases where complete conversion of the carboxylic acid had still not been achieved after 16 h (base, for example on LC-MS analysis), additional quantities of HATU and amine to be coupled were added and stirring of the reaction was continued at RT.

Exemplary work-up of the reaction mixture: Water was added to the reaction solution and the precipitate formed was stirred for another 30 min, filtered off, washed with water and dried under high vacuum overnight. Alternatively, the crude reaction mixture was, either directly after concentration under reduced pressure or after extractive work-up, purified further by preparative HPLC (see general HPLC conditions). The Example Compounds 126 and 127 below are exemplary embodiments of this General Working Procedure.

Example 126

8-[(2,6-Difluorobenzyl)oxy]-6-ethynyl-N-[(2R)-1-hydroxyhexan-2-yl]-2-methylimidazo[1,2-a]-pyridine-3-carboxamide

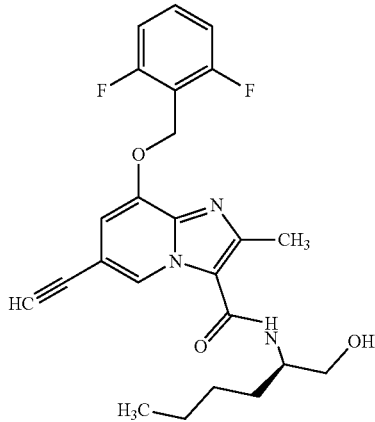 [SMILES: C#Cc1cc(OCc2c(F)cccc2F)c2nc(C)c(C(=O)N[C@@H](CO)CCCC)n2c1]

Under argon, 50 mg (0.15 mmol) of 8-[(2,6-difluorobenzyl)oxy]-6-ethynyl-2-methylimidazo[1,2-a]pyridine-3-carboxylic acid were dissolved in 0.5 ml of dry dimethylformamide, 20.54 mg (0.18 mmol, 1.2 equivalents) of (R)-(−)-2-aminohexanol, 72 µl of diisopropylethylamine (0.44 mmol, 3 equivalents) and 72 mg of HATU (0.19 mmol, 1.3 equivalents) were added and the mixture was stirred at room temperature overnight. A little water was then added, and the mixture was purified directly by preparative HPLC (Method 8). This gave 37.5 mg of the target compound (58% of theory).

LC-MS (Method 2): $R_t$=1.17 min

MS (ESpos): m/z=442.0 (M+H)$^+$ $^1$H NMR (400 MHz, DMSO-d$_6$): δ=0.88 (t, 3H), 1.29-1.39 (m, 4H), 1.40-1.50 (m, 1H), 1.60-1.70 (m, 1H), 2.55 (s, 3H; superimposed by DMSO signal), 3.40-3.52 (m, 2H), 3.90-4.01 (m, 1H), 4.73 (t, 1H), 5.31 (s, 2H), 7.03 (s, 1H), 7.21 (t, 2H), 7.59 (quint., 1H), 7.62 (d, 1H), 8.68 (s, 1H).

Example 127

6-Chloro-8-[(2,6-difluorobenzyl)oxy]-N-[(2R)-1,5-dihydroxypentan-2-yl]-2-methylimidazo[1,2-a]-pyridine-3-carboxamide

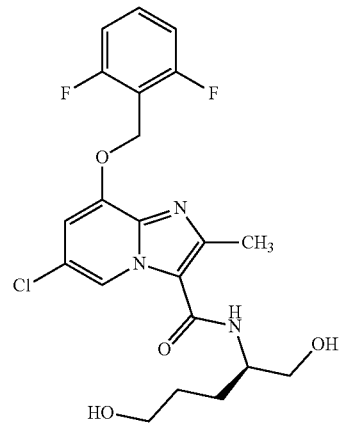 [SMILES: Cc1nc2c(OCc3c(F)cccc3F)cc(Cl)cn2c1C(=O)N[C@@H](CO)CCCO]

Under argon, 70 mg (0.20 mmol) of 6-chloro-8-[(2,6-difluorobenzyl)oxy]-2-methylimidazo[1,2-a]-pyridine-3-carboxylic acid were dissolved in 0.63 ml of dry dimethylformamide, 33.1 mg (0.28 mmol, 1.4 equivalents) of (2R)-2-aminopentan-1,5-diol, 98 µl of diisopropylethylamine (0.60 mmol, 3 equivalents) and 98 mg of HATU (0.26 mmol, 1.3 equivalents) were added and the mixture was stirred at room temperature overnight. A little water was then added, and the mixture was purified directly by preparative HPLC (Method 10). This gave 31.4 mg of the target compound (35% of theory).

LC-MS (Method 1): $R_t$=0.78 min

MS (ESpos): m/z=454.2 (M+H)$^+$ $^1$H NMR (400 MHz, DMSO-d$_6$): δ=1.40-1.60 (m, 3H), 1.60-1.70 (m, 1H), 2.55 (s, 3H; superimposed by DMSO signal), 3.35-3.52 (m, 4H), 3.90-4.01 (m, 1H), 4.40 (t, 1H), 4.73 (t, 1H), 5.31 (s, 2H), 7.18 (s, 1H), 7.23 (t, 2H), 7.59 (quint., 1H), 7.62 (d, 1H), 8.65 (s, 1H).

The further synthesis examples summarized in Table 12 below were prepared analogously to Examples 126 and 127 and General Working Procedure 3 by reacting the appropriate carboxylic acid (see synthesis intermediates above) with the appropriate amines, which were commercially available or prepared as described above.

TABLE 12

| Example | IUPAC name/structure (yield) | Analytical data |
|---|---|---|
| 128 | 6-chloro-8-[(2,6-difluorobenzyl)oxy]-N-[(2R)-1,4-dihydroxybutan-2-yl]-2-methylimidazo[1,2-a]pyridine-3-carboxamide<br>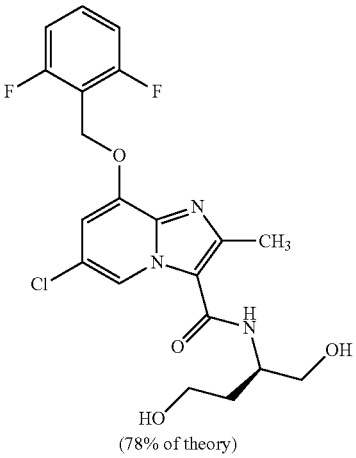<br>(78% of theory) | LC-MS (Method 1): $R_t$ = 0.77 min<br>MS (ESpos): m/z = 486 (M + H)$^+$<br>$^1$H NMR (400 MHz, DMSO-d$_6$):<br>δ = 1.60-1.70 (m, 1H), 1.75-1.87(m, 1H), 2.55 (s, 3H; superimposed by DMSO signal), 3.41-3.57 (m, 4H), 4.02-4.15 (m, 1H), 4.53 (t, 1H), 4.79 (t, 1H), 5.31 (s, 2H), 7.20 (s, 1H), 7.23 (t, 2H), 7.59 (quint, 1H), 7.68 (d, 1H), 8.70 (s, 1H). |
| 129 | 8-[(2,6-difluorobenzyl)oxy]-N-[(2R)-1,4-dihydroxybutan-2-yl]-2-methylimidazo[1,2-a]pyridine-3-carboxamide<br>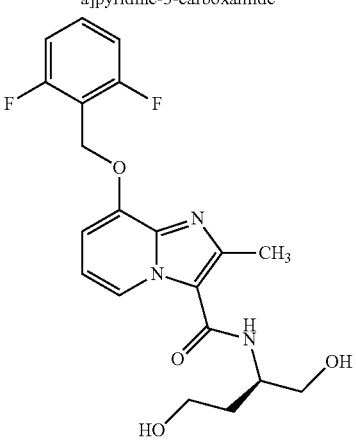<br>(69% of theory) | LC-MS (Method 1): $R_t$ = 0.53 min<br>MS (ESpos): m/z = 406.3 (M + H)$^+$<br>$^1$H NMR (400 MHz, DMSO-d$_6$):<br>δ = 1.60-1.70 (m, 1H), 1.75-1.87 (m, 1H), 2.55 (s, 3H: superimposed by DMSO signal), 3.41-3.57 (m, 4H), 4.02-4.15 (m, 1H), 4.53 (t, 1H), 4.79 (t, 1H), 5.31 (s, 2H), 6.91 (t, 1H), 7.00 (d, 1H), 7.23 (t, 2H), 7.55-7.65 (m, 2 H), 8.59 (d, 1H). |
| 130 | 8-[(2,6-difluorobenzyl)oxy]-N-[(2R)-1,5-dihydroxypentan-2-yl]-2-methylimidazo[1,2-a]pyridine-3-carboxamide<br>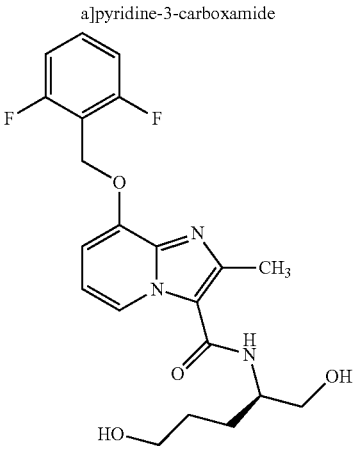<br>(37% of theory) | LC-MS (Method 1): $R_t$ = 0.54 min<br>MS (ESpos): m/z = 420.3 (M + H)$^+$<br>$^1$H NMR (400 MHz, DMSO-d$_6$): δ = 1.40-1.55 (m, 3H), 1.65-1.72 (m, 1H), 2.55 (s, 3H; superimposed by DMSO signal), 3.37-3.52 (m, 4H), 3.95-4.04 (m, 1H), 4.42 (t, 1H), 4.73 (t, 1H), 5.31 (s, 2H), 6.91 (t, 1H), 7.00 (d, 1H), 7.23 (t, 2H), 7.52 (d, 1H), 7.59 (quint., 1H), 8.52 (d, 1H). |

TABLE 12-continued

| Example | IUPAC name/structure (yield) | Analytical data |
|---|---|---|
| 131 | 6-chloro-8-[(2,6-difluorobenzyl)oxy]-N-[(2R)-1-hydroxyhexan-2-yl]-2-methylimidazo[1,2-a]pyridine-3-carboxamide<br>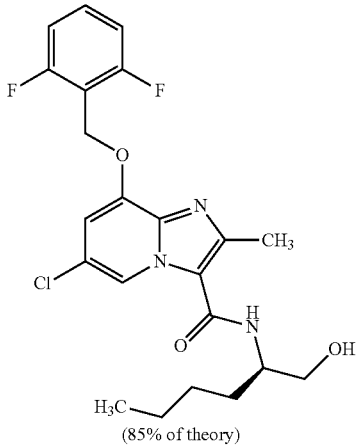<br>(85% of theory) | LC-MS (Method 1): $R_t$ = 1.05 min<br>MS (ESpos): m/z = 452.1/454.1 (M + H)$^+$<br>$^1$H NMR (400 MHz, DMSO-d$_6$):<br>δ = 0.88(t, 3H), 1.25-1.39 (m, 4H), 1.40-1.50 (m, 1H), 1.60-1.70 (m, 1H), 2.55 (s, 3H; superimposed by DMSO signal), 3.40-3.52 (m, 2H), 3.90-4.01 (m, 1H), 4.72 (t, 1H), 5.33 (s, 2H), 7.15 (s, 1H), 7.21 (t, 2H), 7.55-7.65 (m, 2H), 8.62 (s, 1H). |
| 132 | 8-[(2,6-difluorobenzyl)oxy]-6-fluoro-N-[(2R)-1-hydroxyhexan-2-yl]-2-methylimidazo[1,2-a]pyridine-3-carboxamide<br>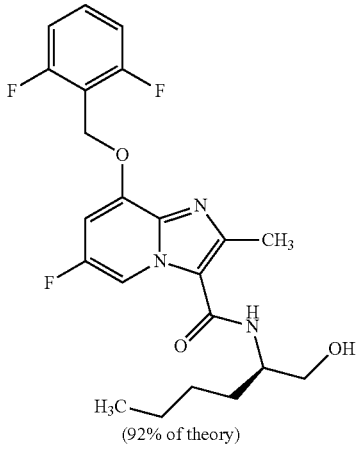<br>(92% of theory) | LC-MS (Method 1): $R_t$ = 0.97 min<br>MS (ESpos): m/z = 436.1 (M + H)$^+$<br>$^1$H NMR (400 MHz, DMSO-d$_6$):<br>δ = 0.86 (t, 3H), 1.21-1.39 (m, 4H), 1.40-1.52 (m, 1H), 1.58-1.71 (m, 1H), 2.55 (s, 3H; superimposed by DMSO signal), 3.40-3.55 (m, 2H), 3.91-4.04 (m, 1H), 4.73 (t, 1H), 5.35 (s, 2H), 7.20-7.30 (m, 3H), 7.55 (d, 1H), 7.59 (quint., 1H), 8.61 (d, 1H). |
| 133 | 8-[(2,6-difluorobenzyl)oxy]-N-[(2R)-1-hydroxyhexan-2-yl]-2,6-dimethylimidazo[1,2-a]pyridine-3-carboxamide<br>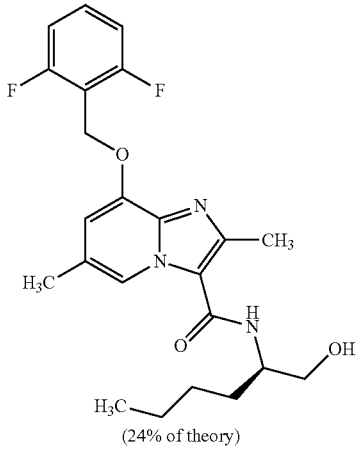<br>(24% of theory) | LC-MS (Method 1): $R_t$ = 0.87 min<br>MS (ESpos): m/z = 432.3 (M + H)$^+$<br>$^1$H NMR (400 MHz, DMSO-d$_6$):<br>δ = 0.88 (t, 3H), 1.21-1.49 (m, 5H), 1.58-1.71 (m, 1H), 2.30 (s, 3H), 2.49 (s, 3H), 3.40-3.55 (m, 2H), 3.91-4.04 (m, 1H), 4.73 (t, 1H), 5.30 (s, 2H), 6.89 (s, 1H), 7.21 (t, 2H), 7.50 (d, 1H), 7.59 (quint., 1H), 8.87(s, 1H). |

TABLE 12-continued

| Example | IUPAC name/structure (yield) | Analytical data |
|---|---|---|
| 134 | 2-cyclopropyl-8-[(2,6-difluorobenzyl)oxy]-N-[(2R)-1-hydroxyhexan-2-yl]imidazo[1,2-a]-pyridine-3-carboxamide<br><br>(12% of theory) | LC-MS (Method 1): $R_t$ = 0.98 min<br>MS (Espos): m/z = 443.3 (M + H)$^+$<br>$^1$H NMR (400 MHz, DMSO-d$_6$):<br>δ = 0.70-1.00 (m, 7H), 1.25-1.39 (m, 4H), 1.40-1.53 (m, 1H), 1.60-1.70 (m, 1H), 2.22-2.31 (m, 1H), 2.55 (s, 3H; superimposed by DMSO signal), 3.43-3.52 (m, 2H), 3.95-4.07 (m, 1H), 4.78 (t, 1H), 5.30 (s, 2H), 6.90 (t, 1H), 6.96 (d, 1H), 7.21 (t, 2H), 7.59 (quint.m 1H), 7.68 (d, 1H), 8.60 (d, 1H). |
| 135 | 8-[(2,6-difluorobenzyl)oxy]-2-methyl-N-[(2R, 5R)-6,6,6-trifluoro-1,5-dihydroxyhexan-2-yl]imidazo[1,2-a]pyridine-3-carboxamide trifluoroacetate (1:1)$^{1)}$<br><br>(22% of theory) | LC-MS (Method 1): $R_t$ = 0.77 min<br>MS (ESpos): m/z = 488 (M + H)$^+$<br>$^1$H NMR (400 MHz, DMSO-d$_6$):<br>δ = 1.49-1.80 (m, 4H), 2.50 (s, 3H), 3.39-3.58 signal under broad singlet (m, 1H), 3.97-4.12 (m, 2H), 5.39 (s, 2H), 6.12 (brs, 1H), 7.09-7.7.36 (m, 4H), 7.59 (quint, 1H), 7.89 (brs, 1H), 8.58 (d, 1H). |
| 136 | 8-[(2,6-difluorobenzyl)oxy]-N-[3-(4-fluorophenoxy)-2-hydroxypropyl]-2-methylimidzao[1,2-a]pyridine-3-carboxamide<br><br>(9% of theory) | LC-MS (Method 1): $R_t$ = 0.84 min<br>MS (ESpos): m/z = 486 (M + H)$^+$<br>$^1$H NMR (400 MHz, DMSO-d$_6$):<br>δ = 2.52 (s, 3H; hidden under DMSO signal), 3.35-3.44 (m, 1H), 3.49-3.59 (m, 1H), 3.87-4.08 (m, 3H), 5.25-5.35 (m, 3H), 6.89-7.04 (m, 4H), 7.09-7.11 (t, 2H), 7.23 (t, 2H), 7.59 (quint, 1H), 7.84 (t, 1H), 8.62 (d, 1H). |

TABLE 12-continued

| Example | IUPAC name/structure (yield) | Analytical data |
|---|---|---|
| 137 | 8-[(2,6-difluorobenzyl)oxy]-N-(2-hydroxy-3-phenoxypropyl)-2-methylimidazo[1,2-a]-pyridine-3-carboxamide<br>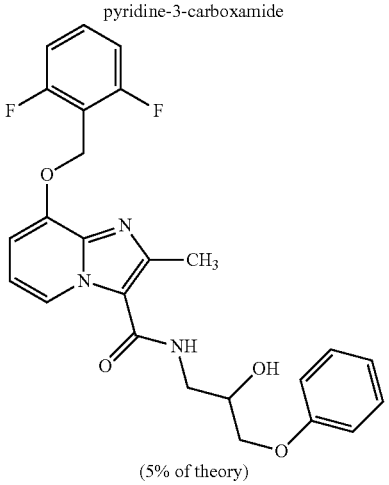<br>(5% of theory) | LC MS (Method 1): $R_t$ = 0.83 min<br>MS (ESpos): m/z = 468 (M + H)$^+$<br>$^1$H NMR (400 MHz, DMSO-d$_6$):<br>δ = 2.52 (s, 3H; hidden under DMSO signal), 3.36-3.45 (m, 1H), 3.50-3.60 (m, 1H), 3.89-4.09 (m, 3H), 5.26-5.35 (m, 3H), 6.89-6.98 (m, 5H), 7.19-7.32 (m, 4H), 7.59 (quint, 1H), 7.85 (t, 1H), 8.63 (d, 1H). |

1)The product was obtained by two preparative HPLC purification:
1) preparative HPLC (RP18 column, mobile phase: acetonitrile/water gradient with addition of 0.1% TFA).
2) column: Sunfire C18, 5 μm, 250 x 20 mm, mobile phase: 44% water, 45% methanol, 11% water + 1% TFA, 40° C., detection: 210 nm.

Example 138

8-[(2,6-Difluorobenzyl)oxy]-2-methyl-N-(6,6,6-trifluoro-1,5-dihydroxyhexan-2-yl)imidazo[1,2-a]-pyridine-3-carboxamide (stereoisomer B)

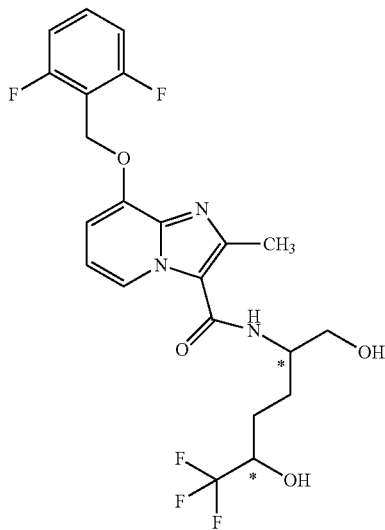 [SMILES: Cc1nc2c(OCc3c(F)cccc3F)cccn2c1C(=O)NC(CO)CCC(O)C(F)(F)F]

Example 135 (44 mg) was separated into the stereoisomers by preparative separation on a chiral phase [column: Daicel Chiralpak AD-H, 5 μm, 250×20 mm, mobile phase: 50% isohexane, 50% ethanol, flow rate 20 ml/min; 25° C., detection: 230 nm].

Yield: 12.4 mg (99% pure, >99% pure stereoisomer)

Stereoisomer B: $R_t$=3.34 min [Chiralpak AD-H, 5 μm, 250×4 mm; mobile phase: 50% isohexane, 50% ethanol; flow rate 1.0 ml/min; 25° C.; detection: 230 nm].

Examples 139 and 140

8-[(2,6-Difluorobenzyl)oxy]-N-[(3R)-2-hydroxyheptan-3-yl]-2-methylimidazo[1,2-a]pyridine-3-carboxamide [diastereomer mixture]

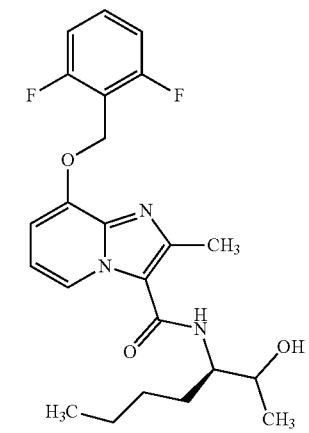 [SMILES: CCCC[C@@H](NC(=O)c1c(C)nc2c(OCc3c(F)cccc3F)cccn12)C(C)O]

282 mg of 8-[(2,6-difluorobenzyl)oxy]-2-methyl-N-[(2R)-1-oxohexan-2-yl]imidazo[1,2-a]pyridine-3-carboxamide (0.68 mmol, 1 equivalent) were initially charged in 20 ml of dry THF, and 450 μl of methylmagnesium bromide solution (3.0 M in diethyl ether 1.36 mmol) were added dropwise at 0° C. The reaction mixture was slowly warmed to RT and stirred for 5 h. The reaction mixture was diluted with ethyl acetate, washed with saturated aqueous sodium bicarbonate solution, dried, filtered and concentrated. Column chromatography (cyclohexane/ethyl acetate gradient) gave 125 mg (43% of theory) of the product as diastereomer mixture (4:1) (HPLC and NMR integration).

Separation by HPLC (for details, see below) gave 20.4 mg of diastereomer 139 (first diastereomer by Method 2; $R_t$=0.99 min) and 85 mg of diastereomer 140 (second diastereomer by Method 2; $R_t$=1.01 min), in each case as trifluoroacetic acid salt. The trifluoroacetic acid salts of the pure diastereomers were taken up in dichloromethane, washed twice with saturated aqueous sodium bicarbonate solution, dried and re-concentrated, thus giving 71 mg of the free base of the main diastereomer 140 and 12.6 mg of the free base of the minor diastereomer 139.

HPLC conditions for diastereomer separation:

| | |
|---|---|
| Sample preparation: | 125 mg dissolved in 3 ml of acetonitrile/2 ml of water. |
| Packing material: | SUNFIRE C 18 OBD 5 μm 19*150 mm |
| Flow rate | 25 ml/min |
| Wavelength | 210 nm |
| Injection volume | 350 μl |
| Temperature | 40° C. |
| Mobile phase | 60/25/15 Milli-Q-water/acetonitrile/1% trifluoroacetic acid. |

Example 139

Minor Diastereomer

LC-MS (Method 2): $R_t$=0.99 min

MS (ESpos): m/z=432 (M+H)$^+$ $^1$H NMR (400 MHz, DMSO-d$_6$): δ=0.87 (t, 3H); 1.11 (d, 3H); 1.23-1.42 (m, 5H); 1.71-1.75 (m, 1H); 2.52 (s, 3H); 3.62-3.67 (m, 1H); 3.82-3.89 (m, 1H); 4.67 (d, 1H); 5.31 (s, 2H); 6.92 (t, 1H); 6.98 (d, 1H); 7.22 (t, 2H); 7.51 (d, 1H); 7.58 (quint., 1H); 8.50 (d, 1H).

Example 140

Main Diastereomer

LC-MS (Method 2): $R_t$=1.01 min

MS (ESpos): m/z=432 (M+H)$^+$ $^1$H NMR (400 MHz, DMSO-d$_6$): δ=0.87 (t, 3H); 1.07 (d, 3H); 1.25-1.36 (m, 4H); 1.50-1.62 (m, 2H); 2.52 (s, 3H); 3.75-3.79 (m, 1H); 3.89-3.94 (m, 1H); 4.72 (d, 1H); 5.31 (s, 2H); 6.93 (t, 1H); 6.99 (d, 1H); 7.21 (t, 2H); 7.27 (d, 1H); 7.58 (quint., 1H); 8.57 (d, 1H).

Example 141 and 142

8-[(2,6-Difluorobenzyl)oxy]-2-methyl-N-[(3R)-1,1,1-trifluoro-2-hydroxyheptan-3-yl]imidazo[1,2-a]pyridine-3-carboxamide

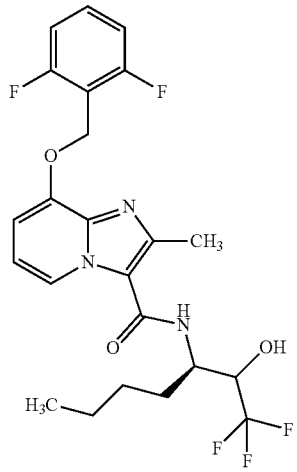 [SMILES: CCCC[C@@H](NC(=O)c1c(C)nc2c(OCc3c(F)cccc3F)cccn12)C(O)C(F)(F)F]

430 mg of 8-[(2,6-difluorobenzyl)oxy]-2-methyl-N-[(2R)-1-oxohexan-2-yl]imidazo[1,2-a]pyridine-3-carboxamide (1.05 mmol) were initially charged in 30 ml of dry THF, and 194 μl of trimethylsilyl trifluoromethane (1.24 mmol) and 621 μl of tetrabutylammonium fluoride solution (1.0 M in THF; 0.62 mmol) were successively added dropwise at 0° C. The reaction mixture was slowly warmed to RT, and stirring was continued overnight. The mixture was then concentrated and the residue was taken up in ethyl acetate, washed with saturated aqueous sodium bicarbonate solution, dried, filtered and concentrated. Preparative HPLC separation (Method 9) afforded 41 mg of the target compound, which was once more purified by HPLC (Method 10). This gave 28.4 mg of the target compound. The diastereomer ratio was about 3:1 ($^1$H NMR integration).

Separation of the diastereomers:

Column: Daicel Chiralpak AD-H, 5 μm 250×20 mm, mobile phase: A=isohexane, B=2-propanol+0.2% TFA+0.1% H$_2$O, 0 to 15 min 1:1 A/B.

Saturated aqueous sodium bicarbonate solution was added to the TFA salts of the pure diastereomers obtained in this manner, the mixture was extracted with ethyl acetate and the extract was washed with saturated sodium chloride solution, dried over magnesium sulphate and concentrated.

Example 141

Main Diastereomer

Yield: 12.3 mg (2% of theory, >98.5% de)

LC (Daicel Chiralpak AD-H, 5 μm 250×4.6 mm, mobile phase: A=isohexane, B=2-propanol+0.2% TFA+0.1% H$_2$O, 0 to 15 min 1:1 A/B) $R_t$=4.52 min $^1$H NMR (400 MHz, DMSO-d$_6$): δ=0.87 (t, 3H), 1.23-1.40 (m, 4H), 1.61-1.75 (m, 2H), 2.56 (s, 3H; obscured by DMSO signal), 4.10 (quint., 1H), 4.40 (q, 1H), 5.30 (s, 2H), 6.64 (d, 1H), 6.92 (t, 1H), 6.98 (d, 1H), 7.21 (t, 2H), 7.46 (d, 1H), 7.58 (quint., 1H), 8.51 (d, 1H).

specific rotation: +39° (0.3 g/100 ml of methanol, 20.0° C., layer thickness 100 mm, 589 nm).

Example 142

Minor Diastereomer

Yield: 4.5 mg (0.9% of theory, >98.5% de)

LC (Daicel Chiralpak AD-H, 5 μm 250×4.6 mm, mobile phase: A=isohexane, B=2-propanol+0.2% TFA+0.1% $H_2O$, 0 to 15 min 1:1 A/B) $R_t$=7.20 min $^1$H NMR (400 MHz, DMSO-$d_6$): δ=0.87 (t, 3H), 1.20-1.42 (m, 4H), 1.57-1.65 (m, 1H), 1.75-1.80 (m, 1H), 2.56 (s, 3H; obscured by DMSO signal), 4.11 (quint., 1H), 4.25 (q, 1H), 5.30 (s, 2H), 6.51 (d, 1H), 6.91 (t, 1H), 6.98 (d, 1H), 7.21 (t, 2H), 7.58 (quint., 1H), 7.80 (d, 1H), 8.50 (d, 1H).

specific rotation: +21° (0.225 g/100 ml of methanol, 19.9° C., layer thickness 100 mm, 589 nm).

Examples 143, 144, 145 and 146

8-[(2,6-Difluorobenzyl)oxy]-2-methyl-N-(4,4,4-trifluoro-3-hydroxybutan-2-yl)imidazo[1,2-a]-pyridine-3-carboxamide (diastereomer mixture)

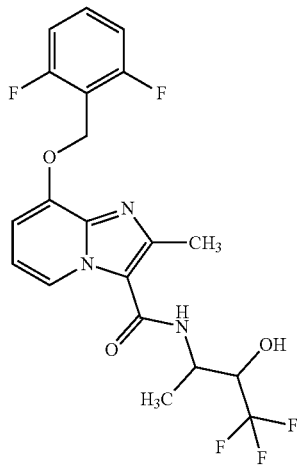 [SMILES: Cc1nc2c(OCc3c(F)cccc3F)cccn2c1C(=O)NC(C)C(O)C(F)(F)F]

250 mg of 8-[(2,6-difluorobenzyl)oxy]-2-methylimidazo[1,2-a]pyridine-3-carboxylic acid (0.785 mmol), 112 mg of 3-amino-1,1,1-trifluorobutan-2-ol (mixture of four stereoisomers; 0.785 mmol) and 277 mg of TBTU (0.864 mmol) were dissolved in 1.5 ml of dichloromethane, and the mixture was stirred at RT for 48 h. The reaction mixture was concentrated and the residue was taken up in methanol and purified by preparative HPLC (Method 7). This gave 186 mg (53% of theory) of the title compound, which was separated by preparative HPLC on a chiral phase.

HPLC conditions for stereoisomer separation:

Column 250×4.6 mm filled with Daicel Chiralpak AD-H, 5 μm separated. Flow rate, 1.0 ml/min, temperature 45° C., mobile phase, 50% isohexane+0.2% trifluoroacetic acid, 50% 2-propanol+2% water.

All isolated stereoisomers were obtained as trifluoroacetic acid salts or with adhering trifluoroacetic acid. The stereoisomers were individually taken up in ethyl acetate and washed with saturated aqueous sodium bicarbonate solution, dried and re-concentrated.

Example 143

Stereoisomer 1

Yield: 24 mg (7% of theory, >96% ee)

Specific rotation: −29° (598 nm, 20.4° C., c=0.275 g/100 ml, methanol)

LC-MS (Method 3): $R_t$=1.65 min; content>98% pure

MS (ESpos): m/z=443 (M+H)$^+$

1H NMR (400 MHz, DMSO-$d_6$): δ=1.27 (d, 3H); 2.49 (s, 3H, superimposed by DMSO signal); 4.08-4.16 (m, 1H); 4.44-4.51 (m, 1H); 5.31 (s, 2H); 6.68 (d, 1H); 6.94 (t, 1H); 7.01 (d, 1H); 7.23 (t, 1H); 7.50 (d, 1H); 7.58 (tt, 1H); 8.63 (d, 1H).

Example 144

Stereoisomer 2

Yield: 13 mg (4% of theory, >96% ee)

Specific rotation: +31° (598 nm, 20.1° C., 0.28 g/100 ml, methanol)

LC-MS (Method 3): $R_t$=1.64 min; content>98% pure

MS (ESpos): m/z=443 (M+H)$^+$ $^1$H NMR (400 MHz, DMSO-$d_6$): δ=1.27 (d, 3H); 2.49 (s, 3H, superimposed by DMSO signal); 4.08-4.16 (m, 1H); 4.44-4.51 (m, 1H); 5.31 (s, 2H); 6.68 (d, 1H); 6.94 (t, 1H); 7.01 (d, 1H); 7.23 (t, 1H); 7.50 (d, 1H); 7.58 (tt, 1H); 8.63 (d, 1H).

Example 145

Stereoisomer 3

Yield: 30 mg (9% of theory, >99% ee)

Specific rotation: −22.7° (598 nm, 20.5° C., c=0.33 g/100 ml, methanol)

LC-MS (Method 3): $R_t$=1.67 min; content>96% pure

MS (ESpos): m/z=443 (M+H)$^+$ $^1$H NMR (400 MHz, DMSO-$d_6$): δ=1.25 (d, 3H); 2.50 (s, 3H, superimposed by DMSO signal); 4.12-4.22 (m, 1H); 4.29-4.37 (m, 1H); 5.31 (s, 2H); 6.53 (d, 1H); 6.95 (t, 1H); 7.00 (d, 1H); 7.23 (t, 1H); 7.58 (tt, 1H); 7.83 (d, 1H); 8.55 (d, 1H).

Example 146

Stereoisomer 2

Yield: 24 mg (7% of theory, >98% ee)

Specific rotation: +21.9° (598 nm, 20.8° C., c=0.33 g/100 ml, methanol)

LC-MS (Method 3): $R_t$=1.66 min; content>98% pure

MS (ESpos): m/z=443 (M+H)$^+$ $^1$H NMR (400 MHz, DMSO-$d_6$): δ=1.25 (d, 3H); 2.50 (s, 3H, superimposed by DMSO signal); 4.14-4.20 (m, 1H);

4.30-4.36 (m, 1H); 5.31 (s, 2H); 6.53 (d, 1H); 6.93 (t, 1H); 7.00 (d, 1H); 7.23 (t, 1H); 7.58 (tt, 1H); 7.83 (d, 1H); 8.55 (d, 1H).

Example 147

8-[(2,6-Difluorobenzyl)oxy]-N-[(3R)-2-hydroxy-2-methylheptan-3-yl]-2-methylimidazo[1,2-a]-pyridine-3-carboxamide

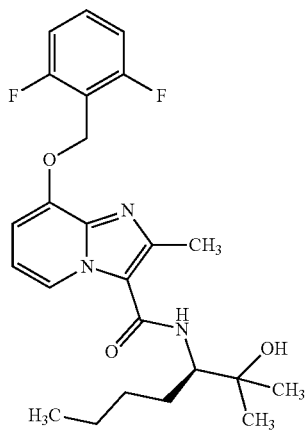 [SMILES: CCCC[C@@H](NC(=O)c1c(C)nc2c(OCc3c(F)cccc3F)cccn12)C(C)(C)O]

Under argon, 100 mg (0.224 mmol) of methyl N-({8-[(2,6-difluorobenzyl)oxy]-2-methylimidazo[1,2-a]pyridin-3-yl}carbonyl)-D-norleucinate were dissolved in 2 ml of dry THF, the mixture was cooled to 0° C., 187 μl of methylmagnesium bromide solution (3.0 M in diethyl ether; 0.561 mmol, 2.5 equivalents) were added dropwise and the mixture was, with stirring, slowly warmed to RT. After 3 h at RT, 1N hydrochloric acid was added and the mixture was diluted with water and ethyl acetate. The organic phase was separated off and the aqueous phase was extracted twice with ethyl acetate. The combined organic phases were washed with saturated aqueous sodium chloride solution, dried with magnesium sulphate, filtered and concentrated. The residue was chromatographed on a 10 g silica gel cartridge (Biotage Isolera, cyclohexane/ethyl acetate gradient as mobile phase). This gave 39 mg of the target compound (38% of theory).

LC-MS (Method 3): $R_t$=1.88 min

MS (ESpos): m/z=446.3 (M+H)$^+$ $^1$H NMR (400 MHz, DMSO-d$_6$): δ=0.85 (t, 3H), 1.10 (s, 3H), 1.15 (s, 3H), 1.20-1.47 (m, 5H), 1.70-1.80 (m, 1H), 2.55 (s, 3H; superimposed by DMSO signal), 3.92 (t, 1H), 4.48 (s, 1H), 5.31 (s, 2H), 6.92 (t, 1H), 6.98 (d, 1H), 7.21 (t, 2H), 7.40 (d, 1H), 7.60 (quint., 1H), 8.51 (d, 1H).

Example 148 rac-8-[(2,6-Difluorobenzyl)oxy]-2-methyl-N-(1,1,1-trifluoro-4-hydroxy-4-methylpentan-3-yl)-imidazo[1,2-a]pyridine-3-carboxamide

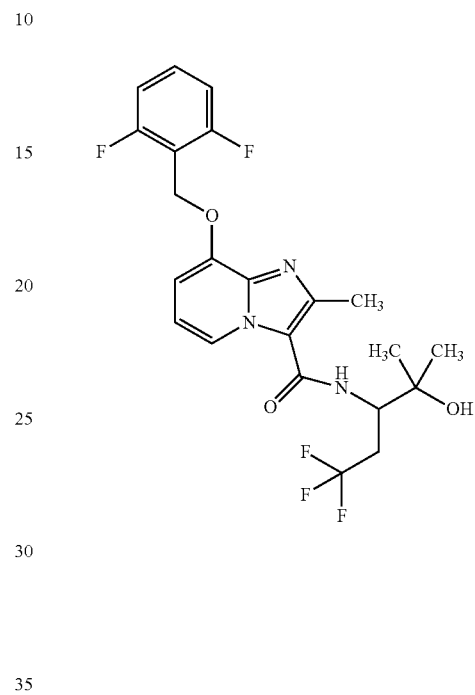

320 mg (0.68 mmol) of methyl 2-[({8-[(2,6-difluorobenzyl)oxy]-2-methylimidazo[1,2-a]pyridin-3-yl}carbonyl)amino]-4,4,4-trifluorobutanoate were initially charged in THF, and the solution was cooled to 0° C. 0.724 ml (2.17 mmol) of methylmagnesium bromide solution (3 M in diethyl ether) was added dropwise, and the mixture was stirred at 0° C. for 15 min. The reaction mixture was slowly brought to RT and stirred at this temperature for 2 h. The mixture was then acidified carefully with 1 N aqueous hydrochloric acid solution and the reaction solution was purified by preparative HPLC (RP18 column, mobile phase: acetonitrile/water gradient with addition of 0.1% TFA). The product fractions were concentrated and dissolved in ethyl acetate, washed with 1 ml of saturated aqueous sodium bicarbonate solution and concentrated, and the residue was taken up in water/acetonitrile and lyophilized. This gave 94 mg of the target compound (29% of theory, purity 96%).

LC-MS (Method 2): $R_t$=0.94 min

MS (ESpos): m/z=483 (M+H)$^+$ $^1$H NMR (400 MHz, DMSO-d$_6$): δ=1.10 (s, 3H), 1.21 (s, 3H), 2.50 (s, 3H), 2.67-2.82 (m, 2H), 4.38 (t, 1H), 4.88 (s, 1H), 5.32 (s, 2H), 6.96 (t, 1H), 7.02 (d, 1H), 7.22 (t, 2H), 7.59 (quint, 1H), 7.82 (d, 1H), 8.43 (d, 1H).

The example compounds shown in Table 13 were prepared analogously to Example 148 by reacting the appropriate methyl esters with methylmagnesium bromide (2.5 to 3.2 equivalents).

TABLE 13

| Example | IUPAC name/structure (yield) | Analytical data |
| --- | --- | --- |
| 149 | rac-8-[(2,6-difluorobenzyl)oxy]-2-methyl-N-(6,6,6-trifluoro-2-hydroxy-2-methylhexan-3-yl)imidazo[1,2-a]pyridine-3-carboxamide[1)]<br>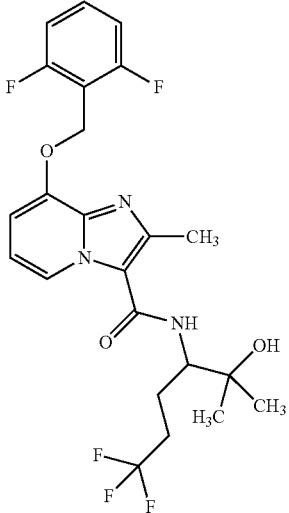 [SMILES: Cc1nc2c(OCc3c(F)cccc3F)cccn2c1C(=O)NC(CCC(F)(F)F)C(C)(C)O]<br>(53% of theory) | LC-MS (Method 1): $R_t$ = 0.95 min<br>MS (ESpos): m/z = 486 (M + H)$^+$<br>$^1$H NMR (400 MHz, DMSO-d6):<br>δ = 1.12 (s, 3H), 1.20 (s, 3H), 1.60-1.74 (m, 1H), 1.95-2.07 (m, 1H), 2.18-2.33 (m, 2H), 2.50 (s, 3H), 3.98-4.07 (m, 1H), 4.69(s, 1H), 5.31 (s, 2H), 6.93 (t,1H), 7.02 (d, 1H), 7.23 (t, 2H), 7.53-7.63 (m, 2H), 8.56 (d, 1H). |
| 150 | rac-8-[(2,6-difluorobenzyl)oxy]-2-methyl-N-(7,7,7-trifluoro-2-hydroxy-2-methylheptan-3-yl)imidazo[1,2-a]pyridine-3-carboxamide<br>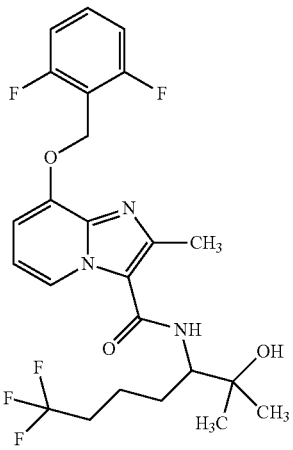 [SMILES: Cc1nc2c(OCc3c(F)cccc3F)cccn2c1C(=O)NC(CCCC(F)(F)F)C(C)(C)O]<br>(30% of theory) | LC-MS (Method 1): $R_t$ = 0.97 min<br>MS (ESpos): m/z = 500 (M + H)$^+$<br>$^1$H NMR (400 MHz, DMSO-d$_6$):<br>δ = 1.12 (s, 3H), 1.19 (s, 3H), 1.42-1.65 (m, 3H), 1.79-1.88 (m, 1H), 2.13-2.29 (m, 1H), 2.33-2.46 (m, 1H), 2.50 (s, 3H), 3.94-4.02 (m, 1H), 4.57(s, 1H). 5.31 (s, 2H), 6.94 (t, 1H), 7.02 (d, 1H), 7.22 (t, 2H), 7.48 (d, 1H), 7.59 (quint, 1H), 8.50(d, 1H). |

TABLE 13-continued

| Example | IUPAC name/structure (yield) | Analytical data |
| --- | --- | --- |
| 151 | rac-N-[1-(4-chlorophenyl)-2-hydroxy-2-methylpropyl]-8-[(2,6-difluorobenzyl)oxy]-2-methylimidazo[1,2-a]pyridine-3-carboxamide [2)] 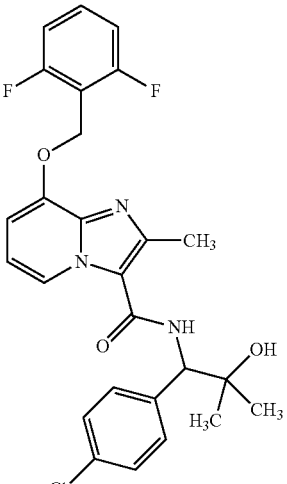 (38% of theory) | LC-MS (Method 1): $R_t$ = 1.15 min<br>MS (ESpos): m/z = 500 (M + H)$^+$<br>$^1$H NMR (400 MHz, DMSO-d$_6$):<br>δ = 1.03 (s, 3H), 1.25 (s, 3H), 2.61 (s, 3H), 4.89 (s, 1H), 4.92 (d, 1H), 5.31 (s, 2H), 6.91 (t, 1H), 7.02 (d, 1H), 7.24 (t, 2H), 7.38 (d, 2H), 7.48 (d, 2H), 7.59 (quint, 1H), 7.91 (d, 1H). 8.58 (d, 1H). |
| 152 | rac-8-[(2,6-difluorobenzyl)oxy]-N-[1-(4-fluorophenyl)-2-hydroxy-2-methylpropyl]-2-methylimidazo[1,2-a]pyridine-3-carboxamide [2)] 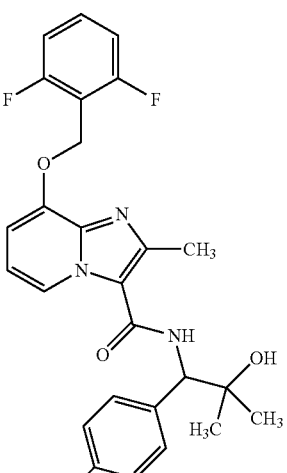 (42% of theory) | LC-MS (Method 1): $R_t$ = 0.97 min<br>MS (ESpos): m/z = 484 (M + H)$^+$<br>$^1$H NMR (400 MHz, DMSO-d$_6$):<br>δ = 1.02 (s, 3H), 1.25 (s, 3H), 2.61 (s, 3H), 4.87 (s, 1H), 4.93 (d, 1H), 5.31 (s, 2H), 6.90 (t, 1H), 7.02 (d, 1H), 7.14 (t, 2H), 7.22 (t, 2H), 7.45-7.51 (m, 2H), 7.59 (quint, 1H), 7.89 (d, 1H), 8.58 (d, 1H). |

TABLE 13-continued

| Example | IUPAC name/structure (yield) | Analytical data |
|---|---|---|
| 153 | 8-[(2,6-difluorobenzyl)oxy]-N-(3-hydroxy-3-methylbutyl)-2-methylimidazo[1,2-a]pyridine-3-carboxamide [2)]<br>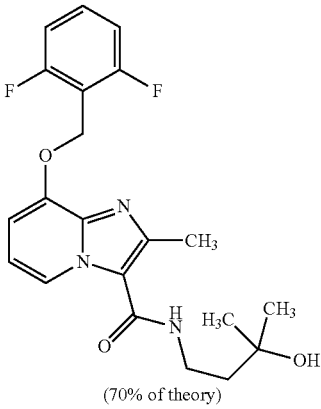<br>(70% of theory) | LC-MS (Method 1): $R_t$ = 0.77 min<br>MS (ESpos): m/z = 404 (M + H)$^+$<br>$^1$H NMR (400 MHz, DMSO-d$_6$):<br>δ = 1.16 (s, 6H), 1.69 (t, 2H), 2.50 (s, 3H), 3.41 (q, 2H), 4.48 (s, 1H), 5.31 (s, 2H), 6.91 (t, 1H), 7.00 (d, 1H), 7.22(t, 2H), 7.59 (quint, 1H), 7.84 (t, 1H), 8.68 (d, 1H). |

[1)]Work-up: The reaction mixture was acidified carefully with 1N aqueous hydrochloric acid solution and extracted three times with ethyl acetate. The combined organic phases were washed with saturated sodium chloride solution, dried over sodium sulphate and filtered, and the filtrate was concentrated. The crude product was purified by silica gel chromatography (mobile phase: dichloromethane:methanol = 100:1 isocratic).
[2)]Work-up and purification: The reaction mixture was acidified carefully with 1N aqueous hydrochloric acid solution and water and ethyl acetate were then added. After phase seperation, the aqueous phase was extracted twice with ethyl acetate and the combined organic phases were washed with saturated aqueous sodium chloride solution. The combined phases were dried over sodium sulphate, filtered and concentrated. The residue was purified by silica gel chromatography (mobile phase: cyclohexane:ethyl acetate gradient).

Example 154 ent-8-[(2,6-Difluorobenzyl)oxy]-2-methyl-N-(1,1,1-trifluoro-4-hydroxy-4-methylpentan-3-yl)-imidazo[1,2-a]pyridine-3-carboxamide (enantiomer B)

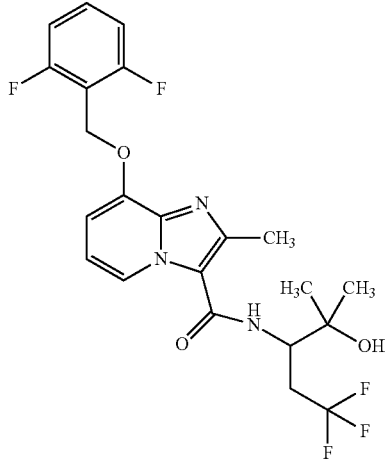 [SMILES: Cc1nc2c(OCc3c(F)cccc3F)cccn2c1C(=O)NC(CC(F)(F)F)C(C)(C)O]

Example 148 (94 mg) was separated into the enantiomers by preparative separation on a chiral phase [column: Daicel Chiralpak AD-H, 5 μm, 250×20 mm, mobile phase: 50% isohexane, 50% isopropanol, flow rate 15 ml/min; 30° C., detection: 220 nm].

Yield: 37 mg (99% pure, >99% ee)

Enantiomer B: $R_t$=6.23 min [Chiralpak AD-H, 5 μm, 250× 4.6 mm; mobile phase: 50% isohexane, 50% isopropanol; flow rate 1.0 ml/min; 30° C.; detection: 220 nm].

Example 155 ent-8-[(2,6-Difluorobenzyl)oxy]-2-methyl-N-(6,6,6-trifluoro-2-hydroxy-2-methylhexan-3-yl)-imidazo[1,2-a]pyridine-3-carboxamide (enantiomer B)

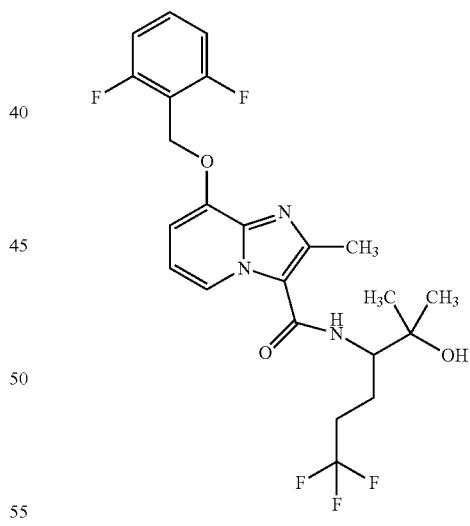

Example 149 (133 mg) was separated into the enantiomers by preparative separation on a chiral phase [column: Daicel Chiralpak AD-H, 5 μm, 250×20 mm, mobile phase: 50% isohexane, 50% isopropanol+0.2% diethylamine, flow rate 15 ml/min; 30° C., detection: 220 nm].

Yield: 51 mg (99% pure, >99% ee)

Enantiomer B: $R_t$=5.41 min [Chiralpak AD-H, 5 μm, 250× 4.6 mm; mobile phase: 50% isohexane, 50% isopropanol+ 0.2% diethylamine; flow rate 1.0 ml/min; 40° C.; detection: 235 nm].

Example 156 ent-8-[(2,6-Difluorobenzyl)oxy]-2-methyl-N-(7,7,7-trifluoro-2-hydroxy-2-methylheptan-3-yl)-imidazo[1,2-a]pyridine-3-carboxamide (enantiomer B)

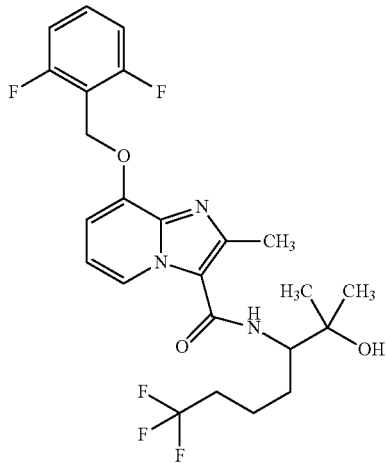 [SMILES: Cc1nc2c(OCc3c(F)cccc3F)cccn2c1C(=O)NC(CCCC(F)(F)F)C(C)(C)O]

Example 150 (83 mg) was separated into the enantiomers by preparative separation on a chiral phase [column: Daicel Chiralpak AD-H, 5 μm, 250×20 mm, mobile phase: 50% isohexane, 50% isopropanol, flow rate 15 ml/min; 30° C., detection: 220 nm].

Yield: 28 mg (99% pure, >99% ee)

Enantiomer B: $R_t$=6.26 min [Chiralpak AD-H, 5 μm, 250×4.6 mm; mobile phase: 50% isohexane, 50% isopropanol; flow rate 1.0 ml/min; 30° C.; detection: 220 nm].

Example 157

6-Cyano-8-[(2,6-difluorobenzyl)oxy]-N-[(2R)-1-hydroxyhexan-2-yl]-2-methylimidazo[1,2-a]-pyridine-3-carboxamide

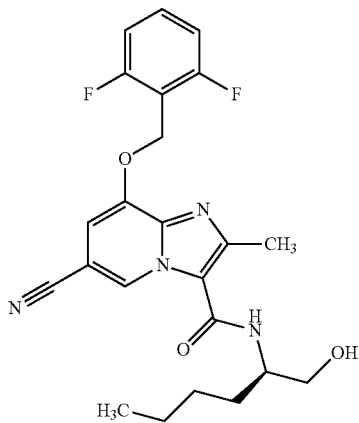 [SMILES: CCCC[C@H](CO)NC(=O)c1c(C)nc2c(OCc3c(F)cccc3F)cc(C#N)cn12]

Under argon, 500 mg (1.0 mmol) of 6-bromo-8-[(2,6-difluorobenzyl)oxy]-N-[(2R)-1-hydroxyhexan-2-yl]-2-methylimidazo[1,2-a]pyridine-3-carboxamide, 70.9 mg of zinc (II) cyanide (0.6 mmol, 0.6 equivalents), 30.4 μl of 1,2-bis(dimethylamino)ethane (TMEDA; 0.2 mmol, 0.2 equivalents), 65 mg of tris(dibenzylideneacetone)dipalladium Pd2 dba3 (0.07 mmol, 7 mol %) and 29 mg of xantphos ligand (0.05 mmol, 5 mol %) were dissolved in 2 ml of DMF and, divided into 5 microwave reaction vessels, heated at 160° C. for 5 min (CEM Discovery microwave, 300 Watt irratiation). The combined reaction mixtures were diluted with ethyl acetate and filtered through kieselguhr. The filter cake was washed thoroughly and the filtrate was washed with water, dried over magnesium sulphate, filtered and concentrated. The residue was chromatographed on a 50 g silica gel cartridge (Biotage Isolera, cyclohexane/ethyl acetate gradient as mobile phase). This gave 289 mg of the target compound (64% of theory).

LC-MS (Method 1): $R_t$=1.05 min

MS (ESpos): m/z=443.3 (M+H)$^+$ $^1$H NMR (400 MHz, DMSO-$d_6$): δ=0.85 (t, 3H), 1.20-1.42 (m, 4H), 1.45-1.57 (m, 1H), 1.60-1.70 (m, 1H), 2.55 (s, 3H; superimposed by DMSO signal), 3.42-3.53 (m, 2H), 3.90-4.02 (m, 1H), 4.75 (t, 1H), 5.31 (s, 2H), 7.21 (t, 2H), 7.33 (s, 1H), 7.60 (quint., 1H), 7.79 (s, 1H), 9.08 (s, 1H).

Example 158

8-(Cyclobutylmethoxy)-N-[(2R)-1-hydroxyhexan-2-yl]-2-methylimidazo[1,2-a]pyridine-3-carboxamide

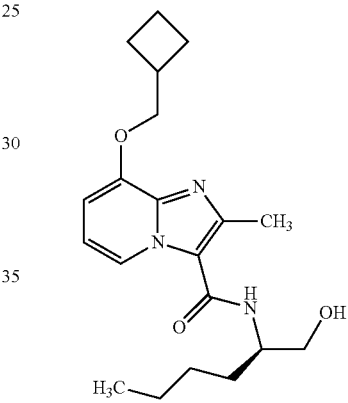

100 mg (0.34 mmol) of 8-hydroxy-N-[(2R)-1-hydroxyhexan-2-yl]-2-methylimidazo[1,2-a]-pyridine-3-carboxamide, 246 mg (0.76 mmol) of caesium carbonate and 56 mg (0.38 mmol) of (bromomethyl)cyclobutane were added to 4.9 ml of dry DMF and the mixture was stirred for 60 min in an oil bath preheated to 60° C. After cooling, about 40 ml of water were added to the reaction mixture and the solution formed was extracted 3× with ethyl acetate. The combined organic phases were concentrated and the residue was purified by preparative HPLC (RP18 column, mobile phase: water/methanol gradient with addition of 0.1% TFA). All product-containing fractions were combined and concentrated. Saturated aqueous sodium bicarbonate solution was added to the residue, and the mixture was extracted three times with ethyl acetate. The combined organic phases were dried over sodium sulphate, filtered, concentrated and dried under high vacuum. This gave 78 mg of the target compound (63% of theory, purity 100%).

LC-MS (Method 1): $R_t$=0.81 min

MS (ESpos): m/z=360 (M+H)$^+$ $^1$H NMR (400 MHz, DMSO-$d_6$): δ=0.88 (t, 3H), 1.21-1.53 (m, 5H), 1.58-1.71 (m, 1H), 1.81-1.99 (m, 4H), 2.09-2.18 (m, 2H), 2.50 (s, 3H), 2.73-2.84 (m, 1H), 3.39-3.54 (m, 2H), 3.92-4.03 (m, 1H), 4.12 (d, 2H), 4.72 (t, 1H), 6.78 (d, 1H), 6.84 (t, 1H), 7.48 (d, 1H), 8.48 (d, 1H).

Example 159

N-[(2R)-1-Hydroxyhexan-2-yl]-2-methyl-8-(3-methylbutoxy)imidazo[1,2-a]pyridine-3-carboxamide

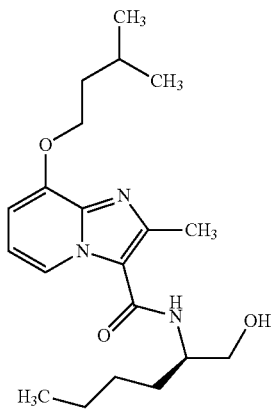 [SMILES: CCCC[C@H](CO)NC(=O)c1c(C)nc2c(OCCC(C)C)cccn12]

100 mg (0.34 mmol) of 8-hydroxy-N-[(2R)-1-hydroxyhexan-2-yl]-2-methylimidazo[1,2-a]-pyridine-3-carboxamide, 246 mg (0.76 mmol) of caesium carbonate and 75 mg (0.38 mmol) of 1-iodo-3-methylbutane were added to 4.9 ml of dry DMF, and the mixture was stirred for 30 min in an oil bath preheated to 60° C. After cooling, about 40 ml of water were added to the reaction mixture and the solution formed was extracted three times with ethyl acetate. The combined organic phases were concentrated and the residue was purified by preparative HPLC (RP18 column, mobile phase: water/methanol gradient with addition of 0.1% TFA). All product-containing fractions were combined and concentrated. Saturated aqueous sodium bicarbonate solution was added to the residue, and the mixture was extracted three times with ethyl acetate. The combined organic phases were dried over sodium sulphate, filtered, concentrated and dried under high vacuum. This gave 82 mg of the target compound (66% of theory, purity 100%).

LC-MS (Method 1): $R_t$=0.85 min

MS (ESpos): m/z=362 (M+H)$^+$ $^1$H NMR (400 MHz, DMSO-$d_6$): δ=0.88 (t, 3H), 0.96 (d, 6H), 1.24-1.53 (m, 5H), 1.59-1.73 (m, 3H), 1.78-1.90 (m, 1H), 2.50 (s, 3H), 3.39-3.53 (m, 2H), 3.92-4.03 (m, 1H), 4.18 (t, 2H), 4.72 (t, 1H), 6.78 (d, 1H), 6.86 (t, 1H). 7.48 (d, 1H), 8.48 (d, 1H).

Example 160 rac-8-[(2,6-Difluorobenzyl)oxy]-N-(1-ethoxy-3-hydroxypropan-2-yl)-2-methylimidazo[1,2-a]-pyridine-3-carboxamide

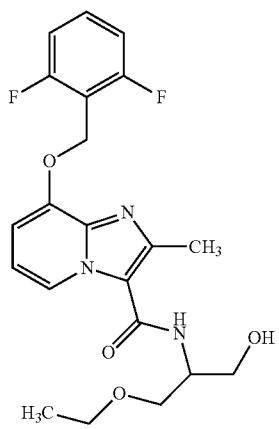 [SMILES: CCOCC(CO)NC(=O)c1c(C)nc2c(OCc3c(F)cccc3F)cccn12]

At 0° C., 750 mg (1.92 mmol) of 8-[(2,6-difluorobenzyl)oxy]-N-(1,3-dihydroxy-propan-2-yl)-2-methylimidazo[1,2-a]pyridine-3-carboxamide were initially charged in 19 ml of DMF, 52 mg (2.11 mmol) of sodium hydride (95%) were added and the mixture was stirred at 0° C. for 30 min. A solution of 239 mg (1.53 mmol) of iodethane in 2 ml of DMF was then slowly added dropwise at 0° C., and the mixture was stirred at RT overnight. At room temperature, another 9.4 mg (0.38 mmol) of sodium hydride (95%) were added, the mixture was stirred for 30 min and another 59.8 mg (0.38 mmol) of iodoethane were then added dropwise, and the mixture was stirred at room temperature overnight. A little methanol was added and the reaction mixture was poured into 20 ml of water and extracted twice with ethyl acetate. The combined organic phases were washed with aqueous saturated sodium chloride solution, dried over sodium sulphate, filtered and concentrated. The residue was purified by silica gel chromatography (mobile phase dichloromethane:methanol=40:1, 20:1). This gave 280 mg of the target compound (33% of theory, purity 96%).

LC-MS (Method 2): $R_t$=0.82 min

MS (ESpos): m/z=420 (M+H)$^+$ $^1$H NMR (400 MHz, DMSO-$d_6$): δ=1.12 (t, 3H), 2.50 (s, 3H), 3.42-3.60 (m, 6H), 4.09-4.18 (m, 1H), 4.72 (t, 1H), 5.31 (s, 2H), 6.93 (t, 1H), 7.00 (d, 1H), 7.22 (t, 2H), 7.53 (d, 1H), 7.59 (quint, 1H), 8.59 (d, 1H).

Example 161 ent-8-[(2,6-Difluorobenzyl)oxy]-N-(1-ethoxy-3-hydroxypropan-2-yl)-2-methylimidazo[1,2-a]-pyridine-3-carboxamide (enantiomer A)

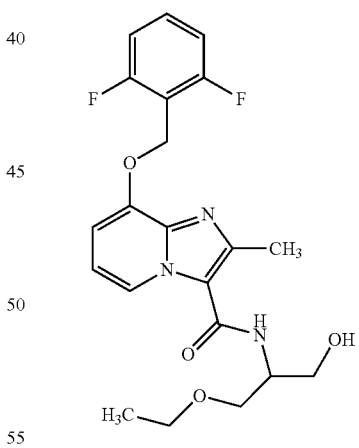

Example 160 (280 mg) was separated into the enantiomers by preparative separation on a chiral phase [column: Daicel Chiralcel OD-H, 5 μm, 250×20 mm; mobile phase: 50% isohexane, 50% isopropanol; flow rate 15 ml/min; 40° C.; detection: 220 nm]

Yield: 116 mg (99% pure, >99% ee)

Enantiomer A: $R_t$=4.88 min [Chiralcel OD-H, 5 μm, 250× 4.6 mm; mobile phase: 50% isohexane, 50% isopropanol+ 0.2% TFA+1% water; flow rate 1.0 ml/min; 40° C.; detection: 220 nm].

Example 162 rac-8-[(2,6-Difluorobenzyl)oxy]-N-(1-hydroxy-3-propoxypropan-2-yl)-2-methylimidazo[1,2-a]-pyridine-3-carboxamide

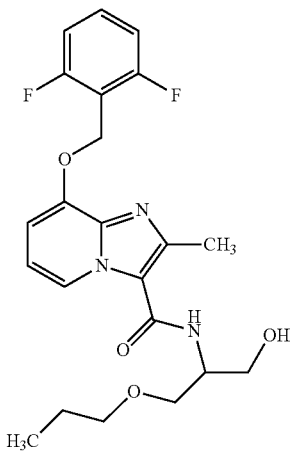 [SMILES: CCCOCC(CO)NC(=O)c1c(C)nc2c(OCc3c(F)cccc3F)cccn12]

At 0° C., 100 mg (0.26 mmol) of 8-[(2,6-difluorobenzyl)oxy]-N-(1,3-dihydroxypropan-2-yl)-2-methylimidazo[1,2-a]pyridine-3-carboxamide were initially charged in 2.4 ml of DMF, 7.1 mg (0.28 mmol) of sodium hydride (95%) were added and the mixture was stirred at 0° C. for 30 min. At 0° C., a solution of 35 mg (0.20 mmol) of iodopropane in 0.4 ml of DMF was then slowly added dropwise, and the mixture was stirred at RT overnight. Another 1.6 mg (0.064 mmol) of sodium hydride (95%) were added at room temperature, the mixture was stirred for 30 min, another 10.6 mg (0.064 mmol) of iodopropane were then added dropwise and the mixture was stirred at room temperature overnight. At RT, another 1.6 mg (0.064 mmol) of sodium hydride (95%) were then added, the mixture was stirred for 30 min and 10.6 mg (0.064 mmol) of iodopropane were then added dropwise, and the mixture was stirred at room temperature overnight. A little methanol was added, and the reaction mixture was poured into 20 ml of water and extracted twice with ethyl acetate. The combined organic phases were washed with aqueous saturated sodium chloride solution, dried over sodium sulphate, filtered and concentrated. The residue was purified by silica gel chromatography (mobile phase: cyclohexane:ethyl acetate=7:3, then dichloromethane:methanol=40:1). The crude product obtained was re-purified by preparative thick-layer chromatography (dichloromethane:methanol=20:1). This gave 44 mg of the target compound (38% of theory, purity 95%).

LC-MS (Method 1): $R_t$=0.82 min

MS (ESpos): m/z=434 (M+H)$^+$ $^1$H NMR (400 MHz, DMSO-d$_6$): δ=0.87 (t, 3H), 1.51 (sextett, 2H), 2.50 (s, 3H), 3.35-3.42 (m, 2H), 3.46-3.60 (m, 4H), 4.10-4.19 (m, 1H), 4.72 (t, 1H), 5.31 (s, 2H), 6.93 (t, 1H), 7.00 (d, 1H), 7.22 (t, 2H), 7.52 (d, 1H), 7.59 (quint, 1H), 8.59 (d, 1H).

Example 163 rac-8-[(2,6-Difluorobenzyl)oxy]-N-(1-hydroxy-3-isobutoxypropan-2-yl)-2-methylimidazo[1,2-a]-pyridine-3-carboxamide

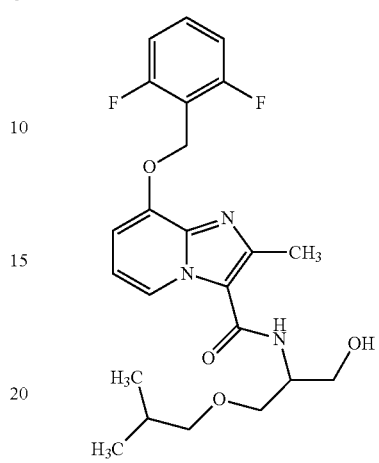

250 mg (0.64 mmol) of 8-[(2,6-difluorobenzyl)oxy]-N-(1,3-dihydroxy-propan-2-yl)-2-methylimidazo[1,2-a]pyridine-3-carboxamide and 4.94 g (26.83 mmol) of 1-iodo-2-methylpropane were initially charged in dry toluene, 1.87 g (7.66 mmol) of silver(I) oxide and 118 mg (0.32 mmol) of tetra-n-butylammonium iodide were added and the mixture was stirred at 40° C. overnight. The reaction mixture was filtered through Celite, the filter cake was washed thoroughly, the filtrate was concentrated and the residue was purified by preparative HPLC (RP18 column, mobile phase: acetonitrile/water gradient with addition of 0.1% TFA). The crude product was then purified by preparative thick-layer chromatography (mobile phase: dichloromethane:methanol=20:1). This gave 13 mg of the target compound (4.5% of theory, purity 100%).

LC-MS (Method 1): $R_t$=0.92 min

MS (ESpos): m/z=448 (M+H)$^+$ $^1$H NMR (400 MHz, DMSO-d$_6$): δ=0.85 (d, 6H), 1.75-1.87 (m, 1H), 2.50 (s, 3H), 3.18-3.24 (m, 2H), 3.46-3.60 (m, 4H), 4.10-4.19 (m, 1H), 4.72 (t, 1H), 5.31 (s, 2H), 6.93 (t, 1H), 7.00 (d, 1H), 7.22 (t, 2H), 7.52 (d, 1H), 7.59 (quint, 1H), 8.59 (d, 1H).

Example 164

Methyl N-({8-[(2,6-difluorobenzyl)oxy]-2-methylimidazo[1,2-a]pyridin-3-yl}carbonyl)-L-serinate

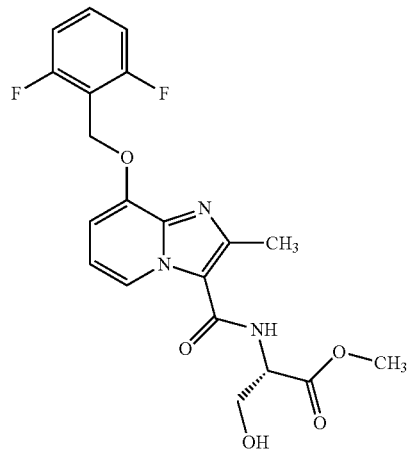 [SMILES: COC(=O)[C@H](CO)NC(=O)c1c(C)nc2c(OCc3c(F)cccc3F)cccn12]

500 mg (1.57 mmol) of 8-[(2,6-difluorobenzyl)oxy]-2-methylimidazo[1,2-a]pyridine-3-carboxylic acid Example 6A, 756 mg (2.36 mmol) of (benzotriazol-1-yloxy)bisdimethylaminomethylium fluoroborate (TBTU) and 794 mg (7.89 mmol) of 4-methylmorpholine were initially charged in 3 ml of DMF. After 10 min at RT, 293 mg (1.89 mmol) of (S)-serine methyl ester hydrochloride were added and the mixture was stirred at RT overnight. About 80 ml of water were added to the reaction solution, and the precipitate formed was stirred for another 30 min, filtered off, washed thoroughly with cold diethyl ether and dried under high vacuum overnight. This gave 601 mg of the target compound (89% of theory, purity 98%).

LC-MS (Method 1): $R_t$=0.74 min

MS (ESpos): m/z=420 (M+H)$^+$ $^1$H NMR (400 MHz, DMSO-d$_6$): δ=2.58 (s, 3H), 3.70 (s, 3H), 3.78-3.88 (m, 2H), 4.59-4.65 (m, 1H), 5.13 (t, 1H), 5.30 (s, 2H), 6.96 (t, 1H), 7.04 (d, 1H), 7.22 (t, 2H), 7.59 (quint, 1H), 7.92 (d, 1H), 8.62 (d, 1H).

Example 165

8-[(2,6-Difluorobenzyl)oxy]-N-[(2S)-1,3-dihydroxy-3-methylbutan-2-yl]-2-methylimidazo[1,2-a]-pyridine-3-carboxamide

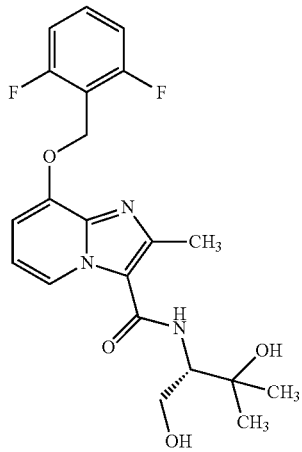 [SMILES: Cc1nc2c(OCc3c(F)cccc3F)cccn2c1C(=O)N[C@@H](CO)C(C)(C)O]

Under argon, 100 mg (0.24 mmol) of methyl N-({8-[(2,6-difluorobenzyl)oxy]-2-methylimidazo[1,2-a]pyridin-3-yl}carbonyl)-L-serinate were suspended in 2.3 ml of dry THF, the mixture was cooled to 0° C., 0.20 ml of methylmagnesium bromide solution (3.0 M in diethyl ether; 0.60 mmol, 2.5 equivalents) was added dropwise and, with stirring, the mixture was slowly brought to RT. The mixture was stirred at RT overnight, and another 0.1 ml of methylmagnesium bromide solution (3.0 M in diethyl ether) was then added dropwise at 0° C. and the mixture was stirred at RT for 6 h. Another 0.1 ml of methylmagnesium bromide solution (3.0 M in diethyl ether) was then added dropwise, and the mixture was stirred at RT overnight. 1N aqueous hydrochloric acid was added, and the mixture was diluted with ethyl acetate. The organic phase was separated off and the aqueous phase was extracted three times with ethyl acetate. The combined organic phases were washed with saturated sodium chloride solution, dried with sodium sulphate, filtered and concentrated. The residue was chromatographed on a silica gel cartridge (dichloromethane:methanol=40:1 as mobile phase). This gave 46 mg of the target compound (45% of theory).

LC-MS (Method 1): $R_t$=0.68 min

MS (ESpos): m/z=420.3 (M+H)$^+$ $^1$H NMR (400 MHz, DMSO-d$_6$): δ=1.12 (s, 3H), 1.20 (s, 3H), 2.55 (s, 3H; superimposed by DMSO signal), 3.56-3.61 (m, 1H), 3.73-3.80 (m, 1H), 3.96-4.03 (m, 1H), 4.57 (s, 1H), 4.61 (t, 1H), 5.31 (s, 2H), 6.92 (t, 1H), 6.99 (d, 1H), 7.23 (t, 2H), 7.30 (d, 1H), 7.59 (quint., 1H), 8.62 (d, 1H).

Example 166

N-[(2R)-1-Hydroxyhexan-2-yl]-2,6-dimethyl-8-(3-methylbutoxy)imidazo[1,2-a]pyridine-3-carboxamide

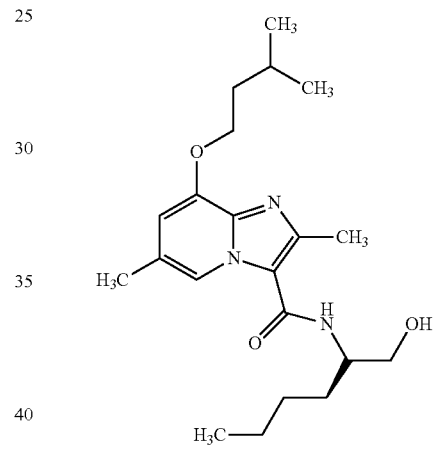

75 mg (0.27 mmol) of 2,6-dimethyl-8-(3-methylbutoxy)imidazo[1,2-a]pyridine-3-carboxylic acid Example 89A, 96 mg (0.30 mmol) of TBTU and 110 mg (1.09 mmol) of 4-methylmorpholine were initially charged in 1.73 ml of DMF. 35 mg (0.30 mmol) of (R)-(–)-2-aminohexanol were then added, and the mixture was stirred at room temperature overnight. The reaction solution was diluted with water/TFA and purified by preparative HPLC (RP18 column, mobile phase: acetonitrile/water gradient with addition of 0.1% TFA). The concentrated fractions were taken up in dichloromethane and washed twice with saturated aqueous sodium bicarbonate solution. The aqueous phase was extracted two more times with dichloromethane, the combined organic phases were dried over sodium sulphate and filtered and the filtrate was concentrated and lyophilized. This gave 91 mg of the target compound (87.5% of theory, purity 98%).

LC-MS (Method 1): $R_t$=0.88 min

MS (ESpos): m/z=376.5 (M+H)$^+$ $^1$H NMR (400 MHz, DMSO-d$_6$): δ=0.88 (t, 3H), 0.96 (d, 6H), 1.23-1.50 (m, 5H), 1.59-1.73 (m, 3H), 1.78-1.88 (m, 1H), 2.28 (s, 3H), 2.56 (s, 3H), 3.38-3.53 (m, 2H), 3.90-4.02 (m, 1H), 4.15 (t, 2H), 4.74 (t, 1H), 6.69 (s, 1H), 7.48 (d, 1H), 8.30 (s, 1H).

Example 167 ent-N-(2-Hydroxy-2-methylheptan-3-yl)-2,6-dimethyl-8-(3-methylbutoxy)imidazo[1,2-a]pyridine-3-carboxamide

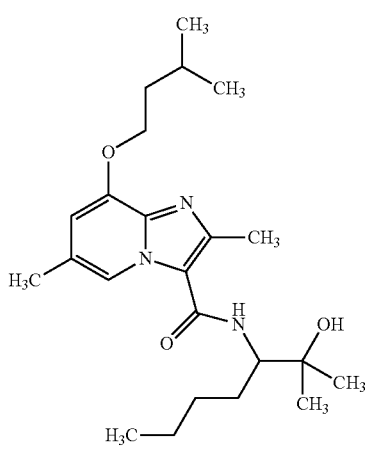 [SMILES: CCCCC(NC(=O)c1c(C)nc2c(OCCC(C)C)cc(C)cn12)C(C)(C)O]

60 mg (0.22 mmol) of 2,6-dimethyl-8-(3-methylbutoxy)imidazo[1,2-a]pyridine-3-carboxylic acid Example 89A, 77 mg (0.24 mmol) of TBTU and 88 mg (0.87 mmol) of 4-methylmorpholine were initially charged in 1.38 ml of DMF. 43 mg (0.24 mmol) of ent-3-amino-2-methylheptan-2-ol hydrochloride from Example 98A were then added, and the mixture was stirred at room temperature overnight. Another 8 mg (0.04 mmol) of ent-3-amino-2-methylheptan-2-ol hydrochloride were then added, and the reaction solution was stirred at RT overnight. The reaction solution was diluted with water/TFA and purified by preparative HPLC (RP18 column, mobile phase: acetonitrile/water gradient with addition of 0.1% TFA). The concentrated fractions were taken up in dichloromethane and washed twice with saturated aqueous sodium bicarbonate solution. The aqueous phase was extracted two more times with dichloromethane, the combined organic phases were dried over sodium sulphate and filtered and the filtrate was concentrated and lyophilized. This gave 48 mg of the target compound (54% of theory, purity 99%).

LC-MS (Method 17): $R_t$=0.91 min

MS (ESpos): m/z=404 (M+H)$^+$ $^1$H NMR (400 MHz, DMSO-d$_6$): δ=0.88 (t, 3H), 0.96 (d, 6H), 1.11 (s, 3H), 1.18 (s, 3H), 1.20-1.48 (m, 5H), 1.66-1.88 (m, 4H), 2.28 (s, 3H), 2.54 (s, 3H), 3.88-3.95 (m, 1H), 4.18 (t, 2H), 4.49 (s, 1H), 6.72 (s, 1H), 7.33 (d, 1H), 8.29 (s, 1H).

Example 168 ent-2,6-Dimethyl-8-(3-methylbutoxy)-N-(7,7,7-trifluoro-2-hydroxy-2-methylheptan-3-yl)imidazo-[1,2-a]pyridine-3-carboxamide

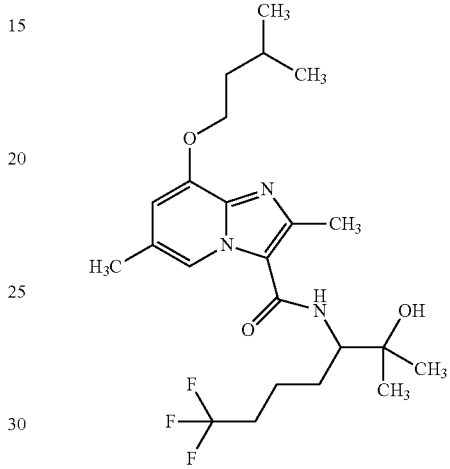

50 mg (0.18 mmol) of 2,6-dimethyl-8-(3-methylbutoxy)imidazo[1,2-a]pyridine-3-carboxylic acid Example 89A, 61 mg (0.19 mmol) of TBTU and 55 mg (0.54 mmol) of 4-methylmorpholine were initially charged in 0.64 ml of DMF. 47 mg (0.20 mmol) of ent-3-amino-7,7,7-trifluoro-2-methylheptan-2-ol hydrochloride Example 104A were then added, and the mixture was stirred at room temperature overnight. Another 17 mg (0.07 mmol) of ent-3-amino-7,7,7-trifluoro-2-methylheptan-2-ol hydrochloride were then added, and the reaction solution was stirred at RT overnight. The mixture was then diluted with a few drops of water/TFA and purified by preparative HPLC (RP18 column, mobile phase: acetonitrile/water gradient with addition of 0.1% TFA). The product-containing fractions were concentrated, saturated aqueous sodium bicarbonate solution was added to the residue and the mixture was extracted three times with dichloromethane. The combined organic phases were dried over sodium sulphate and filtered, and the filtrate was concentrated and dried under high vacuum. This gave 66 mg of the target compound (78% of theory, purity 98%).

LC-MS (Method 17): $R_t$=0.92 min

MS (ESpos): m/z=458 (M+H)$^+$ $^1$H NMR (400 MHz, DMSO-d$_6$): δ=0.96 (d, 6H), 1.11 (s, 3H), 1.18 (s, 3H), 1.42-1.67 (m, 3H), 1.67-1.73 (m, 2H), 1.77-1.88 (m, 2H), 2.12-2.29 (m, 4H), 2.30-2.48 (m, 1H), 2.54 (s, 3H), 3.90-3.99 (m, 1H), 4.18 (t, 2H), 4.56 (s, 1H), 6.72 (s, 1H), 7.43 (d, 1H), 8.28 (s, 1H).

Example 169

N-[(2R)-1-Hydroxyhexan-2-yl]-2,6-dimethyl-8-[4,4,4-trifluoro-3-(trifluoromethyl)butoxy]imidazo-[1,2-a]pyridine-3-carboxamide

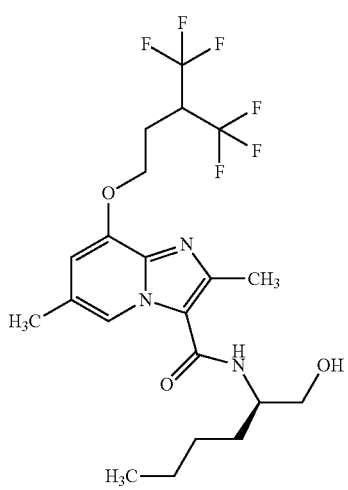 [SMILES: CCCC[C@H](CO)NC(=O)c1c(C)nc2c(OCCC(C(F)(F)F)C(F)(F)F)cc(C)cn12]

150 mg (0.39 mmol) of 2,6-dimethyl-8-[4,4,4-trifluoro-3-(trifluoromethyl)butoxy]imidazo[1,2-a]-pyridine-3-carboxylic acid Example 91A and 163 mg (0.43 mmol) of HATU were initially charged in 2.5 ml of DMF. 0.2 ml (1.17 mmol) of N,N-diisopropylethylamine and 50.3 mg (0.43 mmol) of (R)-(−)-2-amino-1-hexanol were then added, and the mixture was stirred at RT overnight. 10 ml of water were added, the reaction solution was extracted twice with 20 ml of ethyl acetate and the combined organic phases were washed with 20 ml of water and with 20 ml of saturated aqueous sodium chloride solution, dried over magnesium sulphate, filtered and concentrated. The residue was purified by preparative RP-HPLC (acetonitrile-water+0.1% formic acid), the product fractions were combined and concentrated to dryness and the residue was dissolved in a mixture of 1.5 ml of tert-butanol and 2 ml of water and lyophilized overnight. This gave 42 mg of the target compound (95% pure, 21% of theory).

LC-MS (Method 1): $R_t$=0.95 min

MS (ESpos): m/z=484 (M+H)$^+$ $^1$H NMR (400 MHz, DMSO-$d_6$): δ=0.89 (t, 3H), 1.26-1.41 (m, 4H), 1.41-1.54 (m, 1H), 1.58-1.68 (m, 1H), 2.32-2.42 (m, 5H), 2.59 (s, 3H), 3.48 (t, 2H), 3.94-4.02 (m, 1H), 4.24-4.34 (m, 1H), 4.41 (t, 2H), 7.23 (br. s, 1H), 8.05 (br. s, 1H), 8.42 (s, 1H), OH not visible.

Example 170 rac-2,6-Dimethyl-N-(7,7,7-trifluoro-2-hydroxy-2-methylheptan-3-yl)-8-[4,4,4-trifluoro-3-(trifluoromethyl)butoxy]imidazo[1,2-a]pyridine-3-carboxamide

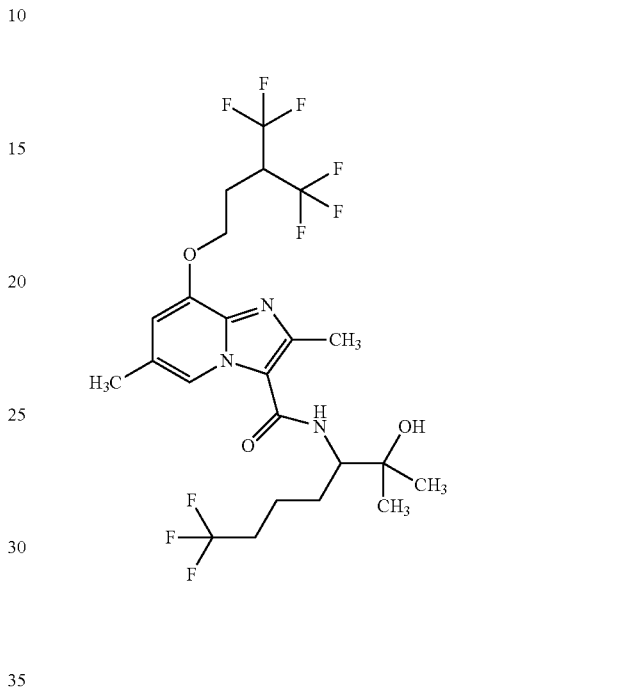

150 mg (0.390 mmol) of 2,6-dimethyl-8-[4,4,4-trifluoro-3-(trifluoromethyl)butoxy]imidazo[1,2-a]-pyridine-3-carboxylic acid Example 91A and 163 mg (0.429 mmol) of HATU were initially charged in 2 ml of DMF. 0.2 ml (1.17 mmol) of N,N-diisopropylethylamine and 101 mg (0.429 mmol) of rac-3-amino-7,7,7-trifluoro-2-methylheptan-2-ol hydrochloride Example 103A were then added, and the mixture was stirred at RT overnight. 10 ml of water were added, the reaction solution was extracted twice with 20 ml of ethyl acetate and the combined organic phases were washed with 20 ml of water and with 20 ml of sat. aqueous NaCl solution, dried over MgSO$_4$, filtered and concentrated. The residue was purified by preparative RP-HPLC (ACN:water+0.1% HCOOH). The product fractions were combined and concentrated to dryness and the residue was dissolved in a mixture of 1.5 ml of tert-butanol and 2 ml of water and lyophilized overnight. This gave 91 mg of the target compound (98% pure, 40% of theory).

LC-MS (Method 1): $R_t$=1.03 min

MS (ESpos): m/z=566 (M+H)$^+$ $^1$H NMR (400 MHz, DMSO-$d_6$): δ=1.12 (s, 3H), 1.19 (s, 3H), 1.40-1.67 (m, 3H), 1.79-1.88 (m, 1H) 2.13-2.29 (m, 2H), 2.29-2.44 (m, 5H), 2.58 (s, 3H), 3.97 (t, 1H), 4.18-4.33 (m, 1H), 4.38 (t, 2H), 4.60 (br. s, 1H), 7.01 (br. s, 1H) 7.70 (br. s, 1H) 8.34 (s, 1H).

Example 171 ent-8-[1-(2,6-Difluorophenyl)ethoxy]-N-(2-hydroxy-2-methylheptan-3-yl)-2,6-dimethylimidazo-[1,2-a]pyridine-3-carboxamide

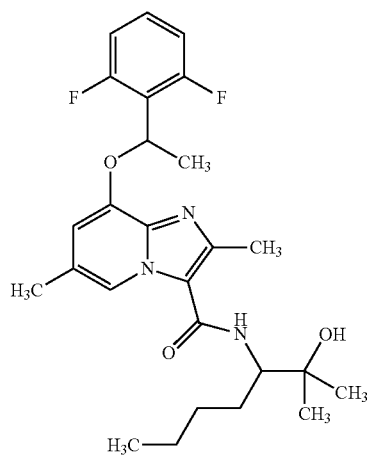 [SMILES: CCCCC(NC(=O)c1c(C)nc2c(OC(C)c3c(F)cccc3F)cc(C)cn12)C(C)(C)O]

40 mg (0.12 mmol) of ent-8-[1-(2,6-difluorophenyl)ethoxy]-2,6-dimethylimidazo[1,2-a]pyridine-3-carboxylic acid Example 94A, 45 mg (0.14 mmol) of TBTU and 47 mg (0.46 mmol) of 4-methylmorpholine were initially charged in 0.77 ml of DMF. 25 mg (0.14 mmol) of ent-3-amino-2-methylheptan-2-ol hydrochloride Example 98A were then added, and the mixture was stirred at room temperature overnight. Another 4 mg (0.02 mmol) of ent-3-amino-2-methylheptan-2-ol hydrochloride were then added, and the reaction solution was stirred at RT overnight. Another 4 mg (0.02 mmol) of ent-3-amino-2-methylheptan-2-ol hydrochloride were then added, and the reaction solution was stirred at RT overnight. The reaction solution was diluted with a few drops of water/TFA and purified by preparative HPLC (RP18 column, mobile phase: acetonitrile/water gradient with addition of 0.1% TFA). The concentrated fractions were taken up in dichloromethane and saturated aqueous sodium bicarbonate solution, and the phases were separated. The aqueous phase was extracted three times with dichloromethane, the combined organic phases were dried over sodium sulphate and filtered and the filtrate was concentrated and lyophilized. This gave 48 mg of the target compound (87% of theory, purity 98%).

LC-MS (Method 1): $R_t$=0.91 min

MS (ESpos): m/z=474 (M+H)$^+$ $^1$H NMR (400 MHz, DMSO-d$_6$): δ=0.85 (t, 3H), 1.11 (s, 3H), 1.17 (s, 3H), 1.20-1.47 (m, 5H), 1.69-1.81 (m, 4H), 2.19 (s, 3H), 2.52 (s, 3H), 3.86-3.93 (m, 1H), 4.42 (br. s, 1H), 6.22 (q, 1H), 6.58 (br. s, 1H), 7.09 (t, 2H), 7.28-7.37 (m, 1H), 7.40 (quintet, 1H), 8.30 (s, 1H).

Example 172

N-(2-Hydroxy-2,3-dihydro-1H-inden-1-yl)-2,6-dimethyl-8-[4,4,4-trifluoro-3-(trifluoromethyl)-butoxy]imidazo[1,2-a]pyridine-3-carboxamide

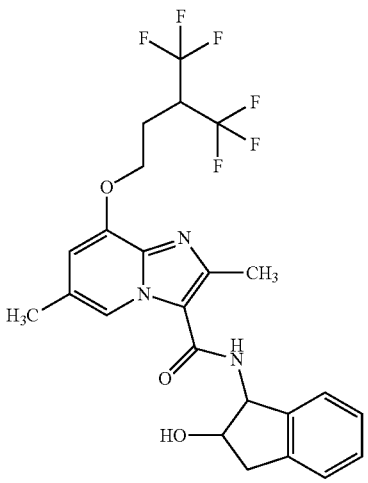 [SMILES: Cc1cc(OCCC(C(F)(F)F)C(F)(F)F)c2nc(C)c(C(=O)NC3c4ccccc4CC3O)n2c1]

12 mg (0.08 mmol) of 1-aminoindan-2-ol were initially charged, 31 mg (0.08 mmol) of 2,6-dimethyl-8-[4,4,4-trifluoro-3-(trifluoromethyl)butoxy]imidazo[1,2-a]pyridine-3-carboxylic acid Example 91A, dissolved in 0.3 ml of DMF, 40 mg (0.104 mmol) of HATU, dissolved in 0.3 ml of DMF, and then 16 mg (0.16 mmol) of 4-methylmorpholine were added and the mixture was shaken at RT overnight. The target compound was isolated by preparative HPLC (Method 11). This gave 15 mg (36% of theory).

LC-MS (Method 12): $R_t$=0.99 min

MS (ESpos): m/z=516 (M+H)$^+$

The example compounds shown in Table 14 were prepared analogously to Example 172 by reacting 2,6-dimethyl-8-[4,4,4-trifluoro-3-(trifluoromethyl)butoxy]imidazo[1,2-a]pyridine-3-carboxylic acid with the appropriate commercially available amines under the conditions described:

TABLE 14

| Example | IUPAC name/structure (yield) | Analytical data |
|---------|------------------------------|-----------------|
| 173 | N-(2-hydroxycyclopentyl)-2,6-dimethyl-8-[4,4,4-trifluoro-3-(trifluoromethyl)butoxy]imidazo[1,2-a]pyridine-3-carboxamide<br />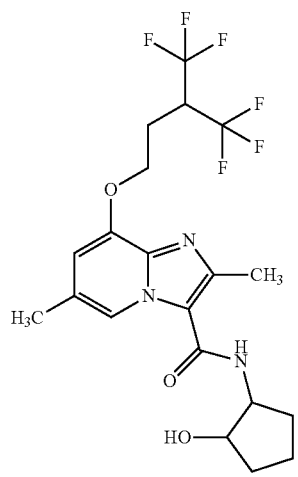<br />(9% of theory) | LC-MS (Method 12): $R_t$ = 0.86 min<br />MS (ESpos): m/z = 456 (M + H)+ |
| 174 | rac-N-(2-hydroxybutyl)-2,6-dimethyl-8-[4,4,4-trifluoro-3-(trifluoromethyl)butoxy]imidazo[1,2-a]pyridine-3-carboxamide<br />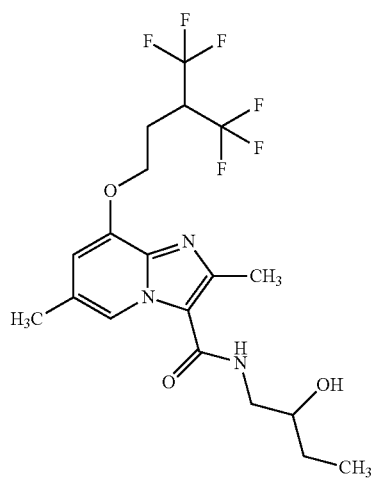 [SMILES: CCC(O)CNC(=O)c1c(C)nc2c(OCCC(C(F)(F)F)C(F)(F)F)cc(C)cn12]<br />(12% of theory) | LC-MC (Method 12): $R_t$ = 0.87 min<br />MS (ESpos): m/z = 456 (M + H)+ |

TABLE 14-continued

| Example | IUPAC name/structure (yield) | Analytical data |
|---|---|---|
| 175 | rac-N-[2-(4-chlorophenyl)-2-hydroxyethyl]-2,6-dimethyl-8-[4,4,4-trifluoro-3-(trifluoromethyl)butoxy]imidazo[1,2-a]pyridine-3-carboxamide<br />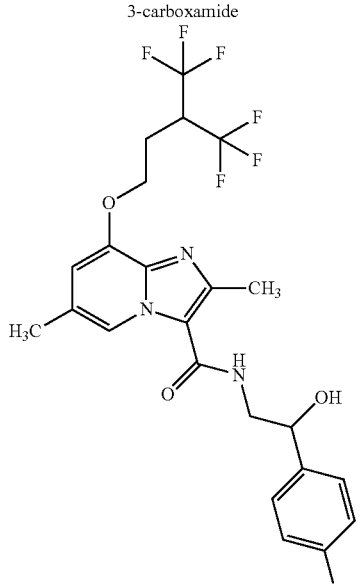<br />(3% of theory) | LC-MS (Method 12): Rt = 0.99 min<br />MS (ESpos): m/z = 538 (M + H)+ |

Example 176 rac-8-[(3,3-Difluorocyclobutyl)methoxy]-2,6-dimethyl-N-(7,7,7-trifluoro-2-hydroxy-2-methylheptan-3-yl)imidazo[1,2-a]pyridine-3-carboxamide

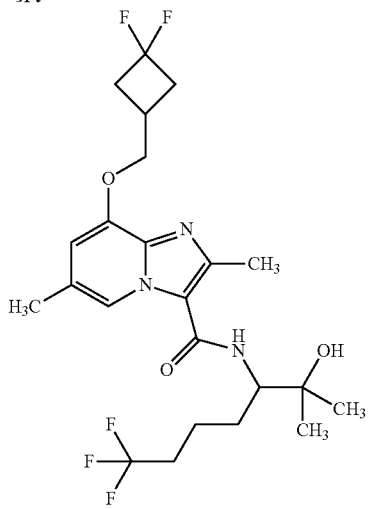

100 mg (0.32 mmol) of 8-[(3,3-difluorocyclobutyl)methoxy]-2,6-dimethylimidazo[1,2-a]pyridine-3-carboxylic acid Example 107A and 135 mg (0.35 mmol) of HATU were initially charged in 2 ml of DMF. 0.16 ml (0.96 mmol) of N,N-diisopropylethylamine and 70.6 mg (0.354 mmol) of rac-3-amino-7,7,7-trifluoro-2-methylheptan-2-ol hydrochloride Example 103A were then added, and the mixture was stirred at RT overnight. 7 ml of water were added, and the reaction solution was extracted twice with 15 ml of ethyl acetate. The combined organic phases were washed with 15 ml of water and with 10 ml of saturated aqueous sodium chloride solution, dried over magnesium sulphate, filtered and concentrated. The residue was purified by preparative RP-HPLC (acetonitrile-water+0.1% formic acid) and the product fractions were combined and concentrated to dryness. This gave 86 mg of the target compound (55% of theory).

LC-MS (Method 1): $R_t$=0.89 min
MS (ESpos): m/z=492 (M+H)$^+$
$^1$H NMR (400 MHz, DMSO-d$_6$): δ=1.13 (s, 3H), 1.18 (s, 3H), 1.41-1.65 (m, 3H), 1.79-1.88 (m, 1H) 2.14-2.29 (m, 2H), 2.29-2.43 (m, 4H), 2.56 (s, 3H), 2.64-2.84 (m, 4H), 3.93-4.00 (m, 1H), 4.28 (d, 2H), 4.57 (br. s, 1H), 6.95 (br. s, 1H), 7.63 (br. s, 1H), 8.33 (s, 1H).

Example 177

8-[(2,6-Difluorobenzyl)oxy]-7-fluoro-N-[(2R)-1-hydroxyhexan-2-yl]-2-methylimidazo[1,2-a]-pyridine-3-carboxamide

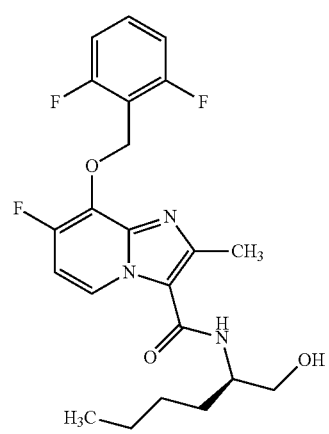 [SMILES: CCCC[C@H](CO)NC(=O)c1c(C)nc2c(OCc3c(F)cccc3F)c(F)ccn12]

14 mg (0.04 mmol) of 8-[(2,6-difluorobenzyl)oxy]-7-fluoro-2-methylimidazo[1,2-a]pyridine-3-carboxylic acid Example 112A, 20 mg (0.06 mmol) of (benzotriazol-1-yloxy)bisdimethylaminomethylium fluoroborate (TBTU) and 17 mg (0.17 mmol) of 4-methylmorpholine were initially charged in 0.28 ml of DMF. 7.5 mg (0.06 mmol) of (2R)-2-aminohexan-1-ol were then added, and the mixture was stirred at RT overnight. Another 2.6 mg of TBTU, 4 mg of 4-methylmorpholine and 1 mg of (2R)-2-aminohexan-1-ol were added, and the mixture was stirred at RT for 2 h. The reaction mixture was concentrated and purified by thick-layer chromatography (mobile phase: dichloromethane/methanol=10/1). This gave 12 mg (66% of theory; purity 99%) of the title compound.

LC-MS (Method 1): $R_t$=1.01 min

MS (ESpos): m/z=436 (M+H)$^+$ $^1$H NMR (400 MHz, DMSO-d$_6$): δ=0.88 (t, 3H), 1.23-1.56 (m, 5H), 1.58-1.70 (m, 1H), 2.57 (s, 3H), 3.38-3.55 (m, 2H), 3.91-4.04 (m, 1H), 4.73 (t, 1H), 5.57-5.63 (m, 2H), 6.96-7.06 (m, 1H), 7.08-7.18 (m, 2H), 7.46-7.62 (m, 2H), 8.63-8.68 (m, 1H).

B. ASSESSMENT OF THE PHARMACOLOGICAL ACTIVITY

The following abbreviations are used:

| | |
|---|---|
| ATP | adenosine triphosphate |
| Brij35 | polyoxyethylene (23) lauryl ether |
| BSA | bovine serum albumin |
| DTT | dithiothreitol |
| TEA | triethanolamine |

The pharmacological effect of the compounds according to the invention can be shown in the following assays:

B-1. Measurement of sGC Enzyme Activity by Detection of PPi

Soluble guanylate cyclase (sGC) converts on stimulation GTP into cGMP and pyrophosphate (PPi). PPi is detected with the aid of the assay described in WO 2008/061626. The signal produced in the assay increases as the reaction progresses and serves as a measure of the sGC enzyme activity. With the aid of a PPi reference curve, the enzyme can be characterized in a known manner, for example with respect to conversion rate, stimulability or Michaelis constant.

Practice of the Test

To carry out the assay, 29 μl of enzyme solution (0-10 nM soluble guanylate cyclase (prepared according to Honicka et al., Journal of Molecular Medicine 77 (1999)14-23) in 50 mM TEA, 2 mM magnesium chloride, 0.1% BSA (fractionV), 0.005% Brij 35, pH 7.5) were initially introduced into the microplate, and 1 μl of the stimulator solution (0-10 μM 3-morpholinosydnonimine, SIN-1, Merck in DMSO) were added. The mixture was incubated at RT for 10 min. 20 μl of detection mix (1.2 nM Firefly Luciferase (*Photinus pyralis* Luziferase, Promega), 29 μM dehydroluciferin (prepared according to Bitler & McElroy, Arch. Biochem. Biophys. 72 (1957) 358), 122 μM luciferin (Promega), 153 μM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by addition of 20 μl of substrate solution (1.25 mM guanosine 5'-triphosphate (Sigma) in 50 mM TEA, 2 mM magnesium chloride, 0.1% BSA (fraction V), 0.005% Brij 35, pH 7.5) and measured continuously in a luminometer.

B-2. Action on Recombinant Guanylate Cyclase Reporter Cell Line

The cellular action of the compounds according to the invention is determined on a recombinant guanylate cyclase reporter cell line, as described in F. Wunder et al., *Anal. Biochem.* 339, 104-112 (2005).

Representative values (MEC=minimal effective concentration) for the compounds according to the invention are shown in the following table (in some cases as mean values obtained from individual determinations):

TABLE A

| Example | MEC [μM] | Example | MEC [μM] |
|---|---|---|---|
| 1 | 0.05 | 101 | 0.1 |
| 2 | 0.03 | 102 | 0.1 |
| 3 | 0.1 | 103 | 0.1 |
| 4 | 0.1 | 104 | 0.1 |
| 5 | 0.1 | 105 | 0.03 |
| 6 | 0.1 | 106 | 0.3 |
| 7 | 0.3 | 107 | 0.1 |
| 8 | 0.3 | 108 | 0.1 |
| 9 | 0.5 | 109 | 0.1 |
| 10 | 0.3 | 110 | 0.3 |
| 11 | 1.5 | 111 | 0.01 |
| 12 | 3.0 | 112 | 0.03 |
| 13 | 3.0 | 113 | 0.03 |
| 14 | 3.0 | 114 | 0.03 |
| 15 | 0.1 | 115 | 0.01 |
| 16 | 1.0 | 116 | 0.3 |
| 17 | 3.0 | 117 | 0.03 |
| 18 | 0.1 | 118 | 0.3 |
| 19 | 1.0 | 119 | 0.3 |
| 20 | 1.0 | 120 | 1.0 |
| 21 | 1.0 | 121 | 0.03 |
| 22 | 1.0 | 122 | 0.03 |
| 23 | 0.3 | 123 | 0.03 |
| 24 | 1.0 | 124 | 0.3 |
| 25 | 0.1 | 125 | 0.3 |
| 26 | 2.0 | 126 | 0.1 |
| 27 | 0.3 | 127 | 0.3 |
| 28 | 0.65 | 128 | 0.3 |
| 29 | 0.1 | 129 | 3.0 |
| 30 | 0.3 | 130 | 1.0 |
| 31 | 1.0 | 131 | 0.01 |
| 32 | 1.0 | 132 | 0.03a |
| 33 | 0.3 | 133 | 0.01 |
| 34 | 0.3 | 134 | 0.3 |
| 35 | 0.3 | 135 | 0.1 |
| 36 | 0.1 | 136 | 3.0 |
| 37 | 0.3 | 137 | 3.0 |
| 38 | 0.3 | 138 | 0.1 |
| 39 | 0.03 | 139 | 0.03 |
| 40 | 0.1 | 140 | 0.03 |
| 41 | 3.0 | 141 | 0.1 |
| 42 | 1.0 | 142 | 0.1 |
| 43 | 0.16 | 143 | 0.03 |
| 44 | 0.3 | 144 | 0.3 |
| 45 | 0.65 | 145 | >10 |
| 46 | 3.0 | 146 | 1.0 |
| 47 | 0.3 | 147 | 0.1 |
| 48 | 1.0 | 148 | 0.03 |
| 49 | 2.0 | 149 | 0.1 |
| 50 | 6.5 | 150 | 0.03 |
| 51 | 5.5 | 151 | 0.3 |
| 52 | 10 | 152 | 0.3 |
| 53 | 10 | 153 | 0.3 |
| 54 | 10 | 154 | 0.03 |
| 55 | 0.1 | 155 | 0.1 |
| 56 | 1.0 | 156 | 0.03 |
| 57 | 1.0 | 157 | 0.065 |
| 58 | 3.0 | 158 | 1.0 |
| 59 | 3.0 | 159 | 1.0 |
| 60 | 0.1 | 160 | 0.3 |
| 61 | 1.0 | 161 | 1.0 |
| 62 | 0.3 | 162 | 0.3 |
| 63 | 3.0 | 163 | 1.0 |
| 64 | 3.0 | 164 | 0.2 |

TABLE A-continued

| Example | MEC [µM] | Example | MEC [µM] |
|---|---|---|---|
| 65 | 0.03 | 165 | 1.0 |
| 66 | 0.01 | 166 | 1.0 |
| 67 | 0.03 | 167 | 2.0 |
| 68 | 0.03 | 168 | 3.0 |
| 69 | 0.1 | 169 | 0.3 |
| 70 | 0.1 | 170 | 3.0 |
| 71 | 0.1 | 171 | 1.0 |
| 72 | 0.1 | 172 | 1.0 |
| 73 | 0.1 | 173 | 3.0 |
| 74 | 0.2 | 174 | 3.0 |
| 75 | 0.22 | 175 | 3.0 |
| 76 | 0.3 | 176 | 3.0 |
| 77 | 0.3 | 177 | 1.0 |
| 78 | 0.3 | | |
| 79 | 0.3 | | |
| 80 | 0.3 | | |
| 81 | 0.65 | | |
| 82 | 0.3 | | |
| 83 | 0.3 | | |
| 84 | 0.3 | | |
| 85 | 0.38 | | |
| 86 | 0.65 | | |
| 87 | 1.0 | | |
| 88 | 1.0 | | |
| 89 | 1.0 | | |
| 90 | 1.0 | | |
| 91 | 1.0 | | |
| 92 | 1.0 | | |
| 93 | 1.0 | | |
| 94 | 3.0 | | |
| 95 | 3.0 | | |
| 96 | 3.0 | | |
| 97 | 1.0 | | |
| 98 | 3.0 | | |
| 99 | 3.0 | | |
| 100 | 0.03 | | |

B-3. Vessel-Relaxing Action In Vitro

Rabbits are stunned with a blow on the back of the neck and exsanguinated. The aorta is removed, freed from adhering tissue, separated into rings with a width of 1.5 mm, and placed individually, with preloading, in 5-ml organ baths with carbogen-gassed Krebs-Henseleit solution at 37° C. with the following composition (mM in each case): sodium chloride: 119; potassium chloride: 4.8; calcium chloride dihydrate: 1; magnesium sulphate heptahydrate: 1.4; potassium dihydrogen phosphate: 1.2; sodium hydrogen carbonate: 25; glucose: 10. The contraction force is recorded with Statham UC2 cells, amplified and digitized via an A/D converter (DAS-1802 HC, Keithley Instruments Munich) and recorded in parallel on a continuous-line recorder. To produce contraction, phenylephrine is added to the bath cumulatively in increasing concentration. After several control cycles, the test substance is added in increasing dosage in each subsequent pass and the level of contraction is compared with the level of contraction reached in the immediately preceding pass. This is used for calculating the concentration that is required to reduce the level of the control value by 50% ($IC_{50}$ value). The standard application volume is 5 µl, and the proportion of DMSO in the bath solution corresponds to 0.1%.

B-4. Measurement of Blood Pressure on Anaesthetized Rats

Male Wistar rats having a body weight of 300-350 g are anaesthetized with thiopental (100 mg/kg i.p.). After tracheotomy, a catheter for measuring the blood pressure is introduced into the femoral artery. The substances to be tested are administered as solutions either orally by gavage or intravenously via the femoral vein (Stasch et al. Br. J. Pharmacol. 2002; 135: 344-355).

B-5. Radiotelemetric Blood Pressure Measurement on Awake, Spontaneously Hypertensive Rats The blood pressure measurement on awake rats described below uses a commercially available telemetry system from the company DATA SCIENCES INTERNATIONAL DSI, USA.

The system consists of 3 main components:
implantable transmitter (Physiotel® Telemetry Transmitter)
receiver (Physiotel® Receiver), which are connected via a multiplexer (DSI Data Exchange Matrix) to a
data acquisition computer.

The telemetry system provides continuous acquisition of blood pressure, heart rate and body movement on awake animals in their usual living space.

Animal Material

The investigations are carried out on adult female, spontaneously hypertensive rats (SHR Okamoto) with a body weight of >200 g. SHR/NCrl from Okamoto Kyoto School of Medicine, 1963 were crossed from male Wistar Kyoto rats with greatly increased blood pressure and females with slightly raised blood pressure and were delivered in F13 to the U.S. National Institutes of Health.

After transmitter implantation, the experimental animals are kept individually in Makrolon cages, type 3. They have free access to standard feed and water.

The day-night rhythm in the testing laboratory is alternated by the room lighting at 06:00 hours in the morning and at 19:00 hours in the evening.

Transmitter Implantation

The TA11 PA-C40 telemetry transmitters used are implanted surgically in the experimental animals under aseptic conditions at least 14 days before the first test. The animals provided with this instrumentation can be used again after the wound has healed and the implant has become incorporated.

For implantation, the fasting animals are anaesthetized with pentobarbital (Nembutal, Sanofi: 50 mg/kg i.p.) and are shaved and disinfected on a wide area of the abdomen. After opening the abdominal cavity along the linea alba, the liquid-filled measuring catheter of the system is inserted above the bifurcation in the cranial direction into the aorta descendens and secured with tissue adhesive (VetBonD™, 3M). The transmitter housing is fixed intraperitoneally on the abdominal wall musculature and the wound is closed layer by layer.

Postoperatively, an antibiotic is administered to prevent infection (Tardomyocel COMP Bayer 1 ml/kg s.c.)

Substances and Solutions

Unless described otherwise, the test substances are in each case administered orally by stomach tube to a group of animals (n=6). Corresponding to an application volume of 5 ml/kg body weight, the test substances are dissolved in suitable solvent mixtures or suspended in 0.5% Tylose.

A group of animals treated with solvents is used as control.

Test Procedure

The present telemetry measuring device is configured for 24 animals. Each test is recorded under a test number (Vtest year month day).

The instrumented rats living in the unit are each assigned their own receiving antenna (1010 Receiver, DSI).

The implanted transmitters can be activated from outside by an in-built magnetic switch. They are switched to transmission at the start of the tests. The signals emitted can be recorded online by a data acquisition system (Dataquest™ A.R.T. for WINDOWS, DSI) and processed appropriately. The data are saved in each case to a folder opened for this, which bears the test number.

In the standard procedure, the following are measured, in each case for 10 seconds:
systolic blood pressure (SBP)
diastolic blood pressure (DBP)
mean arterial pressure (MAP)
heart rate (HR)
activity (ACT).

Recording of the measured values is repeated at 5-minute intervals under computer control. The source data recorded as absolute value are corrected in the diagram with the currently measured barometric pressure (Ambient Pressure Reference Monitor; APR-1) and saved in individual data. Further technical details can be found in the extensive documentation of the manufacturer (DSI).

Unless described otherwise, the test substances are administered on the test day at 09.00 hours. Following application, the parameters described above are measured for 24 hours.

Evaluation

After the end of the test, the individual data recorded are sorted with the analysis software (DATAQUEST™ A.R.T.™ ANALYSIS). The 2 hours before application are taken as the blank value here, so that the selected data set comprises the period from 07:00 hours on the test day to 09:00 hours on the next day.

The data are smoothed for a pre-settable time by mean value determination (15-minute average) and transferred as text file to a storage medium. The pre-sorted and compressed measured values are transferred to Excel templates and presented as tables. The data recorded are saved per test day in a specific folder, which bears the test number. Results and test protocols are filed in folders, sorted in paper form by numbers.

Literature

Klaus Witte, Kai Hu, Johanna Swiatek, Claudia Müssig, Georg Ertl and Bjorn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured with Radio-Telemetry. Physiology & Behavior 55(4): 783-787, 1994

C. EXEMPLARY EMBODIMENTS OF PHARMACEUTICAL COMPOSITIONS

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.
Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.
Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.
Production:
The compound according to the invention is suspended in the mixture of polyethylene glycol and polysorbate with stirring. The stirring process is continued until the compound according to the invention has completely dissolved.

I.V. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. Compound of the formula (I)

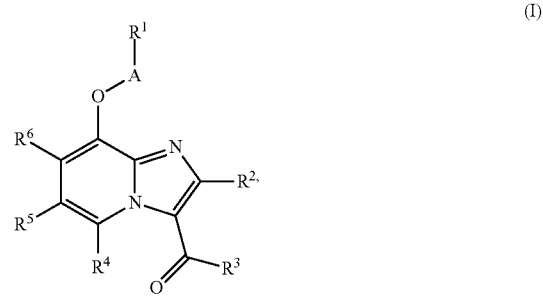

in which
A represents $CH_2$, $CD_2$ or $CH(CH_3)$,
$R^1$ represents $(C_4$-$C_6)$-alkyl, $(C_3$-$C_7)$-cycloalkyl or phenyl,
where $(C_4$-$C_6)$-alkyl may be substituted up to six times by fluorine,
where $(C_3$-$C_7)$-cycloalkyl may be substituted by 1 to 4 substituents independently of one another selected from the group consisting of fluorine, trifluoromethyl and $(C_1$-$C_4)$-alkyl,
and
where phenyl may be substituted by 1 to 4 substituents independently of one another selected from the group consisting of halogen, cyano, monofluoromethyl, difluoromethyl, trifluoromethyl, $(C_1$-$C_4)$-alkyl, $(C_1$-$C_4)$-alkoxy, difluoromethoxy and trifluoromethoxy or at two adjacent carbon atoms of the phenyl group by a difluoromethylenedioxy bridge,
$R^2$ represents hydrogen, $(C_1$-$C_4)$-alkyl, cyclopropyl, monofluoromethyl, difluoromethyl or trifluoromethyl, $R^3$ represents a group of the formula

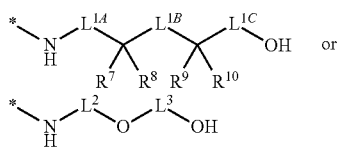

where
* represents the point of attachment to the carbonyl group,
$L^{1A}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$L^{1B}$ represents a bond or $(C_1-C_4)$-alkanediyl,
$L^{1C}$ represents a bond or $(C_1-C_4)$-alkanediyl,
where $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^7$ represents hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
where phenyl, phenoxy and benzyloxy for their part may be substituted by 1 to 3 halogen substituents,
where $(C_3-C_7)$-cycloalkyl may be substituted by 1 or 2 substituents independently of one another selected from the group consisting of fluorine, trifluoromethyl, $(C_1-C_4)$-alkyl, $(C_1-C_4)$-alkoxy and $(C_1-C_4)$-alkylsulphonyl,
and
where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^8$ represents hydrogen or $(C_1-C_4)$-alkyl,
where $(C_1-C_4)$-alkyl may be substituted by hydroxy,
or
$R^7$ and $R^8$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine and $(C_1-C_4)$-alkyl,
$R^9$ represents hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
where $(C_1-C_6)$-alkyl may be substituted by 1 to 3 substituents independently of one another selected from the group consisting of fluorine, trifluoromethyl, difluoromethoxy, trifluoromethoxy, hydroxy, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
where phenyl, phenoxy and benzyloxy for their part may be substituted by 1 to 3 halogen substituents,
where $(C_3-C_7)$-cycloalkyl may be substituted by 1 or 2 substituents independently of one another selected from the group consisting of fluorine, trifluoromethyl, $(C_1-C_4)$-alkyl and $(C_1-C_4)$-alkoxy,
and
where phenyl and 5- or 6-membered heteroaryl may be substituted by 1 to 3 substituents independently of one another selected from the group consisting of halogen, cyano, trifluoromethyl, $(C_1-C_4)$-alkyl, $(C_1-C_4)$-alkoxy and $(C_1-C_4)$-alkylsulphonyl,
$R^{10}$ represents hydrogen or $(C_1-C_4)$-alkyl,
where $(C_1-C_4)$-alkyl may be substituted by hydroxy,
or
$R^9$ and $R^{10}$ together with the carbon atom to which they are attached form a 3- to 7-membered carbocycle or a 4- to 7-membered heterocycle,
where the 3- to 7-membered carbocycle and the 4- to 7-membered heterocycle for their part may be substituted by 1 or 2 substituents independently of one another selected from the group consisting of fluorine and $(C_1-C_4)$-alkyl,
with the proviso that the radicals $R^7$ and $R^9$ do not both represent phenyl,
or
$R^7$ and $R^9$ together with the carbon atoms to which they are attached and with the group $L^{1B}$ form a 5- to 10-membered carbocycle,
with the proviso that not more than one of the radical pairs $R^7$ and $R^8$, $R^9$ and $R^{10}$ and $R^7$ and $R^9$, respectively, forms a carbo- or heterocycle,
$L^2$ represents straight-chain $(C_2-C_4)$-alkanediyl,
$L^3$ represents straight-chain $(C_2-C_4)$-alkanediyl,
$R^4$ represents hydrogen,
$R^5$ represents hydrogen, halogen, cyano, difluoromethyl, trifluoromethyl, $(C_1-C_4)$-alkyl, $(C_3-C_7)$-cycloalkyl, $(C_2-C_4)$-alkynyl, difluoromethoxy, trifluoromethoxy, $(C_1-C_4)$-alkoxy, amino, 4- to 7-membered heterocyclyl or 5- or 6-membered heteroaryl,
$R^6$ represents hydrogen, cyano or halogen,
and its N-oxides, salts, solvates, salts of the N-oxides and solvates of the N-oxides and salts.
2. The compound of claim 1 in which
A represents $CH_2$, $CD_2$ or $CH(CH_3)$,
$R^1$ represents $(C_4-C_6)$-alkyl, $(C_4-C_6)$-cycloalkyl or phenyl,
where $(C_4-C_6)$-alkyl may be substituted up to six times by fluorine,
where $(C_4-C_6)$-cycloalkyl may be substituted by 1 or 2 substituents independently of one another selected from the group consisting of fluorine, trifluoromethyl and methyl,
and
where phenyl may be substituted by 1 to 4 substituents independently of one another selected from the group consisting of fluorine, chlorine, bromine, difluoromethyl, trifluoromethyl and methyl or at 2 adjacent carbon atoms of the phenyl group by a difluoromethylenedioxy bridge, $R^2$ represents hydrogen, $(C_1-C_4)$-alkyl, trifluoromethyl or cyclopropyl, $R^3$ represents a group of the formula where
* represents the point of attachment to the carbonyl group,
$L^{1A}$ represents a bond or methylene,
$L^{1B}$ represents a bond, methylene or 1,2-ethanediyl,
$L^{1C}$ represents a bond or methylene,
  where methylene may be substituted by 1 or 2 substituents independently of one another selected from the group consisting of trifluoromethyl and $(C_1-C_4)$-alkyl,
$R^7$ represents hydrogen, trifluoromethyl, $(C_1-C_6)$-alkyl, $(C_2-C_4)$-alkenyl, $(C_3-C_6)$-cycloalkyl, $(C_1-C_4)$-alkoxycarbonyl, 5- or 6-membered heteroaryl or phenyl,
  where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, $(C_1-C_4)$-alkylthio, $(C_1-C_4)$-alkylsulphonyl, phenyl, phenoxy and benzyloxy,
    where phenyl, phenoxy and benzyloxy for their part may be substituted by 1 or 2 substituents selected from the group consisting of fluorine and chlorine,
  where $(C_3-C_6)$-cycloalkyl may be substituted by 1 or 2 substituents independently of one another selected from the group consisting of fluorine, trifluoromethyl, methyl and ethyl,
  and
  where phenyl and 5- or 6-membered heteroaryl may be substituted by 1 or 3 substituents independently of one another selected from the group consisting of fluorine, chlorine, cyano, trifluoromethyl, $(C_1-C_4)$-alkyl, methoxy and ethoxy,
$R^8$ represents hydrogen, methyl or ethyl,
where methyl and ethyl may be substituted by hydroxy, or
$R^7$ and $R^8$ together with the carbon atom to which they are attached form a 3- to 6-membered carbocycle,
  where the 3- to 6-membered carbocycle may be substituted by 1 or 2 substituents independently of one another selected from the group consisting of fluorine and methyl,
$R^9$ represents hydrogen, trifluoromethyl, $(C_1-C_6)$-alkyl, $(C_2-C_4)$-alkenyl, $(C_3-C_6)$-cycloalkyl, $(C_1-C_4)$-alkoxycarbonyl, 5- or 6-membered heteroaryl or phenyl,
  where $(C_1-C_6)$-alkyl may be substituted by 1 or 2 substituents independently of one another selected from the group consisting of fluorine, trifluoromethyl, difluoromethoxy, trifluoromethoxy, hydroxy, $(C_1-C_4)$-alkoxy, $(C_1-C_4)$-alkylthio, $(C_1-C_4)$-alkylsulphonyl, phenyl, phenoxy and benzyloxy,
    where phenyl, phenoxy and benzyloxy for their part may be substituted by 1 or 2 substituents selected from the group consisting of fluorine and chlorine,
  where $(C_3-C_6)$-cycloalkyl may be substituted by 1 or 2 substituents independently of one another selected from the group consisting of fluorine, trifluoromethyl, methyl and ethyl,
  and
  where phenyl and 5- or 6-membered heteroaryl may be substituted by 1 or 3 substituents independently of one another selected from the group consisting of fluorine, chlorine, cyano, trifluoromethyl, $(C_1-C_4)$-alkyl, methoxy and ethoxy,
$R^{10}$ represents hydrogen, methyl or ethyl,
where methyl and ethyl may be substituted by hydroxy, or
$R^9$ and $R^{10}$ together with the carbon atom to which they are attached form a 3- to 6-membered carbocycle,
  where the 3- to 6-membered carbocycle may be substituted by 1 or 2 substituents independently of one another selected from the group consisting of fluorine and methyl,
with the proviso that the radicals $R^7$ and $R^9$ do not both represent phenyl,
or
$R^7$ and $R^9$ together with the carbon atoms to which they are attached and with the group $L^{1B}$ form a 5- to 10-membered carbocycle,
with the proviso that not more than one of the radical pairs $R^7$ and $R^8$, $R^9$ and $R^{10}$ and $R^7$ and $R^9$, respectively, forms one of the carbo- or heterocycles mentioned above,
$L^2$ represents 1,2-ethanediyl,
$L^3$ represents 1,2-ethanediyl,
$R^4$ represents hydrogen,
$R^5$ represents hydrogen, fluorine, chlorine, bromine, cyano, difluoromethyl, trifluoromethyl, methyl, ethyl, cyclopropyl, ethynyl, morpholinyl or pyrrolidinyl,
$R^6$ represents hydrogen or fluorine,
and its N-oxides, salts, solvates, salts of the N-oxides and solvates of the N-oxides and salts.

3. The compound of claim 1 in which
A represents $CH_2$,
$R^1$ represents a phenyl group of the formula where
# represents the point of attachment to A,
and
$R^{11}$, $R^{12}$ and $R^{13}$ independently of one another represent hydrogen, fluorine or chlorine,
with the proviso that at least two of the radicals $R^{11}$, $R^{12}$, $R^{13}$ are different from hydrogen,
$R^2$ represents methyl,
$R^3$ represents a group of the formula where
* represents the point of attachment to the carbonyl group,
$L^{1A}$ represents a bond,
$L^{1B}$ represents a bond, methylene or 1,2-ethanediyl, $L^{1C}$ represents a bond, $R^7$ represents hydrogen, trifluoromethyl, $(C_1-C_6)$-alkyl or phenyl, where $(C_1-C_6)$-alkyl may be substituted by 1 or 2 substituents independently of one another selected from the group consisting of fluorine, trifluoromethyl, hydroxy, $(C_1-C_4)$-alkoxy and phenyl, and where the phenyl groups mentioned above may be substituted by 1 or 2 substituents independently of one another selected from the group consisting of fluorine and chlorine, $R^8$ represents hydrogen, methyl or ethyl, $R^9$ represents hydrogen, trifluoromethyl, $(C_1-C_6)$-alkyl or phenyl, where $(C_1-C_6)$-alkyl may be substituted by 1 or 2 substituents independently of one another selected from the group consisting of fluorine, trifluoromethyl, hydroxy, $(C_1-C_4)$-alkoxy and phenyl, and where phenyl may be substituted by 1 or 2 substituents independently of one another selected from the group consisting of fluorine and chlorine, $R^{10}$ represents hydrogen, methyl or ethyl, or $R^9$ and $R^{10}$ together with the carbon atom to which they are attached form a 3- to 6-membered carbocycle, with the proviso that the radicals $R^7$ and $R^9$ do not both represent phenyl, or $R^7$ and $R^9$ together with the carbon atoms to which they are attached and the group $L^{1B}$ form a 5- to 9-membered carbocycle, with the proviso that not more than one of the radical pairs $R^9$ and $R^{10}$ and $R^7$ and $R^9$, respectively, forms a carbocycle, $R^4$ represents hydrogen, $R^5$ represents hydrogen, fluorine, chlorine, cyano, methyl or ethyl, $R^6$ represents hydrogen, and its N-oxides, salts, solvates, salts of the N-oxides and solvates of the N-oxides and salts.

4. A process for preparing the compound of formula (I) as defined in claim 1, comprising

[A] reacting a compound of formula (II)

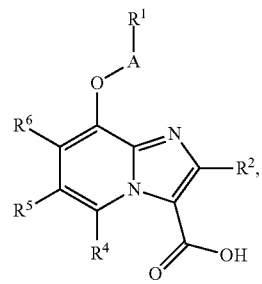
(II)

in which A, $R^1$, $R^2$, $R^4$, $R^5$ and $R^6$ each have the meanings given above and $T^1$ represents $(C_1-C_4)$-alkyl or benzyl, in an inert solvent in the presence of a suitable base or acid to give a carboxylic acid of formula (III)

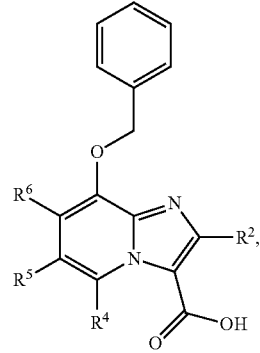
(III)

in which A, $R^1$, $R^2$, $R^4$, $R^5$ and $R^6$ each have the meanings given above, and reacting the compound of formula (III) in an inert solvent under amide coupling conditions with an amine of formula (IV-A) or (IV-B)

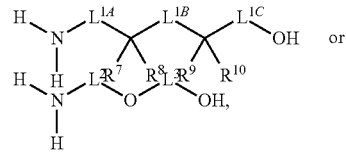
(IV-A)

or

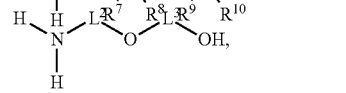
(IV-B)

in which $L^{1A}$, $L^{1B}$, $L^{1C}$, $L^2$, $L^3$, $R^7$, $R^8$, $R^9$ and $R^{10}$ each have the meanings given above or

[B] reacting a compound of formula (III-B)

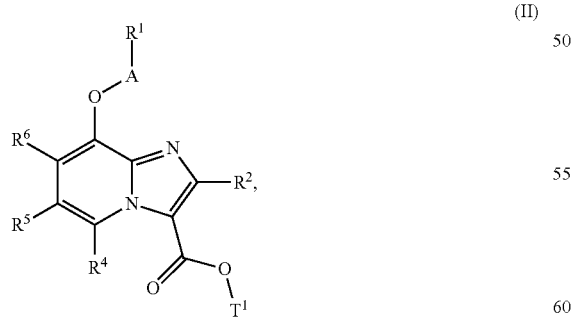
(III-B)

in which $R^2$, $R^4$, $R^5$ and $R^6$ each have the meanings given above, in an inert solvent under amide coupling conditions with an amine of the formula (IV-A) or (IV-B) to give a compound of formula (I-A) or (I-B)

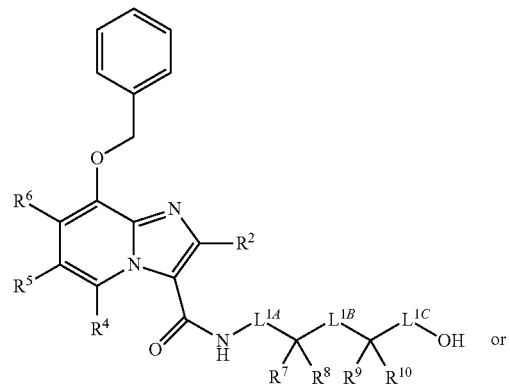
(I-A)

or

-continued (I-B)

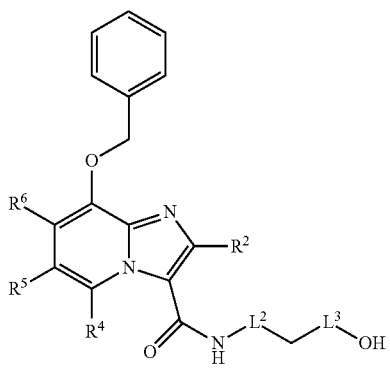

in which $R^2$, $R^4$, $R^5$, $R^6$, $L^{1A}$, $L^{1B}$, $L^{1C}$, $L^2$, $L^3$, $R^7$, $R^8$, $R^9$ and $R^{10}$ each have the meanings given above, removing the benzyl group from the compound of formula (I-A) or (I-B) using methods known to the person skilled in the art and reacting the resulting compound of formula (V-A) or (V-B)

(V-A)

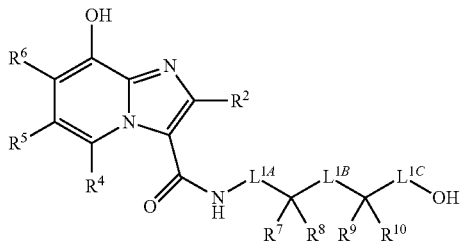

-continued (V-B)

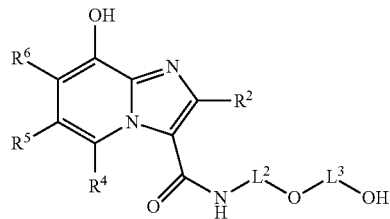

in which $R^2$, $R^4$, $R^5$, $R^6$, $L^{1A}$, $L^{1B}$, $L^{1C}$, $L^2$, $L^3$, $R^7$, $R^8$, $R^9$ and $R^{10}$ each have the meanings given above, in an inert solvent in the presence of a suitable base with a compound of formula (VI)

(VI)

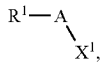

in which A and $R^1$ have the meanings given above and $X^1$ represents a suitable leaving group, in particular chlorine, bromine, iodine, mesylate, triflate or tosylate, and optionally converting the resulting compound of formula (I) with a (i) solvent and/or (ii) acid or base into a solvate, salt and/or solvate of a salt thereof.

5. A pharmaceutical composition, comprising a compound of claim 1 and an inert, non-toxic, pharmaceutically suitable auxiliary.

6. The pharmaceutical composition of claim 1 and an active compound selected from the group consisting of an organic nitrate, an NO donor, a cGMP-PDE inhibitor, an agents having antithrombotic activity, an agent lowering blood pressure, and an agent altering lipid metabolism.

* * * * *